US 7,772,221 B2

(12) United States Patent
Marcin et al.

(10) Patent No.: US 7,772,221 B2
(45) Date of Patent: Aug. 10, 2010

(54) DIAMINOPROPANE DERIVED MACROCYCLES AS INHIBITORS OF β AMYLOID PRODUCTION

(75) Inventors: Lawrence R. Marcin, Bethany, CT (US); Andrew C. Good, Wallingford, CT (US); Yong-Jin Wu, Madison, CT (US); Dmitry S. Zuev, Wallingford, CT (US); Richard E. Olson, Orange, CT (US); Nenghui Wang, Guilford, CT (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 272 days.

(21) Appl. No.: 12/019,986

(22) Filed: Jan. 25, 2008

(65) Prior Publication Data

US 2008/0194535 A1 Aug. 14, 2008

Related U.S. Application Data

(60) Provisional application No. 60/888,993, filed on Feb. 9, 2007.

(51) Int. Cl.
*C07D 403/04* (2006.01)
*C07D 413/04* (2006.01)
*A61K 31/4025* (2006.01)
*A61P 25/28* (2006.01)

(52) U.S. Cl. ...................... 514/183; 540/456
(58) Field of Classification Search ............... 514/183; 540/456
See application file for complete search history.

(56) References Cited

U.S. PATENT DOCUMENTS 7,338,974 B2 3/2008 Marcin et al.

FOREIGN PATENT DOCUMENTS

| WO | WO 02/100856 | 12/2002 |
|---|---|---|
| WO | WO 03/072535 | 9/2003 |
| WO | WO 2004/013098 | 2/2004 |
| WO | WO 2004/062625 | 7/2004 |
| WO | WO 2005/018545 | 3/2005 |
| WO | WO 2005/049585 | 6/2005 |

OTHER PUBLICATIONS

Ghosh, A. K., et al., "Structure-based design of cycloamide-urethane-derived novel inhibitors of human brain memapsin 2 (β-secretase)", *Bioorganic and Medicinal Chem. Lett.* 15 (2005) 15-20.
Hussain, I. et al., "Identification of a Novel Aspartic Protease (Asp 2) as β-Secretase", *Mol. Cell. Neurosci.* 14 (1999) 419-427.
Lin, X. et al., "Human aspartic protease memapsin 2 cleaves the β-secretase site of β-amyloid precursor protein", *Proceedings of the National Academy of Sciences of the USA* (PNAS) 97 (2000) 1456-1460.
Luo, Yi, et al., "Mice deficient in BACE1, the Alzheimer's β-secretase, have normal phenotype and abolished β-amyloid generation", *Nature Neuroscience*4 (2001) 231-232.
U.S. Appl. No. 11/940,597, filed Nov. 15, 2007, Wu, et al.
Roberds, S.L. et al., "BACE knockout mice are healthy despite lacking the primary β-secretase activity in brain: implications for Alzheimer's disease therapeutics", *Human Molecular Genetics* 10 (2001) 1317-1324.
Seiffert, D.; et al., "Presenilin-1 and -2 are molecular targets for γ-secretase inhibitors", *J. Biol. Chem.* 275 (2000) 34086-34091.
Selkoe, D. J., "Cell Biology of the Amyloid-β-Protein Precursor and the Mechanism of Alzheimer's Disease", *Ann. Rev. Cell Biol.* 10 (1994) 373-403.
Selkoe, D. J., "Alzheimer's Disease: Genes, Proteins, and Therapy", *Physiol. Rev.* 81 (2001) 741-766.
Sinha S. et al. "Purification and cloning of amyloid precursor protein β-secretase from human brain", *Nature* 402 (1999) 537-540.
Stachel, S.J., et al., "Macrocyclic Inhibitors of β-Secretase: Functional Activity in an Animal Model", *J. Med. Chem.* 49 (2006) 6147-6150.
Thal, D.R., et al., "Two Types of Sporadic Cerebral Amyloid Angiopathy", *J. Neuropath. Exp. Neuro.* (2002) 61: 282-293.
Vassar, R., et al., "β-Secretase Cleavage of Alzheimer's Amyloid Precursor Protein by the Transmembrane Aspartic Protease BACE", *Science* 286 1999) 735-741.
Walsh, D. M., et al., "Amyloid-β oligomers: their production, toxicity and therapeutic inhibition", *Biochemical Society Transactions* 30 (2002) 552-557.
Wolfe, M. J., "Secretase Targets for Alzheimer's Disease: Identification and Therapeutic Potential", *J. Med. Chem.* 44 (2001) 2039-2060.
Yan, R., et al., "Membrane-anchored aspartyl protease with Alzheimer's disease β-secretase activity", *Nature* 402 (1999) 533-537.

*Primary Examiner*—Bruck Kifle
(74) *Attorney, Agent, or Firm*—John F. Levis; Aldo A. Algieri

(57) ABSTRACT

There is provided a series of macrocyclic diaminopropanes of Formula (I) or a stereoisomer; or a pharmaceutically acceptable salt thereof, wherein $R_1$, $R_2$, $R_3$, m, n, W, X, Y, Z and L as defined herein, their pharmaceutical compositions and methods of use. These novel compounds inhibit the processing of amyloid precursor protein (APP) by β-secretase and, more specifically, inhibit the production of Aβ-peptide. The present disclosure is directed to compounds useful in the treatment of neurological disorders related to β-amyloid production, such as Alzheimer's disease and other conditions affected by anti-amyloid activity.

13 Claims, No Drawings

DIAMINOPROPANE DERIVED MACROCYCLES AS INHIBITORS OF β AMYLOID PRODUCTION

CROSS-REFERENCE TO RELATED APPLICATIONS

This is a non-provisional application which claims the benefit of U.S. Provisional Application No. 60/888,993 filed Feb. 9, 2007.

FIELD OF THE DISCLOSURE

This patent application provides macrocyclic diaminopropane compounds having drug and bio-affecting properties, their pharmaceutical compositions and method of use. In particular, the disclosure is concerned with a series of macrocyclic diaminopropanes which are inhibitors of the β-amyloid peptide (β-AP) production, thereby acting to prevent the accumulation of amyloid protein deposits in the brain and, therefore, are useful in the treatment of neurological disorders related to β-amyloid production. More particularly, the present disclosure relates to the treatment of Alzheimer's Disease (AD) and similar diseases.

BACKGROUND

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J. *Ann. Rev. Cell Biol.* 1994, 10, 373-403).

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP) (Selkoe, D. *Physiol. Rev.* 2001, 81, 741-766; Wolfe, M. *J. Med. Chem.* 2001, 44, 2039-2060). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D.; Bradley, J. et al., *J. Biol. Chem.* 2000, 275, 34086-34091).

In addition to AD, excess production and/or reduced clearance of Aβ causes cerebral amyloid angiopathy (CAA) (reviewed in Thal, D., Gherbremedhin, E. et al., *J. Neuropath. Exp. Neuro.* 2002, 61, 282-293). In these patients, vascular amyloid deposits cause degeneration of vessel walls and aneurysms that may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

A logical approach to reducing Aβ levels is to interfere with the action of the secretases that are directly involved in the cleavage of APP to Aβ. The β-secretase enzyme (BACE) is responsible for cleaving APP and forms the amino-terminus of Aβ, initiating the amyloidogenic pathway. The BACE enzyme is a transmembrane aspartyl protease and was described in the literature by several independent groups [see Hussain, I. et al., *Mol. Cell. Neurosci.*, 1999, 14, 419-427; Lin, X. et al., *Proceedings of the National Academy of Sciences of the United States of America* 2000, 97: 1456-1460; Sinha, S., et al., *Nature* 1999, 402, 537-540; Vassar, R., et al., *Science* 1999, 286, 735-741; Walsh, D. M., et al., *Biochemical Transactions* 2002, 30, 552-557; Wolfe, M. *J. Med. Chem.* 2001, 44, 2039-2060; Yan, R. et al., *Nature* 1999, 402, 533-537].

Removal of BACE activity in mice by gene targeting completely abolishes Aβ production [see Luo, Y., et al., *Nature Neuroscience* 2001, 4, 231-232; Roberds, S. L., et al., *Human Molecular Genetics* 2001, 10, 1317-1324]. BACE −/− mice also show no detectable negative phenotypes, suggesting that disruption of BACE-mediated cleavage of APP does not produce additional undesired effects. This demonstrates that a drug substance capable of inhibiting β-secretase activity should lower or halt the synthesis of Aβ and should provide a safe treatment for Alzheimer's disease.

PCT Publication WO 2005049585, published Jun. 2, 2005 discloses novel macrocyclic lactams for the treatment of neurological and vascular disorders related to β-amyloid generation and/or aggregation.

PCT Publication WO 2005018545 A2, published Mar. 3, 2005 discloses macrocyclic BACE inhibitors for the treatment of Alzheimers.

Published article Ghosh, A. K. et al., *Bioorganic and Medicinal Chem. Lett.* 2005, 15, 15-20 discloses macrocyclic amide-urethane inhibitors of BACE.

PCT Publication WO 2004062625 A2, published Jul. 29, 2004 discloses macrocyclic BACE inhibitors for the treatment of Alzheimers.

PCT Publication WO 2002100856 A1, published Dec. 19, 2002 discloses macrocycles useful in the treatment of Alzheimers.

PCT Publication WO 2004013098, published Feb. 12, 2004, discloses lactam derivatives as beta-secretase inhibitors.

PCT Publication WO 2003072535, published Sep. 4, 2003, discloses substituted hydroxyethylamines in the treatment of Alzheimer's Disease.

At present there remains an urgent need to develop pharmaceutical agents capable for effective treatment in halting, slowing, preventing, and/or reversing the progression of Alzheimer's disease. Compounds that are effective inhibitors of beta-secretase, that inhibit beta-secretase mediated cleavage of APP, that are effective inhibitors of Aβ protein production by beta-secretase, and/or are effective in reducing soluble Aβ protein, amyloid beta deposits or amyloid beta plaques, are needed for effective treatment in halting, slowing, preventing, and/or reversing neurological disorders related to Aβ protein production, such as Alzheimer's disease.

SUMMARY OF THE DISCLOSURE

A series of macrocyclic diaminopropanes having the Formula (I)

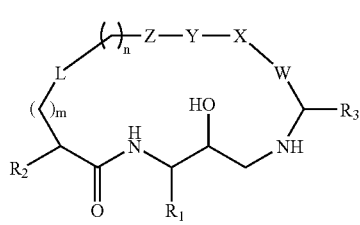

(I)

or a stereoisomer; or a pharmaceutically acceptable salt thereof, wherein $R_1$, $R_2$, $R_3$, L, W, X, Y, Z, m, and n as defined below are effective inhibitors of the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds or a pharmaceutical composition containing a therapeutically effective amount of at least one of these compounds to patients suffering from, or susceptible to, these conditions involves reducing β-AP available for accumulation and deposition in brains of these patients.

DETAILED DESCRIPTION

The present application comprises compounds of Formula I, their pharmaceutical formulations, and their use in inhibiting β-AP production in patients suffering from or susceptible to AD or other disorders resulting from β-AP accumulation in brain tissue. The compounds of Formula I which include stereoisomers and pharmaceutically acceptable salts thereof have the following formula and meanings:

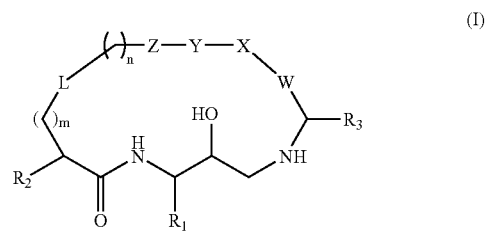

(I)

wherein $R_1$ is $C_{1-6}$alkyl, phenyl or phenyl($C_{1-4}$alkyl) in which each group is optionally substituted with one or two groups selected from halogen, $C_{1-4}$alkyl, OH, $CF_3$, $OCF_3$ and CN;

$R_2$ is hydrogen, $C_{1-6}$alkyl, $C_{3-6}$alkenyl, $C_{3-6}$cycloalkyl or $C_{3-6}$cylcoalkyl($C_{1-4}$alkyl) in which each group is optionally substituted with a group selected from halogen, $C_{1-4}$alkyl, OH, $C_{1-4}$alkoxy, $CF_3$, $CF_2H$, $OCF_3$ and CN; or $NHR_4$, $NR_4C(=O)R_5$, $NR_4C(=O)OR_5$ or $NR_4S(=O)_2R_5$;

$R_3$ is hydrogen, $C_{1-6}$alkyl, phenyl or phenyl($C_{1-4}$alkyl) in which each group is optionally substituted with one to two groups selected from halogen, $C_{1-4}$alkyl, OH, $CF_3$, $OCF_3$ and CN;

$R_4$ is hydrogen or $C_{1-6}$alkyl;

$R_5$ is $C_{1-6}$alkyl, phenyl or thiophenyl in which each group is optionally substituted with one to two groups selected from halogen, $C_{1-4}$alkyl, OH, $CF_3$, $OCF_3$ and CN;

m is 1 or 2;

n is 1 or 2;

W is $CH_2$; or W and $R_3$ are joined together to form the following ring system

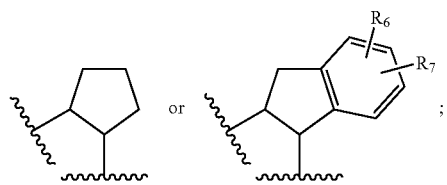

;

X is a bond or $CH_2$; or when W is $CH_2$, X and $R_3$ are joined together to form the following ring system

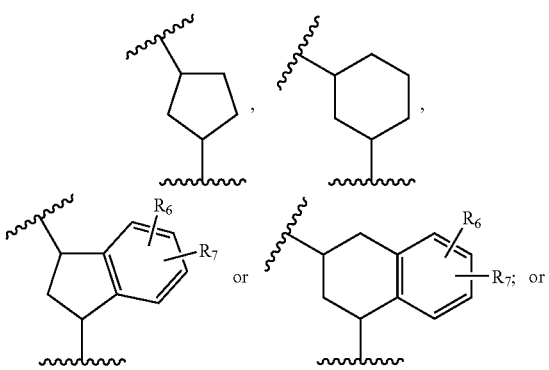

; or

X and W are joined together to form the following ring system

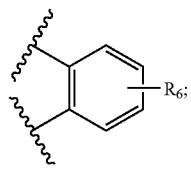

Y is a bond or $C_{1-3}$alkyl;

Z is a bond, oxygen or $NR_8$;

$R_6$ and $R_7$ each are independently hydrogen, halogen, $C_{1-6}$alkyl, $C_{3-6}$cycloalkyl, $C_{3-6}$cylcoalkyl($C_{1-4}$alkyl), phenyl, 4-morpholinophenyl, $C_{1-6}$alkoxy, $OCF_3$, phenoxy, indanyl, pyrazoyl, piperizinyl, 4-(5-tert-butoxycarbonyl)-hexahydropyrrolo[3,4-c]pyrrol-2(1H)-yl), 5-methyl-hexahydropyrrolo[3,4-c]pyrrol-2(1H)-yl and pyrrolidinyl in which each group is optionally substituted with a group selected from halogen, $C_{1-4}$alkyl, $CF_3$, $CF_2H$, OH, $OCF_3$ and $C_{1-4}$alkoxy;

$R_8$ is hydrogen, $C_{1-4}$alkyl or $C(=O)OR_9$;

$R_9$ is $C_{1-6}$alkyl, phenyl or phenyl($C_{1-4}$alkyl);

L is $-CH(R_{10})-CH(R_{11})-$ or $-C(R_{10})=C(R_{11})-$; and $R_{10}$ and $R_{11}$ are each independently hydrogen or methyl.

The present application also provides a method for the treatment or alleviation of disorders associated with β-amyloid peptide, especially Alzheimer's Disease, cerebral amyloid angiopathy, Down's Syndrome and which comprises administering together with a conventional adjuvant, carrier or diluent a therapeutically effective amount of a compound of Formula (I) or a pharmaceutically acceptable salt thereof.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Dingwall, C. *Journal of Clinical Investigation* 2001, 108, 1243-1246; as well as PCT international patent application WO 01/92235, published Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The term "substituted," as used herein and in the claims, means that any one or more hydrogens on the designated atom is replaced with a selection from the indicated group, provided that the designated atom's normal valency is not exceeded, and that the substitution results in a stable compound.

As used herein and in the claims, "alkyl" or "alkylene" is intended to include both branched and straight-chain saturated aliphatic hydrocarbon groups having the specified number of carbon atoms; for example, "$C_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, pentyl and hexyl. Preferred "alkyl" group, unless otherwise specified, is "$C_{1-4}$ alkyl". Additionally, unless otherwise specified, "propyl" denotes n-propyl or i-propyl; "butyl" denotes n-butyl, i-butyl, sec-butyl or t-butyl.

As used herein and in the claims, "alkenyl" or "alkenylene" is intended to include hydrocarbon chains of either a straight or branched configuration and one or more unsaturated carbon-carbon bonds which may occur in any stable point along the chain, for example, "$C_{3-6}$ alkenyl" include but are not limited to 1-propenyl, 2-propenyl, 1-butenyl, 2-butenyl, 3-butenyl, 3-methyl-2-butenyl, 2-pentenyl, 3-pentenyl, hexenyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

As used herein and in the claims, "halogen" refers to fluoro, chloro, bromo, and iodo. Unless otherwise specified, preferred halogens are fluoro and chloro. "Counterion" is used to represent a small, negatively charged species such as chloride, bromide, hydroxide, acetate, sulfate, and the like.

"Cycloalkyl" is intended to include saturated ring groups, having the specified number of carbon atoms. For example, "$C_{3-6}$ cycloalkyl" denotes such as cyclopropyl, cyclobutyl, cyclopentyl and cyclohexyl.

The compounds described herein may have asymmetric centers. An example of a preferred stereochemical configuration is the isomer:

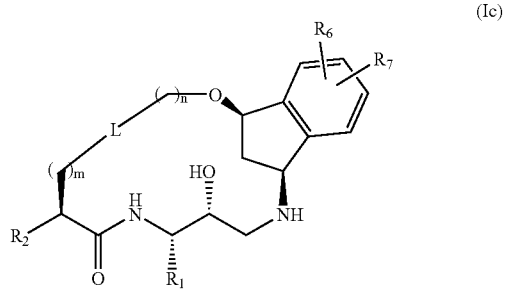

(Ic)

or pharmaceutically acceptable salt thereof, but is not intended to be limited to this example. It is understood, that whether a chiral center in an isomer is "R" or "S" depends on the chemical nature of the substituents of the chiral center. All configurations of compounds of the invention are considered part of the invention. Compounds of the present disclosure containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, EtOAc, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

In the method of the present application, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The macrocyclic compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In general, the macrocyclic diaminopropanes represented by Formula Ia (General Reaction Scheme A) can be prepared by metal catalyzed hydrogenation of the corresponding macrocyclic alkenes represented by Formula Ib. The macrocyclic alkenes Ib can be obtained by ring-closing metathesis (RCM) of diene intermediate 2. Intermediate 2 can be obtained by coupling, under standard conditions known to one skilled in the art, a substituted carboxylic acid 4 and a substituted 2-hydroxy-1-3-diaminopropane 3. Preparations of the requisite diaminopropanes 3 (General Reaction Scheme B) and carboxylic acids 4 are disclosed in detail in the discussion given below.

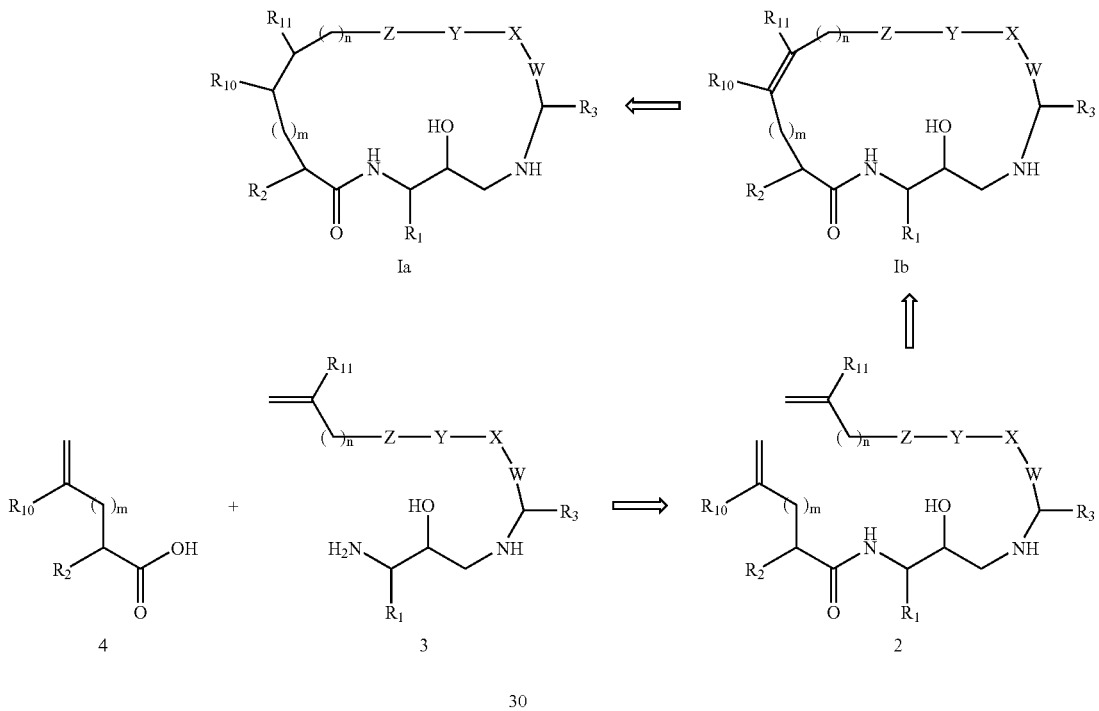

General Reaction Scheme A

In general, 2-hydroxy-1-3-diaminopropanes 3 can be prepared from N-protected α-amino epoxides 5 and primary amines 6 (General Reaction Scheme B). The synthesis of N-protected α-amino epoxides 5 from activated amino esters 7 is known to one skilled in the art and is disclosed in a number of references including but not limited to those given below. The synthesis of olefin appended primary amines represented by formula 6 is disclosed in detail in the discussion given below.

The synthesis of N-protected α-amino epoxides 5a is known to one skilled in the art and is disclosed in a number of references including, but not limited to those listed below (Reaction Scheme 1). The starting materials for the process of preparing N-protected α-amino epoxides 5a are activated esters, represented by formula 7, wherein $R_1$ is as defined above and LG is Cl or a phenyl ester substituted in the ortho or para position on the phenyl ring by hydrogen, halogen, or a nitro group (Kronenthal, D. et al., WO 02/14256 A1 and

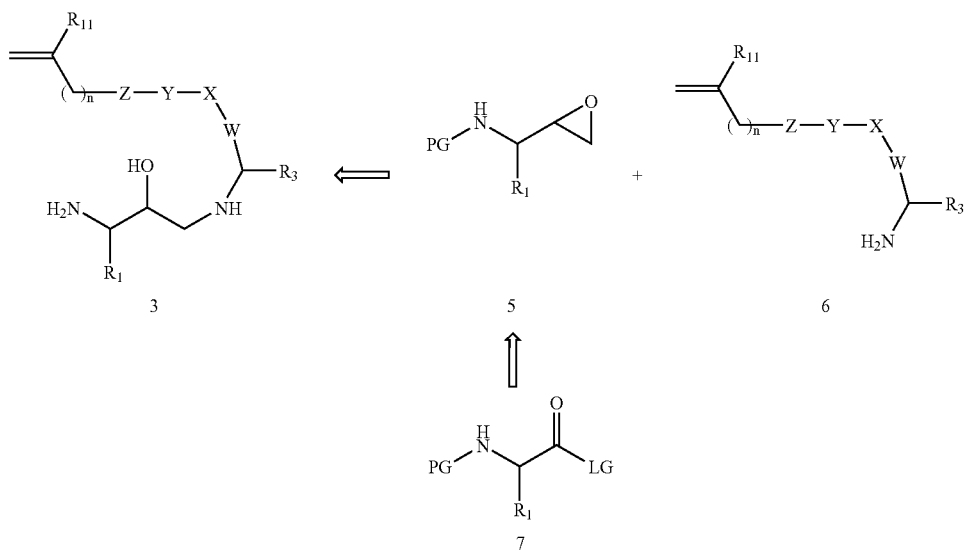

General Reaction Scheme B

Decicco, C. P. et al. WO 2004/013098 A1.). The compounds represented by formula 7, are commercially available or can be prepared by techniques well known to those skilled in the art. The protecting group (PG) on the amino function is preferably Boc or CBz, but can also be other amino protecting groups which are recognized by those skilled in the art of organic synthesis.

In accordance with the present invention, an activated ester 7 is treated with a sulfur ylide to produce an intermediate keto ylide compound represented by 9. The sulfur ylide reagent is conveniently prepared from a sulfoxonium salt, such as trimethylsulfoxonium iodide, by reaction with a suitable base, such as sodium hydride, in an organic solvent. The keto-ylide compound 9 is then converted to the bromoketone 10 by reaction with a source of bromide, preferably lithium bromide, and an organic acid, such as methanesulfonic acid. The carbonyl group of the bromoketone 10 is then diastral selectively reduced using a suitable hydride source such as borohydride or aluminum hydride, most preferably sodium borohydride, to afford an intermediate alcohol represented by formula 11, that spontaneously cyclizes to afford erythro epoxide 5a (Albeck, A.; Persky, R. *Tetrahedron* 1994, 50, 6333-6346.).

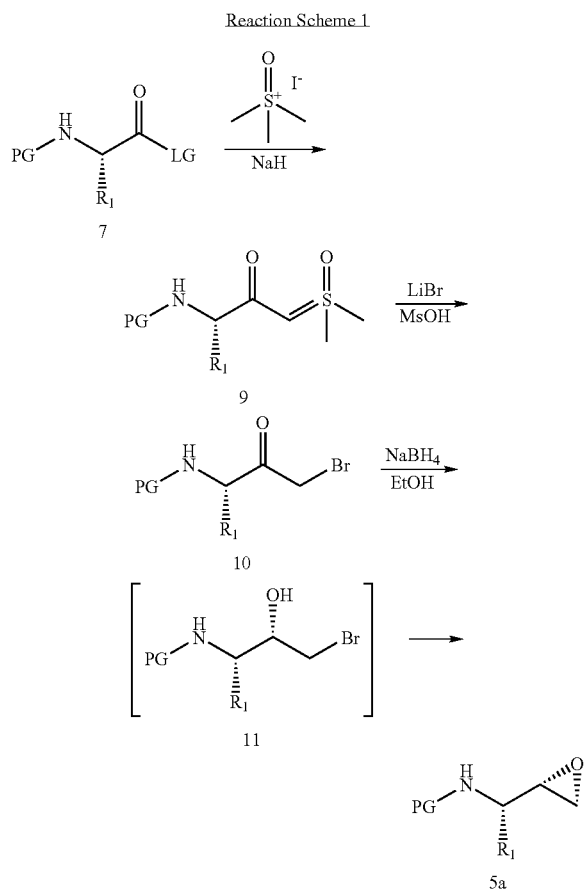

A preferred subset of primary amines of formula 6 are represented by formula 6a and are known as 3-allyloxy-1-aminoindanes. Routes for the preparation of 3-allyloxy-1-aminoindanes 6a and other preferred primary amines are provided below.

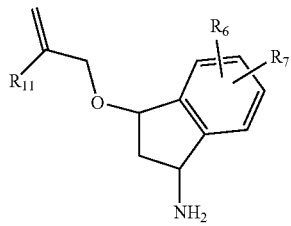

A variety of N-protected aminoindan-1-ones 16 can be prepared from aryl aldehydes 12 using known literature methods (Reaction Scheme 2) (see, for instance, Dallemagne, P.; Pilo, J. C.; Rault, S.; Robba, M. *Bull Chem. Soc. Fr.* 1993, 130, 121-124. Quermonne, M. A.; Dallemagne, P.; Louchahi-Raoul, J.; Pilo, J. C.; Rault, S.; Robba, M. *Eur. J. Med. Chem.* 1992, 27, 961-965.). Propionic acids 13 can be prepared from the condensation of aryl aldehydes 12 and malonic acid in the presence of ammonium formate. When $R_6$ and/or $R_7$ are an electron rich donating groups (i.e. alkyl or alkoxy), cyclization of propionic acids 13 to afford indanones 16 can be accomplished in a single step using trifluoroacetic anhydride and trifluoroacetic acid. In other cases, when $R_6$ and/or $R_7$ are an electron withdrawing groups (i.e. halogen), cyclization to indanones 16 can be performed using a three step protocol involving protection of the amino group as a trifluoroacetate 14, conversion of the carboxylic acid to an acid chloride 15, and Lewis-acid catalyzed cyclization. Reduction of the indanone 16 with borane.THF can provide a mixture of the cis- and trans-3-aminoindan-1-ols 17, favoring the cis diasteromer. Separation of the cis and trans diastereomers can be accomplished using silica gel column chromatography. Reduction of the indanone 16 with L-Selectride can exclusively provide the cis-aminoindan-1-ols 17. Deprotonation of alcohols 17, followed by alkylation with an electrophile, such as allyl bromide or 3-bromo-2-methylpropene, can provide the corresponding allyl ethers 18. Cleavage of the trifluoroacetate protecting group of intermediate 18 to afford aminoindane allyl ethers 6a can be accomplished using aqueous potassium carbonate in refluxing methanol. This method can be used to prepare either the cis- or trans-aminoindane allyl ethers 6a from cis- or trans-17, respectively.

Enantiomerically enriched samples of cis- or trans-indane allyl ethers 6a can be prepared from enantiomerically enriched β-aminoacids 13 (Reaction Scheme 2). Enantiomerically enriched β-aminoacids 13 can be obtained from commercial sources or they can prepared by literature methods which are known to one skilled in the art (for a general overview, see: *Enantioselective Synthesis of b-amino Acids*; Juaristi, E., Ed.; Wiley-VCH: New York, 1996). Enantiomerically enriched indane allyl ethers 6a can also be obtained after chiral HPLC separation of the racemic intermediates, preferably compounds 17 or 18, and transformation of the enantiomerically enriched intermediates to amine 6a as described in Reaction Scheme 2.

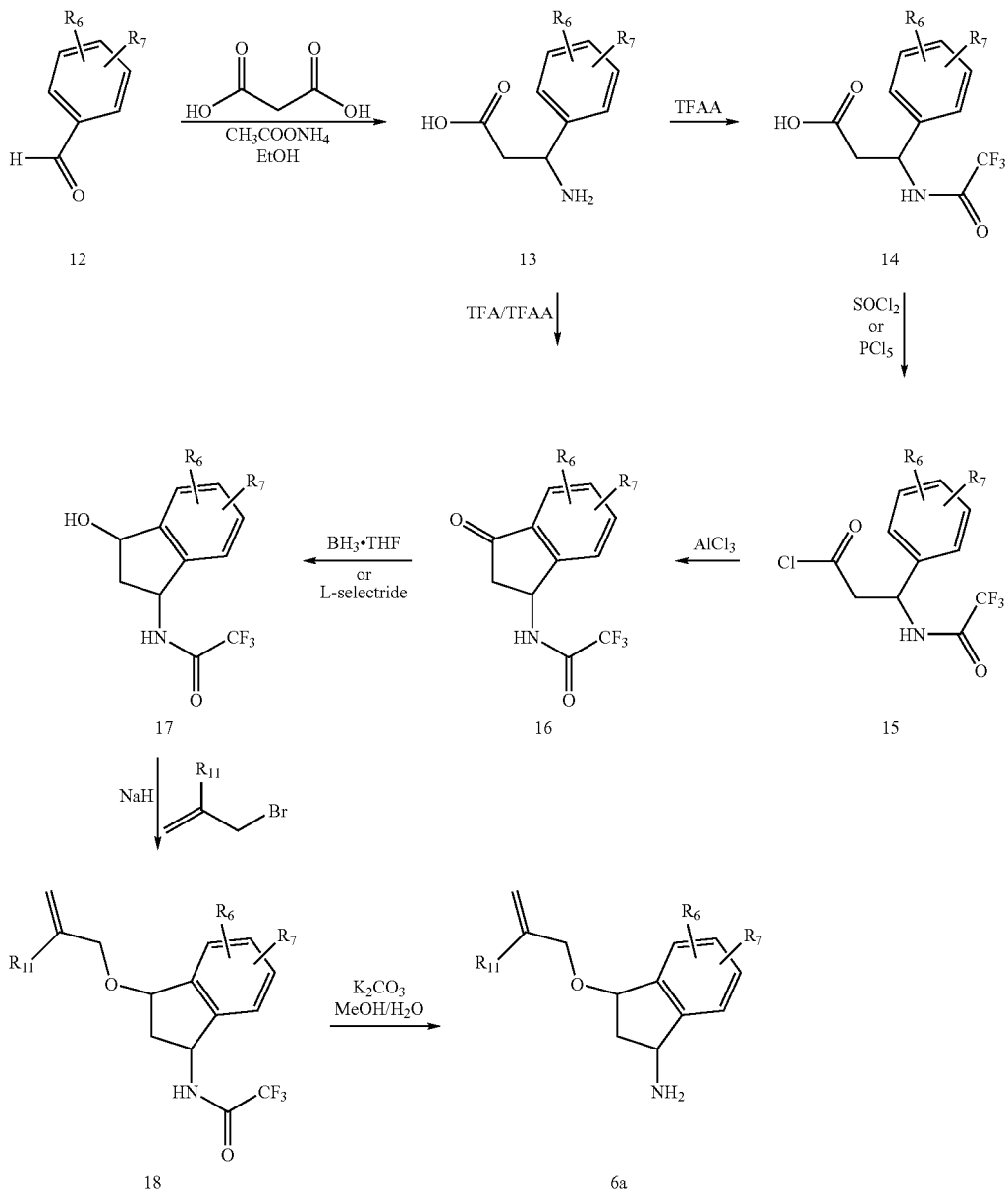

Reaction Scheme 3 discloses a method for preparing preferred subset of 1,3-diaminoindanes 6b from N-protected 3-aminoindanones 16. Condensation of indanones 16 with allyl amine or 3-butenamine and subsequent reduction of the resulting imines with sodium borohydride can provide the diamines 20 as a mixture of cis- and trans-isomers. The cis- and trans-diamines can be separated by reverse phase preparative HPLC. The diamines 20 can be converted to the carbamates 21 upon treatment with a chloroformate reagent and a suitable base, preferably sodium bicarbonate. Cleavage of the trifluoroacetate protecting group of intermediate 21 to afford 1,3-diaminoindanes 6b can be accomplished using aqueous potassium carbonate in refluxing methanol.

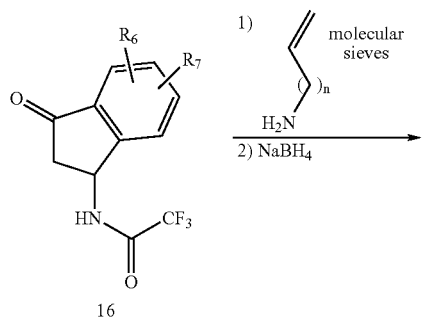

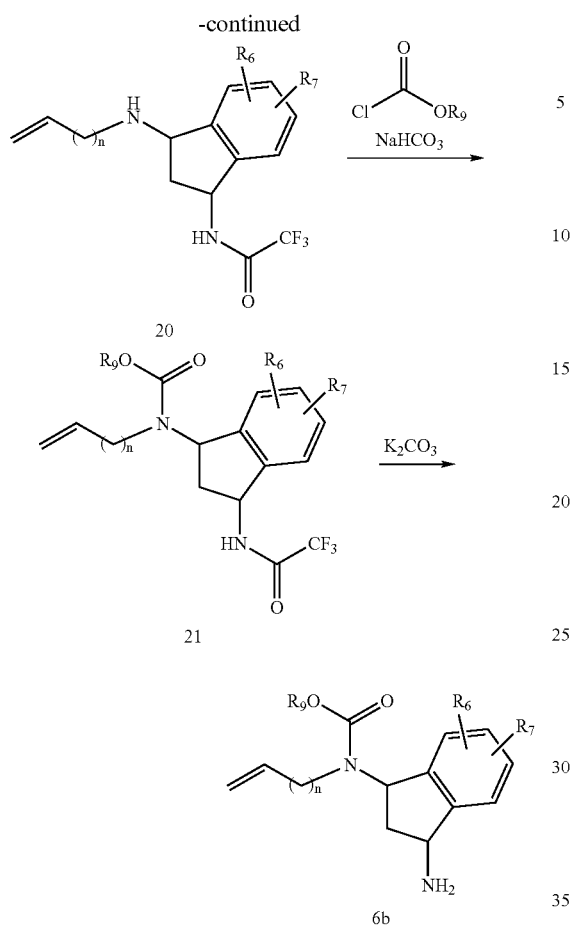

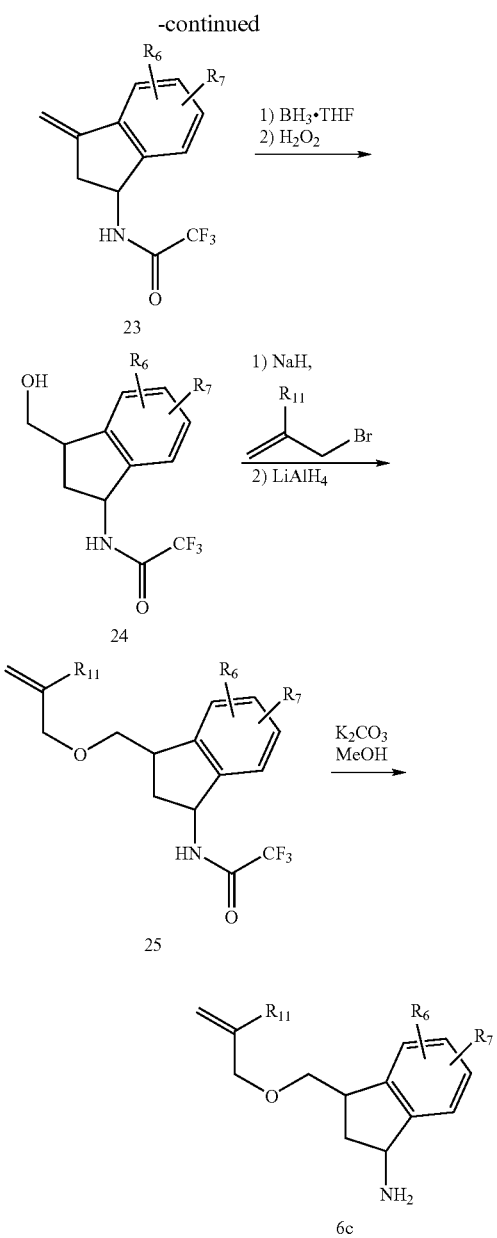

Reaction Scheme 4 outlines a method for preparing a preferred subset of 3-allyloxymethyl-1-aminoindanes 6c from N-protected 3-aminoindanones 16. Wittig methylenation of indanones 16 can provide the exo-olefin 23. Borane reduction, followed by an oxidative workup, can afford the hydroxymethyl analogs 24. Allylation, under standard conditions, followed by trifluoroacetate deprotection, can provide the substituted allyloxymethyl-aminoindanes 6c.

Reaction Scheme 4

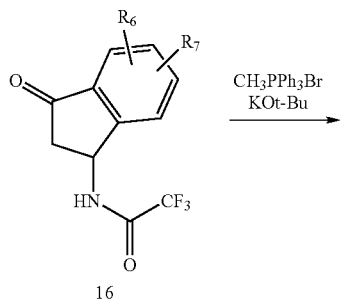

Cis- and trans-2-allyloxy-1-aminoindanes 6d can be prepared as illustrated in Reaction Scheme 5. m-Chloroperoxybenzoic acid oxidation of substituted indenes 27, can provide the corresponding racemic expoxides. Epoxide opening with sodium azide can afford the azidoalcohols trans-28. Mitsunobu inversion using 4-nitrobenzoic acid, followed by ester hydrolysis, can afford the azidoalcohol cis-28. O-Allylation of the azidoacohols 28 and azide reduction of resulting intermediate, using lithium aluminum hydride, can provide the corresponding racemic cis- and trans-2-allyloxy-1-aminoindanes 6d. Scalemic samples of allyloxy-1-aminoindanes cis-6d and trans-6d, can be obtained when epoxidation of the starting indenes 27 is conducted under asymmetric catalytic conditions as described by E. N. Jacobsen (*Tetrahedron Lett.* 1995, 36, 5457).

Reaction Scheme 5

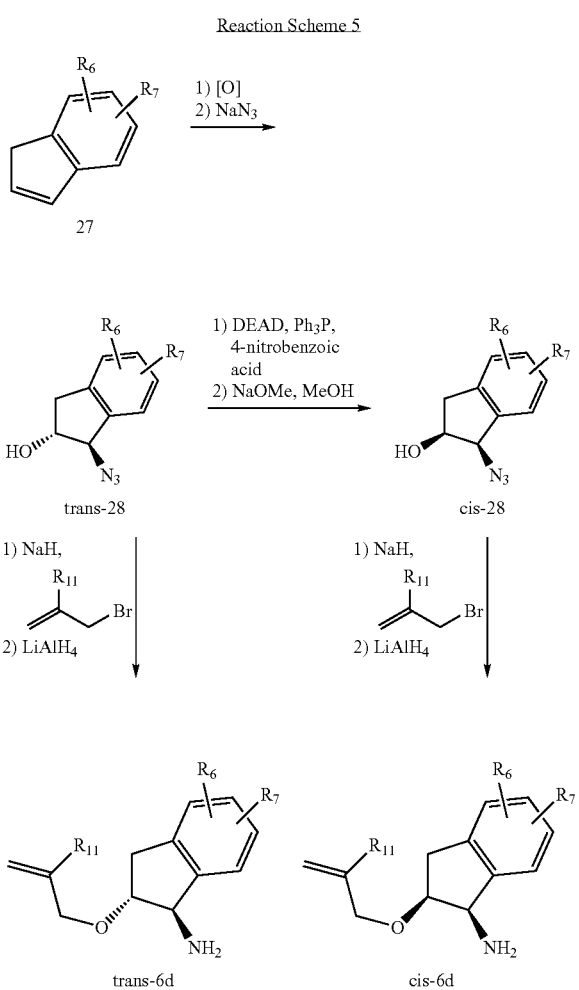

Allyloxy-bearing benzylic amines 6e can be prepared from readily available phenolic benzylamines 30 applying a standard three step protocol (Reaction Scheme 6). Protection of the primary amines 30 using trifluoroacetic anhydride can provide the N-trifluoroacetates 31. Deprotonation of alcohols 31, followed by alkylation with an electrophile, such as allyl bromide or 3-bromo-2-methylpropene, can provide the corresponding allyl ethers. Cleavage of the trifluoroacetate protecting group to reveal primary amines 6e can be accomplished using aqueous potassium carbonate in refluxing methanol.

Reaction Scheme 6

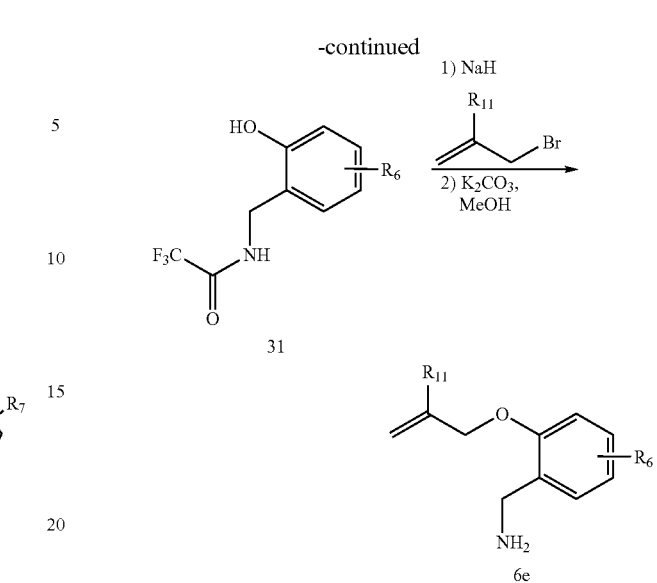

Preferred benzylamines of the type 6f may be prepared in several steps from ortho-bromobenzaldehydes 33 (Reaction Scheme 7). The reaction of readily obtained aldehydes 33 with methanol and p-toluenesulfonic acid can provide the dimethylketals 34. Halogen/metal exchange of compounds 34 with n-butyllithium, followed by reaction with an electrophile, such as 6-bromo-1-hexene, 5-bromo-1-pentene, 4-bromo-1-butene, or allylbromide, can provide, after aqueous acid workup, aldehydes 35. Reductive amination of aldehydes 35 with ammonium acetate and sodium cyanoborohydride can afford the desired benzylamines 6f.

Reaction Scheme 7

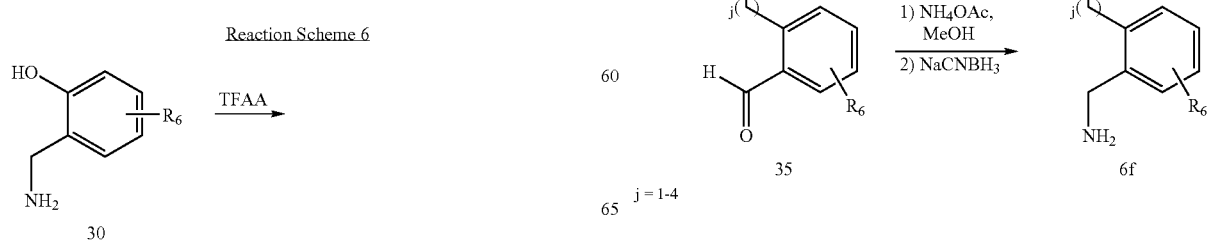

The epoxides 5a and primary amines of the preferred subtype 6g can be combined, in a polar solvent such as tetrahydrofuran, acetonitrile, or alcohol, to afford protected amino alcohols 36 (Reaction Scheme 8). The reaction can be promoted under thermal conditions or using a Lewis-acid additive such as lithium-based salts, titanium-based salts, or aluminum-based salts, preferably lithium perchlorate. The reaction is carried out at a temperature range of 20-80° C. The amine protecting group of intermediate 36 can be removed using a variety of reagents and conditions to give amine 3a. The reagents and conditions of choice for protecting group removal are dictated by the nature of the protecting group and are widely known to those skilled in the art. Barium hydroxide hydrate, in refluxing dimethoxyethane/water, is the preferred method when benzyloxycarbonyl (CBz) is used as the amine protecting group (PG). A two step protocol employing TBSOTf/lutidine, followed by reaction of the crude products with tetrabutylammonium fluoride, is the preferred method when tert-butyloxycarbonyl (BOC) is used as the amine protecting group. In certain cases, the BOC protecting group may be removed under acidic conditions, preferably trifluoroacetic acid in DCM, when the allyl group is not sufficiently activated and prone to decomposition or elimination. Primary amines of the formulas 6a-f, which are not represented by general formula 6g, may also be transformed into 1,3-diamino-2-propanols 3 according to the general method described in Reaction Scheme 8.

Reaction Scheme 8

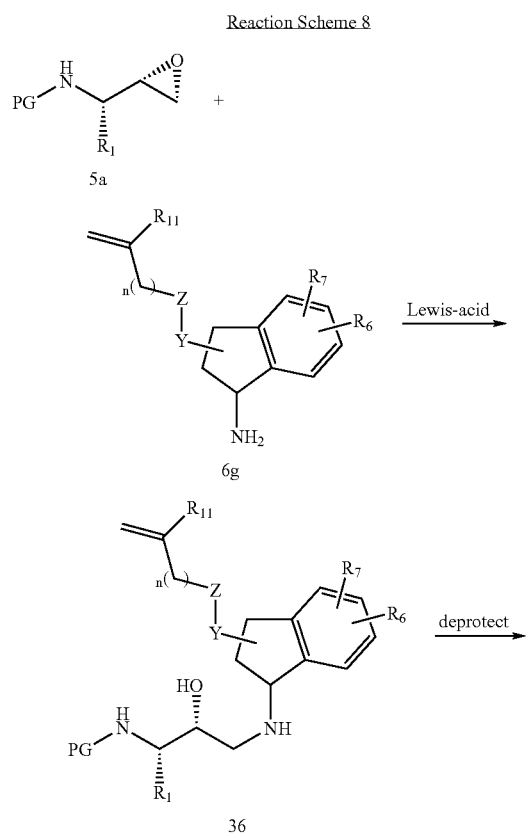

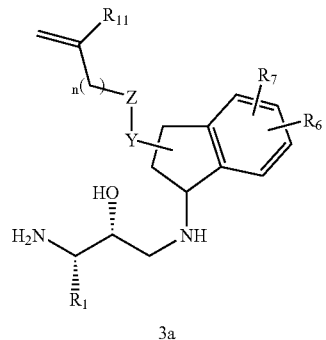

Preferred carboxylic acids represented by formulas 4a, 4b, and 4c can be prepared in five steps from aminoacids 37 (Reaction Scheme 9). The amino acids 37 or their BOC protected derivatives 38 may be purchased from commercial sources or prepared by standard literature methods known to one skilled in the art (for a general overview, see: R. M. Williams, *Synthesis of Optically Active Amino Acids*; Pergamon: Oxford, 1989). The free amino acids 37 (preferably (S)-2-aminohex-5-enoic acid and (S)-2-aminopent-4-enoic acid) can be converted to their corresponding BOC derivatives 38 upon reaction with di-tert-butyl dicarbonate. The amides 38 may be deprotonated with sodium hydride and alkylated with an alkyl halide, preferably methyl iodide. The BOC group can be removed and the carboxylic acid esterified upon reaction with thionyl chloride in methanol to afford the amino methyl esters 39. Through appropriate reagent selection the amine can be readily functionalized to afford a variety of derivatives including but not limited to amides, sulfonamides, carbamates, and tertiary amines. Amides 40 can be prepared from amines 39 and a carboxylic acid using standard coupling reagents like HATU (O-(7-azabenzotriazol-1-yl)-1,1,3,3,-tetramethyluronium hexafluorophosphate), PyBOP (benzotriazole-1-yl-oxy-tris-pyrrolidino-phosphonium hexafluorophosphate), or EDC (1-(3-dimethylaminopropyl)-3-ethylcarbodiimide hydrochloride)/HOBt (1-hydroxybenzotriazole hydrate) in the presence of a tertiary amine base such as triethylamine, N,N-diisopropyl-ethylamine (DIEA), or N-methylmorpholine. Sulfonamides 41 can be prepared from amines 39 and sulfonyl chlorides in the presence of a tertiary amine base. The intermediates 40 and 41 can be hydrolyzed under basic conditions, preferably aqueous lithium hydroxide in tetrahydrofuran, to afford the carboxylic acids 4a and 4b. Carbamates 4c can be prepared in two steps by the reaction of amines 39 with a chloroformate or dicarbonate reagent in the presence of a tertiary amine base, followed by basic hydrolysis of the resulting ester. Scalemic carboxylic acids 4 can be prepared according to the route depicted in Reaction Scheme 9 when the synthesis starts with enantiomerically enriched amino acids.

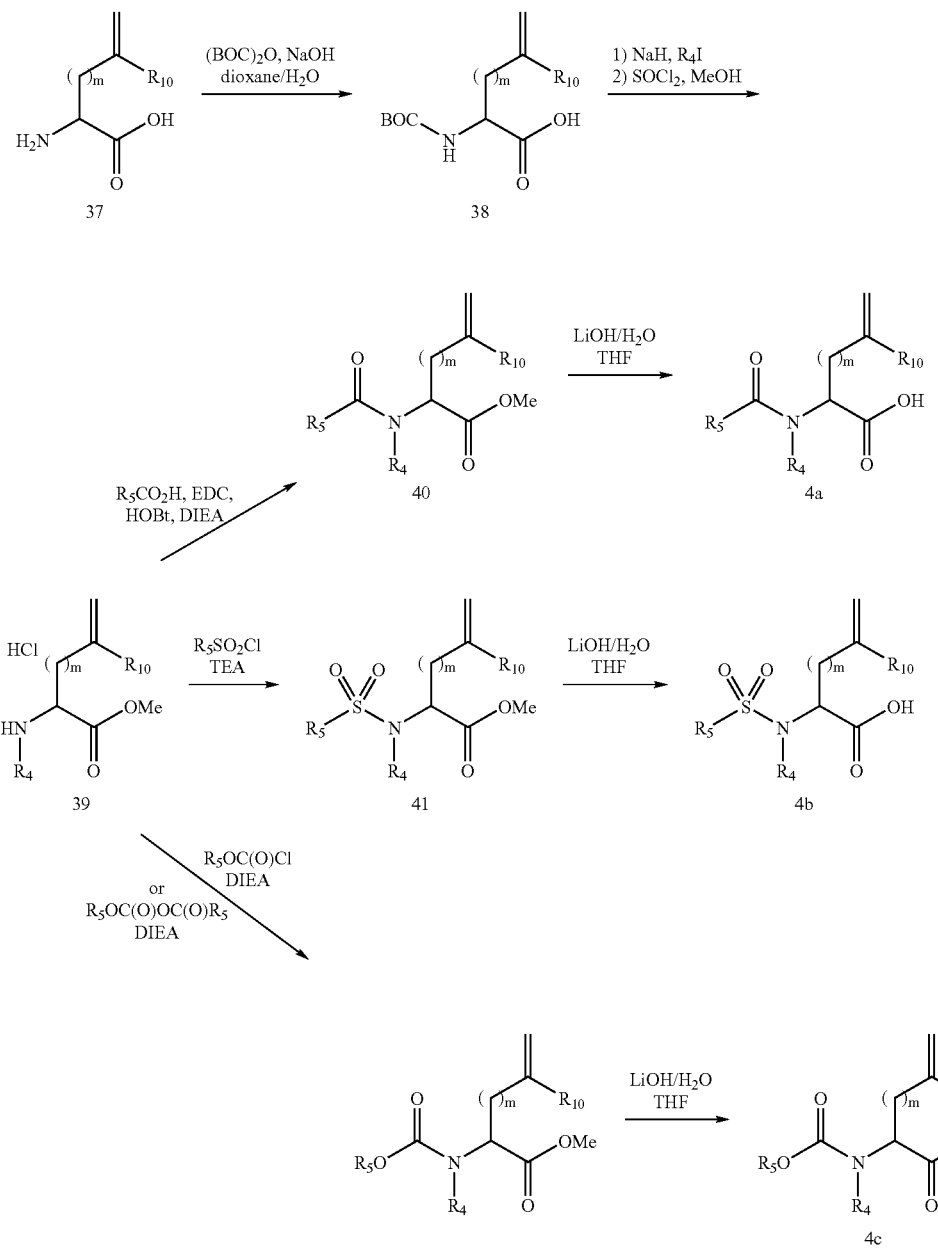

A another preferred subset of carboxylic acids of formula 4 are represented by formula 4d (Reaction Scheme 10) and are known as alpha-allyl carboxylic acids. A variety of alpha-allyl carboxylic acids 4d are available utilizing known asymmetric alkylation methodology (for a review, see: Jones, S. *J. Chem. Soc. Perkins I* 2002, 1-21.). Evan's asymmetric alkylation methodology employing N-acyloxazolidinones has proven particularly useful to prepare alpha-allyl acids in scalemic form [(a) Munoz, L. et. al. *J. Org. Chem.* 2001, 66, 4206. (b) Evans, D. A. et. al. *J. Org. Chem.* 1999, 64, 6411.]

Reaction Scheme 10

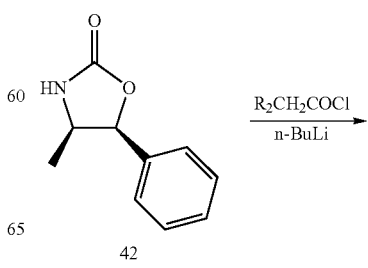

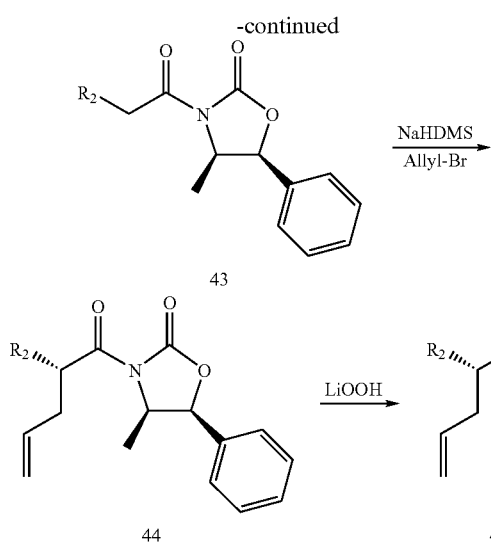

In a preferred embodiment of the chemistry, the carboxylic acids 4 can be coupled with 3-allyloxy-1-aminoindanes 3a, using coupling methods previously described for the making amide bonds, such as EDC, HOBt, and DIEA in DMF, to provide dienes of formula 2a. The protonated salt of a diene 2a, such as trifluoroacetate or p-toluenesulfonate, can undergo ring closing metathesis to afford the unsaturated macrocycle 45 (for a comprehensive review of RCM chemistry see Trnka, T.; Grubbs, R. Accounts of Chemical Research 2001, 34, 18-29). The Grubbs Catalyst 2nd Generation A and the Hoveyda-Grubbs Catalyst B are preferable for promoting the RCM of protonated salts (i.e. hydrochloride, p-toluenesulfonic acid) of secondary amine containing substrates such as 2a (Furstner, A.; Grabowski, J.; Lehmann, C. W. J. Org. Chem. 1999, 64, 8275-8280. Wright, D. L.; Schulte, J. P.; Page, M. A. Org. Lett. 2000, 2, 1847-1850.). Additionally, the Hoveyda-Grubbs Catalyst may provide access to macrocycles possessing tri- and tetrasubstituted double bonds (Garber, S.; Kingsbury, J. S.; Gray, B.; Hoveyda, A. J. Am. Chem. Soc. 2000, 122, 8168-8179). Reduced macrocyclic diaminopropanes represented by formula 46 can be prepared by palladium catalyzed hydrogenation of the protonated salts, preferably trifluoroacetate salts, of unsaturated macrocycles 45. The synthetic route outlined in Reaction Scheme 11 can be used to provide a wide variety of diaminopropane-derived macrocycles of Formula I, from amines of the general formula 3 and carboxylic acids of the general formula 4. In a preferred embodiment of the present invention, macrocycles Ia or Ib can be further elaborated to provide derivatives of Ia or Ib by metal-catalyzed cross coupling reactions if one of the aryl ring substituents $R_6$ or $R_7$ is a halogen atom, preferably bromine (For a general review of modern cross-coupling technology see: Corbet, J.-P.; Mignani, G. Chemical Reviews 2006, 106, 2651-2710).

Reaction Scheme 11

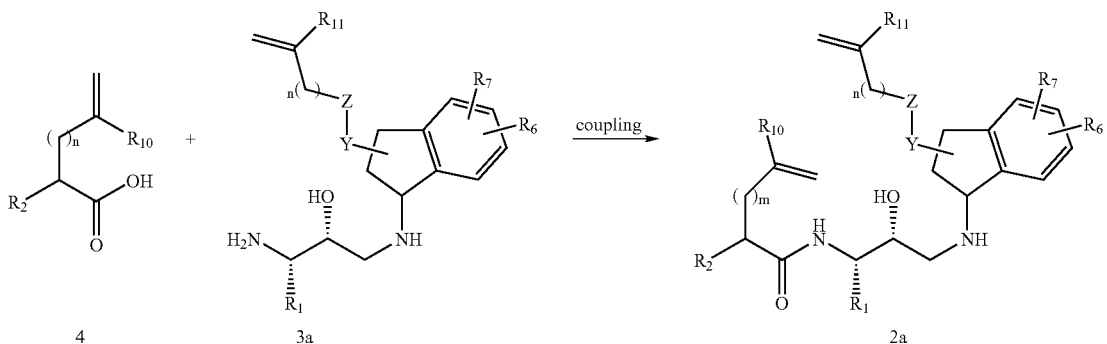

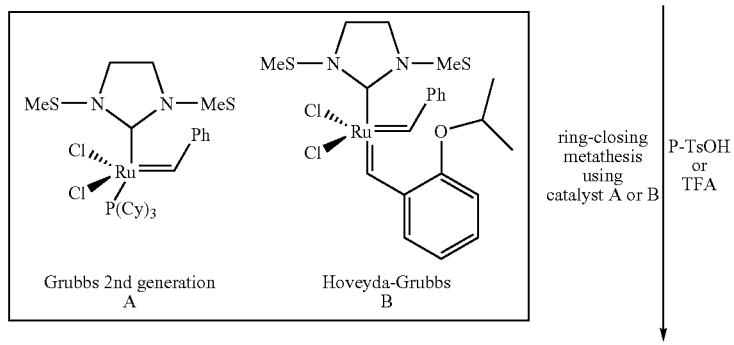

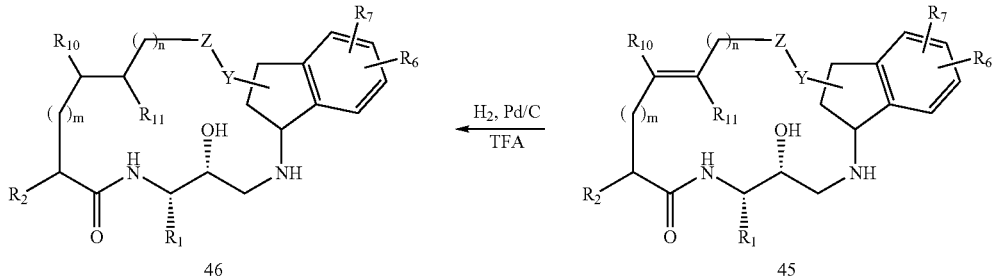

DESCRIPTION OF THE SPECIFIC EMBODIMENTS

The compounds of this application and their preparation can be understood further by the following working examples. These examples are meant to be illustrative of the present application, and are not to be taken as limiting thereof.

Chemical abbreviations used in the specification and Examples are defined as follows:
"Ac" for acetate,
"Boc" or "BOC" for t-butyloxycarbonyl,
"BOP" for benzotriazol-1-yloxytris-(dimethylamino)-phosphonium hexafluorophosphate,
"Cbz" for benzyloxycarbonyl,
"CDCl$_3$" for deuterochloroform,
"CD$_3$OD" for deuteromethanol,
"DCC" for 1,3-dicyclohexylcarbodiimide,
"DCM" for dichloromethane
"DEAD" for diethyl azodicarboxylate,
"DIEA", "Hunig's base", or "DIPEA" for N,N-diisopropylethylamine,
"DME" for 1,2-dimethoxyethane,
"DMF" for N,N-dimethylformamide,
"DMAP" for 4-dimethylaminopyridine,
"DMPU" for 1,3-dimethyl-3,4,5,6-tetrahydro-2(1H)-pyrimidone,
"DMSO" for dimethylsulfoxide,
"DPPA" for diphenylphosphorylazide
"EDC" or "EDCI" for 1-(3-dimethylaminopropyl)-3-ethylcarbodiimide hydrochloride,
"Et" for ethyl,
"EtOAc" for ethyl acetate,
"HOAc" for acetic acid,
"HOBt" for 1-hydroxybenzotriazole hydrate,
"HATU" for O-(7-azabenzotriazol-1-yl)-N,N,N',N'-tetramethyluronium hexafluorophosphate,
"HMPA" for hexamethylphosphoramide,
"LDA" for lithium diisopropylamide,
"LiHMDS" for lithium bis(trimethylsilyl)amide,
"NaHMDS" for sodium bis(trimethylsilyl)amide,
"n-BuLi" for n-butyllithium,
"NMM" for 4-methylmorpholine,
"PyBOP" for benzotriazole-1-yl-oxy-tris-pyrrolidino-phosphonium hexafluorophosphate,
"TBAF" for tetrabutylammonim fluoride
"TBSOTf" for tert-butyldimethylsilyl trifluoromethanesulfonate
"TBTU" for O-(1H-benzotriazol-1-yl)-N,N,N',N'-tetramethyluronium tetrafluoroborate,
"TEA" for triethylamine,
"TES" for triethylsilane,
"TFA" for trifluoroacetic acid,
"THF" for tetrahydrofuran,
"TMSCH$_2$N$_2$" for (trimethylsilyl)diazomethane, and
"TMSN$_3$" for Azidotrimethylsilane.

Abbreviations used in the Examples are defined as follows: "° C." for degrees Celsius, "MS" for mass spectrometry, "ESI" for electrospray ionization mass spectroscopy, "HRMS" for high resolution mass spectrometry, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimoles, "µmol" for micromoles, "M" for molar, "min" for minute or minutes, "rt" for room temperature, "$^1$H NMR" for proton nuclear magnetic resonance spectroscopy, "tlc" for thin layer chromatography, "atm" for atmosphere, and "α", "β", "R", "S", "E", and "Z" are stereochemical designations familiar to one skilled in the art. "HPLC" is an abbreviation used herein for high pressure liquid chromatography. "LC-MS" refers to high pressure liquid chromatography carried out according to the definition for HPLC with a mass spectrometry detector. HPLC solvent conditions: When described as performed under "standard conditions", samples were dissolved in methanol (1 mg/mL) and run using a gradient program with a solvent flow rate of 1.0 mL/min. Retention times "R$_t$" are reported in minutes. "Method A" refers to analyses conducted using a Phenomenex-Luna C18 S10 (4.6×50 mm) column, Start % B=0, Final % B=100, Gradient Time=2 min, Flow rate 5 ml/min. Wavelength=220 nm, Solvent A=10% MeOH/90% H$_2$O/0.1% TFA, Solvent B=90% MeOH/10% H$_2$O/0.1% TFA; and R$_t$ in min. "Method B" is the same as method A with the exception of 4 mL/min flow rate. "Method C" refers to analysis conducted using a XTERRA C18 S5 (4.6×30 mm) column, Start % B=0, Final % B=100, Gradient Time=3 min, Flow rate 4 ml/min. Wavelength=220 nm, Solvent A=10% MeOH/90% H$_2$O/0.1% TFA, Solvent B=90% MeOH/10% H$_2$O/0.1% TFA; and R$_t$ in min.

Reverse phase preparatory HPLC: When described as performed under "standard conditions", samples (approx. 20 mg) were dissolved in methanol (10 mg/mL) and purified on a 30 mm×100 mm Waters-Atlantis S5 column or a Phenomenex-Luna 30×100 mm 10 µm C18 column using a 10 minute gradient elution from 0% to 100% buffer B in buffer A (buffer A=10% MeOH/90% water/0.1% TFA and buffer B=90% MeOH/10% water/0.1% TFA) at 40 mL/minute.

Proton NMR spectra (referenced to tetramethylsilane) were obtained on a Bruker Avance 300, Avance 400, or Avance 500 spectrometer. Data were referred to the lock solvent. Electrospray Ionization (ESI) experiments were performed on a Micromass II Platform single-quadrupole mass spectrometer, or on a Finnigan SSQ7000 mass spectrometer.

The examples provided are intended to assist in a further understanding of the present disclosure. Particular materials employed, species and conditions are intended to further illustrate the specific embodiments of the invention and not limit the reasonable scope thereof.

Synthesis of Intermediates

Preparation A (S)-2-(N-methyl-2-propylpentanamido)pent-4-enoic acid

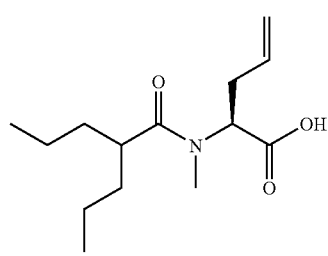

Step A (1): DIEA (2.52 mL, 14.5 mmol) was added to a mixture of (S)-methyl 2-aminopent-4-enoate hydrochloride (500 mg, 3.03 mmol) [Del Valle, J. R.; Goodman, M. *J. of Org. Chem.* 2004, 69, 8946-8948], 2-propylpentanoic acid (417 mg, 2.89 mmol), EDC (581 mg, 3.03 mmol), and HOBt (409 mg, 3.03 mmol) in DMF (15 mL) at rt. The mixture was stirred for 18 h and subsequently poured into 200 mL 1M HCl. The aqueous layer was extracted with EtOAc/hexanes (95:5) (2×200 mL). The combined organic extracts were washed with brine, dried with MgSO$_4$, filtered, and concentrated in vacuo. The residue was purified by silica gel chromatography to give (S)-methyl 2-(2-propylpentanamido)pent-4-enoate 852 mg (quantitative yield) as a white solid. LC-MS (M+H)$^+$=256.16. $^1$H NMR (500 MHz, CDCl$_3$) δ 5.90 (s, 1H) 5.64-5.85 (m, 1H) 4.95-5.14 (m, 2H) 4.04 (dd, J=5.04, 2.29 Hz, 2H) 3.75 (s, 3H) 2.28-2.46 (m, 1H) 2.07-2.29 (m, 2H) 1.62-1.64 (m, 1H) 1.46-1.47 (m, 1H) 1.18-1.36 (m, 4H) 0.87 (t, J=6.87 Hz, 3H).

Step A (2): (S)-Methyl 2-(2-propylpentanamido)pent-4-enoate (852 mg, 3.34 mmol) from Step A (1) was dissolved in THF (20 mL). Iodomethane (620 µL, 10 mmol) was added and resulting mixture chilled to 0° C. Sodium hydride (120 mg, 5.00 mmol) was added and the ice-bath was removed. After 75 min, the reaction was chilled again to 0° C. and quenched with aqueous 1 N HCl. The slurry was poured into H$_2$O, and extracted with EtOAc (3×200 mL). The combined organic extracts were washed with brine, dried over Na$_2$SO$_4$, and concentrated in vacuo. The residue was purified by silica gel chromatography to give (S)-methyl 2-(N-methyl-2-propylpentanamido)pent-4-enoate 230 mg (26% yield). LC-MS (M+H)$^+$=270.22. $^1$H NMR (300 MHz, CDCl$_3$) δ 0.78-0.90 (m, 5H) 1.10-1.41 (m, 6H) 1.49-1.69 (m, 3H) 2.36-2.50 (m, 1H) 2.60-2.79 (m, 2H) 2.92 (s, 3H) 3.67 (s, 3H) 4.96-5.12 (m, 2H) 5.29 (dd, J=10.98, 4.76 Hz, 1H) 5.58-5.77 (m, 1H).

Step A (3): A solution of LiOH/H$_2$O (2 M, 1.2 mL) was added to (S)-methyl 2-(N-methyl-2-propylpentanamido) pent-4-enoate (230 mg, 0.85 mmol) from Step A (2) in THF (4.0 mL) at rt. The reaction was stirred for 3 days. The mixture was poured into 1N HCl and the aqueous layer was extracted with EtOAc. The combined organic layers were washed with brine, dried over NaSO$_4$, and concentrated in vacuo to give 206 mg (95% yield) of the title compound as a white solid. LC-MS (M+H)$^+$=256.23. $^1$H NMR (300 MHz, CDCl$_3$) δ 0.78-0.92 (m, 6H) 1.11-1.44 (m, 7H) 1.50-1.69 (m, 2H) 2.47-2.83 (m, 3H) 2.97 (s, 3H) 4.98-5.16 (m, 3H) 5.59-5.78 (m, 1H).

Preparation B (2S)-2-(2-ethyl-N-methylhexanamido)pent-4-enoic acid (diastereomer A) and

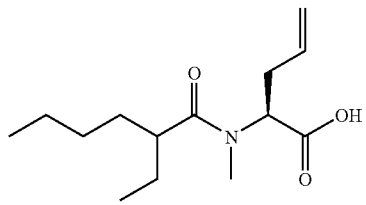

(2S)-2-(2-ethyl-N-methylhexanamido)pent-4-enoic acid (diastereomer B)

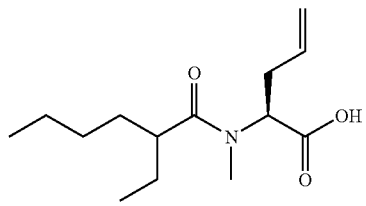

Step B (1): Same procedure as Step A (1). 2-Ethylhexanoic acid was used in place of 2-propylpentanoic acid. The crude reaction products were purified by silica-gel column chromatography to give 258 mg (33% yield) of diastereomer A and 284 mg (37% yield) of diastereomer B of (2S)-methyl 2-(2-ethylhexanamido)pent-4-enoate. Data for diasteromer A: LC-MS (M+H)$^+$=256.16, $^1$H NMR (300 MHz, CDCl$_3$) δ 0.76-0.93 (m, 5H) 1.11-1.66 (m, 10H) 1.87-2.00 (m, 1H) 2.41-2.63 (m, 2H) 3.72 (s, 3H) 4.66-4.77 (m, 1H) 5.03-5.14 (m, 2H) 5.55-5.72 (m, 1H) 5.91 (d, J=7.32 Hz, 1H). Data for diastereomer B: LC-MS (M+H)$^+$=256.17, $^1$H NMR (300 MHz, CDCl$_3$) δ ppm 0.77-0.93 (m, 5H) 1.14-1.65 (m, 10H) 1.87-2.00 (m, 1H) 2.41-2.66 (m, 2H) 3.72 (s, 3H) 4.64-4.77 (m, 1H) 5.01-5.16 (m, 2H) 5.56-5.72 (m, 1H) 5.90 (d, J=7.68 Hz, 1H).

Step B (2): Same procedure as Step A (2). Diastereomers A and B of (2S)-methyl 2-(2-ethylhexanamido)pent-4-enoate from Step B (1) were independently subjected to the N-methylation protocol. The crude products were purified by silica gel chromatography to give (2S)-methyl 2-(2-ethyl-N-methylhexanamido)pent-4-enoate (diastereomer A) 146 mg (54% yield) and (2S)-methyl 2-(2-ethyl-N-methylhexanamido) pent-4-enoate (diastereomer B) 68 mg (23% yield). Data for diastomer A: LC-MS (M+H)$^+$=270.43. $^1$H NMR (300 MHz, CDCl$_3$) δ ppm 0.74-0.93 (m, 5H) 1.10-1.71 (m, 9H) 2.40-2.62 (m, 2H) 2.69-2.80 (m, 1H) 2.92 (s, 3H) 3.67 (s, 3H) 4.96-5.14 (m, 2H) 5.25-5.37 (m, 1H) 5.60-5.76 (m, 1H). Data for diasteromer B: LC-MS (M+H)$^+$=270.45.

Step B (3): Same procedure as Step A (3). Diastereomers A and B of (2S)-methyl 2-(2-ethyl-N-methylhexanamido)pent-4-enoate from Step B (2) were independently subjected to the ester hydrolysis protocol. The procedure provided 142 mg (quantitative yield) of the title compound (diastereomer A) as a colorless residue and 68 mg (quantitative yield) of the title compound (diastereomer B) as a colorless residue. Data for diastereomer A: LC-MS (M+H)$^+$=256.42. Data for diastereomer B: LC-MS (M+H)$^+$=256.41.

Preparation C (S)-2-(N,2,2-trimethylhexanamido)pent-4-enoic acid

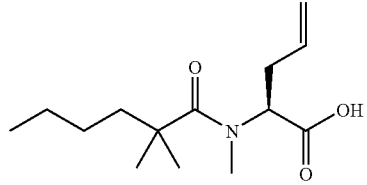

Step C (1): Same procedure as Step A (1). 2,2-Dimethylhexanoic acid was used in place of 2-propylpentanoic acid. The crude reaction products were purified by silica-gel column chromatography to give 650 mg (88% yield) of (S)-methyl 2-(2,2-dimethylhexanamido)pent-4-enoate as a pale-yellow oil. LC-MS (M+H)$^+$=256.15. $^1$H NMR (300 MHz, CDCl$_3$) δ ppm 0.84 (t, J=7.14 Hz, 3H) 1.09-1.28 (m, 9H) 1.39-1.52 (m, 2H) 1.59 (s, 1H) 2.39-2.63 (m, 2H) 3.71 (s, 3H) 4.58-4.69 (m, 1H) 5.02-5.14 (m, 2H) 5.54-5.73 (m, 1H) 6.09 (d, J=6.59 Hz, 1H).

Step C (2): Same procedure as Step A (2). (S)-methyl 2-(2,2-dimethylhexanamido)pent-4-enoate from Step C (1) was subjected to the N-methylation protocol. The crude products were purified by silica gel chromatography to afford 76 mg (11% yield) of (S)-methyl 2-(N,2,2-trimethylhexanamido)pent-4-enoate as a colorless residue. LC-MS (M+H)$^+$=270.24. $^1$H NMR (300 MHz, CDCl$_3$) δ ppm 0.75-0.87 (m, 3H) 1.03-1.26 (m, 12H) 1.35-1.58 (m, 2H) 2.35-2.59 (m, 2H) 2.97 (s, 1H) 3.57-3.69 (m, 1H) 4.07-4.21 (m, 1H) 4.50-4.64 (m, 1H) 4.98-5.10 (m, 2H) 5.51-5.69 (m, 1H) 6.09 (d, J=6.95 Hz, 1H).

Step C (3): Same procedure as Step A (3). (S)-Methyl 2-(N,2,2-trimethylhexanamido)pent-4-enoate from Step C (2) was subjected to the ester hydrolysis protocol. The procedure provided 14.9 mg (21% yield) of the title compound. LC-MS (M+H)$^+$=255.99.

Preparation D (S)-2-((S)-N,2-dimethylhexanamido)pent-4-enoic acid (diastereomer A)

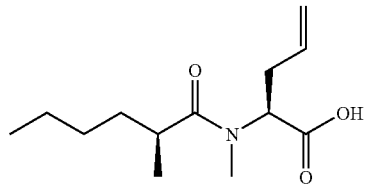

and (S)-2-((R)-N,2-dimethylhexanamido)pent-4-enoic acid (diastereomer B)

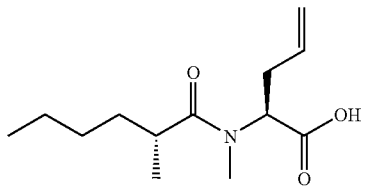

Step D (1): Same procedure as step A (1). 2-Methylhexanoic acid was used in place of 2-propylpentanoic acid. The crude products were purified using silica gel chromatography (EtOAc/hexanes, 1-50% linear gradient) to afford 484 mg (33% yield) of (S)-methyl 2-((S)-2-methylhexanamido)pent-4-enoate (diastereomer A, first to elute) as a white solid and 526 mg (36% yield) of (S)-methyl 2-((R)-2-methylhexanamido)pent-4-enoate (diastereomer B, second to elute) as a white solid. Data for diastereomer A: LRMS (M−H)$^-$=240.0; [α]$_D$ +27.4 (c=10.2 mg/mL, dichloroethane). $^1$H NMR (500 MHz, CDCl$_3$) δ ppm 0.87 (t, J=7.02 Hz, 3H) 1.07-1.16 (m, 3H) 1.21-1.41 (m, 5H) 1.56-1.67 (m, 1H) 2.15-2.25 (m, 1H) 2.44-2.52 (m, 1H) 2.56-2.65 (m, 1H) 3.74 (s, 3H) 4.64-4.73 (m, 1H) 5.06-5.18 (m, 2H) 5.60-5.72 (m, 1H) 5.92 (d, J=6.71 Hz, 1H). Data for diastereomer B: LRMS (M−H)$^-$=240.0; [α]$_D$ +13.7 (c=8.36 mg/mL, dichloroethane). $^1$H NMR (500 MHz, CDCl$_3$) δ ppm 0.87 (t, J=7.02 Hz, 3H) 1.12 (d, J=6.71 Hz, 3H) 1.20-1.41 (m, 5H) 1.54-1.68 (m, 1H) 2.15-2.25 (m, 1H) 2.46-2.54 (m, 1H) 2.55-2.62 (m, 1H) 3.74 (s, 3H) 4.65-4.74 (m, 1H) 5.04-5.16 (m, 2H) 5.59-5.71 (m, 1H) 5.93 (d, J=6.71 Hz, 1H).

Step D (2): Same procedure as Step A (3). Diastereomers A and B of (2S)-methyl 2-(2-methylhexanamido)pent-4-enoate from Step D (1) were independently subjected to the ester hydrolysis protocol. The procedure provided 445 mg (97% yield) of (S)-2-((S)-2-methylhexanamido)pent-4-enoic acid (diastereomer A) as a white solid and 550 mg (quantitative yield) of (S)-2-((R)-2-methylhexanamido)pent-4-enoic acid (diastereomer B) as a white solid. Data for diastereomer A: LRMS (M−H)$^-$=226.01. $^1$H NMR (500 MHz, DMSO-d$_6$) δ ppm 0.84 (t, J=7.02 Hz, 3H) 0.96 (d, J=7.02 Hz, 3H) 1.15-1.29 (m, 3H) 1.44-1.53 (m, 1H) 2.26-2.38 (m, 1H) 2.42-2.52 (m, 5H) 4.20-4.28 (m, 1H) 5.01-5.12 (m, 1H) 5.69-5.80 (m, 1H) 7.96 (d, J=7.93 Hz, 1H) 12.49 (s, 1H). Data for diastereomer B: LRMS (M−H)$^-$=226.08; $^1$H NMR (500 MHz, CDCl$_3$) δ ppm 0.87 (t, J=7.17 Hz, 3H) 1.13 (d, J=7.02 Hz, 3H) 1.20-1.43 (m, 5H) 1.55-1.68 (m, 1H) 2.20-2.29 (m, 1H) 2.52-2.70 (m, 2H) 4.60-4.68 (m, 1H) 5.11-5.20 (m, 2H) 5.65-5.78 (m, 1H) 6.01 (d, J=7.32 Hz, 1H).

Step D (3): General procedure: Sodium hydride (60% dispersion in mineral oil, 231 mg, 5.79 mmol) was carefully added portionwise to a solution of (S)-2-((S)-2-methylhexanamido)pent-4-enoic acid (diastereomer A from Step D (2), 440 mg, 1.93 mmol) and iodomethane (961 μL, 15.4 mmol) in THF (25 mL) at 0° C. The resulting mixture was allowed to warm to rt and stirred overnight (18 h). The reaction was chilled to 0° C. and quenched with EtOAc. The mixture was diluted with water and poured into 1 N NaOH. The aqueous layer was extracted with diethyl ether. The aqueous layer was then acidified with 1 N HCl and extracted with EtOAc. The second organic extract was sequentially washed with aqueous sodium bisulfite solution and brine solution. The organic layer was dried over magnesium sulfate, filtered, and concentrated in vacuo to provide 370 mg (80% yield) of the title compound (diastereomer A) as a clear viscous oil. Diastereomer B from Step D (2) was subject to the same procedure to afford 580 mg (97% yield) of the title compound (diastereomer B) as a clear viscous oil. Data for diastereomer A: LRMS (M−H)⁻=240.1 ¹H NMR (500 MHz, CDCl₃) δ ppm 0.82-0.90 (m, 3H) 1.05-1.13 (m, 3H) 1.17-1.42 (m, 5H) 1.62-1.73 (m, 1H) 2.52-2.61 (m, 1H) 2.63-2.87 (m, 2H) 2.99 (d, J=3.36 Hz, 3H) 5.00-5.16 (m, 3H) 5.64-5.76 (m, 1H). Data for diastereomer B: LRMS (M−H)⁻=240.2; ¹H NMR (500 MHz, CDCl₃) δ ppm 0.82-0.90 (m, 3H) 1.10 (dd, J=11.29, 6.71 Hz, 3H) 1.17-1.43 (m, 5H) 1.60-1.75 (m, 1H) 2.52-2.83 (m, 3H) 2.99 (d, J=3.05 Hz, 3H) 5.01-5.16 (m, 3H) 5.63-5.77 (m, 1H).

Preparation E (S)-2-(butoxycarbonyl(methyl)amino)pent-4-enoic acid

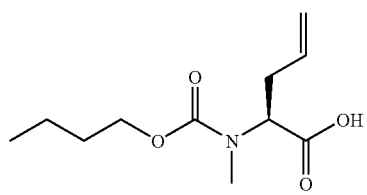

Step E (1): Butyl chloroformate (408 mg, 3.0 mmol), followed by DIEA (1.23 mL, 9.0 mmol), was added to a 250-mL single neck round bottom flask charged with a solution of the (S)-methyl 2-aminopent-4-enoate hydrochloride (500 mg, 3.00 mmol) in DCM (50 mL) at 0° C. Warmed the mixture to rt and after 2 h, poured into 1N HCl (200 mL). Extracted with EtOAc. Washed the combined organic extracts with 0.1 N NaOH, brine, dried over MgSO₄, filtered and concentrated in vacuo. Purification by silica-gel column chromatography afforded 357 mg (52% yield) of (S)-methyl 2-(butoxycarbonylamino)pent-4-enoate. LC-MS (M+H)⁺=230.2; ¹H NMR (500 MHz, CDCl₃) δ ppm 0.91 (t, J=7.48 Hz, 3H) 1.30-1.40 (m, 2H) 1.54-1.61 (m, 2H) 2.43-2.59 (m, 2H) 3.73 (s, 3H) 4.05 (t, J=6.71 Hz, 2H) 4.38-4.46 (m, 1H) 5.08-5.20 (m, 3H) 5.62-5.72 (m, 1H).

Step E (2): Same procedure as Step A (2). (S)-methyl 2-(butoxycarbonylamino)pent-4-enoate from Step E (1) was subjected to the N-methylation protocol. The crude products were purified by silica gel chromatography to afford 211 mg (57% yield) of (S)-methyl 2-(butoxycarbonyl(methyl)amino) pent-4-enoate. LC-MS (M+H)⁺=244.2; ¹H NMR (500 MHz, CDCl₃) δ ppm 0.86-0.97 (m, 3H) 1.30-1.43 (m, 2H) 1.49-1.67 (m, 3H) 2.41-2.54 (m, 1H) 2.65-2.76 (m, 1H) 2.79-2.90 (m, 3H) 3.66-3.76 (m, 3H) 4.09 (t, J=6.56 Hz, 2H) 5.03-5.18 (m, 2H) 5.65-5.77 (m, 1H).

Step E (3): Same procedure as Step A (3). (S)-methyl 2-(butoxycarbonyl(methyl)amino)pent-4-enoate (210 mg, 864 μmol) from Step E (2) was subjected to the ester hydrolysis protocol. The procedure provided 193 mg (98% yield) of the title compound as a clear viscous oil. ¹H NMR (500 MHz, CDCl₃) δ ppm 0.83-0.97 (m, 3H) 1.28-1.44 (m, 2H) 1.54-1.66 (m, 2H) 2.44-2.58 (m, 1H) 2.81-2.91 (m, 3H) 4.01-4.14 (m, 2H) 4.64 (dd, J=10.38, 4.58 Hz, 1H) 4.82 (dd, J=10.68, 4.88 Hz, 1H) 5.04-5.20 (m, 2H) 5.64-5.81 (m, 1H).

Preparation F (S)-2-(N-methylhexanamido)pent-4-enoic acid

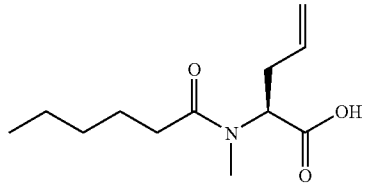

Step F (1): Same procedure as Step E (1). Hexanoyl chloride was used in place of butyl chloroformate. The crude reaction products were purified by silica-gel column chromatography to give 1.36 g (99% yield) of (S)-methyl 2-hexanamidopent-4-enoate. LC-MS (M+H)⁺=228.3; ¹H NMR (500 MHz, CDCl₃) δ ppm 0.81-0.89 (m, 3H) 1.23-1.33 (m, 4H) 1.54-1.64 (m, 2H) 2.18 (t, J=7.32 Hz, 2H) 2.42-2.51 (m, 1H) 2.52-2.60 (m, 1H) 3.71 (s, 3H) 4.63-4.70 (m, 1H) 5.03-5.11 (m, 2H) 5.59-5.70 (m, 1H) 5.99 (s, 1H).

Step F (2): Same procedure as Step A (2). (S)-Methyl 2-hexanamidopent-4-enoate (1.0 g, 4.40 mmol) from Step F (1) was subjected to the N-methylation protocol. The crude products were purified by silica gel chromatography to afford 309 mg (29% yield) of (S)-methyl 2-(N-methylhexanamido) pent-4-enoate. LC-MS (M+H)⁺=242.1; ¹H NMR (400 MHz, CDCl₃) δ ppm 0.79-0.94 (m, 3H) 1.21-1.38 (m, 4H) 1.53-1.70 (m, 3H) 2.24-2.36 (m, 2H) 2.67-2.82 (m, 1H) 2.90 (s, 3H) 3.65-3.76 (m, 3H) 4.96-5.19 (m, 2H) 5.28 (dd, J=10.83, 5.04 Hz, 1H) 5.56-5.75 (m, 1H).

Step F (3): According to the general procedure outlined in Step A (3), a solution of LiOH/H₂O (2M, 2.5 mL), was added to a mixture of (S)-methyl 2-(N-methylhexanamido)pent-4-enoate (254 mg, 1.05 mmol) in THF (2.5 mL) to afford 229 mg (96% yield) of (S)-2-(N-methylhexanamido)pent-4-enoic acid as a clear viscous oil. LC-MS (M+H)⁺=228.2; ¹H NMR (500 MHz, CDCl₃) δ ppm 0.82-0.93 (m, 3H) 1.23-1.36 (m, 4H) 1.55-1.70 (m, 2H) 2.26-2.38 (m, 2H) 2.47-2.59 (m, 1H) 2.71-2.80 (m, 1H) 2.94 (s, 3H) 4.99-5.19 (m, 3H) 5.61-5.75 (m, 1H) 5.91 (br s, 1H).

Preparation G (S)-methyl 2-(methylamino)pent-4-enoate hydrochloride

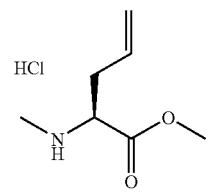

Step G (1): Thionyl chloride (1.7 g, 14.4 mmol) was added to a round bottom flask charged with a solution of (S)-2-(tert-butoxycarbonyl(methyl)-amino)pent-4-enoic acid (1.66 g, 7.2 mmol) [Tetrahedron (1991), 47(29), pp. 5453-62] in MeOH at 0° C. After complete addition, the reaction mixture was heated at reflux for 2 h, then cooled to rt. The resulting solution was concentrated in vacuo and the residual volatiles were removed on high vacuum overnight to afford 1.32 g (quantitative yield) of the title compound as an off-white solid. LC-MS (M+H)$^+$=143.96; $[\alpha]_D$ +3.7 (c=7.57 mg/mL, methanol); $^1$H NMR (500 MHz, CD$_3$OD) δ ppm 2.71-2.84 (m, 5H) 3.88 (s, 2H) 4.19 (t, J=5.65 Hz, 1H) 4.84 (s, 2H) 5.26-5.38 (m, 1H) 5.68-5.83 (m, 1H).

Preparation H (S)-2-(5,5,5-trifluoro-N-methylpentanamido)pent-4-enoic acid

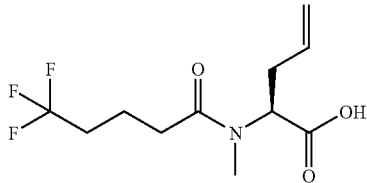

Step H (1): 5,5,5-Trifluoropentanoic acid and (S)-methyl 2-(methylamino)pent-4-enoate from Step G (1) were coupled according to the conditions described in Step A (1). The crude reaction products were purified by silica-gel column chromatography to give 191 mg (48% yield) of (S)-methyl 2-(5,5,5-trifluoro-N-methylpentanamido)pent-4-enoate as a clear oil. LC-MS (M+H)$^+$=282.1; $^1$H NMR (500 MHz, CDCl$_3$) δ ppm 1.86-1.95 (m, 2H) 2.12-2.23 (m, 2H) 2.38-2.50 (m, 3H) 2.70-2.80 (m, 1H) 2.91 (s, 3H) 3.67-3.76 (m, 3H) 5.00-5.17 (m, 2H) 5.27 (dd, J=10.83, 5.04 Hz, 1H) 5.61-5.74 (m, 1H).

Step H (2): Same procedure as Step A (3). (S)-Methyl 2-(5,5,5-trifluoro-N-methylpentanamido)pent-4-enoate subjected to the ester hydrolysis protocol. The procedure provided 179 mg (quantitative yield) of the title compound as a clear viscous oil. LRMS (M–H)$^-$=265.96; $^1$H NMR (500 MHz, CDCl$_3$) δ ppm 1.86-1.96 (m, 2H) 2.10-2.22 (m, 2H) 2.39-2.48 (m, 2H) 2.50-2.60 (m, 1H) 2.72-2.82 (m, 1H) 2.94 (s, 3H) 5.03-5.18 (m, 3H) 5.63-5.75 (m, 1H).

Preparation I (S)-2-(3,3,3-trifluoro-N-methylpropylsulfonamido) pent-4-enoic acid

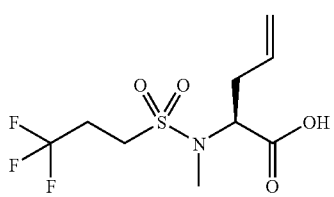

Step I (1): DIEA (436 μL, 3.2 mmol) was added to a solution of (S)-methyl 2-(methylamino)pent-4-enoate hydrochloride (229 mg, 1.28 mmol) and 3,3,3-trifluoropropane-1-sulfonyl chloride (250 mg, 1.28 mmol) in DCM. The reaction mixture was stirred for 24 h at rt. The resulting solution was poured into 1 N HCl and extracted with EtOAc. The combined organic layers were washed with brine, dried over magnesium sulfate, and concentrated in vacuo. The crude residue was purified by silica gel column chromatography (1-50% EtOAc/hexanes, linear gradient) to afford 288 mg (74% yield) of (S)-methyl 2-(3,3,3-trifluoro-N-methylpropylsulfonamido)pent-4-enoate as a viscous oil. LC-MS (M+H)$^+$=303.9; $^1$H NMR (500 MHz, CDCl$_3$) δ ppm 2.42-2.51 (m, 1H) 2.58-2.69 (m, 2H) 2.73-2.81 (m, 1H) 2.87 (s, 3H) 3.17-3.29 (m, 2H) 3.77 (s, 3H) 4.63 (dd, J=10.53, 5.34 Hz, 1H) 5.13-5.23 (m, 2H) 5.70-5.83 (m, 1H).

Step I (2): Same procedure as Step A (3). (S)-Methyl 2-(3,3,3-trifluoro-N-methylpropylsulfonamido)pent-4-enoate from Step I (1) was subjected to the ester hydrolysis protocol. The procedure provided 248 mg (95% yield) of the title compound as a clear viscous oil. LRMS (M–H)$^-$=287.9; $^1$H NMR (500 MHz, CDCl$_3$) δ ppm 2.46-2.55 (m, 1H) 2.59-2.71 (m, 2H) 2.77-2.84 (m, 1H) 2.87-2.92 (m, 3H) 3.18-3.29 (m, 2H) 4.70 (dd, J=10.68, 4.88 Hz, 1H) 5.16-5.27 (m, 2H) 5.71-5.83 (m, 1H).

Preparation J (S)-2-(N-methylpentylsulfonamido)pent-4-enoic acid

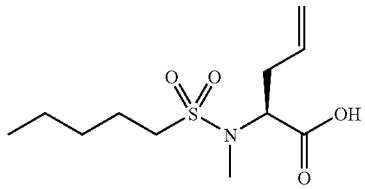

Step J (1): Same procedure as Step I (1). Pentane-1-sulfonyl chloride was used in place of 3,3,3-trifluoropropane-1-sulfonyl chloride. The procedure provided 248 mg (41% yield) of (S)-methyl 2-(N-methylpentylsulfonamido)-pent-4-enoate. LC-MS (M+H)$^+$=278.1; $^1$H NMR (500 MHz, CDCl$_3$) δ ppm 0.90 (t, J=7.02 Hz, 3H) 1.28-1.41 (m, 3H) 1.54 (s, 1H) 1.74-1.83 (m, 2H) 2.40-2.51 (m, 1H) 2.68-2.76 (m, 1H) 2.82-2.88 (m, 3H) 2.92-3.07 (m, 2H) 3.74 (s, 3H) 4.62 (dd, J=10.07, 5.49 Hz, 1H) 5.10-5.22 (m, 2H) 5.72-5.84 (m, 1H).

Step J (2): Same procedure as Step A (3). (S)-Methyl 2-(N-methylpentyl-sulfonamido)pent-4-enoate from Step J (1) was subjected to the ester hydrolysis protocol. The procedure provided 188 mg (80% yield) of the title compound as a clear viscous oil. LRMS (M–H)$^-$=262.31; $^1$H NMR (500 MHz, CDCl$_3$) δ ppm 0.85-0.94 (m, 3H) 1.29-1.44 (m, 4H) 1.75-1.86 (m, 2H) 2.44-2.55 (m, 1H) 2.71-2.80 (m, 1H) 2.84-

2.92 (m, 3H) 2.94-3.08 (m, 2H) 4.67 (dd, J=10.38, 5.19 Hz, 1H) 5.12-5.24 (m, 2H) 5.72-5.85 (m, 1H).

Preparation K (S)-methyl 2-(methylamino)hex-5-enoate hydrochloride

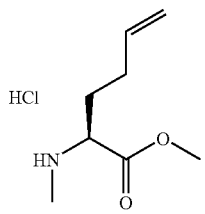

Step K (1): Same procedure as Step D (3). (S)-2-(tert-Butoxycarbonyl-amino)hex-5-enoic acid (was used in place of (2S)-2-(2-methylhexanamido)pent-4-enoic acid. The procedure provided 2.06 g (98% yield) of (S)-2-(tert-butoxycarbonyl(methyl)amino)hex-5-enoic acid. LRMS (M−H)⁻=242.1; ¹H NMR (500 MHz, CDCl₃) δ ppm 1.45 (d, J=15.26 Hz, 9H) 1.86 (s, 1H) 1.99-2.19 (m, 3H) 2.82 (d, J=18.01 Hz, 3H) 4.36-4.72 (m, 1H) 4.96-5.12 (m, 2H) 5.71-5.87 (m, 1H).

Step K (2): Thionyl chloride (1.22 mL, 16.9 mmol) was added to a round bottom flask charged with a solution of (S)-2-(tert-butoxycarbonyl(methyl)amino)hex-5-enoic acid (2.06 g, 8.47 mmol) from Step K (1) in MeOH at 0° C. After complete addition, heated at reflux for 2 h. Cooled to rt, concentrated in vacuo, and removed residuals on high vacuum overnight. This afforded 1.64 g (quantitative yield) of the title compound as an off-white solid. LC-MS (M+H)⁺=158.3; ¹H NMR (500 MHz, CDCl₃) δ ppm 2.09-2.27 (m, 3H) 2.29-2.43 (m, 1H) 2.71-2.81 (m, 3H) 3.77-3.88 (m, 3H) 5.04 (d, J=10.07 Hz, 1H) 5.12 (d, J=17.09 Hz, 1H) 5.68-5.82 (m, 1H) 9.59-9.72 (br s, 1H) 9.99-10.12 (br s, 1H).

Preparation L (S)-2-(5,5,5-trifluoro-N-methylpentanamido)hex-5-enoic acid

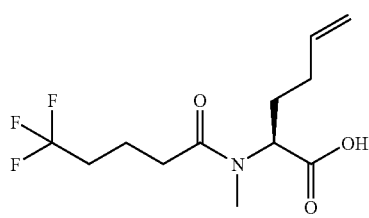

Step L (1): 5,5,5-Trifluoropentanoic acid and (S)-methyl 2-(methylamino)hex-5-enoate hydrochloride from Step K (2) were coupled according to the conditions described in Step A (1). The crude reaction products were purified by silica-gel column chromatography to give 276 mg (65% yield) of (S)-methyl 2-(5,5,5-trifluoro-N-methylpentanamido)hex-5-enoate. LC-MS (M+H)⁺=296.3; ¹H NMR (500 MHz, CDCl₃) δ ppm 1.73-1.83 (m, 1H) 1.84-2.25 (m, 7H) 2.37-2.52 (m, 2H) 2.78-2.96 (m, 3H) 3.66-3.75 (m, 3H) 4.94-5.09 (m, 2H) 5.17 (dd, J=10.53, 4.73 Hz, 1H) 5.70-5.84 (m, J=6.71 Hz, 1H).

Step L (2): Same procedure as Step A (3). (S)-Methyl 2-(5,5,5-trifluoro-N-methylpentanamido)hex-5-enoate from Step L (1) was subjected to the ester hydrolysis protocol. The procedure provided 258 mg (98% yield) of (S)-2-(5,5,5-trifluoro-N-methylpentanamido)hex-5-enoic acid as a white waxy solid. LRMS (M−H)⁻=280.3. ¹H NMR (500 MHz, CDCl₃) δ ppm 1.79-1.98 (m, 3H) 1.98-2.25 (m, 5H) 2.38-2.52 (m, 2H) 2.95 (s, 3H) 4.96-5.12 (m, 3H) 5.70-5.86 (m, J=6.71 Hz, 1H) 9.55-10.90 (m, 1H).

Preparation M (S)-2-(3,3,3-trifluoro-N-methylpropylsulfonamido)hex-5-enoic acid

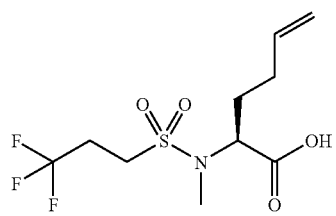

Step M (1): Same procedure as Step I (1). (S)-Methyl 2-(methylamino)hex-5-enoate hydrochloride from Step K (2) was sulfonylated with 3,3,3-trifluoropropane-1-sulfonyl chloride according to the procedure outlined in Step I (1). The procedure provided 242 mg (56% yield) of (S)-methyl 2-(3,3,3-trifluoro-N-methylpropylsulfonamido)hex-5-enoate. LC-MS (M+H)⁺=318.3; ¹H NMR (500 MHz, CDCl₃) δ ppm 1.73-1.85 (m, 1H) 2.02-2.21 (m, 3H) 2.59-2.73 (m, 2H) 2.87 (s, 3H) 3.16-3.32 (m, 2H) 3.76 (s, 3H) 4.55 (dd, J=10.68, 4.58 Hz, 1H) 4.99-5.14 (m, 2H) 5.74-5.87 (m, 1H).

Step M (2): Same procedure as Step A (3). (S)-Methyl 2-(3,3,3-trifluoro-N-methylpropylsulfonamido)hex-5-enoate from Step M (1) was subjected to the ester hydrolysis protocol. The procedure provided 218 mg (94% yield) of the title compound as a clear viscous oil. LRMS (M−H)⁻=302.3. ¹H NMR (500 MHz, CDCl₃) δ ppm 1.79-1.91 (m, 1H) 2.06-2.25 (m, 3H) 2.57-2.73 (m, 2H) 2.90 (s, 3H) 3.17-3.33 (m, 2H) 4.63 (dd, J=10.83, 4.43 Hz, 1H) 5.03-5.16 (m, 2H) 5.75-5.90 (m, J=6.41 Hz, 1H) 9.38-10.76 (m, 1H).

Preparation N (S)-2-(3-ethoxy-N-methylthiophene-2-carboxamido)pent-4-enoic acid

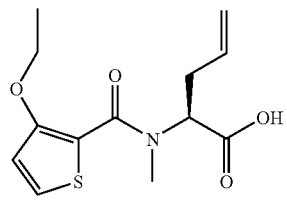

Step N (1): (S)-Methyl 2-(methylamino)pent-4-enoate from Step G (1) and 3-ethoxythiophene-2-carboxylic acid were coupled according to the procedure outlined in Step A (1). The product was purified using silica gel column chromatography to provide 80 mg (quantitative yield) of (S)- methyl 2-(3-ethoxy-N-methylthiophene-2-carboxamido)pent-4-enoate. LC-MS (M+H)+=298.29; ¹H NMR (300 MHz, CDCl₃) δ ppm 1.32 (t, J=6.77 Hz, 3H) 2.48-2.64 (m, 1H) 2.68-2.82 (m, 1H) 3.01 (s, 3H) 3.72 (s, 3H) 4.06 (q, J=6.83 Hz, 2H) 5.00-5.20 (m, 3H) 5.63-5.84 (m, 1H) 6.70 (d, J=5.49 Hz, 1H) 7.29 (d, J=5.49 Hz, 1H).

Step N (2): Same procedure as Step A (3). (S)-Methyl 2-(3,3,3-trifluoro-N-methylpropylsulfonamido)hex-5-enoate from Step N (1) was subjected to the ester hydrolysis protocol. The procedure provided 68 mg (89% yield) of the title compound as a colorless oil. LC-MS (M+H)+=284.27.

Preparation O (2S)-2-(4,4,4-trifluoro-N,2-dimethylbutanamido)pent-4-enoic acid (diastereomer A)

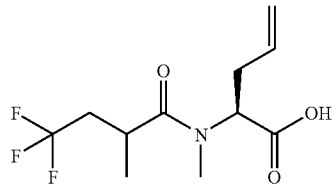

and (2S)-2-(4,4,4-trifluoro-N,2-dimethylbutanamido)pent-4-enoic acid (diastereomer B)

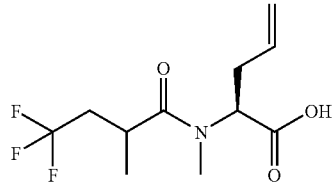

Step O (1): Same procedure as step A (1). 4,4,4-Trifluoro-2-methylbutanoic acid was used in place of 2-propylpentanoic acid. The crude products were purified using silica gel chromatography (EtOAc/hexanes, 1-50% linear gradient) to afford 1.73 g (40% yield) of (2S)-methyl 2-(4,4,4-trifluoro-2-methylbutanamido)pent-4-enoate (diastereomer A, 1st to elute) and 1.77 g (41% yield) of (2S)-methyl 2-(4,4,4-trifluoro-2-methylbutanamido)pent-4-enoate (diastereomer B, 2nd to elute). Both diastereomers were obtained as waxy white solids. Data for diasteromer A: ¹H NMR (500 MHz, CDCl₃) δ ppm 1.26 (d, J=7.02 Hz, 3H) 2.03-2.19 (m, 1H) 2.41-2.75 (m, 4H) 3.75 (s, 3H) 4.57-4.72 (m, 1H) 5.03-5.19 (m, 2H) 5.56-5.73 (m, 1H) 5.99-6.10 (d, J=6.41 Hz, 1H). Data for diasteromer B: LRMS (M+H)+=268.32. ¹H NMR (500 MHz, CDCl₃) δ ppm 1.25 (d, J=6.71 Hz, 3H) 2.00-2.19 (m, 1H) 2.43-2.79 (m, 4H) 3.71-3.80 (m, 3H) 4.59-4.73 (m, 1H) 5.03-5.19 (m, 2H) 5.56-5.72 (m, 1H) 6.05 (d, J=7.02 Hz, 1H).

Step O (2): Same procedure as Step A (3). Diastereomers A and B of (2S)-methyl 2-(4,4,4-trifluoro-2-methylbutanamido)pent-4-enoate from Step O (1) were independently subjected to the ester hydrolysis protocol. The procedure provided 1.66 g (100% yield) of (2S)-2-(4,4,4-trifluoro-2-methylbutanamido)pent-4-enoic acid (diastereomer A) and 1.72 g (100% yield) of (2S)-2-(4,4,4-trifluoro-2-methylbutanamido)pent-4-enoic acid (diastereomer B). Data for diastereomer A: LRMS (M−H)−=252.0. ¹H NMR (500 MHz, CDCl₃) δ ppm 1.22-1.32 (m, 3H) 2.04-2.22 (m, 1H) 2.47-2.75 (m, 4H) 4.60-4.73 (m, 1H) 5.07-5.20 (m, 2H) 5.63-5.77 (m, 1H) 6.18 (d, J=7.63 Hz, 1H) 6.27-6.65 (br s, 1H). Data for diastereomer B: LRMS (M−H)−=252.0; ¹H NMR (500 MHz, CDCl₃) δ ppm 1.26 (d, J=7.02 Hz, 3H) 2.05-2.17 (m, 1H) 2.52-2.75 (m, 4H) 4.64-4.72 (m, 1H) 4.72-5.09 (br s, 1H) 5.12-5.21 (m, 2H) 5.63-5.75 (m, 1H) 6.10 (d, J=7.63 Hz, 1H).

Step O (3): Diastereomers A and B of (2S)-2-(4,4,4-trifluoro-2-methylbutanamido)pent-4-enoic acid from Step O (2) were independently N-methylated according to the general procedure outlined in Step D (3). The procedure provided 1.23 g (71% yield) of the title compound (diastereomer A) and 1.60 g (90% yield) of the title compound (diastereomer B). Data for diastereomer A: LRMS (M−H)−=266.02; ¹H NMR (500 MHz, CDCl₃) δ ppm 1.15-1.27 (m, 3H) 2.06-2.20 (m, 1H) 2.47-2.61 (m, 1H) 2.68-2.89 (m, 2H) 2.96-3.14 (m, 4H) 4.99-5.20 (m, 3H) 5.60-5.76 (m, 1H). Data for diastereomer B: LRMS (M−H)−=266.02; ¹H NMR (500 MHz, CDCl₃) δ ppm 1.15-1.26 (m, 3H) 2.02-2.18 (m, 1H) 2.45-2.61 (m, 1H) 2.66-2.84 (m, 2H) 2.96-3.13 (m, 4H) 4.98-5.26 (m, 3H) 5.59-5.78 (m, 1H).

Preparation P (S)-2-(N-methylacetamido)pent-4-enoic acid

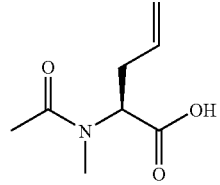

Step P (1): To a solution of (S)-2-methylamino-pent-4-enoic acid methyl ester hydrochloride (200 mg, 1.1 mmol, from Preparation G) in 5 mL anhydrous methylene chloride was added triethylamine (464 μl, 3.4 mmol) followed by addition of acetyl chloride (88 μl, 1.2 mmol) at 0° C. The resulting mixture was stirred at rt for 1 h and concentrated in vacuo. The residue was purified by silica gel chromatography eluting with EtOAc/hexane (00%~60%) to afford 196 mg (95% yield) of (S)-2(N-methylacetamido)-pent-4-enoic acid methyl ester as a colorless oil. LC-MS (M+H)+=186. ¹H NMR (400 MHz, CDCl₃) δ ppm 5.69 (m, 1H) 5.28 (dd, J=10.70, 5.16 Hz, 1H) 5.10 (m, 2H) 3.69 (s, 3H) 2.90 (s, 3H) 2.73 (m, 1H) 2.45 (1H, m), 2.10 (s, 3H).

Step P (2): The product from Step P (1) (196 mg, 1.06 mmol) and 2 mL THF/2 mL methanol/1 mL aqueous lithium hydroxide (100 mg, 4.17 mmol) was refluxed for 2 h. The reaction concentrated and the residue partitioned between EtOAc/1N HCl. The organic layer was dried over magnesium sulfate. The solvent was removed in vacuo to afford 180 mg of the title compound as colorless oil. LC-MS (M+H)+=172; ¹H NMR (400 MHz, CDCl₃) δ ppm 5.75 (m, 1H) 5.10 (m, 3H) 2.96 (s, 3H) 2.74 (m, 1H) 2.55 (m, 1H) 2.10 (s, 3H).

Preparation Q (2R,3S)-1-((R)-2-(allyloxy)-1-phenylethylamino)-3-amino-4-(3,5-difluorophenyl)butan-2-ol

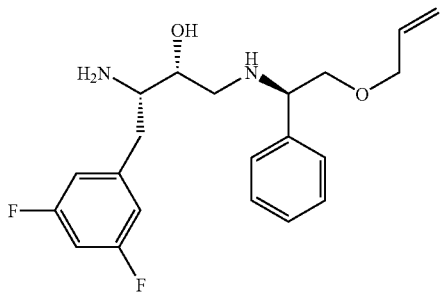

Step Q (1): (R)-(−)-Phenylglycinol (2.18 g, 15.9 mmol) was dissolved in DCM (200 mL) and to this was added pyridine (3.86 mL, 47.7 mmol) followed by trifluoroacetic anhydride (2.25 mL, 15.9 mmol). After 2 hr, the crude reaction mixture was concentrated in vacuo. The residue was purified using silica-gel column chromatography (10-55% EtOAc/Hexanes, linear gradient) to afford 3.34 g (90% yield) of (R)-2,2,2-trifluoro-N-(2-hydroxy-1-phenylethyl)acetamide as a white solid. LC-MS (M+H)$^+$=234.08; $^1$H NMR (300 MHz, CDCl$_3$) δ ppm 2.38-2.73 (m, 2H) 3.95 (dd, J=4.39, 1.83 Hz, 2H) 5.04-5.13 (m, 1H) 7.02-7.12 (m, 1H) 7.25-7.41 (m, 4H).

Step Q (2): (R)-2,2,2-Trifluoro-N-(2-hydroxy-1-phenylethyl)acetamide from step Q (1) (3.34 g, 14.3 mmol) was dissolved in THF (30 mL) and chilled to −78° C. n-BuLi (12 mL, 29 mmol, 2.5 M in hexanes) and DMPU (3.45 mL, 29 mmol) were added to the mixture. After 10 min, allyl bromide (12 mL, 143 mmol) was added. The mixture was warmed to rt and then heated to reflux for 16 h. The mixture was quenched with saturated NH$_4$Cl, diluted with 1 N NaOH, and extracted with EtOAc. The combined organic layers were dried over Na$_2$SO$_4$, filtered, and concentrated in vacuo. Purification by silica-gel column chromatography (0-25% EtOAc/Hexanes) afforded 2.88 g (73% yield) of (R)-N-(2-(allyloxy)-1-phenylethyl)-2,2,2-trifluoroacetamide as a yellow residue. LC-MS (M+H)$^+$=274.06. $^1$H NMR (300 MHz, CDCl$_3$) δ ppm 3.66-3.79 (m, 2H) 3.95-4.01 (m, 2H) 5.07-5.26 (m, 3H) 5.73-5.89 (m, 1H) 6.95-7.06 (m, 1H) 7.24-7.37 (m, 4H).

Step Q (3): (R)-N-(2-(Allyloxy)-1-phenylethyl)-2,2,2-trifluoroacetamide (3.0 g, 11.0 mmol) from step Q (2), potassium carbonate (7.59 g, 55 mmol), methanol (300 mL) and H$_2$O (20 mL) were heated to reflux for 16 h. The mixture was concentrated in vacuo. Water was added, and the aqueous layer was repeatedly extracted with EtOAc. The combined organics were washed with brine, dried over Na$_2$SO$_4$, and concentrated in vacuo to afford 1.06 g (54% yield) of (R)-2-(allyloxy)-1-phenylethanamine as a yellow oil. The crude mixture was used without further purification. LC-MS (M+H)$^+$=178.18. $^1$H NMR (300 MHz, CDCl$_3$) δ ppm 2.02 (s, 2H) 3.38 (t, J=9.15 Hz, 1H) 3.48-3.63 (m, 1H) 3.99 (d, J=5.49 Hz, 2H) 4.19 (dd, J=9.15, 3.66 Hz, 1H) 5.05-5.31 (m, 2H) 5.74-5.99 (m, 1H) 7.15-7.42 (m, 5H).

Step Q (4): Lithium perchlorate (1.59 g, 15 mmol) was added to a solution of (R)-2-(allyloxy)-1-phenylethanamine (530 mg, 2.99 mmol) from Step Q (3) and benzyl (S)-2-(3,5-difluorophenyl)-1-((S)-oxiran-2-yl)ethylcarbamate (996 mg, 2.99 mmol) in CH$_3$CN (10 mL). The resulting mixture was stirred at 50° C. for 16 h, then poured into a solution of brine and saturated aqueous NaHCO$_3$. The aqueous layer was extracted with EtOAc. The combined organic layers were washed with brine, dried over dried over Na$_2$SO$_4$, filtered and concentrated in vacuo. The residue was purified by silica gel column chromatography to give 1.1 g (72% yield) of benzyl (2S,3R)-4-((R)-2-(allyloxy)-1-phenylethylamino)-1-(3,5-difluorophenyl)-3-hydroxybutan-2-ylcarbamate. LC-MS (M+H)$^+$=511.5; $^1$H NMR (300 MHz, CDCl$_3$) δ ppm 2.36-2.53 (m, J=10.98 Hz, 1H) 2.55-3.00 (m, 3H) 3.25-3.74 (m, 3H) 3.77-4.19 (m, 3H) 4.71-4.84 (m, 1H) 5.00 (s, 2H) 5.09-5.37 (m, 2H) 5.74-6.00 (m, 1H) 6.50-6.78 (m, 3H) 7.16-7.42 (m, 10H).

Step Q (5): A mixture of benzyl (2S,3R)-4-((R)-2-(allyloxy)-1-phenylethylamino)-1-(3,5-difluorophenyl)-3-hydroxybutan-2-ylcarbamate (1.1 g, 2.15 mmol) from step Q (4), Ba(OH)$_2$.H$_2$O (1.23 g, 6.47 mmol), and DME/H$_2$O (12 mL/8 mL) was heated at 110° C. in a sealed tube. After 18 h, the vessel was cooled to rt and the precipitate was removed by filtration. The vessel and filtercake were rinsed with fresh DME and the combined filtrates were concentrated in vacuo. The crude product was purified by silica gel chromatography to give 550 mg (68% yield) of the title compound as a yellow viscous oil. LC-MS (M+H)$^+$=377.4; $^1$H NMR (300 MHz, CDCl$_3$) δ ppm 2.46-3.01 (m, 3H) 3.13-3.72 (m, 7H) 3.89-4.04 (m, 2H) 5.10-5.28 (m, 2H) 5.77-5.96 (m, 1H) 6.52-6.78 (m, 3H) 7.24-7.41 (m, 4H).

Preparation R (2R,3S)-1-(3-(allyloxy)-1-(3-methoxyphenyl)propylamino)-3-amino-4-phenylbutan-2-ol

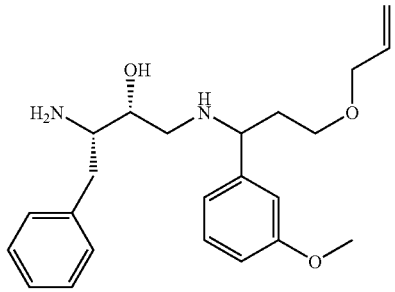

Step R (1): According to the procedure outlined in Step Q (1), 3-amino-3-(3-methoxyphenyl)propan-1-ol [Shih, Y.-E.; Wang, J.-S; Chen, C.-T. *Heterocycles* 1978, 9, 1277-1285] was converted to its corresponding ditrifluoroacetate. After concentration in vacuo, the residue was dissolved in methanol and a catalytic amount of potassium carbonate was added. After 2 h, the mixture was filtered. The filtrate concentrated in vacuo to afford 1.34 g (49% yield) of 2,2,2-trifluoro-N-(3-hydroxy-1-(3-methoxyphenyl)propyl)acetamide as a yellow oil. LC-MS (M+H)$^+$=278.07; $^1$H NMR (300 MHz, CDCl$_3$) δ ppm 1.89-2.02 (m, 1H) 2.10-2.25 (m, 1H) 3.60-3.74 (m, 2H) 3.74-3.80 (m, 3H) 5.13-5.23 (m, 1H) 6.77-6.87 (m, 3H) 7.24-7.30 (m, 1H).

Step R (2): 2,2,2-Trifluoro-N-(3-hydroxy-1-(3-methoxyphenyl)propyl)acetamide from step R (1) (1.99 g, 7.18 mmol) was dissolved in THF (20 mL) and chilled to −78° C. n-BuLi (5.76 mL, 14.4 mmol, 2.5 M in hexanes) and DMPU (1.73 mL, 14.4 mmol) were added and the resulting mixture was stirred for 45 min. Allyl bromide (3.04 mL, 36 mmol) was added. The mixture was warmed to rt and then heated to reflux for 3 days. The mixture was quenched with saturated NH₄Cl. After 15 min, the mixture was diluted with 1 N NaOH and the aqueous mixture was extracted with EtOAc. The combined organic layers were dried over Na₂SO₄, filtered, and concentrated in vacuo. Purification by silica-gel column chromatography (0%-25% EtOAc/Hexanes) afforded 610 mg (27% yield) of N-(3-(allyloxy)-1-(3-methoxyphenyl)propyl)-2,2,2-trifluoroacetamide as a viscous yellow oil. LC-MS (M+H)⁺=318.37; ¹H NMR (300 MHz, CDCl₃) δ ppm 1.89-2.01 (m, 1H) 2.14-2.29 (m, 1H) 3.34-3.52 (m, 2H) 3.77 (s, 3H) 3.91 (d, J=5.86 Hz, 2H) 5.10-5.30 (m, 3H) 5.79-5.95 (m, 1H) 6.70-6.82 (m, 3H) 7.19-7.29 (m, 1H).

Step R (3): N-(3-(Allyloxy)-1-(3-methoxyphenyl)propyl)-2,2,2-trifluoroacetamide from step R (2) (610 mg, 1.92 mmol), potassium carbonate (1.33 g, 9.26 mmol), methanol (50 mL) and H₂O (4 mL) were heated to reflux for 16 h. The mixture was concentrated in vacuo. H₂O was added, and the aqueous layer was extracted several times with EtOAc. The combined organics were washed with brine, dried over Na₂SO₄, and concentrated in vacuo to afford 390 mg (92% yield) of 3-(allyloxy)-1-(3-methoxyphenyl)propan-1-amine as a pale-yellow oil. The crude mixture was used without further purification. LC-MS (M+H)⁺=222.95; ¹H NMR (300 MHz, CDCl₃) δ ppm 1.82-2.18 (m, 2H) 3.23-3.54 (m, 3H) 3.72-3.82 (m, 3H) 3.83-4.00 (m, 2H) 4.14 (t, J=6.95 Hz, 1H) 5.08-5.31 (m, 2H) 5.76-5.95 (m, 1H) 6.71-6.86 (m, 1H) 6.86-6.97 (m, 1H) 7.14-7.29 (m, 2H).

Step R (4): Lithium perchlorate (936 mg, 8.80 mmol) was added to a mixture of 3-(allyloxy)-1-(3-methoxyphenyl)propan-1-amine (390 mg, 1.76 mmol) from Step R(3) and tert-butyl (S)-1-((S)-oxiran-2-yl)-2-phenylethylcarbamate (464 mg, 1.76 mmol) from Aldrich, dissolved in CH₃CN (10 mL). The resulting mixture was heated at 50° C. for 16 h. The reaction mixture was poured into a mixture of brine and saturated aqueous NaHCO₃ solution. Extracted with EtOAc, washed combined extracts with brine, dried over Na₂SO₄, filtered, and concentrated. The residue was purified by silica gel chromatography to give 700 mg (quantitative yield) of tert-butyl (2S,3R)-4-(3-(allyloxy)-1-(3-methoxyphenyl)propylamino)-3-hydroxy-1-phenylbutan-2-ylcarbamate as a mixture of two diastereomers. LC-MS (M+H)⁺=485.57; ¹H NMR (300 MHz, CDCl₃) δ ppm 1.14-1.43 (m, 9H) 2.56-3.04 (m, 4H) 3.24-3.38 (m, 1H) 3.39-3.58 (m, 2H) 3.69-4.01 (m, 7H) 4.60 (t, J=9.88 Hz, 1H) 5.04-5.30 (m, 2H) 5.72-5.99 (m, 1H) 6.73-7.00 (m, 2H) 7.09-7.33 (m, 7H).

Step R (5): Tin (II) triflate (1.2 g, 2.89 mmol) was added to a 0° C. solution of tert-butyl (2S,3R)-4-(3-(allyloxy)-1-(3-methoxyphenyl)propylamino)-3-hydroxy-1-phenylbutan-2-ylcarbamate from Step R (4) (700 mg, 1.45 mmol) in dry DCM (30 mL). The reaction was warmed to rt and stirred for 16 h. The reaction was neutralized with saturated NaHCO₃ and the product was extracted with EtOAc. The organic phase was separated, dried over Na₂SO₄, and concentrated in vacuo. The crude product was purified by silica gel chromatography to give 320 mg (57% yield) of the title compound. LC-MS (M+H)⁺=385.42; ¹H NMR (300 MHz, CDCl₃) δ ppm 2.05-2.80 (m, 4H) 2.78-3.54 (m, 4H) 3.63-3.97 (m, 6H) 4.99-5.30 (m, 2H) 5.65-5.94 (m, 1H) 6.76-7.33 (m, 10H) 7.53-7.74 (m, 1H).

Preparation S cis-2,2,2-trifluoro-N-3-hydroxy-6-methoxy-2,3-dihydro-1H-inden-1-yl)acetamide (diastereomer A)

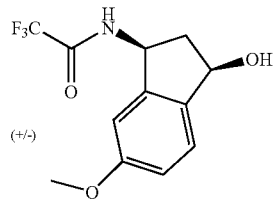

and trans-2,2,2-trifluoro-N-3-hydroxy-6-methoxy-2,3-dihydro-1H-inden-1-yl)acetamide (diastereomer B)

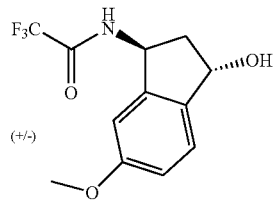

Step S (1): BH₃.THF (1.0 M, 44 mL, 43.8 mmol) was added to a solution of 2,2,2-trifluoro-N-(6-methoxy-3-oxo-2,3-dihydro-1H-inden-1-yl)acetamide (6.0 mg, 21.9 mmol) [Dallemagne, P.; Pilo, J. C.; Rault, S.; Robba, R. M. *Bull. Soc. Chim. Fr.* 1993, 130, 121-124] in THF at −20° C. The reaction mixture was warmed to rt and stirred overnight. Carefully quenched with MeOH. Poured the mixture into H₂O and extracted with EtOAc. Washed with brine, dried over MgSO₄, filtered, and concentrated in vacuo. The residue was purified by silica gel chromatography (33-75% EtOAc/hexanes linear gradient) to give 4.49 g (74% yield) of cis-2,2,2-trifluoro-N-3-hydroxy-6-methoxy-2,3-dihydro-1H-inden-1-yl)acetamide (diastereomers A, first to elute) as a white solid and 1.29 g (21% yield) of trans-2,2,2-trifluoro-N-3-hydroxy-6-methoxy-2,3-dihydro-1H-inden-1-yl)acetamide (diastereomers B, second to elute) as a white solid. Both diastereomers were independently recrystallized from EtOAc/Hex to provide 4.0 g (66% yield) of diastereomer A and 1.0 g (17% yield) of diasteromer B as white crystalline solids. Data for cis-2,2,2-trifluoro-N-3-hydroxy-6-methoxy-2,3-dihydro-1H-inden-1-yl)acetamide (diastereomer A): LC-MS (M+Na)⁺=298.1; ¹H NMR (500 MHz, DMSO-d₆) δ 9.79 (d, J=8.24 Hz, 1H) 7.29 (d, J=8.24 Hz, 1H) 6.78-7.06 (m, 1H) 6.66 (s, 1H) 5.44 (d, J=5.80 Hz, 1H) 5.14-5.16 (m, 1H) 4.92-4.96 (m, 1H) 3.74 (s, 3H) 2.67-2.83 (m, 1H) 1.73-1.91 (m, 1H). Data for trans-2,2,2-trifluoro-N-3-hydroxy-6-methoxy-2,3-dihydro-1H-inden-1-yl)acetamide (diastereomer B): ¹H NMR (500 MHz, DMSO-d₆) δ 9.71 (d, J=7.94 Hz, 1H) 7.29 (d, J=8.24 Hz, 1H) 6.90 (dd, J=8.39, 1.98 Hz, 1H) 6.74 (d, J=2.14 Hz, 1H) 5.38-5.58 (m, 1H) 5.11-5.13 (m, 2H) 3.74 (s, 3H) 2.13-2.37 (m, 2H).

Preparation T 2,2,2-trifluoro-N-((1S,3R)-3-hydroxy-6-methoxy-2,3-dihydro-1H-inden-1-yl)acetamide (enantiomer A)

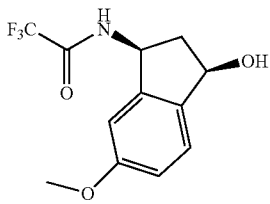

and 2,2,2-trifluoro-N-((1R,3S)-3-hydroxy-6-methoxy-2,3-dihydro-1H-inden-1-yl)acetamide (enantiomer B)

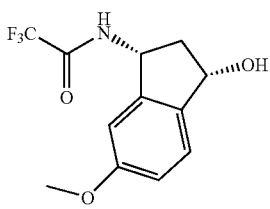

Step T (1): cis-2,2,2-Trifluoro-N-3-hydroxy-6-methoxy-2,3-dihydro-1H-inden-1-yl)acetamide (diastereomer A, from Step S (1)) (2.5 g) was separated into its individual enantiomers using a Chiralpak AD column (50×500 mm, 20 μm) [solvent=85:15 heptane/EtOH, flow rate=75 mL/min, run time=37 min]. Enantiomer A eluted at 14.7 min, enantiomer B eluted at 25.4 min. The separation provided 1.04 g of 2,2,2-trifluoro-N-((1S,3R)-3-hydroxy-6-methoxy-2,3-dihydro-1H-inden-1-yl)acetamide (enantiomer A, peak 1, ee>99%) and 1.14 g of 2,2,2-trifluoro-N-((1R,3S)-3-hydroxy-6-methoxy-2,3-dihydro-1H-inden-1-yl)acetamide (enantiomer B, peak 2, ee>99%). Data for enantiomer A: ESI (M−H)⁻=274.09; [α]$_D$ −124.16 (c=6.84 mg/mL, methanol). Data for enantiomer B: ESI (M−H)⁻=274.09; [α]$_D$ +126.09 (c=7.62 mg/mL, methanol).

Preparation U (1S,3R)-3-(allyloxy)-6-methoxy-2,3-dihydro-1H-inden-1-amine

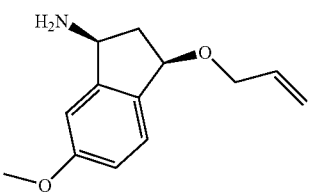

Step U (1): A solution of 2,2,2-trifluoro-N-((1S,3R)-3-hydroxy-6-methoxy-2,3-dihydro-1H-inden-1-yl)acetamide (enantiomer A, 2.65 g, 9.63 mmol) from step T (1) was cooled to −78° C. in THF. Added n-BuLi (7.7 mL, 19.3 mmol, 2.5M in Hex, Aldrich). Allowed the precipitous mixture to stir at −78° C. for 30 min. Added allyl bromide (4.6 mL, 48.2 mmol, Aldrich), warmed to rt and the reaction became homogeneous. The mixture was stirred for 18 h. Quenched with 1M HCl. Extracted with EtOAc. Washed with brine, dried over Na$_2$SO$_4$, filtered and concentrated. The residue was purified by silica gel column chromatography to afford 1.38 g (46% yield) of N-((1S,3R)-3-(allyloxy)-6-methoxy-2,3-dihydro-1H-inden-1-yl)-2,2,2-trifluoroacetamide as white solid. LC-MS (M+Na)⁺=337.9; [α]$_D$ −115.43 (c=6.79 mg/mL, dioxane); Anal. Calcd for C$_{15}$H$_{16}$F$_3$NO$_3$: C, 57.14; H, 5.11; N, 4.44. Found: C, 57.19; H, 4.88; N, 4.31. ¹H NMR (500 MHz, CDCl$_3$) δ ppm 1.55 (s, 2H) 2.09 (d, J=14.04 Hz, 1H) 2.61-2.73 (m, 1H) 3.80 (s, 2H) 4.06 (dd, J=3.05, 1.53 Hz, 2H) 4.79 (dd, J=5.49, 1.83 Hz, 1H) 5.19 (dd, J=10.53, 1.37 Hz, 1H) 5.28 (dd, J=17.24, 1.68 Hz, 1H) 5.39 (s, 1H) 5.83-5.97 (m, 1H) 6.85-6.98 (m, 2H) 7.32 (d, J=8.24 Hz, 1H).

Step U (2): N-((1S,3R)-3-(allyloxy)-6-methoxy-2,3-dihydro-1H-inden-1-yl)-2,2,2-trifluoroacetamide (1.28 g, 4.06 mmol) from Step U (1), potassium carbonate (2.85 g, 20.8 mmol) and MeOH (92 mL)/H$_2$O (6 mL) were heated at reflux for 16 h. The reaction mixture was concentrated in vacuo. Added water to the residue, extracted with EtOAc, washed the organic layers with brine, dried over Na$_2$SO$_4$, filtered and concentrated to afford 780 mg (quantitative yield) of the title compound as light brown oil. HRMS (M+H)⁺=220.1336; [α]$_D$ +18.72 (c=8.86 mg/mL, ethanol) ¹H NMR (500 MHz, CDCl$_3$) δ ppm 1.66 (s, 1H) 1.76 (d, J=12.82 Hz, 1H) 2.74-2.83 (m, 1H) 3.81 (s, 3H) 4.04-4.18 (m, 3H) 4.77 (t, J=5.80 Hz, 1H) 5.18 (dd, J=10.38, 1.53 Hz, 1H) 5.32 (dd, J=17.24, 1.68 Hz, 1H) 5.97 (dd, 1H) 6.90 (d, J=2.44 Hz, 1H) 7.30 (d, J=8.24 Hz, 1H).

Preparation V (2R,3S)-1-((1S,3R)-3-(allyloxy)-6-methoxy-2,3-dihydro-1H-inden-1-ylamino)-3-amino-4-phenylbutan-2-ol

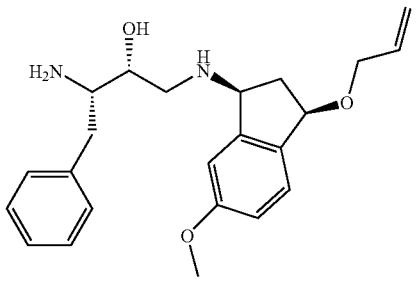

Step V (1): Lithium perchlorate (838 mg, 7.88 mmol) was added to a solution of (1S,3R)-3-(allyloxy)-6-methoxy-2,3-dihydro-1H-inden-1-amine (765 mg, 3.49 mmol, from Step U(2)) and benzyl (S)-1-((S)-oxiran-2-yl)-2-phenylethyl-carbamate (1.04 g, 3.49 mmol) in CH$_3$CN (50 mL). The reaction mixture was stirred at 50° C. for 36 h. The reaction mixture was poured into brine/NaHCO$_3$ solution. Extracted with EtOAc, washed combined extracts with brine, dried over Na$_2$SO$_4$, filtered and concentrated in vacuo. The residue was purified by silica gel chromatography (1-10% MeOH (with 0.1% triethylamine)/chloroform, linear gradient) to give 700 mg (39% yield) of benzyl (2S,3R)-4-((1S,3R)-3-(allyloxy)-6-methoxy-2,3-dihydro-1H-inden-1-ylamino)-3-hydroxy-1- phenylbutan-2-ylcarbamate. LC-MS (M+H)$^+$=517.06; HRMS (M+H)$^+$=517.2700; [α]$_D$ +14.45 (c=6.50 mg/mL, dichloroethane); $^1$H NMR (500 MHz, CDCl$_3$) δ ppm 1.59 (s, 3H) 1.82-1.93 (m, 1H) 2.58-2.75 (m, 2H) 2.80-2.93 (m, 2H) 2.97-3.07 (m, 1H) 3.44-3.54 (m, 1H) 3.78 (s, 3H) 3.88 (t, 1H) 4.09 (t, J=5.19 Hz, 2H) 4.76 (s, 1H) 4.84-4.94 (m, 1H) 5.02 (s, 2H) 5.18 (d, J=10.38 Hz, 1H) 5.31 (dd, J=17.24, 1.37 Hz, 1H) 5.89-6.01 (m, 1H) 6.79-6.92 (m, 2H) 7.14-7.37 (m, 11H).

Step V (2): A mixture of benzyl (2S,3R)-4-((1S,3R)-3-(allyloxy)-6-methoxy-2,3-dihydro-1H-inden-1-ylamino)-3-hydroxy-1-phenylbutan-2-ylcarbamate (700 mg, 1.36 mmol, from step N(1)), Ba(OH)$_2$.H$_2$O (1.46 g, 7.72 mmol), and DME/H$_2$O (18 mL/12 mL) was heated at 110° C. in a sealed tube. After 16 h, cooled to rt, filtered of solid. Rinsed the vessel and filtercake with fresh DME and concentrated the filtrate in vacuo. The crude product was purified by silica-gel column chromatography (1-20% MeOH (containing 0.1% triethylamine)/chloroform, linear gradient) to provide 255 mg (49% yield) of the title compound. LC-MS (M+H)=383.0; HRMS (M+H)$^+$=383.2332; [α]$_D$ +29.84 (c=6.43 mg/mL, methanol); $^1$H NMR (500 MHz, CDCl$_3$) δ ppm 1.67 (d, 4H) 1.97 (d, J=13.43 Hz, 1H) 2.43-2.54 (m, 1H) 2.60-2.71 (m, 1H) 2.81 (dd, J=11.90, 8.55 Hz, 1H) 2.90-3.05 (m, 2H) 3.10-3.18 (m, 1H) 3.47 (s, 1H) 3.57 (s, 1H) 3.81 (s, 3H) 4.02-4.16 (m, 2H) 4.77 (dd, J=6.10, 3.97 Hz, 1H) 5.18 (dd, J=10.38, 1.53 Hz, 1H) 5.31 (dd, J=17.24, 1.68 Hz, 1H) 5.96 (dd, 1H) 6.85 (dd, J=8.24, 2.44 Hz, 1H) 6.95 (d, J=2.14 Hz, 1H) 7.15-7.35 (m, 6H).

Preparation W (2R,3S)-1-((1S,3R)-3-(Allyloxy)-6-methoxy-2,3-dihydro-1H-inden-1-ylamino)-3-amino-4-(3,5-difluorophenyl)butan-2-ol

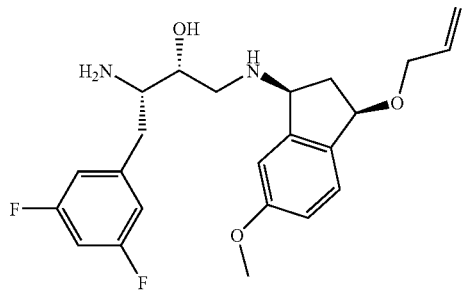

Step W (1): (1S,3R)-3-(Allyloxy)-6-methoxy-2,3-dihydro-1H-inden-1-amine from Step U(2) was reacted with benzyl (S)-2-(3,5-difluorophenyl)-1-((S)-oxiran-2-yl)ethylcarbamate according to the conditions described in Step V (1). The crude product was purified using silica gel column chromatography (1-10% MeOH (with 0.1% triethylamine)/chloroform, linear gradient) to provide 1.72 g mg (34% yield) of benzyl (2S,3R)-4-((1S,3R)-3-(allyloxy)-6-methoxy-2,3-dihydro-1H-inden-1-ylamino)-1-(3,5-difluorophenyl)-3-hydroxybutan-2-ylcarbamate. HRMS (M+H)$^+$=553.2534; $^1$H NMR (500 MHz, DMSO-d$_6$) δ 7.21-7.35 (m, 4H) 7.14-7.21 (m, 2H) 7.03 (t, J=9.46 Hz, 1H) 6.87-6.99 (m, 3H) 6.83 (dd, J=8.24, 2.14 Hz, 1H) 5.88-6.00 (m, 1H) 5.30 (dd, J=17.09, 1.83 Hz, 1H) 5.14 (dd, J=10.53, 1.98 Hz, 1H) 4.96-5.02 (m, 1H) 4.83-4.95 (m, 2H) 4.75 (t, J=6.41 Hz, 1H) 4.01-4.13 (m, 2H) 3.91-4.00 (m, 1H) 3.72-3.76 (m, 3H) 3.64-3.72 (m, 1H) 3.44-3.53 (m, 1H) 3.06 (dd, J=13.73, 3.05 Hz, 1H) 2.65-2.75 (m, 1H) 2.54-2.65 (m, 2H) 1.92-2.02 (m, 1H) 1.57-1.67 (m, 1H).

Step W (2): Benzyl (2S,3R)-4-((1S,3R)-3-(allyloxy)-6-methoxy-2,3-dihydro-1H-inden-1-ylamino)-1-(3,5-difluorophenyl)-3-hydroxybutan-2-ylcarbamate from Step W (1) was deprotected using Ba(OH)$_2$.H$_2$O according to the conditions described in Step V (2) to give 74 mg (38% yield) of the of the title compound as a clear viscous oil. LC-MS (M+H)$^+$=419.24; $^1$H NMR (500 MHz, CDCl$_3$) δ 7.32 (d, J=8.24 Hz, 1H) 6.92 (d, J=2.14 Hz, 1H) 6.85 (dd, J=8.24, 2.44 Hz, 1H) 6.71-6.80 (m, 2H) 6.60-6.71 (m, 1H) 5.84-6.03 (m, 1H) 5.30 (dd, J=17.24, 1.68 Hz, 1H) 5.18 (dd, J=10.38, 1.53 Hz, 1H) 4.77 (dd, J=6.10, 3.97 Hz, 1H) 4.08-4.12 (m, 2H) 4.05 (dd, J=6.87, 4.43 Hz, 1H) 3.79 (s, 3H) 3.47-3.52 (m, 1H) 3.04-3.10 (m, 1H) 2.90-3.00 (m, 2H) 2.75 (dd, J=11.90, 8.55 Hz, 1H) 2.61-2.68 (m, 1H) 2.49 (dd, J=13.43, 9.77 Hz, 1H) 1.94-2.00 (m, 1H).

Preparation X

Diastereomeric Mixture of (2R,3S)-1-((1S,3S)-3-(allyloxy)-6-methoxy-2,3-dihydro-1H-inden-1-ylamino)-3-amino-4-(3,5-difluorophenyl)butan-2-ol

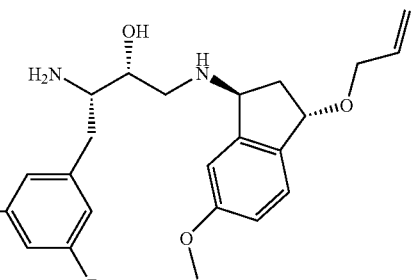

and (2R,3S)-1-((1R,3R)-3-(allyloxy)-6-methoxy-2,3-dihydro-1H-inden-1-ylamino)-3-amino-4-(3,5-difluorophenyl)butan-2-ol

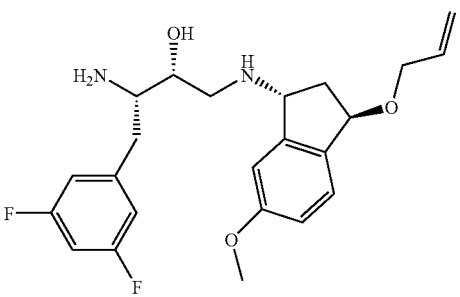

Step X (1): A solution of trans-2,2,2-trifluoro-N-3-hydroxy-6-methoxy-2,3-dihydro-1H-inden-1-yl)acetamide (1.40 g, 5.09 mmol, diastereomer B from step S(1)) and allyl bromide (728 μL, 7.60 mmol) was cooled to 0° C. in THF. To this mixture was added NaH (407 mg, 10.2 mmol, 60% mineral oil dispersion, Aldrich). Allowed the mixture to warm to rt and stir for 16 h. Quenched with 0.1 M HCl. Extracted with EtOAc. Washed with brine, dried over MgSO$_4$, filtered and concentrated. The residue was purified by silica gel chromatography and recrystallized from EtOAc/Hex to afford 428 mg (27% yield) of trans-N-(3-(allyloxy)-6-methoxy-2,3-dihydro-1H-inden-1-yl)-2,2,2-trifluoroacetamide as white fluffy needles. LRMS (M−H)$^−$=314.37; $^1$H NMR (500 MHz, CDCl$_3$) δ ppm 2.04-2.16 (m, 1H) 2.67-2.80 (m, 1H) 3.80 (s, 3H) 4.02 (dd, J=5.49, 1.22 Hz, 2H) 4.98 (dd, J=6.10, 1.83 Hz, 1H) 5.18 (dd, J=10.53, 1.37 Hz, 1H) 5.29 (dd, J=17.09, 1.53 Hz, 1H) 5.69 (q, J=7.32 Hz, 1H) 5.82-5.98 (m, 1H) 6.25-6.39 (m, J=6.71 Hz, 1H) 6.80 (d, J=1.83 Hz, 1H) 6.89 (dd, J=8.24, 2.14 Hz, 1H) 7.34 (d, J=8.55 Hz, 1H) Anal. calcd for C$_{15}$H$_{16}$F$_3$NO$_3$: C, 57.14; H, 5.11; N, 4.44. Found: C, 57.23; H, 4.88; N, 4.34.

Step X (2): Same procedure as Step U(2). trans-N-(3-(allyloxy)-6-methoxy-2,3-dihydro-1H-inden-1-yl)-2,2,2-trifluoroacetamide from Step X (1) was deprotected to provide 533 mg (quantitative yield) of trans-3-(allyloxy)-6-methoxy-2,3-dihydro-1H-inden-1-amine. LC-MS (M+H)$^+$=not observed; $^1$H NMR (500 MHz, CDCl$_3$) δ ppm 1.79-1.96 (m, 3H) 2.54-2.67 (m, 1H) 3.73-3.88 (m, 3H) 4.01 (d, J=5.80 Hz, 2H) 4.59 (t, J=7.02 Hz, 1H) 4.86-4.94 (m, 1H) 5.16 (d, J=10.38 Hz, 1H) 5.27 (dd, J=17.24, 1.68 Hz, 1H) 5.80-6.00 (m, 1H) 6.80 (dd, J=8.24, 2.14 Hz, 1H) 6.91 (d, J=1.83 Hz, 1H) 7.19-7.33 (m, 1H).

Step X (3): trans-3-(allyloxy)-6-methoxy-2,3-dihydro-1H-inden-1-amine from Step X (2) was reacted with benzyl (S)-2-(3,5-difluorophenyl)-1-((S)-oxiran-2-yl)ethylcarbamate according to the conditions described in Step V (1). The crude product was purified using silica gel column chromatography to provide 900 mg (69% yield) of a mixture of benzyl (2S,3R)-4-((1S,3S)-3-(allyloxy)-6-methoxy-2,3-dihydro-1H-inden-1-ylamino)-1-(3,5-difluorophenyl)-3-hydroxybutan-2-ylcarbamate and benzyl (2S,3R)-4-((1R,3R)-3-(allyloxy)-6-methoxy-2,3-dihydro-1H-inden-1-ylamino)-1-(3,5-difluorophenyl)-3-hydroxybutan-2-ylcarbamate. LRMS (M+H)$^+$=553.3; $^1$H NMR (500 MHz, CDCl$_3$) δ ppm 1.87-2.05 (m, 1H) 2.38-2.50 (m, 1H) 2.69-2.92 (m, 3H) 2.96-3.12 (m, 1H) 3.41-3.51 (m, 1H) 3.72-3.91 (m, 4H) 4.01 (t, J=5.49 Hz, 2H) 4.37-4.47 (m, 1H) 4.80 (d, J=9.16 Hz, 1H) 4.92 (dd, J=15.26, 4.58 Hz, 1H) 4.97-5.08 (m, 2H) 5.17 (d, J=10.38 Hz, 1H) 5.23-5.33 (m, 1H) 5.84-5.99 (m, 1H) 6.60-6.68 (m, 1H) 6.74 (d, J=6.41 Hz, 2H) 6.82 (dd, J=8.24, 1.83 Hz, 1H) 6.91 (s, 1H) 7.20-7.38 (m, 7H).

Step X (4): The mixture of the products from step X (3) was deprotected using Ba(OH)$_2$.H$_2$O according to the conditions described in Step V (2) to give 98 mg (52% yield) of the title diastereomers. LC-MS (M+H)$^+$=419.3; $^1$H NMR (500 MHz, CDCl$_3$) δ ppm 1.76-1.94 (m, 1H) 1.96-2.07 (m, 1H) 2.44-2.57 (m, 2H) 2.67-2.80 (m, 1H) 2.85-3.02 (m, 2H) 3.03-3.11 (m, 1H) 3.45-3.51 (m, 1H) 3.51-3.57 (m, 1H) 3.76-3.82 (m, 3H) 3.97-4.04 (m, 2H) 4.47 (q, J=6.92 Hz, 1H) 4.93 (dd, J=6.10, 2.14 Hz, 1H) 5.16 (dd, J=10.38, 1.22 Hz, 1H) 5.28 (dd, J=17.24, 1.68 Hz, 1H) 5.86-5.96 (m, 1H) 6.62-6.69 (m, 1H) 6.73 (t, J=6.41 Hz, 2H) 6.78-6.84 (m, 1H) 6.87-6.96 (m, 1H) 7.20-7.34 (m, 1H).

Preparation Y

Diasteromeric Mixture of (2R,3S)-1-((1R,3S)-3-(allyloxy)cyclopentylamino)-3-amino-4-(3,5-difluorophenyl)butan-2-ol

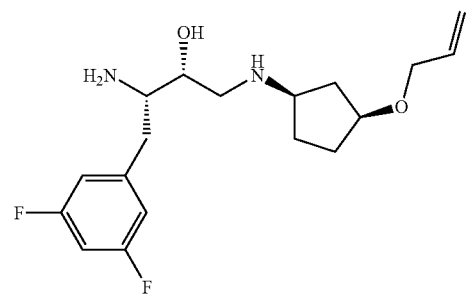

and (2R,3S)-1-((1S,3R)-3-(allyloxy)cyclopentylamino)-3-amino-4-(3,5-difluorophenyl)butan-2-ol

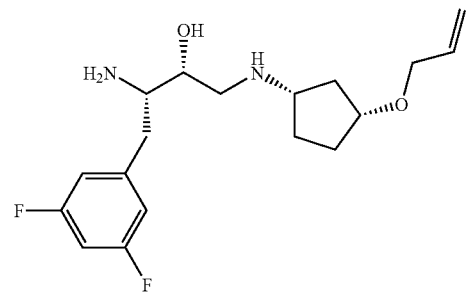

Step Y (1): A racemic mixture of cis-2,2,2-trifluoro-N-3-hydroxy-cyclopentyl)acetamide was O-allylated according to the procedure described in Step X (1) to afford 3.05 g (67% yield) of cis-N-3-(allyloxy)cyclopentyl)-2,2,2-trifluoroacetamide. LRMS (M−H)$^−$=236.1; $^1$H NMR (500 MHz, CDCl$_3$) δ ppm 1.71-1.85 (m, 3H) 1.87-2.12 (m, 3H) 3.87-3.94 (m, 1H) 3.94-4.01 (m, 1H) 4.08 (t, J=4.58 Hz, 1H) 4.46-4.55 (m, 1H) 5.18 (dd, J=10.38, 1.22 Hz, 1H) 5.24 (dd, J=17.24, 1.68 Hz, 1H) 5.80-5.93 (m, 1H).

Step Y (2): N-((1R,3S)-3-(allyloxy)cyclopentyl)-2,2,2-trifluoroacetamide from step Y (1) was N-deprotected according to the procedure described in Step U (2) to provide 2.1 g (quantitative yield) of racemic cis-3-(allyloxy)cyclopentanamine as a yellow oil. LRMS (M+H)$^+$=142.3; $^1$H NMR (500 MHz, CDCl$_3$) δ ppm 1.56-1.69 (m, 2H) 1.70-1.80 (m, 1H) 1.85-2.05 (m, 4H) 3.05 (s, 2H) 3.36-3.50 (m, 1H) 3.88-4.00 (m, 2H) 5.11-5.19 (m, 1H) 5.25 (dd, J=17.24, 1.68 Hz, 1H) 5.80-5.98 (m, 1H)

Step Y (3): Racemic cis-3-(allyloxy)cyclopentanamine from step Y (2) was reacted with benzyl (S)-2-(3,5-difluorophenyl)-1-((S)-oxiran-2-yl)ethylcarbamate according to the conditions described in Step V (1). Purification by silica gel column chromatography provided 726 mg (51% yield) of a mixture of benzyl (2S,3R)-4-((1R,3S)-3-(allyloxy)cyclopentylamino)-1-(3,5-difluorophenyl)-3-hydroxybutan-2-ylcarbamate and benzyl (2S,3R)-4-((1S,3R)-3-(allyloxy)cyclopentylamino)-1-(3,5-difluorophenyl)-3-hydroxybutan-2-ylcarbamate. LC-MS (M+H)$^+$=475.3; $^1$H NMR (500 MHz, CDCl$_3$) δ ppm 1.61-1.92 (m, 3H) 1.93-2.30 (m, 3H) 2.72 (dd, J=13.89, 10.83 Hz, 1H) 3.00 (d, J=9.16 Hz, 1H) 3.18 (t, J=14.34 Hz, 1H) 3.31-3.48 (m, 1H) 3.55-4.18 (m, 5H) 4.39 (dd, J=36.01, 4.88 Hz, 1H) 4.91-5.07 (m, 2H) 5.10-5.31 (m, 2H) 5.43 (dd, J=15.87, 8.55 Hz, 1H) 5.77-5.94 (m, 1H) 6.55-6.81 (m, 3H) 7.00-7.51 (m, 7H).

Step Y (4): The mixture of products from Step Y (3) was deprotected using Ba(OH)$_2$.H$_2$O according to the conditions described in Step V (2) to give 88 mg (49% yield) of the title diastereomers. LC-MS (M+H)$^+$=341.2; $^1$H NMR (500 MHz, CDCl$_3$) δ ppm 1.63-2.07 (m, 6H) 2.43-2.55 (m, 1H) 2.89-3.02 (m, 2H) 3.02-3.15 (m, 2H) 3.37-3.49 (m, 1H) 3.65-4.04 (m, 8H) 5.04-5.15 (m, 1H) 5.16-5.27 (m, 1H) 5.75-5.89 (m, 1H) 6.63 (t, J=8.85 Hz, 1H) 6.74 (d, J=6.10 Hz, 2H).

Preparation Z (1S,3R)-3-(allyloxy)-6-bromo-2,3-dihydro-1H-inden-1-amine

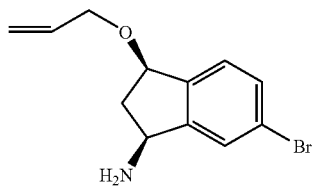

Step Z (1). A mixture of 200 grams (1.08 mol) of 3-bromobenzaldehyde, 112 grams (1.08 mol) of malonic acid, and 166.5 g (2.16 mol) of ammonium acetate was suspended in 1.125 liters of absolute ethanol. The mixture was mechanically stirred and brought to reflux temperature, whereupon the solution clarified. The mixture was kept at reflux for 16 h, and a precipitate formed. The mixture was chilled to 0° C., and the solid product was collected by filtration and washed with cold ethanol to yield 184 grams (70%) of 3-amino-3-(3-bromophenyl)propanoic acid as a white solid which was carried forward without further purification or analytical characterization.

Step Z (2). A 500 g (2.4 mol) portion of trifluoroacetic anhydride was placed in a flask and the product from Step Z(1) (184 g, 0.75 mol) was added in tablespoon-sized portions with mechanical stirring, allowing each to dissolve. After addition was completed (30 minutes) the homogeneous reaction solution was allowed to stir for an additional 1 h at rt. The volatiles were then removed by rotary evaporation, and the crude product was dissolved in 500 mL of EtOAc and then treated carefully with a satd. solution of NaHCO$_3$ until all bubbling ceased. The mixture was stirred for an additional 15 min at rt and then the aqueous layer reacidified with conc. HCl to pH 1. The organic layer was removed, dried, and concentrated to provide 3-(3-bromophenyl)-3-(2,2,2-trifluoroacetamido)propanoic acid (245 g, 96%) which was used without further purification. ESI MS (M+H)$^+$=340.07, 342.07. $^1$H NMR (300 MHz, CDCl$_3$) δ ppm 3.28 (ddd, J=44.37, 17.66, 6.40 Hz, 2H) 5.30-5.54 (m, 1H) 6.50-6.78 (m, 2H) 7.18-7.34 (m, 2H) 7.36-7.58 (m, 2H).

Step Z(3). The product from step Z (2) (245 g, 0.72 mol) was dissolved in 800 mL of thionyl chloride and heated to reflux temperature for 1 h. The reaction solution was directly concentrated, dissolved in 100 mL of DCM, and redried to the crude acid chloride. This material was then dissolved in 2.5 L of DCM, stirred with a mechanical stirrer, and 180 g of AlCl$_3$ was added. The reaction mixture was brought to reflux temperature for 1 h, and then allowed to cool to rt and stirred for 16 h. Separately, 1 L of 1 N HCl was placed in a 4 L beaker in an ice bath, and approximately half of the reaction mixture was then quenched by slowly adding it to the HCl (Caution-exthermic). EtOAc was also added as needed to dissolve precipitated solids. This procedure was then repeated on the other half of the reaction mixture. The combined organic layers were then washed with 500 mL of a satd. NH$_4$Cl solution, and 500 mL of brine followed by concentration. This crude material was crystallized by dissolving in hot EtOAc and then diluted with 2 volumes of pentane to yield a total of 175 g (2 batches of 140 g and 35 g) (75%) of a 4:1 mixture of N-(6-bromo-3-oxo-2,3-dihydro-1H-inden-1-yl)-2,2,2-trifluoroacetamide and N-(4-bromo-3-oxo-2,3-dihydro-1H-inden-1-yl)-2,2,2-trifluoroacetamide. ESI MS (M+H-water)$^+$=322.07, 324.06; $^1$H NMR (500 MHz, CD$_3$OD, regioisomer mixture) δ ppm 2.59-2.76 (m, J=18.69, 18.69, 3.81 Hz, 2H) 3.13-3.27 (m, J=18.92, 10.99, 7.93 Hz, 2H) 5.60-5.73 (m, 1H) 7.60 (d, J=4.88 Hz, 1H) 7.66 (d, 1H) 7.69-7.77 (m, 3H) 7.82 (s, 1H).

Step Z (4). The product mixture from step Z (3) (70 g, 217 mmol) was dissolved in 1 L of THF and chilled to −78° C., inducing some precipitation. To the cold reaction mixture was added 300 mL of a 1 M solution of L-Selectride in THF at a fast dropwise rate. The reaction solution clarified, and after stirring for 1 h tlc analysis indicated complete reaction. The reaction was then quenched with the slow, dropwise addition of 200 mL of water, and the mixture was brought to rt, diluted with brine, and extracted 3× with EtOAc. The organic layer was concentrated to a yellow oil which was then redissolved with heating in 250 mL of a 1:1 solution of EtOAc and methanol and reconcentrated onto 240 grams of powdered sodium sulfate, followed by azeotropic removal of excess methanol using benzene twice. The resulting material was loaded onto a Flash 75 chromatography system in 3 equal batches and purified by eluting with a gradient of 10-75% EtOAc in hexanes to provide 40 g (57%) of pure cis-N-((1S,3R)-6-bromo-3-hydroxy-2,3-dihydro-1H-inden-1-yl)-2,2,2-trifluoroacetamide. The racemate was then separated by chiral chromatography eluting with 15% isopropyl alcohol in supercritical CO$_2$ on a Chiralpak AD-H column (3×25 cM, 5 μm) at 35° C. to provide 20 g of N-((1S,3R)-6-bromo-3-hydroxy-2,3-dihydro-1H-inden-1-yl)-2,2,2-trifluoroacetamide (first-eluting enantiomer) as a white powder. MS (M+H-water)$^+$=306.08, 308.08. $^1$H NMR (500 MHz, CD$_3$OD) δ ppm 2.95 (dt, J=12.82, 7.32 Hz, 1H) 5.09 (t, J=7.17 Hz, 1H) 5.32 (t, J=7.93 Hz, 1H) 7.28-7.44 (m, 2H) 7.52 (d, J=8.24 Hz, 1H), [α]$_D$ (MeOH)=−82.27.

Step Z (5). A solution of 1.7 g (5.25 mmol) of N-((1S,3R)-6-bromo-3-hydroxy-2,3-dihydro-1H-inden-1-yl)-2,2,2-trifluoroacetamide from step Z (4) was dissolved in 30 mL of DMF, and a suspension of 60% NaH in mineral oil (630 mg, 15.75 mmol) was added in portions to minimize gas evolution. The resulting reaction mixture was stirred at rt for 10 min, and then allyl bromide (953 mg, 7.8 mmol) was added. After stirring at rt for 3 h, the starting material was consumed. The reaction solution was diluted with 60 mL of ether and the remaining NaH was slowly quenched with water. Brine (20 mL) was then added, and the organic layer was removed followed by extraction of the aqueous layer with 2 more portions of ether. The combined organics were dried and concentrated, and the crude product was purified by chromatography eluting with a gradient of 0 to 15% EtOAc in hexanes to provide 1.26 g (74% yield) of N-((1S,3R)-3-(allyloxy)-6-bromo-2,3-dihydro-1H-inden-1-yl)-2,2,2-trifluoroacetamide. $^1$H NMR (500 MHz, CDCl$_3$) δ ppm 2.06 (ddd, J=13.89, 3.05, 2.90 Hz, 1H) 2.70 (ddd, J=13.89, 7.17, 5.49 Hz, 1H) 4.07 (ddd, J=5.65, 1.53, 1.37 Hz, 2H) 4.80 (dd, J=5.65, 2.59 Hz, 1H) 5.22 (dd, J=10.38, 1.22 Hz, 1H) 5.29 (ddd, J=17.32, 3.13, 1.53 Hz, 1H) 5.37-5.44 (m, 1H) 5.84-5.95 (m, 1H) 6.81 (d, J=7.63 Hz, 1H) 7.30 (d, J=7.93 Hz, 1H) 7.49 (dd, J=7.93, 1.83 Hz, 1H) 7.58 (d, J=1.53 Hz, 1H).

Step Z (6). N-((1S,3R)-3-(allyloxy)-6-bromo-2,3-dihydro-1H-inden-1-yl)-2,2,2-trifluoroacetamide from Step Z (5) was deprotected by a procedure analogous to Step U(2) to afford the title compound. $^1$H NMR (500 MHz, CDCl$_3$) δ ppm 1.67 (s, 2H) 2.75-2.84 (m, 1H) 4.03-4.17 (m, 4H) 4.72 (t, J=6.26 Hz, 1H) 5.18 (dd, J=10.38, 1.53 Hz, 1H) 5.30 (dd, J=17.24, 1.68 Hz, 1H) 5.94 (ddd, 1H) 7.23 (d, J=7.93 Hz, 1H) 7.36 (dd, J=8.09, 1.37 Hz, 1H) 7.47 (s, 1H).

Preparation AA trans-2-(allyloxy)-6-methoxy-2,3-dihydro-1H-inden-1-amine

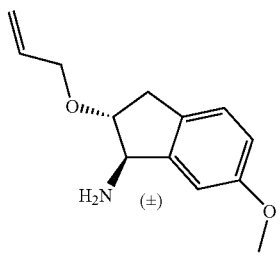

Step AA (1): To a solution of 6-methoxy-2,3-dihydro-1H-inden-1-one (24 g) in methanol (150 mL) and THF (50 mL) at 0° C. was added sodium borohydride (5.6 g), and the resulting suspension was stirred at 0° C. for 1 h and rt for 30 min. Solvents were evaporated, and water was added. The aqueous solution was extracted with EtOAc (×4), and the combined organic layers were washed with brine, dried over anhydrous sodium sulfate, and filtered. The filtrate was evaporated in vacuo to give methyl 6-methoxy-2,3-dihydro-1H-inden-1-ol as a colorless oil (24.3 g), which was carried forward without purification. $^1$H NMR (400 MHz, CDCl$_3$): 7.12 (1H, d), 6.95 (1H, d), 6.81 (1H, dd), 5.19 (1H, br. S), 3.79 (3H, s), 2.95 (1H, m), 2.74 (1H, m), 2.50 (1H, m), 1.94 (1H, m).

Step AA (2): To a solution of crude methyl 6-methoxy-2,3-dihydro-1H-inden-1-ol from Step AA (1) (24.3 g) in benzene (100 mL) was added pTSA (250 mg), and the resulting solution was heated at 90° C. for 3 h with a Dean-Stark trap to remove water. Saturated sodium bicarbonate was added, the aqueous layer was extracted with EtOAc (×3), and the combined organic layers were washed with brine, dried over anhydrous sodium sulfate, filtered, and evaporated. The crude product was distilled under vacuum to provide 5-methoxy-1H-indene as a colorless liquid (10 g). $^1$H NMR (400 MHz, CDCl$_3$): 7.33 (1H, d), 6.96 (1H, d), 6.81 (1H, m), 6.75 (1H, m), 6.56 (1H, m), 3.82 (3H, s), 3.33 (2H, m).

Step AA (3): To a solution of 5-methoxy-1H-indene (586 mg) from Step AA (2) in DCM (14 mL) and water (14 mL) was added mCPBA (77% purity, 1.35 g) and sodium bicarbonate (1.35 g), and the resulting mixture was stirred at rt for 12 h. Saturated sodium thiosulfate (10 mL) was added, and the reaction mixture was stirred at room temperature for 30 min. The two layers were separated, the aqueous layer was extracted with DCM (×4), and the combined organic layers were washed with brine, dried over anhydrous sodium sulfate, and filtered. The filtrate was evaporated in vacuo and the residue was purified by Biotage chromatography eluting with 5-10% EtOAc/hexanes to give (±)-5-Methoxy-1H-indene epoxide as a colorless oil (352 mg). $^1$H NMR (400 MHz, CDCl$_3$) δ 7.11 (1H, d), 7.06 (1H, d), 6.78 (1H, dd), 4.21 (1H, m), 4.11 (1H, m), 3.79 (3H, s), 3.13 (1H, d), 2.92 (1H, dd).

Step AA (4): A mixture of (±)-5-methoxy-1H-indene epoxide (352 mg) from Step AA (3), sodium azide (226 mg), ammonium chloride (184 mg) in ethanol-water (4:1) (7 mL) was heated under reflux for 3 h. Ethanol was removed in vacuo, the aqueous layer was extracted with EtOAc (×3), and the combined organic layers were washed with brine, dried over anhydrous sodium sulfate, and filtered. The filtrate was evaporated in vacuo and the residue was purified by Biotage chromatography eluting with 10-20% EtOAc/hexanes to give trans-1-azido-6-methoxy-2,3-dihydro-1H-inden-2-ol as a colorless oil (385 mg). $^1$H NMR (400 MHz, CDCl$_3$) δ 7.13 (1H, d), 6.83 (2H, m), 4.65 (1H, d), 4.51 (1H, m), 3.80 (3H, s), 3.24 (1H, dd), 2.79 (1H, dd), 2.21 (1H, d).

Step AA (5): To a solution of (1RS,2RS)-1-azido-6-methoxy-2,3-dihydro-1H-inden-2-ol (64 mg) from Step AA (4) in DMF (0.30 mL) at rt was added sodium hydride (95% purity, 20 mg), and the resulting mixture was stirred at rt for 5 min. Allyl bromide (40 μL) was added, and the reaction mixture was stirred for 5 min. Water was added, the aqueous layer was extracted with EtOAc (×3), and the combined organic layers were washed with brine, dried over anhydrous sodium sulfate, and filtered. The filtrate was evaporated in vacuo to give trans-2-(allyloxy)-1-azido-6-methoxy-2,3-dihydro-1H-indene as a slightly yellowish oil (71 mg). $^1$H NMR (400 MHz, CDCl$_3$) δ 7.09 (1H, d), 6.84 (2H, m), 5.96 (1H, m), 5.34 (1H, d), 5.23 (1H, d), 4.75 (1H, d), 4.23 (1H, q), 4.16 (2H, q), 3.80 (3H, s), 3.21 (1H, dd), 2.78 (1H, dd).

Step AA (6): To a solution of (1RS,2RS)-2-(allyloxy)-1-azido-6-methoxy-2,3-dihydro-1H-indene from Step AA (5) (71 mg) in THF (4 mL) at rt was added LiAlH$_4$ (33 mg), and the resulting suspension was stirred at rt for 10 min. Five crystals of Na$_2$SO$_4$.10H$_2$O was added followed by anhydrous sodium sulfate, and the reaction mixture was stirred at rt for 30 min and filtered through a pad of Celite. The filtrate was evaporated in vacuo to give the title compound as a slightly yellowish oil (53 mg). retention time: 1.31 min (method A). MS (ESI) (M+H)$^+$ 220.15.

Preparation AB

Diastereomeric Mixture of (2R,3S)-1-((1R,2R)-2-(allyloxy)-6-methoxy-2,3-dihydro-1H-inden-1-ylamino)-3-amino-4-phenylbutan-2-ol and (2R,3S)-1-((1S,2S)-2-(allyloxy)-6-methoxy-2,3-dihydro-1H-inden-1-ylamino)-3-amino-4-phenylbutan-2-ol

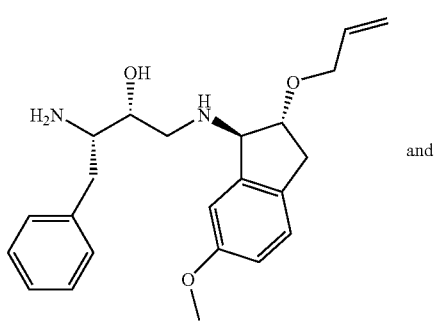

and

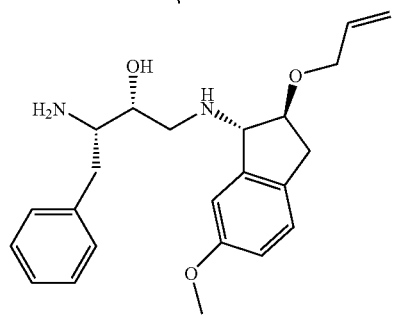

Step AB (1): A solution of tert-butyl (S)-1-((S)-oxiran-2-yl)-2-phenylethylcarbamate (70 mg) and LiClO$_4$ (29 mg) in acetonitrile (0.40 mL) was stirred at rt for 10 min. To the above solution was added trans-2-(allyloxy)-6-methoxy-2,3-dihydro-1H-inden-1-amine (53 mg) from Step AA (1) in acetonitrile (0.40 mL), and the reaction mixture was heated at 45° C. for 12 h. Solvents were removed in vacuo, and the residue was purified by preparative TLC eluting with 90% DCM/9% methanol/1% NH$_3$.H$_2$O to give 60 mg of a 1:1 mixture of tert-butyl (2S,3R)-4-((1R,2R)-2-(allyloxy)-6-methoxy-2,3-dihydro-1H-inden-1-ylamino)-3-hydroxy-1-phenylbutan-2-ylcarbamate and tert-butyl (2S,3R)-4-((1S,2S)-2-(allyloxy)-6-methoxy-2,3-dihydro-1H-inden-1-ylamino)-3-hydroxy-1-phenylbutan-2-ylcarbamatethe as a white solid. HPLC retention time: 1.88 min (method A). MS (ESI) (M+H)$^+$ 483.35.

Step AB (2): To a solution of the products from Step AB (1) (60 mg) in DCM (0.10 mL) was added TFA (0.10 mL), and the reaction mixture was stirred at rt for 2 h. Solvents were removed in vacuo to give the TFA salt of the title compounds (1:1 mixture) as a yellowish oil. The crude product was carried forward without purification. Retention time: 1.35 min (method A). MS (ESI) (M+H)$^+$ 383.34.

Preparation AC (2R,3S)-1-((1R,2S)-2-(allyloxy)-6-methoxy-2,3-dihydro-1H-inden-1-ylamino)-3-amino-4-phenylbutan-2-ol

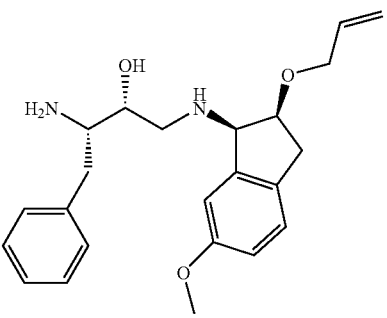

Step AC (1): To a solution of 5-methoxy-1H-indene (1.07 g) in dichloriomethane (60 mL) was added (S,S)-Jacobsen catalyst (232 mg) (Jacobsen, E. N., et. al *Tetrahedron. Lett.* 1995, 36, 5457-5460) and NMO (4.29 g), and the resulting solution was cooled to −78° C. A precooled (−78° C.) mCPBA (3.29 g, 77% purity) was added to the above reaction mixture portionwise over a period of 10 min, and the dark solution was stirred at −78° C. for 2 h. A precooled (−78° C.) domethyl sulfide (2.69 mL) was added, and 5 min later, saturated sodium bicarbonate solution was added. The two layers were separated, the aqueous layer was extracted with DCM (×4), and the combined organic layers were washed with brine, dried over anhydrous sodium sulfate, and filtered. The filtrate was evaporated in vacuo and the residue was purified by Biotage chromatography eluting with 5-10% EtOAc/hexanes to give (1S,2R)-5-methoxy-1H-indene epoxide as a colorless oil (977 mg). $^1$H NMR (400 MHz, CDCl$_3$) δ 7.11 (1H, d), 7.06 (1H, d), 6.78 (1H, dd), 4.21 (1H, m), 4.11 (1H, m), 3.79 (3H, s), 3.13 (1H, d), 2.92 (1H, dd). The ee of this epoxide was determined in Step AC (2).

Step AC (2): (1S,2R)-5-Methoxy-1H-indene epoxide (970 mg) from Step AC (1) was converted to (920 mg) of (1R,2R)-1-azido-6-methoxy-2,3-dihydro-1H-inden-2-ol by a procedure analogous to Step AA (3). $^1$H NMR (400 MHz, CDCl$_3$) δ 7.13 (1H, d), 6.83 (2H, m), 4.65 (1H, d), 4.51 (1H, m), 3.80 (3H, s), 3.24 (1H, dd), 2.79 (1H, dd), 2.21 (1H, d). This ee of this product was 87% by chiral HPLC (chircel OJ-H column, 4.6×250 mm, 5 μm; mobile phase: 5% ethanol in CO$_2$; flow rate: 2.0 mL/min). Retention time of the title compound: 9.54 min; Retention time of the other enantiomer: 7.97 min.

Step AC (3): To a solution of (1R,2R)-1-azido-6-methoxy-2,3-dihydro-1H-inden-2-ol (400 mg) from Step AC (2), 4-nitrobenzoic acid (813 mg), triphenyl phosphine (1.28 g) in benzene (10 mL) at rt was added DEAD dropwise (0.77 mL), and the reaction mixture was stirred at rt for 12 h. Saturated sodium bicarbonate was added, the aqueous layer was separated, and the aqueous layer was extracted with EtOAc (×3). The combined organic layers were washed with brine, dried over anhydrous sodium sulfate, and filtered. The filtrate was evaporated in vacuo, and the residue was purified by preparative TLC eluting with 30% EtOAc/70% hexanes to give (1R, 2S)-1-azido-6-methoxy-2,3-dihydro-1H-inden-2-yl 4-nitrobenzoate compound as a colorless oil (284 mg). NMR (400

MHz, CDCl₃) δ 8.28 (2H, dd), 8.22 (2H, dd), 7.20 (1H, d), 6.93 (2H, m), 7.79 (1H, q), 4.94 (1H, d), 3.83 (3H, s), 3.29 (1H, dd), 3.22 (1H, dd).

Step AC (4): To a solution of (1R,2S)-1-azido-6-methoxy-2,3-dihydro-1H-inden-2-yl 4-nitrobenzoate (248 mg) from Step AC (3) in methanol (2.8 mL) and DCM (2.4 mL) was added sodium methoxide (114 mg), and the reaction mixture was stirred at rt for 30 min. the solvents were removed in vacuo, and water was added. The aqueous layer was separated, and the aqueous layer was extracted with EtOAc (×3). The combined organic layers were washed with brine, dried over anhydrous sodium sulfate, and filtered. The filtrate was evaporated in vacuo, and the residue was purified by preparative TLC eluting with 30% EtOAc/70% hexanes to give (1R,2S)-1-azido-6-methoxy-2,3-dihydro-1H-inden-2-ol compound as a white solid (100 mg). ¹H NMR (400 MHz, CDCl₃) δ 7.15 (1H, d), 6.91 (1H, d), 6.87 (1H, dd), 4.72 (1H, d), 4.57 (1H, t), 3.80 (3H, s), 3.09 (1H, dd), and 2.84 (1H, dd). The ee of this product was 86% by chiral HPLC (chircel OJ-H column, 4.6×250 mm, 5 μm; mobile phase: 5% ethanol in $CO_2$; flow rate: 2.0 mL/min). Retention time of the title compound: 10.04 min; Retention time of the other enantiomer: 7.38 min.

Step AC (5): (1R,2S)-1-Azido-6-methoxy-2,3-dihydro-1H-inden-2-ol (50 mg) from Step AC (4) was converted to (1R,2S)-2-(allyloxy)-1-azido-6-methoxy-2,3-dihydro-1H-indene by a procedure analogous to Step AA (4). ¹H NMR (400 MHz, CDCl₃) δ 7.25 (1H, d), 6.90 (1H, d), 6.85 (1H, dd), 5.95 (1H, m), 5.35 (1H, d), 5.22 (1H, d), 4.62 (1H, d), 4.35 (1H, q), 4.20 (2H, m), 3.79 (3H, s), 3.05 (2H, t), 2.90 (2H, m).

Step AC (6): (1R,2S)-2-(Allyloxy)-1-azido-6-methoxy-2,3-dihydro-1H-indene (50 mg) from Step AC (5) was converted to 48 mg of (1R,2S)-2-(allyloxy)-6-methoxy-2,3-dihydro-1H-inden-1-amine (slightly yellowish oil) by a procedure analogous to Step AA (5). Retention time: 1.09 min (method A). MS (ESI) (M+H)⁺ 220.29.

Step AC (7): The product from Step AC (6) (48 mg) was converted to tert-butyl (2S,3R)-4-((1R,2S)-2-(allyloxy)-6-methoxy-2,3-dihydro-1H-inden-1-ylamino)-3-hydroxy-1-phenylbutan-2-ylcarbamate (28 mg, white solid) by a procedure analogous to Step AB (1). Retention time: 1.87 min (method A). MS (ESI) (M+H)⁺ 483.35.

Step AC (8): The product from Step AC (7) (28 mg) was converted to the title compound (TFA salt, yellowish oil) by a procedure analogous to Step AB (2). This crude product was used for the next step without purification. Retention time: 1.44 min (method A). MS (ESI) (M+H)⁺ 383.26.

Preparation AD (2R,3S)-1-((1R,2R)-2-(allyloxy)-6-methoxy-2,3-dihydro-1H-inden-1-ylamino)-3-amino-4-phenylbutan-2-ol

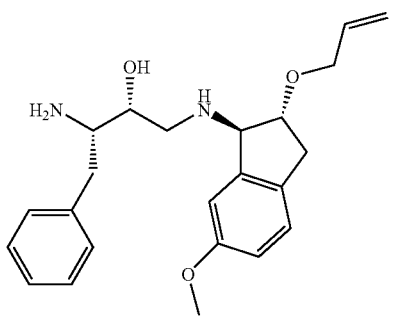

Step AD (1): (1R,2R)-1-Azido-6-methoxy-2,3-dihydro-1H-inden-2-ol from Step AC (2) was converted to the title compound by a set of procedures analogous to Steps AA (5-6) and Steps AB (1-2). Retention time: 1.51 min (method A). MS (ESI) (M+H)⁺ 383.16.

Preparation AE (2R,3S)-1-((1R,2S)-2-(allyloxy)-6-methoxy-2,3-dihydro-1H-inden-1-ylamino)-3-amino-4-phenylbutan-2-ol

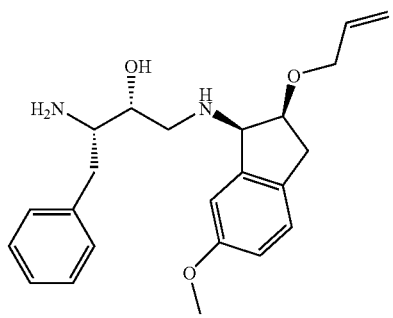

Step AE (1): To a solution of (1R,2S)-1-amino-6-methoxy-2,3-dihydro-1H-inden-2-ol (500 mg) [E. N. Jacobsen, et. al *Organic Synthesis* 1999, 76, 46-56] in methanol (10 mL) was added ethyl trifluoroacetate (0.83 mL) followed by triethylamine (0.65 mL), and the reaction mixture was stirred at rt for 12 h. The solvents were removed in vacuo to give 2,2,2-trifluoro-N-((1R,2S)-2-hydroxy-6-methoxy-2,3-dihydro-1H-inden-1-yl)acetamide as an oil. HPLC retention time: 1.77 min (method B). MS (ESI) (M+Na)⁺ 298.13.

Step AE (2): To a solution of 2,2,2-trifluoro-N-((1R,2S)-2-hydroxy-6-methoxy-2,3-dihydro-1H-inden-1-yl)acetamide in DMF (4.5 mL) at rt was added sodium hydride (95% purity, 205 mg). The resulting mixture was stirred at rt for 5 min. Allyl bromide (0.26 mL) was added, and the reaction mixture was stirred for 30 min. Water was added, the aqueous layer was extracted with EtOAc (×3), and the combined organic layers were washed with brine, dried over anhydrous sodium sulfate, and filtered. The filtrate was evaporated in vacuo to give N-((1R,2S)-2-(allyloxy)-6-methoxy-2,3-dihydro-1H-inden-1-yl)-2,2,2-trifluoroacetamide as a slightly yellowish oil (660 mg). ¹H NMR (400 MHz, CDCl₃) δ 7.14 (1H, d), 6.85 (1H, d), 6.83 (1H, s), 5.88 (1H, m), 5.44 (1H, d), 5.28 (1H, dt), 5.12 (1H, dt), 4.38 (1H, q), 4.06 (1H, m), 3.76 (3H, s), 3.05 (1H, d).

Step AE (3): N-((1R,2S)-2-(allyloxy)-6-methoxy-2,3-dihydro-1H-inden-1-yl)-2,2,2-trifluoroacetamide (650 mg) in methanol (15 mL) was added saturated potassium carbonate (570 mg), and the resulting solution was heated at 73° C. for 12 h. The reaction mixture was filtered through a pad of Celite to give, and the filtrate was evaporated in vacuo to give (1R,2S)-2-(allyloxy)-6-methoxy-2,3-dihydro-1H-inden-1-amine as a solid. HPLC Retention time: 1.34 min (method B). MS (ESI) (M+H)⁺ 220.27.

Step AE (4): A solution of tert-butyl (S)-1-((S)-oxiran-2-yl)-2-phenylethylcarbamate (298 mg) and LiClO₄ (mg) in acetonitrile (3.0 mL) was stirred at rt for 10 min. To the above solution was added 1R,2S)-2-(allyloxy)-6-methoxy-2,3-dihydro-1H-inden-1-amine from Step AE (3) (137 mg) in acetonitrile (0.50 mL), and the reaction mixture was heated at 45° C. for 36 h. Solvents were removed in vacuo, and the residue was purified by HPLC to give tert-butyl (2S,3R)-4-((1R,2S)-2-(allyloxy)-6-methoxy-2,3-dihydro-1H-inden-1- ylamino)-3-hydroxy-1-phenylbutan-2-ylcarbamate as an oil (77 mg). retention time: 1.85 min (method B). MS (ESI) (M+H)+ 483.30.

Step AE (5): To a solution of tert-butyl (2S,3R)-4-((1R, 2S)-2-(allyloxy)-6-methoxy-2,3-dihydro-1H-inden-1-ylamino)-3-hydroxy-1-phenylbutan-2-ylcarbamate (77 mg) in DCM (0.50 mL) was added TFA (0.27 mL), and the reaction mixture was stirred at rt for 1 h. Solvents were removed in vacuo to give the TFA salt of the title compound as a yellowish oil. This crude product was used for the next step without purification. HPLC Retention time: 1.43 min (method B). MS (ESI) (M+H)+ 383.28.

Preparation AF (1S,3R)-3-(allyloxymethyl)-6-methoxy-2,3-dihydro-1H-inden-1-amine

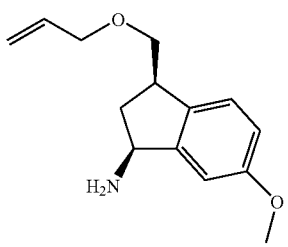

Step AF (1): Pyridinium chlorochromate (362 mg) was added to a stirred suspension of 4A° MS and 2,2,2-trifluoro-N-((1S,3R)-3-hydroxy-6-methoxy-2,3-dihydro-1H-inden-1-yl)acetamide (200 mg) from Step T (1) in DCM (6 mL) at rt. The resulting mixture was stirred for 2 h. The reaction mixture was filtered through a pad of Celite, and the filtrate was evaporated in vacuo to give (S)-2,2,2-trifluoro-N-(6-methoxy-3-oxo-2,3-dihydro-1H-inden-1-yl)acetamide. This crude product was carried forward without purification. $^1$H NMR (400 MHz, CD$_3$OD) δ ppm 2.56 (m, 1H) 3.08 (m, 1H) 3.83 (s, 3H) 5.58 (m, 1H) 6.96 (m, 2H) 7.29 (m, 1H) 7.62 (s, 1H). Optical rotation $[α]_D$=−124.16 (c=6.84 mg/mL, methanol).

Step AF (2): To a solution of methyltriphenylphosphonium bromide (1.6 g) in THF (5 mL) was added potassium t-butoxide (700 mg), and the mixture was stirred at rt for 30 min to form a deep yellow solution. A solution of (S)-2,2,2-trifluoro-N-(6-methoxy-3-oxo-2,3-dihydro-1H-inden-1-yl)acetamide (500 mg) in THF (2 mL) was added, and the reaction was continued for 40 min. Water was added, the aqueous layer was extracted with EtOAc (×3), and the combined organic layers were washed with brine, dried over anhydrous sodium sulfate, and filtered. The filtrate was evaporated in vacuo, and the residue was purified by Biotage chromatography eluting with 1-10% EtOAc/hexanes to give (S)-2,2,2-trifluoro-N-(6-methoxy-3-methylene-2,3-dihydro-1H-inden-1-yl)-acetamide as a white solid (460 mg). $^1$H NMR (400 MHz, CDCl$_3$) δ 7.45 (1H, d), 6.91 (1H, dd), 6.83 (1H, d), 6.45 (1H, br. S), 5.38 (1H, dt), 5.38 (1H, t), 4.99 (1H, t), 3.81 (3H, s), 3.45 (1H, m), and 2.62 (1H, m).

Step AF (3): To a solution of the product from Step AF (2) (460 mg) in THF (9 mL) at 0° C. was added BH$_3$.THF (1.0 M solution, 5.10 mL) and the solution was stirred at rt for 12 h. 38% Hydrogen peroxide (6.42 mL) was added followed by 1 N sodium hydroxide (12 mL), and the solution was stirred at rt for 40 min. Water was added, the aqueous layer was extracted with EtOAc (×3), and the combined organic layers were washed with brine, dried over anhydrous sodium sulfate, and filtered. After evaporation, the residue was purified by preparative TLC eluting with 50% EtOAc/hexanes to give 130 mg of 2,2,2-trifluoro-N-((1S,3R)-3-(hydroxymethyl)-6-methoxy-2,3-dihydro-1H-inden-1-yl)acetamide (diastereomer A) as a colorless oil and 74 mg of 2,2,2-trifluoro-N-((1S,3S)-3-(hydroxymethyl)-6-methoxy-2,3-dihydro-1H-inden-1-yl)acetamide (diastereomer B) as a white solid. Data for diastereomer A: HPLC Retention time: 1.35 min (method A); MS (ESI) (M+Na)+ 312.15; $^1$H NMR (400 MHz, CDCl$_3$) δ 7.95 (1H, br. S), 7.15 (1H, d), 6.88 (1H, s), 6.87 (1H, d), 5.46 (1H, t), 3.8-4.0 (2H, m), 3.77 (3H, s), 3.33 (1H, m), 2.79 (1H, m), 1.89 (1H, dt), 1.68 (1H, br. t). Data for diastereomer B: HPLC Retention time: 1.22 min (method A); MS (ESI) (M+Na)+ 312.15; $^1$H NMR (400 MHz, CDCl$_3$) δ 7.24 (1H, s), 6.88 (1H, m), 6.81 (1H, d), 6.40 (1H, m), 5.52 (1H, q), 3.79 (3H, s), 3.70 (3H, m), 3.43 (1H, m), 2.54 (1H, m), 2.12 (1H, m).

Step AF (4): 2,2,2-Trifluoro-N-((1S,3R)-3-(hydroxymethyl)-6-methoxy-2,3-dihydro-1H-inden-1-yl)acetamide (130 mg) (diasteromer A) from Step AF (3) was converted to N-((1S,3R)-3-(allyloxymethyl)-6-methoxy-2,3-dihydro-1H-inden-1-yl)-2,2,2-trifluoroacetamide by a procedure analogous to Step AA (4). The crude product was purified by preparative TLC eluting with 30% EtOAc/70% hexanes to give the product as a white solid. HPLC retention time: 1.72 min (method A). MS (ESI) (M+Na)+ 352.20.

Step AF (5): To a solution of the product from Step AF (4) (42 mg) was added saturated potassium carbonate in methanol (0.80 mL), and the resulting solution was heated at 73° C. for 3 h. The reaction mixture was filtered through a pad of Celite and the filtrate was evaporated in vacuo to give the title compound as a white solid (36 mg). HPLC retention time: 1.34 min (method A). MS (ESI) (M+H)+ 234.20.

Preparation AG (2R,3S)-1-((1S,3R)-3-(allyloxymethyl)-6-methoxy-2,3-dihydro-1H-inden-1-ylamino)-3-amino-4-phenylbutan-2-ol

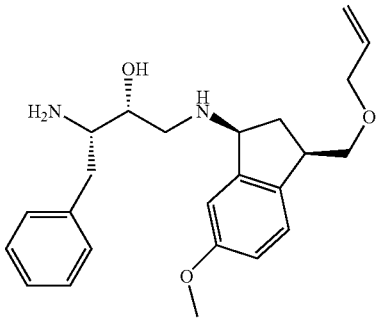

Step AG (1): The product from Step AF (5) (36 mg) was converted to tert-butyl (2S,3R)-4-((1S,3R)-3-(allyloxymethyl)-6-methoxy-2,3-dihydro-1H-inden-1-ylamino)-3-hydroxy-1-phenylbutan-2-ylcarbamate (40 mg, white solid) by a procedure analogous to Step AB (1). Retention time: 1.83 min (method A). MS (ESI) (M+H)+ 497.35.

Step AG (2): The product from Step AG (1) (40 mg) was converted to the title compound (TFA salt, yellowish oil) by a procedure analogous to Step AB (2). This crude product was used for the next step without purification. HPLC Retention time: 1.44 min (method A). MS (ESI) (M+H)+ 383.26.

Preparation AH (2R,3S)-3-amino-4-(3,5-difluorophenyl)-1-(5-methoxy-2-(pent-4-enyl)benzylamino)butan-2-ol

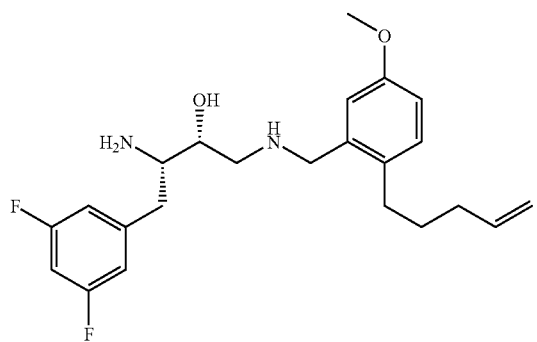

Step AH (1): To a solution of 2-bromo-5-hydroxybenzaldehyde (1000.0 mg, 4.975 mmol) in DMF (20 mL) were added methyl iodide (0.31 mL, 5.000 mmol) and potassium carbonate (1036.6 mg, 7.500 mmol). The reaction mixture was stirred at rt for 2.5 days. Water was added and the reaction mixture was extracted with hexanes-ether (1:1) solvent system. The combined organic phases were dried over $Na_2SO_4$, filtered and concentrated in vacuum to yield 2-bromo-5-methoxybenzaldehyde (1069.8 mg, 100%) as colorless oil. LC-MS (M+H)+=215.11. $^1$H NMR (500 MHz, DMSO-$d_6$) δ 10.18 (s, 1H). 7.70 (d, J=10 Hz, 1H) 7.35 (d, J=3 Hz, 1H) 7.23 (dt, $J_1$=7.0 Hz, $J_2$=2.0 Hz, 1H) 3.83 (s, 3H).

Step AH (2): 2-Bromo-5-methoxybenzaldehyde (1069 mg, 4.975 mmol) was dissolved in a mixture of methanol (20 mL) and triethylorthoformate (20 mL). p-Toluenesulfonic acid monohydrate (180.0 mg, 0.946 mmol) was added and the reaction mixture was stirred under reflux for 5 h. The reaction was quenched with aqueous $NaHCO_3$ and extracted with DCM. The combined organic phases were dried over $Na_2SO_4$, filtered and concentrated in vacuum at the temperature, not exceeding 35° C. The residue was purified by silica gel chromatography to give 1-bromo-2-(dimethoxymethyl)-4-methoxybenzene (688.5 mg, 53%) as colorless oil. LC-MS (M+H)+=261.00. $^1$H NMR (CDCl$_3$, 500 MHz) δ 7.42 (d, J=7.0 Hz, 1H) 7.16 (d, J=3.0 Hz, 1H) 6.76 (dd, $J_1$=10 Hz, $J_2$=3.0 Hz, 1H) 5.50 (s, 1H) 3.80 (s, 3H) 3.39 (s, 6H).

Step AH (3): To a solution of 1-bromo-2-(dimethoxymethyl)-4-methoxybenzene (688.5 mg, 2.637 mmol) in THF (7.0 mL) at −78° C. was added n-butyl lithium (3.46 mL, 5.538 mmol). The resulting mixture was stirred at −78° C. for 15 min. 5-Bromopent-1-ene (0.31 mL, 2.637 mmol) was added by drops. The reaction mixture was warmed to rt and stirred overnight. Aqueous hydrochloric acid solution (1N) was added and the reaction mixture was stirred at rt for 3 h. The reaction was extracted with DCM. The combined organic phases were dried over $Na_2SO_4$, filtered and concentrated in vacuum. The residue was purified by silica gel chromatography to give 5-methoxy-2-(pent-4-enyl)benzaldehyde (538.6 mg, 100%) as colorless oil. LC-MS (M+H)+=205.36. $^1$H NMR (CDCl$_3$, 500 MHz) δ 10.30 (s, 1H) 7.35 (d, J=3.0 Hz, 1H) 7.17 (m, 1H) 7.06 (m, 1H) 5.82 (m, 1H) 5.05-4.98 (m, 2H) 3.84 (s, 3H) 2.12 (m, 2H) 1.69 (m, 2H) 1.57 (m, 2H).

Step AH (4): To a solution of 5-methoxy-2-(pent-4-enyl)benzaldehyde (140.0 g, 0.685 mmol) and ammonium acetate (7.549 g, 97.941 mmol) in methanol (28 mL) was added sodium cyanoborohydride (258.3 g, 4.110 mmol). The reaction mixture was stirred at 65° C. in a high-pressure vessel for 1 h. Aqueous sodium bicarbonate solution was added and the reaction mixture was extracted with DCM. The combined organic phases were dried over $Na_2SO_4$, filtered and concentrated in vacuum. The residue was purified by reverse phase chromatography to give (5-methoxy-2-(pent-4-enyl)phenyl)methanamine trifluoroacetate salt (54.4 mg, 39%) as colorless oil. LC-MS (M+H)+=206.15.

Step AH (5): A solution of benzyl (S)-2-(3,5-difluorophenyl)-1-((S)-oxiran-2-yl)ethylcarbamate (88.3 mg, 0.265 mmol) and amine (54.4 mg, 0.265 mmol) in iso-propanol (2.3 mL) was stirred at 85° C. in a high-pressure vessel for 18 h. The solvent was removed in vacuum and the residue was purified by reverse phase chromatography to give benzyl (2S,3R)-1-(3,5-difluorophenyl)-3-hydroxy-4-(5-methoxy-2-(pent-4-enyl)benzylamino)butan-2-ylcarbamate trifluoroacetate salt (91.3 mg, 91%) as a colorless oil. LC-MS (M+H)+=539.52. $^1$H NMR (CD$_3$OD, 500 MHz) δ 7.70-7.14 (m, 11H) 6.25 (m, 1H) 5.37 (m, 2H) 4.62-4.60 (m, 2H) 4.25 (m, 1H) 4.19 (s, 3H) 3.71-3.64 (m, 2H) 3.42 (m, 1H) 3.05-3.01 (m, 2H) 2.51 (m, 2H) 2.04 (m, 2H) 1.91 (m, 2H) 1.74 (m, 2H).

Step AH (6): To a solution of benzyl (2S,3R)-1-(3,5-difluorophenyl)-3-hydroxy-4-(5-methoxy-2-(pent-4-enyl)benzylamino)butan-2-ylcarbamate trifluoroacetate salt (91.3 mg, 0.140 mmol) in DME (9.0 mL) and water (6.0 mL) was added barium hydroxide monohydrate (831.2 mg, 4.389 mmol). The reaction mixture was stirred at 110° C. in a high-pressure vial for 18 h. The reaction was filtered through a pad of celite and the filtrate was concentrated in vacuum. The residue was purified by silica gel chromatography to give (2R,3S)-3-amino-4-(3,5-difluorophenyl)-1-(5-methoxy-2-(pent-4-enyl)benzylamino)butan-2-ol double trifluoroacetate salt (45.8 mg, 52%) as colorless oil. LC-MS (M+H)+=405.42. $^1$H NMR (CD$_3$OD, 500 MHz) δ 7.30-6.75 (m, 6H) 5.86 (m, 1H) 5.02 (m, 2H) 4.33 (m, 1H) 3.81 (s, 3H) 3.72 (m, 2H) 3.37 (m, 1H) 3.12-2.92 (m, 2H) 2.75-2.60 (m, 2H) 2.14 (m, 2H) 1.65 (m, 2H) 1.53 (m, 2H).

Preparation AI (5-methyl-2-(pent-4-enyl)phenyl)methanamine

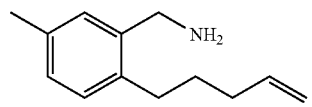

Step AI (1): To a solution of 2-bromo-5-methylbenzoic acid (1000.0 mg, 4.65 mmol) in DMF (100 mL) were added N,O-dimethylhydroxylamine hydrochloride (454 mg, 4.65 mmol), EDC (891 mg, 4.65 mmol), and HOBT (628 mg, 4.65 mmol). The reaction mixture was stirred at rt for 2.5 days. The reaction mixture was diluted with water and extracted with EtOAc. The combined organic phases were dried over $Na_2SO_4$, filtered and concentrated in vacuum. The residue was purified by silica gel chromatography to give 2-bromo-N-methoxy-N,5-dimethylbenzamide (656 mg, 55%) as a colorless oil. LC-MS (M+H)+=258.21.

Step AI (2): 2-Bromo-N-methoxy-N,5-dimethylbenzamide (656 mg, 2.54 mmol) was dissolved in THF (20 mL).

The reaction mixture was cooled down to −78° C. and a 1.0M solution of DIBAL-H (7.62 mL, 7.62 mmol) was added. The reaction mixture was stirred at −78° C. for 1 h. The reaction was quenched with acetone and stirred at rt with Rochelle's salt. The mixture was extracted with DCM. The combined organic phases were dried over $Na_2SO_4$, filtered and concentrated in vacuum to yield 2-bromo-5-methylbenzaldehyde (500 mg, 99%) as a colorless oil. LC-MS (M+H)$^+$=199.21.

Step AI (3): 2-Bromo-5-methylbenzaldehyde (500 mg, 2.51 mmol) was dissolved in methanol (5.0 mL). p-Toluenesulfonic acid monohydrate (90 mg, 0.52 mmol) and trimethoxymethane (5 mL) were added. The reaction mixture was heated at reflux for 5 h. The reaction mixture was extracted with DCM and washed with saturated aqueous sodium bicarbonate. The combined organic phases were dried over $Na_2SO_4$, filtered and concentrated in vacuum to yield 1-bromo-2-(dimethoxymethyl)-4-methylbenzene (615 mg, 99%) as a colorless oil. LC-MS (M−OCH$_3$)$^+$=213.25. $^1$H NMR (CD$_3$OD, 500 MHz) δ 7.41-7.39 (m, 2H) 6.98 (d, J=10 Hz, 1H) 5.51 (s, 1H) 3.37 (s, 6H) 2.30 (s, 3H).

Step AI (4): 1-Bromo-2-(dimethoxymethyl)-4-methylbenzene (615 mg, 2.51 mmol) was dissolved in THF (10 mL) under $N_2$ atmosphere at −78° C. n-Butyllithium (1.6 M, 3.1 mL) was added and the reaction mixture was stirred for 30 min. 5-Bromopent-1-ene (0.31 mL, 2.64 mmol) was added. The reaction mixture was warmed to rt and stirred for 18 h. The reaction was quenched with the addition of HCl (1.0 N) and was further stirred at rt for 1 h. The reaction mixture was extracted with EtOAc and washed with brine. The combined organic phases were dried over $Na_2SO_4$, filtered and concentrated in vacuum. The residue was purified by silica gel chromatography to give 5-methyl-2-(pent-4-enyl)benzaldehyde (45 mg, 10%) as a colorless oil. LC-MS (M+H)$^+$=189.41.

Step AI (5): 5-Methyl-2-(pent-4-enyl)benzaldehyde (170 mg, 0.90 mmol) and ammonium acetate (10.44 g, 135.5 mmol) was dissolved in methanol (35 mL). Sodium cyanoborohydride (341 mg, 5.42 mmol) was added. The reaction mixture was stirred at 65° C. in a high-pressure vessel for 1 h. Aqueous sodium bicarbonate solution was added and the reaction mixture was extracted with DCM. The combined organic phases were dried over $Na_2SO_4$, filtered and concentrated in vacuum. The residue was purified by reverse phase chromatography to give (5-methyl-2-(pent-4-enyl)phenyl)methanamine (57 mg, 33%) as a colorless oil. LC-MS (M+H)$^+$=190.09.

Preparation AJ (2-(pent-4-enyl)-5-(trifluoromethyl)phenyl)methanamine

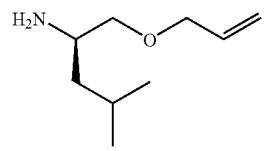

Step AJ (1): 2-Bromo-5-(trifluoromethyl)benzaldehyde (1069 mg, 4.975 mmol) was dissolved in a mixture of methanol (20 mL) and triethylorthoformate (20 mL). p-Toluenesulfonic acid monohydrate (180.0 mg, 0.946 mmol) was added and the reaction mixture was stirred under reflux for 5 h. The reaction was quenched with aqueous NaHCO$_3$ and extracted with DCM. The combined organic phases were dried over $Na_2SO_4$, filtered and concentrated in vacuum at the temperature, not exceeding 35° C. The residue was purified by silica gel chromatography to give 1-bromo-2-(dimethoxymethyl)-4-methoxybenzene (1060 mg, 71%) as a colorless oil. LC-MS (M−OCH$_3$)$^+$=267.23.

Step AJ (2): To a solution of 1-bromo-2-(dimethoxymethyl)-4-(trifluoromethyl)benzene (1060 mg, 3.544 mmol) in THF (10 mL) at −78° C. was added 1.6N solution of n-butyl lithium in hexanes (4.43 mL, 7.088 mmol). The resulting mixture was stirred at −78° C. for 15 min. 5-Bromopent-1-ene (0.42 mL, 3.544 mmol) was added by drops. The reaction mixture was warmed to rt and stirred overnight. Aqueous hydrochloric acid solution (1N) was added and the reaction mixture was stirred at rt for 3 h. The reaction was extracted with DCM. The combined organic phases were dried over $Na_2SO_4$, filtered and concentrated in vacuum. The residue was purified by silica gel chromatography to give 2-(pent-4-enyl)-5-(trifluoromethyl)benzaldehyde (858.0 mg, 100%) as a brown oil. LC-MS (M+H)$^+$=243.09. $^1$H NMR (CDCl$_3$, 500 MHz) δ 10.30 (s, 1H) 8.22-7.35 (m, 3H) 7.06 (m, 1H) 5.83 (m, 1H) 5.10-5.00 (m, 2H) 3.84 (s, 3H) 2.16 (m, 2H) 1.75 (m, 2H) 1.60 (m, 2H).

Step AJ (3): 2-(Pent-4-enyl)-5-(trifluoromethyl)benzaldehyde (200 mg, 0.83 mmol) and ammonium acetate (9.6 g, 124 mmol) was dissolved in methanol (35 mL). Sodium cyanoborohydride (311 mg, 4.95 mmol) was added. The reaction mixture was stirred at 65° C. in a high-pressure vessel for 2 h. Aqueous sodium bicarbonate solution was added and the reaction mixture was extracted with DCM. The combined organic phases were dried over $Na_2SO_4$, filtered and concentrated in vacuum. The residue was purified by reverse phase chromatography to give (2-(pent-4-enyl)-5-(trifluoromethyl) phenyl)methanamine (65 mg, 32%) as a colorless oil. LC-MS (M+H)$^+$=244.21.

Preparation AK (R)-1-(allyloxy)-4-methylpentan-2-amine

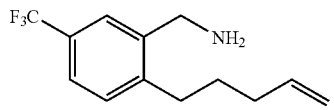

Step AK (1): (R)-2-amino-4-methylpentan-1-ol (1.0 g, 8.53 mmol) was dissolved in ethyl trifluoroacetate (2.5 mL). The reaction mixture was stirred overnight at rt. The reaction mixture was diluted with water and extracted with EtOAc. The combined organic phases were washed with water and brine. The organic phases were dried over $Na_2SO_4$, filtered and concentrated in vacuum. The residue was purified by silica gel chromatography to give (R)-2,2,2-trifluoro-N-(1-hydroxy-4-methylpentan-2-yl)acetamide (1.48 g, 81%) as a colorless oil. LC-MS (M+H)$^+$=214.81.

Step AK (2): (R)-2,2,2-trifluoro-N-(1-hydroxy-4-methyl-pentan-2-yl)-acetamide (200 mg, 0.94 mmol) was dissolved in THF (5 mL) under nitrogen atmosphere. Sodium hydride (80 mg, 1.9 mmol) was added to the reaction mixture in portions. 3-Bromoprop-1-ene (0.16 mL, 1.9 mmol) was added dropwise to the reaction mixture. The reaction mixture was stirred at rt for 3 h and was extracted with EtOAc. The combined organic phases were washed with water and brine and dried over $Na_2SO_4$, filtered and concentrated in vacuum. The residue was purified by silica gel chromatography to give (R)-N-(1-(allyloxy)-4-methylpentan-2-yl)-2,2,2-trifluoroacetamide (210 mg, 88%) as a colorless oil. LC-MS (M+H)⁺ =254.06. ¹H NMR (CD₃OD, 500 MHz) δ 5.91 (m, 1H) 5.31-5.17 (m, 2H) 4.21 (m, 1H) 4.05-3.97 (m, 2H) 3.49-3.42 (m, 2H) 1.63 (m, 1H) 1.52 (m, 1H) 1.39 (m, 1H) 0.97-0.93 (m, 6H).

Step AK (3): To a mixture of methanol (90 mL) and water (10 mL), (R)-N-(1-(allyloxy)-4-methylpentan-2-yl)-2,2,2-trifluoroacetamide (1.9 g, 7.5 mmol) and potassium carbonate (3.1 g, 22.5 mmol) were added. The mixture was heated at reflux for 16 h and concentrated in vacuum to remove methanol. The mixture was poured into excess NaOH (1 M) and extracted with EtOAc. The combined organic phases were washed with brine, dried over Na₂SO₄, filtered and concentrated in vacuum to yield (R)-1-(allyloxy)-4-methylpentan-2-amine (1.12 g, 95%) as a colorless oil. LC-MS (M+H)⁺=158.07.

Preparation AL (2R,3S)-3-amino-4-(3,5-difluorophenyl)-1-(5-methyl-2-(pent-4-enyl)benzylamino)butan-2-ol

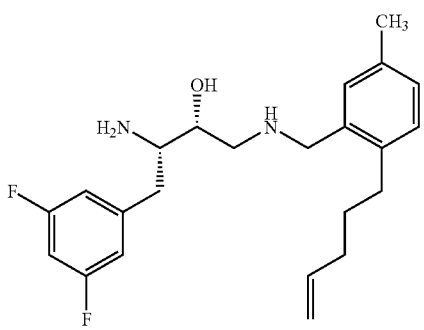

Step AL (1): A solution of benzyl (S)-2-(3,5-difluorophenyl)-1-((S)-oxiran-2-yl)ethylcarbamate (100 mg, 0.301 mmol) and (5-methyl-2-(pent-4-enyl)phenyl)methanamine (57 mg, 0.301 mmol) in iso-propanol (2.6 mL) was stirred at 80° C. in a high-pressure vessel for 18 h. The solvent was removed in vacuum and the residue was purified by reverse phase chromatography to give benzyl (2S,3R)-1-(3,5-difluorophenyl)-3-hydroxy-4-(5-methyl-2-(pent-4-enyl)benzylamino)butan-2-ylcarbamate trifluoroacetate salt (65 mg, 34%) as a colorless oil. LC-MS (M+H)⁺=523.78.

Step AL (2): To a solution of benzyl (2S,3R)-1-(3,5-difluorophenyl)-3-hydroxy-4-(5-methyl-2-(pent-4-enyl)benzylamino)butan-2-ylcarbamate trifluoroacetate salt (65 mg, 0.102 mmol) in DME (7.0 mL) and water (4.5 mL) was added barium hydroxide monohydrate (625 mg, 3.3 mmol). The reaction mixture was stirred at 110° C. in a high pressure vial for 18 h. The reaction mixture was filtered through a pad of celite and the filtrate was concentrated in vacuum. The residue was purified by reverse phase chromatography to give (2R,3S)-3-amino-4-(3,5-difluorophenyl)-1-(5-methyl-2-(pent-4-enyl)benzylamino)butan-2-ol double trifluoroacetate salt (22 mg, 35%) as a colorless oil. LC-MS (M+H)⁺=389.63.

Preparation AM (2R,3S)-3-amino-4-(3,5-difluorophenyl)-1-(2-(pent-4-enyl)-5-(trifluoromethyl)benzylamino)butan-2-ol

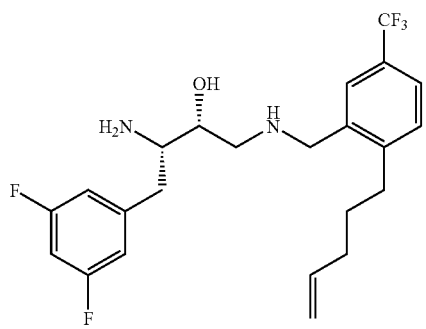

Step AM (1): A solution of benzyl (S)-2-(3,5-difluorophenyl)-1-((S)-oxiran-2-yl)ethylcarbamate (89 mg, 0.267 mmol) and (2-(pent-4-enyl)-5-(trifluoromethyl)phenyl)methanamine (65 mg, 0.267 mmol) in iso-propanol (2.0 mL) was stirred at 80° C. in a high-pressure vessel for 18 h. The solvent was removed in vacuum and the residue was purified by reverse phase chromatography to give benzyl (2S,3R)-1-(3,5-difluorophenyl)-3-hydroxy-4-(2-(pent-4-enyl)-5-(trifluoromethyl)benzylamino)butan-2-ylcarbamate trifluoro-acetate salt (88 mg, 48%) as a colorless oil. LC-MS (M+H)⁺=577.48.

Step AM (2): To a solution of benzyl (2S,3R)-1-(3,5-difluorophenyl)-3-hydroxy-4-(2-(pent-4-enyl)-5-(trifluoromethyl)benzylamino)butan-2-ylcarbamate trifluoroacetate salt (88 mg, 0.128 mmol) in DME (9.0 mL) and water (6.0 mL) was added barium hydroxide monohydrate (852 mg, 4.5 mmol). The reaction mixture was stirred at 110° C. in a high pressure vial for 18 h. The reaction mixture was filtered through a pad of celite and the filtrate was concentrated in vacuum. The residue was purified by reverse phase chromatography to give (2R,3S)-3-amino-4-(3,5-difluorophenyl)-1-(2-(pent-4-enyl)-5-(trifluoromethyl)-benzylamino)butan-2-ol double trifluoro-acetate salt (64 mg, 74%) as a colorless oil. LC-MS (M+H)⁺=443.36.

Preparation AO (2R,3S)-1-((R)-1-(allyloxy)-methylpentan-2-ylamino)-3-amino-4-(3,5-difluorophenyl)butan-2-ol

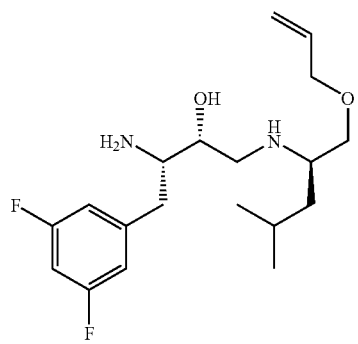

Step AO (1): A solution of benzyl (S)-2-(3,5-difluorophenyl)-1-((S)-oxiran-2-yl)ethylcarbamate (750 mg, 2.25 mmol) and (R)-1-(allyloxy)-4-methylpentan-2-amine (354 mg, 2.25 mmol) in iso-propanol (10.0 mL) was stirred at 80° C. in a high-pressure vessel for 18 h. The solvent was removed in vacuum and the residue was purified by reverse phase chromatography to give benzyl(2S,3R)-4-((R)-1-(allyloxy)-4-methylpentan-2-ylamino)-1-(3,5-difluorophenyl)-3-hydroxybutan-2-ylcarbamate trifluoroacetate salt (560 mg, 53%) as a colorless oil. LC-MS (M+H)$^+$=491.30.

Step AO (2): To a solution of benzyl (2S,3R)-4-((R)-1-(allyloxy)-4-methylpentan-2-ylamino)-1-(3,5-difluorophenyl)-3-hydroxybutan-2-ylcarbamate trifluoroacetate salt (560 mg, 1.19 mmol) in DME (9.0 mL) and water (6.0 mL) was added barium hydroxide monohydrate (1.35 g, 7.11 mmol). The reaction mixture was stirred at 110° C. in a high pressure vial for 18 h. The reaction mixture was filtered through a pad of celite and the filtrate was concentrated in vacuum. The residue was purified by reverse phase chromatography to give (2R,3S)-1-((R)-1-(allyloxy)-4-methylpentan-2-ylamino)-3-amino-4-(3,5-difluorophenyl)butan-2-ol double trifluoroacetate salt (243 mg, 57%) as a colorless oil. LC-MS (M+H)$^+$=357.09.

Preparation AP benzyl trans-allyl(3-amino-5-methoxy-2,3-dihydro-1H-inden-1-yl)carbamate

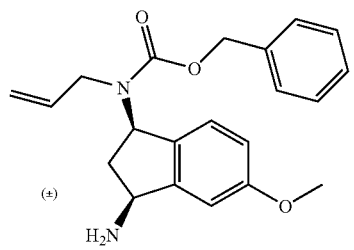

Step AP (1). 2,2,2-Trifluoro-N-(6-methoxy-3-oxo-2,3-dihydro-1H-inden-1-yl)acetamide (1.37 g, 5.0 mmole) was stirred in neat allylamine (18 mL) with dried 4 Å molecular sieves (10 g) for 2 days at rt. LC-MS analysis showed complete conversion of the starting material to N-(3-(allylimino)-6-methoxy-2,3-dihydro-1H-inden-1-yl)-2,2,2-trifluoroacetamide with (M+H)$^+$=313.05. The reaction was concentrated by rotary evaporation to dryness. The residue was suspended in 100 mL MeOH at 0° C. and treated with NaBH$_4$ (284 mg, 7.5 mmole), then warmed to rt and stirred for 0.5 h. The reaction was filtered and concentrated by rotary evaporation. The residue was taken up in 100 mL EtOAc, washed twice with 50 mL brine, and concentrated to an oil. Purification of the crude mixture into the two racemic diastereomers was accomplished by reverse phase prep-HPLC. For trans-N-((1S,3R)-3-(allylamino)-6-methoxy-2,3-dihydro-1H-inden-1-yl)-2,2,2-trifluoroacetamide (189 mg, 9% yield): LC-MS (M+H)$^+$=315.1; $^1$H NMR (400 MHz, CD$_3$OD) δ ppm 2.48 (dt, J=14.86, 7.43 Hz, 1H) 2.77 (ddd, J=14.86, 7.81, 2.27 Hz, 1H) 3.73 (d, J=6.80 Hz, 2H) 3.81 (s, 3H) 4.88 (dd, J=7.93, 2.14 Hz, 1H) 5.48 (dd, J=10.20, 0.88 Hz, 1H) 5.55 (dd, J=17.12, 1.01 Hz, 1H) 5.74 (t, J=7.43 Hz, 1H) 5.88-6.01 (m, J=17.09, 10.29, 6.70, 6.70 Hz, 1H) 6.87 (d, J=2.01 Hz, 1H) 7.00 (dd, J=8.31, 2.27 Hz, 1H) 7.53 (d, J=8.56 Hz, 1H). For cis-N-((1S,3R)-3-(allylamino)-6-methoxy-2,3-dihydro-1H-inden-1-yl)-2,2,2-trifluoroacetamide (822 mg, 38% yield): LC-MS (M+H)$^+$=315.2; $^1$H NMR (400 MHz, CD$_3$OD) δ ppm 2.19 (dt, J=14.04, 6.33 Hz, 1H) 3.10 (ddd, J=13.98, 8.18, 8.06 Hz, 1H) 3.77 (d, J=6.80 Hz, 2H) 3.80 (s, 3H) 4.76 (t, J=6.92 Hz, 1H) 5.31 (t, J=7.30 Hz, 1H) 5.51 (dd, J=10.20, 0.88 Hz, 1H) 5.58 (dd, J=17.00, 1.13 Hz, 1H) 5.90-6.07 (m, J=17.12, 10.32, 6.80, 6.80 Hz, 1H) 6.88 (d, J=2.01 Hz, 1H) 7.01 (dd, J=8.56, 2.27 Hz, 1H) 7.50 (d, J=8.56 Hz, 1H).

Step AP (2). cis-N-((1S,3R)-3-(Allylamino)-6-methoxy-2,3-dihydro-1H-inden-1-yl)-2,2,2-trifluoroacetamide from Step AP (1) and NaHCO$_3$ were dissolved in 25 mL THF and 10 mL H$_2$O at 0 C. Benzyl chloroformate was added and the reaction was stirred for 2 h. The reaction was diluted into 75 mL EtOAc and extracted 25 mL 0.1 N HCl followed by 25 mL brine. The organic layer was dried over Na$_2$SO$_4$, concentrated by rotary evaporation, and dried to give benzyl trans-allyl(5-methoxy-3-(2,2,2-trifluoroacetamido)-2,3-dihydro-1H-inden-1-yl)carbamate (735 mg, 93%). LC-MS (M+Na)$^+$=471.2; $^1$H NMR (500 MHz, CDCl$_3$) δ ppm 1.97 (d, J=14.65 Hz, 1H) 3.03 (ddd, J=14.88, 9.16, 8.93 Hz, 1H) 3.78 (s, 3H) 3.94-4.05 (m, 1H) 4.06-4.14 (m, 1H) 4.69 (s, 1H) 4.96 (d, J=12.51 Hz, 1H) 5.10 (d, J=12.21 Hz, 1H) 5.15-5.28 (m, 2H) 5.48 (s, 1H) 5.82-5.94 (m, J=16.79, 10.61, 5.84, 5.84 Hz, 1H) 6.81 (s, 1H) 6.87 (dd, J=8.24, 1.83 Hz, 1H) 7.13 (d, J=8.24 Hz, 1H) 7.26-7.39 (m, 5H) 8.44 (s, 1H).

Step AP (3): benzyl trans-allyl(5-methoxy-3-(2,2,2-trifluoroacetamido)-2,3-dihydro-1H-inden-1-yl)carbamate (735 mg, 164 mmol) from Step AP (2) and K$_2$CO$_3$ (1.13 g, 8.20 mmol) were refluxed in 30 mL methanol and 3 mL H$_2$O for 24 h. the reaction was concentrated to an oil, which was dissolved in 50 mL EtOAc and extracted three times with 50 mL brine. The organic layer was dried over Na$_2$SO$_4$, concentrated by rotary evaporation, and dried to give the title compound (600 mg, 100%). LC-MS (M+H)$^+$=353.2; $^1$H NMR (400 MHz, CDCl$_3$) δ ppm 1.63-1.83 (m, 1H) 2.80 (s, 1H) 3.51-3.65 (m, 1H) 3.81 (s, 3H) 3.88-4.03 (m, 1H) 4.24 (s, 1H) 4.99-5.19 (m, 4H) 5.23-5.54 (m, 1H) 5.81 (s, 1H) 6.80 (dd, J=8.31, 2.01 Hz, 1H) 6.83-6.97 (m, 1H) 7.01 (d, J=8.06 Hz, 1H) 7.18 (s, 1H) 7.26-7.41 (m, 4H).

Preparation AQ

Diastereomeric Mixture of allyl-[(1R,3S)-3-((2R,3S)-3-amino-2-hydroxy-4-phenyl-butylamino)-5-methoxy-indan-1-yl]-carbamic acid benzyl ester and allyl-[(1S,3R)-3-((2R,3S)-3-amino-2-hydroxy-4-phenyl-butylamino)-5-methoxy-indan-1-yl]-carbamic acid benzyl ester

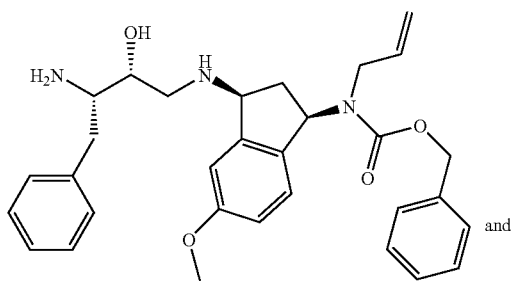

and

-continued

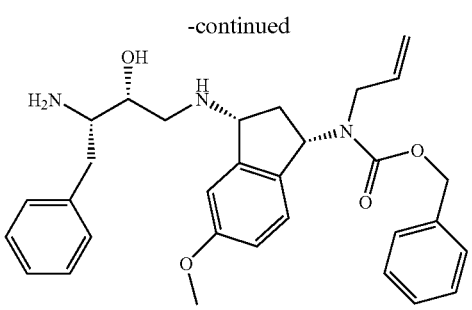

Step AQ (1): The products from Step AP (3) (600 mg, 1.7 mmol), tert-butyl[S-(R*,R*)]-(−)-(1-oxiranyl-2-phenylethyl)carbamate (500 mg, 1.9 mmol), and lithium perchlorate (368 mg, 3.46 mmol) were stirred in 23 mL of acetonitrile at 45° C. for 65 h. After cooling to rt the reaction was diluted into 200 mL EtOAc, then extracted with 100 mL saturated aqueous NaHCO$_3$ and 100 mL brine. The organic layer was dried over Na$_2$SO$_4$, concentrated by rotary evaporation, and purified by flash chromatography on 40 g silica gel with a 40 min gradient of 0 to 100% EtOAc in hexane. Desired fractions were pooled, concentrated by rotary evaporation, and dried to give allyl-[(1R,3S)-3-((2R,3S)-3-tert-butoxycarbonylamino-2-hydroxy-4-phenyl-butylamino)-5-methoxy-indan-1-yl]-carbamic acid benzyl ester and allyl-[(1S,3R)-3-((2R,3S)-3-tert-butoxycarbonylamino-2-hydroxy-4-phenyl-butylamino)-5-methoxy-indan-1-yl]-carbamic acid benzyl ester (595 mg, 57%) as a 1:1 mixture of diastereomers. LC-MS (M+H)$^+$=616.5; $^1$H NMR (400 MHz, CDCl$_3$) δ ppm 1.35 (2s, 9H) 1.70-1.83 (m, 1H) 2.55-3.14 (m, 5H) 3.27-3.70 (m, 3H) 3.72-3.78 (m, 1H) 3.80 (2s, 3H) 3.85-4.20 (m, 2H) 4.45-4.85 (m, 1H) 4.95-5.21 (m, 4H) 5.21-5.60 (m, 1H) 5.70-5.92 (m, 1H) 6.75-6.87 (m, J=7.81 Hz, 1H) 6.87-7.11 (m, 2H) 7.14-7.39 (m, 10H).

Step AQ (2). A solution of the products from Step AQ (1) in 50 mL DCM and 10 mL TFA was stirred for 1 h at rt. The reaction was concentrated by rotary evaporation, chased several times with ether to remove excess TFA, and dried to give a 1:1 mixture of the titled compounds as the di-TFA salt (0.72 g, 100%). LC-MS (M+H)$^+$=516.4; $^1$H NMR (400 MHz, CD$_3$OD) δ ppm 2.10-2.41 (m, 1H) 2.86-3.10 (m, 3H) 3.15-3.40 (m, 2H) 3.65-3.74 (m, 1H) 3.81 (2s, 3H) 3.91-4.04 (m, 1H) 4.05-4.17 (m, 1H) 4.24 (dd, J=19.51, 11.21 Hz, 1H) 4.68-4.78 (m, 1H) 4.94-5.14 (m, 3H) 5.16-5.30 (m, 2H) 5.82-6.03 (m, 1H) 7.00 (t, J=6.17 Hz, 1H) 7.08-7.16 (m, 1H) 7.17-7.40 (m, 11H).

Preparation AR benzyl (3S)-3-((2R,3S)-3-amino-2-hydroxy-4-phenylbutylamino)-5-methoxy-2,3-dihydro-1H-inden-1-yl(but-3-enyl)carbamate

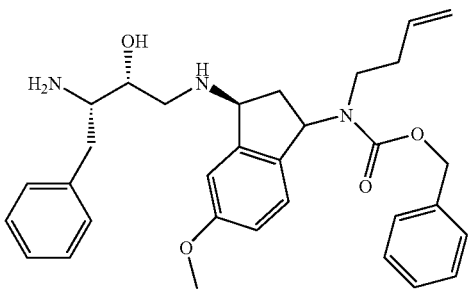

Step AR (1). N-((1S)-3-(but-3-enylamino)-6-methoxy-2,3-dihydro-1H-inden-1-yl)-2,2,2-trifluoroacetamide (0.40 g) was prepared in 74% yield from (S)-2,2,2-trifluoro-N-(6-methoxy-3-oxo-2,3-dihydro-1H-inden-1-yl)acetamide (0.45 g, 1.6 mmol, from Step AF (1)) by a method analogous to that used for Step AP (1). Cis and trans diastereomers were not separated. LC-MS (M+H)$^+$=329.2.

Step AR (2): Benzyl but-3-enyl((3S)-5-methoxy-3-(2,2,2-trifluoroacetamido)-2,3-dihydro-1H-inden-1-yl)carbamate (0.70 g, mixture of cis and trans diastereomers) was prepared in 55% yield from the products of Step AR (1) (0.90 g, 2.7 mmol) by a method analogous to that used for the preparation of Step AP (2), except that the reaction time was 3 days. LC-MS (M+H)$^+$=463.2; $^1$H NMR (400 MHz, CD$_3$OD) δ 7.20-7.42 (m, 5H) 6.70-7.16 (m, 3H) 4.85-5.72 (m, 7H) 3.75 (s, 3H) 3.10 (m, 2H) 2.40-2.80 (m, 1H) 2.00-2.38 (m, 3H).

Step AR (3): Benzyl (3S)-3-amino-5-methoxy-2,3-dihydro-1H-inden-1-yl(but-3-enyl)carbamate (1.1 g) was prepared in 93% yield from the products of Step AR (2) (1.5 g, 3.2 mmol) by a method analogous to that used for Step AP (3). LC-MS (M+H)$^+$=367.2; $^1$H NMR (400 MHz, CD$_3$OD) δ 7.20-7.42 (m, 5H) 6.72-7.18 (m, 3H) 4.80-5.80 (m, 6H) 4.20-4.50 (m, 1H) 3.80 (s, 3H) 2.80-3.40 (m, 3H) 1.70-2.48 (m, 3H).

Step AR (4): But-3-enyl-[(S)-3-((2R,3S)-3-tert-butoxycarbonylamino-2-hydroxy-4-phenyl-butylamino)-5-methoxy-indan-1-yl]-carbamic acid benzyl ester (1.4 g) was prepared in 75% yield from the products of Step AR (3) (1.1 g, 3.0 mmol) by a method analogous to that used for Step AQ (1). LC-MS (M+H)$^+$=630.4; $^1$H NMR (400 MHz, CD$_3$OD) δ 7.10-7.40 (m, 12H) 7.00 (m, 1H) 5.75-5.85 (m, 1H) 4.95-5.15 (m, 5H) 4.70 (m, 1H) 3.81 (s, 3H) 3.37-3.80 (m, 4H) 2.96-3.25 (m, 4H) 2.27-2.70 (m, 4H) 1.28 (2s, 9H).

Step AR (5): The titled compound (0.50 g) was prepared in 53% yield from the products of Step AR (4) (0.78 g, 1.1 mmol) by a method analogous to that used for Step AQ (1). LC-MS (M+H)$^+$=530.3; $^1$H NMR (400 MHz, CD$_3$OD) δ 7.10-7.40 (m, 12H) 6.98 (m, 1H) 5.70-5.80 (m, 1H) 4.90-5.15 (m, 4H) 4.70 (m, 1H) 4.20 (m, 1H) 3.81 (s, 3H) 3.28-3.68 (m, 4H) 2.80-3.20 (m, 5H) 2.10-2.56 (m, 3H).

Preparation AS (2R,3S)-1-(2-(allyloxy)-5-methoxybenzylamino)-3-amino-4-phenylbutan-2-ol

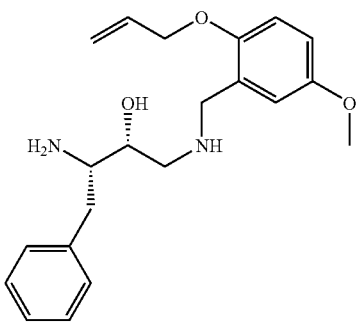

Step AS (1). A mixture of 10 g (55 mmol) of methyl 5-methoxysalicylate, 9.3 mL (110 mMol) of allyl bromide and 36 g (110 mmol) of cesium carbonate in 100 mL of acetonitrile was stirred at rt for 2 h. The reaction was filtered to remove cesium carbonate and concentrated under vacuum to yield 13.3 g (100%) of methyl 2-allyloxy-5-methoxybenzoate as a yellowish solid, which was used directly in the next reaction without purification. LC-MS (M+H)⁺=223; ¹H NMR (400 MHz, CDCl₃) δ ppm 3.77 (s, 3H) 3.88 (s, 3H) 4.49-4.58 (m, 2H) 5.20-5.29 (m, 1H) 5.39-5.50 (m, 1H) 5.96-6.11 (m, 1H) 6.89 (d, J=9.06 Hz, 1H) 6.98 (dd, J=9.07, 3.27 Hz, 1H) 7.32 (d, J=3.02 Hz, 1H).

Step AS (2). To a solution of methyl 2-allyloxy-5-methoxybenzoate (12 g, 55 mmol) in 100 mL anhydrous THF was added slowly 55 mL of a 1.0 M solution of lithium aluminum hydride (55 mmol) in THF at −50° C. The resulting solution was stirred at −50° C. for 1.5 h. EtOAc (100 mL) was added, followed by addition of 30 mL of aqueous ammonium chloride. The organic layer was filtered, washed with aqueous ammonium chloride and brine, then dried over magnesium sulfate. After concentration, 2-allyloxy-5-methoxybenzyl alcohol was obtained as a colorless oil (10.5 g, 100%), which was used directly for the next reaction without purification. LC-MS (M+H)⁺=195; ¹H NMR (400 MHz, CDCl₃) δ ppm 3.75 (s, 3H) 4.46-4.55 (m, 2H) 4.66 (s, 2H) 5.21-5.29 (m, 1H) 5.34-5.42 (m, 1H) 5.95-6.09 (m, 1H) 6.74 (dd, J=9.05, 3.02 Hz, 1H) 6.78 (d, J=9.05 Hz, 1H) 6.88 (d, J=3.02 Hz, 1H).

Step AS (3). To a solution of 2-allyloxy-5-methoxybenzyl alcohol (5 g, 26 mmol) in 75 mL of anhydrous THF was added diphenylphosphoryl azide (6 mL, 28.5 mmol) and 1,8-diazabicyclo[5,4,0]undec-7-ene (DBU) (4.6 mL, 31 mmol) at 0° C. The mixture was refluxed for 1 h. The reaction was concentrated and the residue purified by silica gel chromatography eluting with 25% EtOAc in hexane to yield 2-allyloxy-5-methoxybenzyl azide as a colorless oil (4.9 g, 87%). (M−N₃)⁺=177; ¹H NMR (400 MHz, CDCl₃) δ ppm 3.76 (s, 3H) 4.36 (s, 2H) 4.47-4.57 (m, 2H) 5.21-5.31 (m, 1H) 5.31-5.46 (m, 1H) 5.95-6.14 (m, 1H) 6.79-6.82 (m, 2H) 6.83-6.85 (m, 1H).

Step AS (4). To a solution of 2-allyloxy-5-methoxybenzyl azide (4.5 g, 21 mmol) in 150 mL of anhydrous THF was added triphenylphosphine (10.8 g, 41 mmol) and 0.5 mL of water. The mixture was stirred at rt for 7 h. The reaction was concentrated under vacuum and the residue was partitioned between Et₂O and 2 N HCl. The aqueous layer was basified with 2 N NaOH to pH 10 and extracted with EtOAc (3×40 mL). The organic layers were combined and washed with brine then dried over magnesium sulfate. After concentration, the residue was purified by silica gel chromatography, eluting with a mixture of 30% 2N ammonia in methanol and 70% EtOAc to yield 2-allyloxy-5-methoxybenzylamine as colorless oil (2.2 g, 55%). LC-MS (M+H)⁺=194; ¹H NMR (400 MHz, CD₃OD) δ ppm 3.75 (s, 3H) 4.08 (s, 2H) 4.60 (d, J=5.29 Hz, 2H) 5.22-5.30 (m, J=10.58 Hz, 1H) 5.35-5.44 (m, J=17.37 Hz, 1H) 6.01-6.15 (m, 1H) 6.89-6.96 (m, 2H) 6.96-7.02 (m, 1H).

Step AS (5). A mixture of 2-allyloxy-5-methoxybenzylamine (375 mg, 1.94 mmol), (2S,3S)-1,2-epoxy-3-(BOC-amino)-4-phenylbutane (818 mg, 3.1 mmol), and lithium perchlorate (514 mg, 4.85 mmol) in acetonitrile (6 mL) was stirred at 60° C. for 2.5 h. The reaction was concentrated and the residue was purified by silica gel chromatography, eluting with a mixture of 5% 2N ammonia in methanol and 95% EtOAc to yield 0.8 g of tert-butyl (2S,3R)-4-(2-(allyloxy)-5-methoxybenzylamino)-3-hydroxy-1-phenylbutan-2-ylcarbamate. The BOC-protected amine was dissolved in 10 mL 10% TFA/DCM and stirred at rt for 3 h. The reaction was concentrated under vacuum and the residue purified by reverse phase prep-HPLC to yield the titled compound as the ditrifluoroacetic acid salt (440 mg, 39%). LC-MS (M+H)⁺=357; ¹H NMR (400 MHz, CD₃OD) δ 7.30 (m, 5H) 7.00 (m, 3H) 6.10 (m, 1H) 5.40 (m, 1H) 5.30 (m, 1H) 4.61 (m, 2H) 4.22 (m, 3H) 3.76 (s, 3H) 3.66 (m, 1H) 3.18 (m, 2H) 2.90 (m, 3H).

Preparation AT (2R,3S)-1-((1S,3R)-3-(allyloxy)-6-methoxy-2,3-dihydro-1H-inden-1-ylamino)-3-amino-5-methylhexan-2-ol

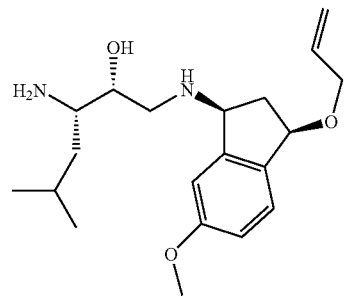

Step AT (1). To a solution of (2S,3S)-3-azido-2-hydroxy-5-methylhexyl 4-nitrobenzenesulfonate (15.2 g, 42.4 mmol) and 2,6-lutidine (10 mL, 86 mmol) in 250 mL DCM was added TBSOTf (15 mL, 65 mmol) at rt. The mixture was stirred for 2 h, then quenched with water. The organic layer was washed with 1.0 N HCl twice, dried over Na₂SO₄, filtered and concentrated in vacuo. Purification by silica-gel column chromatography (5-10% EtOAc/Hexane) afforded 18 g (90%) of product (2S,3S)-3-azido-2-(tert-butyldimethylsilyloxy)-5-methylhexyl 4-nitrobenzenesulfonate. ¹H NMR (300 MHz, CDCl₃) δ 0.03-0.06 (d, 6H) 0.83 (s, 9H) 0.85-0.91 (dd, 6H) 1.2-1.3 (m, 2H) 1.6-1.8 (m, 1H) 3.3-3.5 (m, 1H) 3.8-3.9 (m, 1H) 4.0-4.2 (m, 2H) 8.0-8.1 (d, 2H) 8.3-8.4 (d, 2H).

Step AT (2). A solution of the product from Step AT (1) (3.0 g, 6.4 mmol) and (1S,3R)-3-(allyloxy)-6-methoxy-2,3-dihydro-1H-inden-1-amine (1.2 g, 5.5 mmol, from Step U (2)) in 10 mL NMP was heated at 90° C. for 18 h. The mixture was purified using silica-gel column chromatography (10-20% EtOAc/Hexane) to afford (1S,3R)-3-(allyloxy)-N-((2R,3S)-3-azido-2-(tert-butyldimethylsilyloxy)-5-methylhexyl)-6-methoxy-2,3-dihydro-1H-inden-1-amine (1.1 g, 41% yield). LC-MS (M+H)⁺=489.22. ¹H NMR (300 MHz, CDCl₃) δ 0.05-0.08 (d, 6H) 0.85 (s, 9H) 0.87-0.95 (m, 6H) 1.2-1.4 (m, 2H) 1.7-1.9 (m, 3H) 2.6-2.8 (m, 2H) 2.8-3.0 (m, 1H) 3.5-3.6 (m, 1H) 3.76 (s, 3H) 4.0-4.2 (m, 3H) 4.7-4.9 (m, 1H) 5.1-5.4 (m, 2H) 5.8-6.0 (m, 1H) 6.8-6.9 (d, 1H) 6.9 (s, 1H) 7.2-7.4 (d, 1H).

Step AT (3). To a solution of LAH (200 mg, 5.26 mmol) in THF (20 mL) at rt was added the solution of the product from Step (AT) 3 in THF (10 mL) slowly. The mixture was stirred for 1 h. The reaction mixture was quenched with 10 mL 10% NaOH and the resulting solution was extracted with EtOAc (100 mL×2). The combined organic layer was dried over Na₂SO₄, concentrated in vacuo to afford (2R,3S)-N1-((1S,3R)-3-(allyloxy)-6-methoxy-2,3-dihydro-1H-inden-1-yl)-2-(tert-butyldimethylsilyloxy)-5-methylhexane-1,3-diamine as an oil. LC-MS (M+H)⁺ 463.25.

Step AT (4). To a solution of the product from Step AT (3) in 30 mL THF at rt was added TBAF (5 mL, 5 mmol). The resulting mixture was stirred overnight. The crude mixture was purified in silica-gel column chromatography (10-20% CH₃OH/DCM) to afford (2R,3S)-1-((1S,3R)-3-(allyloxy)-6-methoxy-2,3-dihydro-1H-inden-1-ylamino)-3-amino-5-methylhexan-2-ol (310 mg, 40% yield over two steps) as a white solid. LC-MS (M+H)⁺ 349.15. ¹H NMR (300 MHz, CDCl₃) δ 0.8-0.9 (dd, 6H) 1.1-1.3 (m, 2H) 1.6-1.8 (m, 1H) 1.9-2.1 (m, 1H) 2.5-3.1 (m, 4H) 3.5-3.6 (m, 1H) 3.7 (s, 3H) 4.0-4.2 (m, 3H) 4.7-4.8 (m, 1H) 5.1-5.4 (m, 2H) 5.8-6.0 (m, 1H) 6.8-7.0 (m, 2H) 7.2-7.4 (d, 1H).

Preparation AU 2,2,2-trifluoro-N-((1S,3R)-3-hydroxy-6-isopropoxy-2,3-dihydro-1H-inden-1-yl)acetamide

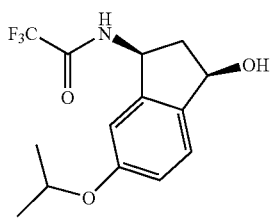

Step AU (1). A solution of 3-hydroxybenzaldehyde (67 g, 549 mmol), 2-iodopropane (100 g, 588 mmol) and $K_2CO_3$ (130 g, 942 mmol) in 400 mL DMF was stirred for 18 h. To the above solution was added 2-iodopropane (20 g, 117 mmol) and $K_2CO_3$ (20 g, 145 mmol) and the mixture was stirred for another 24 h. The reaction mixture was poured into 300 mL water which was extracted with EtOAc (200 mL×3). The combined organic layers were washed with water (100 mL×3), dried over $Na_2SO_4$, filtered, and concentrated in vacuo to afford 77 g (85% yield) of 3-isopropoxybenzaldehyde as an oil. $^1H$ NMR (300 MHz, $CDCl_3$) δ 1.29-1.31 (d, 6H) 4.5-4.6 (m, 1H) 7.0-7.1 (m, 1H) 7.3-7.4 (m, 3H).

Step AU (2). A solution of 3-isopropoxybenzaldehyde (77 g, 470 mmol), malonic acid (52 g, 496 mmol) and ammonium acetate (65 g, 844 mmol) in 1.0 L of ethanol was refluxed at 120° C. for 24 h. The solvent was evaporated in vacuo. The residue was purified using silica-gel column chromatography with (100% EtOAc, then 30% methanol/methylene chloride) to afford 65 g (62% yield) of 3-amino-3-(3-isopropoxyphenyl)propanoic acid as a white solid. LC-MS $(M+H)^+=224.14$. $^1H$ NMR (300 MHz, DMSO-$d_6$) δ 1.2-1.3 (d, 6H) 2.4-2.5 (m, 2H) 4.2-4.4 (m, 1H) 4.5-4.7 (m, 1H) 6.8-6.9 (m, 1H) 6.9-7.0 (m, 2H) 7.2-7.3 (m, 1H).

Step AU (3). To a solution of 3-amino-3-(3-isopropoxyphenyl)propanoic acid (65 g, 291 mmol) and TFA (100 mL) was added TFAA (100 mL). The mixture was warmed up to 95° C. for 2 h. The solvent was evaporated under high vacuum to afford a sticky oil which was taken into EtOAc (500 mL) and water (300 mL). The organic layer was separated, dried over $Na_2SO_4$, and concentrated in vacuo. The residue was purified using silica-gel chromatography (10-30% EtOAc/Hexane) to afford 20 g (23% yield) of 2,2,2-trifluoro-N-(6-isopropoxy-3-oxo-2,3-dihydro-1H-inden-1-yl)acetamide as a white solid.

Step AU (4). To a solution of 2,2,2-trifluoro-N-(6-isopropoxy-3-oxo-2,3-dihydro-1H-inden-1-yl)acetamide (20 g, 66 mmol) in THF (200 mL) at −78° C. was added L-Selectride (70 mL, 70 mmol). The reaction mixture was allowed to warm to rt and stir for 6 h. The reaction was quenched with HCl (1.0 N, 70 mL) and the resulting mixture was extracted with EtOAc (200 mL×2). The combined organic layers were dried over $Na_2SO_4$, filtered, and concentrated in vacuo. The crude product was purified by silica gel column chromatography (10-40% EtOAc/Hexane) to afford 5 g (25% yield) of cis-2,2,2-trifluoro-N-(3-hydroxy-6-isopropoxy-2,3-dihydro-1H-inden-1-yl)acetamide. LC-MS $(M-H_2O+H)^+=286.14$, $(M+Na)^+=326.10$. $^1H$ NMR (300 MHz, $CDCl_3$) δ 1.31-1.32 (d, 6H) 1.5 (s, 1H) 1.9-2.0 (m, 1H) 2.0-2.2 (m, 1H) 2.8-2.9 (m, 1H) 4.5-4.6 (m, 1H) 5.1-5.2 (m, 1H) 5.3-5.4 (m, 1H) 6.8-6.9 (m, 2H) 7.3-7.4 (d, 1H).

Step AU (5). cis-2,2,2-Trifluoro-N-(3-hydroxy-6-isopropoxy-2,3-dihydro-1H-inden-1-yl)acetamide was separated into its individual enantiomers by chiral HPLC with 10% EtOH in supercritical $CO_2$ on a Chiralpak AD-H column (3×25 cm, 5 μM) at 35° C. to provide 1.8 g of 2,2,2-trifluoro-N-((1S,3R)-3-hydroxy-6-isopropoxy-2,3-dihydro-1H-inden-1-yl)acetamide (first eluting enantiomer). $^1H$ NMR (300 MHz, $CDCl_3$) δ 1.3-1.31 (d, 6H) 1.8-2.0 (m, 1H) 2.7-2.9 (m, 1H) 4.4-4.6 (m, 1H) 5.0-5.2 (m, 1H) 5.2-5.4 (m, 1H) 6.8-6.9 (m, 2H) 7.3-7.4 (d, 1H).

Preparation AV (1S,3R)-3-(allyloxy)-6-isopropoxy-2,3-dihydro-1H-inden-1-amine

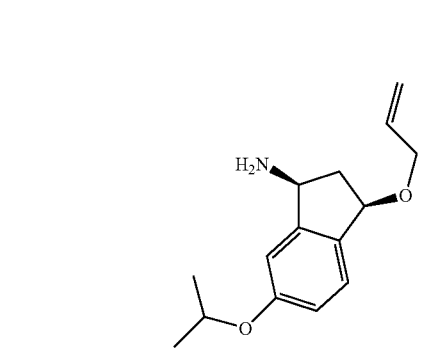

Step AV (1). 2,2,2-Trifluoro-N-((1S,3R)-3-hydroxy-6-isopropoxy-2,3-dihydro-1H-inden-1-yl)acetamide from Step AU (5) was converted into (1S,3R)-3-(allyloxy)-6-isopropoxy-2,3-dihydro-1H-inden-1-amine using methods analogous to those described in Steps X (1) and U (2). $^1H$ NMR (300 MHz, $CDCl_3$) δ 1.2-1.4 (d, 6H) 1.8-1.9 (m, 1H) 2.5-2.6 (m, 1H) 3.3-3.4 (m, 2H) 4.0-4.1 (m, 1H) 4.4-4.6 (m, 1H) 4.9-5.0 (m, 1H) 5.0-5.4 (m, 2H) 5.8-6.0 (m, 1H) 6.7-6.9 (m, 2H) 7.2-7.4 (d, 1H).

Preparation AW (2R,3S)-1-((1S,3R)-3-(allyloxy)-6-isopropoxy-2,3-dihydro-1H-inden-1-ylamino)-3-amino-4-phenylbutan-2-ol

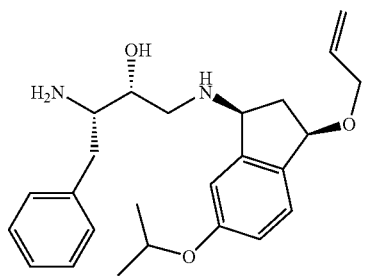

Step AW (1): A solution of (1S,3R)-3-(allyloxy)-6-isopropoxy-2,3-dihydro-1H-inden-1-amine (1.3 g, 5.3 mmol), (S)-(1-oxiranyl-2-phenylethyl)-carbamic acid tert-butyl ester (1.7 g, 6.5 mmol), and lithium perchlorate (2.8 g, 26.3 mmol) in 40 mL CH$_3$CN was stirred at 50° C. for 18 h. The mixture was poured into brine/NaHCO$_3$ solution, extracted with EtOAc (200 mL×2). The combined organic layers were washed with brine, dried over Na$_2$SO$_4$, filtered, and concentrated in vacuo. The residue was purified using silica-gel column chromatography (30-80% EtOAc/Hexane) to afford 1.2 g (45% yield) of tert-butyl (2S,3R)-4-((1S,3R)-3-(allyloxy)-6-isopropoxy-2,3-dihydro-1H-inden-1-ylamino)-3-hydroxy-1-phenylbutan-2-ylcarbamate. LC-MS (M+H)$^+$=511.25. $^1$H NMR (300 MHz, CDCl$_3$) δ 1.2-1.4 (m, 15H) 2.5-2.7 (m, 1H) 2.7-2.9 (m, 2H) 3.0-3.1 (m, 2H) 3.5-3.7 (m, 1H) 3.7-3.9 (m, 1H) 4.0-4.1 (m, 2H) 4.2-4.3 (m, 1H) 4.5-4.7 (m, 2H) 4.7-4.8 (m, 1H) 5.1-5.3 (m, 2H) 5.8-6.0 (m, 1H) 6.8-6.9 (m, 1H) 7.0-7.3 (m, 7H).

Step AW (2): To a solution of the product from Step AW (1) (1.2 g, 2.4 mmol) and 2,6-lutidine (2 mL, 17 mmol) in DCM (30 mL) at −78° C. was added TBSOTf (2.2 mL, 9.5 mmol). The reaction mixture was stirred at 0° C. for 1 h. LC-MS analysis of the crude reaction indicated conversion of the starting material to a 70/30 mixture of (2R,3S)-N-1-((1S,3R)-3-(allyloxy)-6-isopropoxy-2,3-dihydro-1H-inden-1-yl)-2-(tert-butyldimethylsilyloxy)-4-phenylbutane-1,3-diamine [(M+H)$^+$=525.27] and tert-butyldimethylsilyl (2S,3R)-4-((1S,3R)-3-(allyloxy)-6-isopropoxy-2,3-dihydro-1H-inden-1-ylamino)-3-(tert-butyldimethylsilyloxy)-1-phenylbutan-2-ylcarbamate [(M+H)$^+$=683.31)]. The reaction was quenched with saturated NaHCO$_3$ and extracted with EtOAc (100 mL×2). The combined organic layers were washed with brine, dried over Na$_2$SO$_4$, filtered, and concentrated in vacuo. The crude product mixture was carried forward to the next reaction without purification.

Step AW (3): A solution of TBAF (1.0 M in THF, 5 mL, 5 mmol) was added to a solution of the crude products from Step AW (2) in 30 mL THF at rt. The resulting mixture was stirred for 18 h and concentrated in vacuo. The residue was purified using silica gel column chromatography (10-25% CH$_3$OH/DCM) to afford 1.0 g (100% yield) of (2R,3S)-1-((1S,3R)-3-(allyloxy)-6-isopropoxy-2,3-dihydro-1H-inden-1-ylamino)-3-amino-4-phenylbutan-2-ol. LC-MS (M+H) 411.28.

Preparation AX (2R,3S)-1-((1S,3R)-3-(allyloxy)-6-isopropoxy-2,3-dihydro-1H-inden-1-ylamino)-3-amino-4-(3,5-difluorophenyl)butan-2-ol

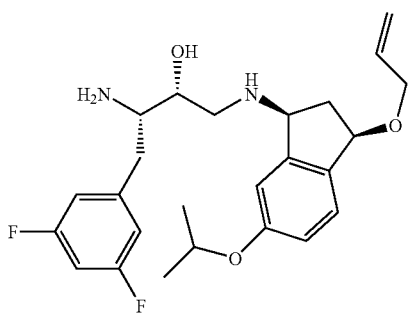

Step AX (1): (2R,3S)-1-((1S,3R)-3-(Allyloxy)-6-isopropoxy-2,3-dihydro-1H-inden-1-ylamino)-3-amino-4-(3,5-difluorophenyl)butan-2-ol (39 mg, was prepared from (1S,3R)-3-(allyloxy)-6-isopropoxy-2,3-dihydro-1H-inden-1-amine and tert-butyl (S)-2-(3,5-difluorophenyl)-1-((S)-oxiran-2-yl)ethylcarbamate in three steps and 30% overall yield using procedures analogous to the Steps AW (1-3).

Preparation AY (1S,3R)-3-(allyloxy)-6-propoxy-2,3-dihydro-1H-inden-1-amine

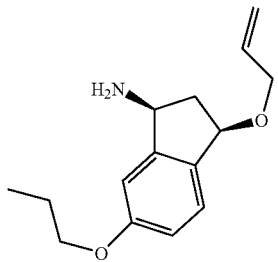

Step AY (1). (1S,3R)-3-(Allyloxy)-6-propoxy-2,3-dihydro-1H-inden-1-amine was prepared from 3-hydroxybenzaldehyde using a series of procedures analogous to Steps AU (1-5), X (1) and U (2). $^1$H NMR (300 MHz, CDCl$_3$) δ 0.9-1.0 (t, 3H) 1.6-1.8 (m, 2H) 2.6-2.8 (m, 1H) 3.8-3.9 (t, 2H) 4.0-4.2 (m, 3H) 4.7-4.8 (t, 1H) 5.1-5.4 (m, 2H) 5.8-6.0 (m, 1H) 6.7-6.9 (m, 2H) 7.2-7.3 (d, 1H).

Preparation AZ (2R,3S)-1-((1S,3R)-3-(allyloxy)-6-propoxy-2,3-dihydro-1H-inden-1-ylamino)-3-amino-4-phenylbutan-2-ol

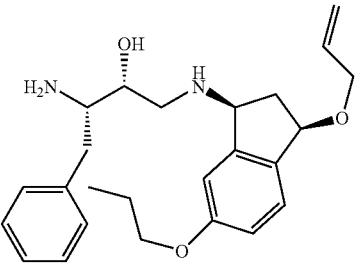

Step AZ (1): (2R,3S)-1-((1S,3R)-3-(Allyloxy)-6-propoxy-2,3-dihydro-1H-inden-1-ylamino)-3-amino-4-phenylbutan-2-ol (590 mg) was prepared from (1S,3R)-3-(allyloxy)-6-propoxy-2,3-dihydro-1H-inden-1-amine (1.2 g, 4.9 mmol, from Step AY (1)) and (S)-(1-oxiranyl-2-phenylethyl)-carbamic acid tert-butyl ester in three steps and 30% overall yield using procedures analogous to the Steps AW (1-3). LC-MS (M+H)$^+$=411.19. $^1$H NMR (300 MHz, CDCl$_3$) δ 0.9-1.0 (t, 3H) 1.7-1.9 (m, 2H) 2.0-2.2 (m, 1H) 2.4-2.6 (m, 2H) 2.7-3.0 (m, 3H) 3.1-3.2 (m, 1H) 3.8-4.1 (m, 5H) 4.2-4.4 (m, 1H) 4.6-4.8 (m, 1H) 5.1-5.3 (m, 2H) 5.7-5.9 (m, 1H) 6.9-7.0 (m, 1H) 7.0-7.3 (m, 7H).

Preparation BA (2R,3S)-1-((1S,3R)-3-(allyloxy)-6-propoxy-2,3-di-hydro-1H-inden-1-ylamino)-3-amino-4-(3,5-difluorophenyl)butan-2-ol

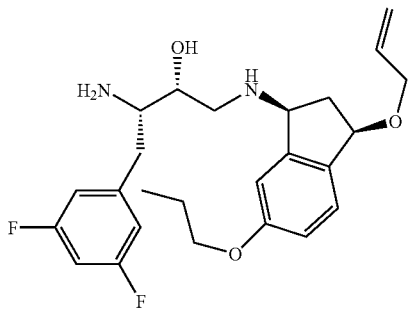

Step BA (1): (1S,3R)-3-(allyloxy)-6-propoxy-2,3-dihydro-1H-inden-1-amine (940 mg, 3.8 mmol, from Step AY (1)) was reacted with tert-butyl (S)-2-(3,5-difluorophenyl)-1-((S)-oxiran-2-yl)ethylcarbamate (1.0 g, 3.3 mmol) following a procedure analogous to Step AW (1) to afford, after purification, 1.2 g (66% yield) of (2R,3S)-1-((1S,3R)-3-(allyloxy)-6-propoxy-2,3-dihydro-1H-inden-1-ylamino)-3-amino-4-(3,5-difluorophenyl)butan-2-ol. LC-MS (M+H)$^+$=547.20. $^1$H NMR (300 MHz, CDCl$_3$) δ 0.9-1.1 (t, 3H) 1.3 (s, 9H) 1.7-1.9 (m, 2H) 1.9-2.0 (m, 1H) 2.5-3.1 (M, 5H) 3.4-3.5 (m, 1H) 3.7-3.8 (m, 1H) 3.8-4.0 (t, 2H) 4.0-4.1 (m, 2H) 4.5-4.6 (m 1H) 4.7-4.8 (m, 1H) 5.1-5.4 (m, 2H) 5.8-6.0 (m, 1H) 6.5-6.9 (m, 5H) 7.2-7.3 (d, 1H).

Step BA (2): The products from Step BA (1) were converted into 1.2 g (92% yield over two steps) of (2R,3S)-1-((1S,3R)-3-(allyloxy)-6-propoxy-2,3-dihydro-1H-inden-1-ylamino)-3-amino-4-(3,5-difluorophenyl)butan-2-ol following procedures analogous to Steps AW (2-3). LC-MS (M+H)$^+$=447.13. $^1$H NMR (300 MHz, CDCl$_3$) δ 0.9-1.1 (t, 3H) 1.7-1.9 (m, 2H) 2.0-2.2 (m, 1H) 2.5-2.7 (m, 2H) 2.7-3.4 (m, 4H) 3.5-4.1 (m, 5H) 4.1-4.2 (m, 1H) 4.7-4.8 (m, 1H) 5.1-5.3 (m, 2H) 5.7-6.0 (m, 1H) 6.6-6.8 (m, 3H) 6.8-6.9 (m, 1H) 7.1-7.2 (m, 2H).

Preparation BB 3-(allyloxy)-6-phenoxy-2,3-dihydro-1H-inden-1-amine

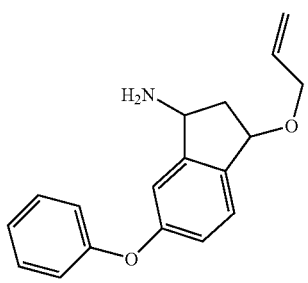

Step BB (1). 3-(Allyloxy)-6-phenoxy-2,3-dihydro-1H-inden-1-amine was prepared using a series of procedures analogous to Steps AU (1-5), X (1) and U (2). $^1$H NMR (300 MHz, CDCl$_3$) δ 1.6-1.8 (m, 1H) 2.7-2.9 (m, 1H) 4.0-4.2 (m, 3H) 4.7-4.8 (t, 1H) 5.1-5.4 (m, 2H) 5.8-6.0 (m, 1H) 6.8-7.1 (m, 5H) 7.2-7.4 (m, 3H).

Preparation BC (2R,3S)-N$^1$-(3-(allyloxy)-6-phenoxy-2,3-dihydro-1H-inden-1-yl)-2-(tert-butyldimethylsilyloxy)-phenylbutane-1,3-diamine

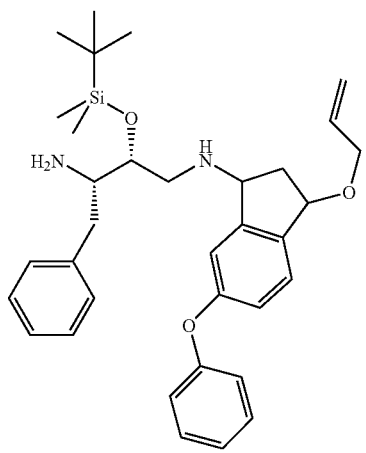

Step BC (1): 3-(Allyloxy)-6-phenoxy-2,3-dihydro-1H-inden-1-amine (2.7 g, 9.6 mmol, from Step BB (1)) was reacted with (S)-(1-oxiranyl-2-phenylethyl)-carbamic acid tert-butyl ester (3.0 g, 11.4 mmol) following a procedure analogous to Step AW (1) to afford, after purification, 3.3 g (63% yield) of tert-butyl (2S,3R)-4-(3-(allyloxy)-6-phenoxy-2,3-dihydro-1H-inden-1-ylamino)-3-hydroxy-1-phenylbutan-2-ylcarbamate. LC-MS (M+H)$^+$=545.36. $^1$H NMR (300 MHz, CDCl$_3$) δ 1.3 (s, 9H) 1.8-1.9 (m, 1H) 2.6-3.0 (m, 4H) 3.3-3.5 (m, 1H) 3.7-3.9 (m, 1H) 4.0-4.2 (m, 3H) 4.5-4.7 (m, 1H) 4.7-4.8 (m, 1H) 5.1-5.4 (m, 2H) 5.8-6.0 (m, 1H) 6.8-7.1 (m, 5H) 7.1-7.4 (m, 8H).

Step BC (2): The product from Step BC (1) was converted to a mixture of (2R,3S)-N$^1$-(3-(allyloxy)-6-phenoxy-2,3-dihydro-1H-inden-1-yl)-2-(tert-butyldimethylsilyloxy)-4-phenylbutane-1,3-diamine and tert-butyldimethylsilyl (2S,3R)-4-(3-(allyloxy)-6-phenoxy-2,3-dihydro-1H-inden-1-ylamino)-3-(tert-butyldimethylsilyloxy)-1-phenylbutan-2-ylcarbamate by following a procedure analogous to Step AW (2). The crude product mixture was carried forward to the next reaction without purification or analytical characterization.

Step BC (3): Anhydrous KF (300 mg) was added to a solution of the crude product mixture from Step BC (2) dissolved in CH$_3$OH (30 mL). The reaction mixture was stirred for 1 h and concentrated in vacuo. The crude residue was diluted with water and extracted with EtOAc. The combined organic layers were washed with brine, dried over Na$_2$SO$_4$, filtered, and concentrated in vacuo to afford 3.3 g of the title compound as a white solid. LC-MS (M+H)$^+$=559.38.

Preparation BD (2R,3S)-1-((1S,3R)-3-(allyloxy)-6-bromo-2,3-dihydro-1H-inden-1-ylamino)-3-amino-4-phenylbutan-2-ol

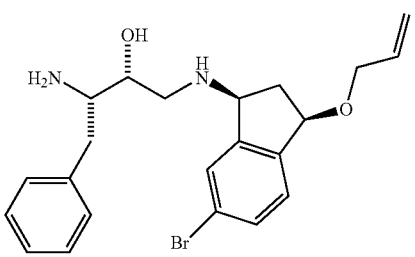

Step BD (1). (1S,3R)-3-(Allyloxy)-6-bromo-2,3-dihydro-1H-inden-1-amine from Step Z(1) was reacted with tert-butyl (S)-1-((S)-oxiran-2-yl)-2-phenylethylcarbamate (Aldrich) according to the procedures described in Step V (1) to afford, after purification, 275 mg (82% yield) of tert-butyl (2S,3R)-4-((1S,3R)-3-(allyloxy)-6-bromo-2,3-dihydro-1H-inden-1-ylamino)-3-hydroxy-1-phenylbutan-2-ylcarbamate. MS (M+H)$^+$ 531.43. $^1$H NMR (500 MHz, CDCl$_3$) δ ppm 1.36 (s, 9H) 1.82 (ddd, J=12.67, 6.26, 6.10 Hz, 1H) 2.69-2.79 (m, 3H) 2.87 (dd, J=13.89, 8.09 Hz, 1H) 3.03 (dd, J=14.04, 4.58 Hz, 1H) 3.38-3.46 (m, 1H) 3.79 (s, 1H) 4.01-4.05 (m, 2H) 4.06-4.15 (m, 2H) 4.54 (d, J=9.16 Hz, 1H) 4.75 (t, J=6.10 Hz, 1H) 5.19 (dd, J=10.38, 1.53 Hz, 1H) 5.31 (ddd, J=17.24, 3.20, 1.53 Hz, 1H) 5.94 (ddd, J=22.74, 10.53, 5.49 Hz, 1H) 7.18-7.32 (m, 7H) 7.40 (d, J=8.24 Hz, 1H) 7.50 (s, 1H).

Step BD (2). The product from Step BD (1) was N-deprotected by procedures analogous to those described in Steps AW (2-3) to provide the titled compound in 89% yield. MS (M+H)$^+$ 431.40. $^1$H NMR (500 MHz, CD$_3$OD) δ ppm 1.24-1.34 (m, 1H) 1.81-1.92 (m, 1H) 2.59 (dd, J=13.58, 9.00 Hz, 1H) 2.73-2.84 (m, 2H) 2.85-2.92 (m, 1H) 3.00 (dd, J=13.58, 4.73 Hz, 1H) 3.10-3.17 (m, 1H) 3.62-3.70 (m, 1H) 4.12-4.25 (m, 3H) 4.83 (t, J=5.95 Hz, 1H) 5.20 (dd, J=10.38, 1.83 Hz, 1H) 5.36 (dd, J=17.24, 1.68 Hz, 1H) 5.95-6.06 (m, 1H) 7.15-7.37 (m, 7H) 7.40-7.50 (m, 1H) 7.65 (s, 1H).

Preparation BE tert-butyl (2S,3R)-((1S,3R)-3-(allyloxy)-6-bromo-2,3-dihydro-1H-inden-1-ylamino)-1-(3,5-difluorophenyl)-3-hydroxybutan-2-ylcarbamate

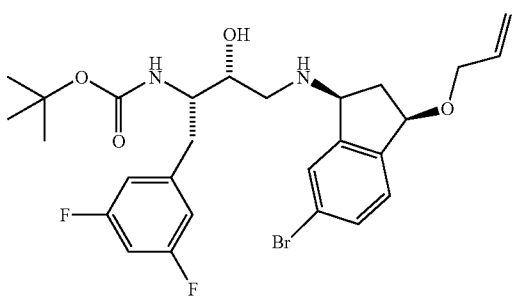

Step BE (1). (1S,3R)-3-(Allyloxy)-6-bromo-2,3-dihydro-1H-inden-1-amine from Step Z(1) was reacted with tert-butyl (S)-2-(3,5-difluorophenyl)-1-((S)-oxiran-2-yl)ethylcarbamate following a procedure analogous to Step AW (1) to afford 1.5 g (76% yield) of tert-butyl (2S,3R)-4-((1S,3R)-3-(allyloxy)-6-bromo-2,3-dihydro-1H-inden-1-ylamino)-1-(3,5-difluorophenyl)-3-hydroxybutan-2-ylcarbamate. LC-MS (M+H)$^+$ 568.97. $^1$H NMR (300 MHz, CDCl$_3$) δ ppm 1.35 (s, 9H) 1.79-1.90 (m, 2H) 2.64-2.82 (m, 4H) 3.03 (dd, J=14.09, 4.21 Hz, 1H) 3.36-3.44 (m, 1H) 3.68-3.80 (m, J=8.42, 4.03 Hz, 1H) 4.01-4.12 (m, 3H) 4.50 (d, J=9.51 Hz, 1H) 4.73 (t, J=6.04 Hz, 1H) 5.18 (dd, J=10.43, 1.28 Hz, 1H) 5.24-5.34 (m, J=17.20, 1.46 Hz, 1H) 5.92 (ddd, J=22.60, 10.52, 5.67 Hz, 1H) 6.63 (tt, J=9.01, 2.33 Hz, 1H) 6.70-6.78 (m, 2H) 7.25 (d, J=8.05 Hz, 1H) 7.39 (dd, J=7.87, 1.65 Hz, 1H) 7.49 (s, 1H).

Preparation BF benzyl (S)-2-(3,5-dichlorophenyl)-1-((S)-oxiran-2-yl)ethylcarbamate Step BF (1): To a slurry of N-(Benzyloxycarbonyl)-alpha-phosphonoglycine trimethyl ester (76.37 g, 230.5 mmol) in THF (210 mL) just thawed from a −78° C. bath was added tetramethylguanidine (28.85 mL, 230.0 mmol) dropwise. A cold solution of 3,5-dichlorobenzaldehyde (36.70 g, 209.7 mmol) in THF (52.5 mL) was added via cannula. The cold yellow solution was stirred for 1 hour, at which time TLC revealed no aldehyde remained. The THF was removed in vacuo, and EtOAc and 1M HCl was added. The mixture was extracted three times into EtOAc, and the combined organic layers were washed with water, brine, and then dried over MgSO$_4$. Concentration in vacuo followed by recrystallization of the desired olefin isomer from EtOAc/hexane yielded pure product. Concentration of the mother liquor and recrystallization of the residue yielded, over 4 crops, 68.22 g (86% yield) of (Z)-methyl 2-(benzyloxycarbonylamino)-3-(3,5-dichlorophenyl)acrylate. $^1$H NMR (500 MHz, CDCl$_3$) δ 7.28-7.42 (m, 7H) 7.16 (s, 2H) 6.55 (s, 1H) 5.10 (s, 2H) 3.79-3.90 (m, 3H).

Step BF (2): To a solution of (Z)-methyl 2-(benzyloxycarbonylamino)-3-(3,5-dichlorophenyl)acrylate (46.08 g, 121.3 mmol) in methylene chloride (435 mL) was added (+)-1,2-bis((2S,5S)-2,5-Diethylpholano)benzene(cyclooctadiene)Rhodium(I) trifluoromethanesulfonate (4.02 g, 6.08 mmol). The solution was split between two Parr bottles and shaken under 50 psi hydrogen for 8 h. The combined reactions were concentrated in vacuo and subjected to silica gel chromatography (25% EtOAc/hexane) to yield (S)-methyl 2-(benzyloxycarbonylamino)-3-(3,5-dichlorophenyl)propanoate (40.94 g, 88% yield). $^1$H NMR (500 MHz, CDCl$_3$) δ 7.28-7.39 (m, 5H) 7.24 (d, J=7.02 Hz, 1H) 7.00 (s, J=1.53 Hz, 2H) 5.34 (d, J=7.63 Hz, 1H) 5.10 (q, J=12.21 Hz, 2H) 4.58-4.68 (m, 1H) 3.73 (s, 3H) 3.05-3.15 (m, 1H) 2.95-3.05 (m, 1H).

Step BF (3): To a solution of (S)-methyl 2-(benzyloxycarbonylamino)-3-(3,5-dichlorophenyl)propanoate (20.60 g, 53.94 mmol) in THF was added 2M LiOH (250 mL). After the reaction was stirred at rt for 18 h, the THF was removed in vacuo. The pH was adjusted to below two by 6M HCl. The mixture was extracted three times into EtOAc, and the combined organic layers were dried with MgSO$_4$. Concentration in vacuo afforded pure (S)-2-(benzyloxycarbonylamino)-3-(3,5-dichlorophenyl)propanoic acid. This material was taken up in methylene chloride (250 mL), and p-nitrophenol (7.50 g, 53.94 mmol) was added. EDC was added portionwise (12.43 g, 64.73 mmol), followed by Hunig's base (11.3 mL, 64.73 mmol). The reaction was allowed to stir at rt for 80 h. The reaction was extracted 3 times with 1M HCl, then with brine. The reaction was next extracted with 0.5M NaOH (yellow color formed), and again with brine. The organic layer was dried with MgSO$_4$, and concentrated to a yellow gum. Silica gel chromatography (EtOAc/hexane gradient) afforded (S)-4-nitrophenyl 2-(benzyloxycarbonylamino)-3-(3,5-dichlorophenyl)propanoate (26.37 g, 58% yield).

Step BF (4): To a mixture of trimethylsulfoxonium iodide (20.72 g, 94.2 mmol) in THF (175 mL) was added solid potassium t-butoxide (8.792 g, 78.7 mmol) and the mixture was refluxed for 3 h. The mixture was cooled to 0° C., to which a solution of (S)-4-nitrophenyl 2-(benzyloxycarbonylamino)-3-(3,5-dichlorophenyl)propanoate (15.35 g, 31.40 mmol) in THF (70 mL) was added. The mixture was brought to rt, and stirred for 16 h. Solvents were removed in vacuo. Water and EtOAc were then added, and the solid material filtered (Buchner funnel). The yellowish solid was washed with water and hexane until a white solid remained. The solid was dried in a vacuum oven. All liquid layers were combined and extracted 3 times to EtOAc. The combined organic layers were back-extracted with dilute NaOH, washed with brine, dried over MgSO4, and concentrated in vacuo. The combined material was the desired compound (13.40 g, 97% yield). $^1$H NMR (500 MHz, CDCl$_3$) δ 6.99-7.39 (m, 8H) 5.80 (d, J=7.93 Hz, 1H) 5.01-5.15 (m, 2H) 4.25-4.37 (m, 2H) 3.31 (s, 3H) 3.26 (s, 3H) 2.96 (d, J=6.41 Hz, 2H).

Step BF (5): To a solution of the product of step KB(4) (11.20 g, 25.35 mmol) in THF (101 mL) at 0° C. was added LiBr (2.21 g, 25.4 mmol), then methanesulfonic acid (1.848 mL, 28.5 mmol) dropwise. After letting the reaction come to rt, the reaction was heated to reflux for 2 h. After cooling to rt, the reaction was diluted with water and EtOAc. The mixture was extracted three times to EtOAc, dried over MgSO4, and concentrated in vacuo. The crude solid was suspended in minimal methylene chloride, and filtered on a Buchner funnel. The filtrate was concentrated and the procedure was repeated to obtain a second crop. The combined material was the desired (S)-benzyl 4-bromo-1-(3,5-dichlorophenyl)-3-oxobutan-2-ylcarbamate (5.59 g, 50% yield). LC-MS (M+H)$^+$=505.94. $^1$H NMR (500 MHz, CDCl$_3$) δ 7.27-7.41 (m, 6H) 7.05 (s, 2H) 5.25 (d, J=7.32 Hz, 1H) 5.02-5.15 (m, 2H) 4.78 (q, J=7.32 Hz, 1H) 3.89-4.00 (m, 2H) 3.15 (dd, J=14.19, 5.95 Hz, 1H) 2.92 (dd, J=14.04, 7.63 Hz, 1H).

Step BF (6): A 1M solution of LiAlH(OtBu)$_3$ in THF (22.9 mL, 22.9 mmol) was diluted with THF (30.5 mL) and ethanol (56 mL) and cooled to −78° C. A solution of (S)-benzyl 4-bromo-1-(3,5-dichlorophenyl)-3-oxobutan-2-ylcarbamate (5.093 g, 11.45 mmol) in THF (56 mL) was then added dropwise down the side of the flask. After 15 min, TLC indicated no starting material remained. The reaction was carefully quenched with 1M HCl and let warm to rt. The organic solvents were removed in vacuo. The residue was taken up in EtOAc, and the aluminum salts removed via filtration. The organic layer was dried over MgSO$_4$, and concentrated to afford benzyl (2S,3S)-4-bromo-1-(3,5-dichlorophenyl)-3-hydroxybutan-2-ylcarbamate (4.08 g, 80% yield). $^1$H NMR (500 MHz, DMSO-d$_6$) δ 7.05-7.50 (m, 9H) 5.55 (d, J=5.80 Hz, 1H) 4.99 (d, J=12.8 Hz, 1H) 4.87 (d, J=12.8 Hz, 1H) 3.66-3.77 (m, 1H) 3.56-3.65 (m, 2H) 3.36-3.45 (m, 1H) 3.01 (dd, J=13.73, 3.05 Hz, 1H) 2.59 (dd, J=13.43, 10.38 Hz, 1H).

Step BF (7): To a suspension of benzyl (2S,3S)-4-bromo-1-(3,5-dichlorophenyl)-3-hydroxybutan-2-ylcarbamate (100 mg, 224 umol) in MeOH (2.4 mL) was added K$_2$CO$_3$ (12 mg). The reaction was stirred vigorously overnight. Solvents were removed in vacuo, and the residue partitioned between EtOAc and water three times. The combined organic layers were dried over MgSO$_4$ and concentrated in vacuo to afford the solid benzyl (S)-2-(3,5-dichlorophenyl)-1-((S)-oxiran-2-yl)ethylcarbamate (78.9 mg, 97% yield). $^1$H NMR (DMSO-d$_6$) δ 7.08-7.55 (m, 9H) 4.99 (d, J=12.8 Hz, 1H) 4.89 (d, J=12.8 Hz, 1H) 3.60-3.78 (m, 1H) 2.89-3.06 (m, 2H) 2.60-2.79 (m, 3H).

Preparation BG (2R,3S)-1-((1S,3R)-3-(allyloxy)-6-methoxy-2,3-dihydro-1H-inden-1-ylamino)-3-amino-4-(3,5-chlorophenyl)butan-2-ol

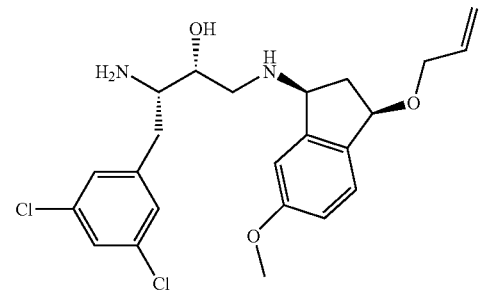

Step BG (1): A mixture of 130 mg (0.59 mmoles) benzyl (S)-2-(3,5-dichlorophenyl)-1-((S)-oxiran-2-yl)ethyl-carbamate from Preparation BF, 216 mg (0.59 mmoles) of (1S, 3R)-3-(allyloxy)-6-methoxy-2,3-dihydro-1H-inden-1-amine from Preparation U, 324 mg lithium perchlorate and 1.5 mL acetonitrile was stirred at rt for 18 h and then heated in an oil bath at 50° for 24 h. The reaction mixture was directly applied to a silica gel column and eluted with 15% methanol in DCM, collecting the Rf 0.6 spot. Yield 192.4 mg (55.7%) of benzyl (2S,3R)-4-((1S,3R)-3-(allyloxy)-6-methoxy-2,3-dihydro-1H-inden-1-ylamino)-1-(3,5-dichlorophenyl)-3-hydroxybutan-2-ylcarbamate as a clear oil. LC-MS retention time (RT) 2.11 min; (M+H)$^+$=585.1; $^1$H NMR (500 MHz, CDCl$_3$) δ 7.37-7.22 (m, 6H) 7.20 (s, 1H) 7.10 (s, 2H) 6.93 (s, 1H) 6.85 (d of d, J=8.2, 2.4, 1H) 5.94 (m, 1H) 5.30 (d, J=14.6, 1H) 5.18 (d, J=9.1, 1H) 5.03 (m, 2H) 4.93 (d, J=8.5, 1H) 4.76 (m, 1H) 4.09 (m, 2H) 3.79 (s+m, 4H) 3.53 (s, 1H) 2.96 (m, 2H) 2.74 (m, 2H) 2.61 (m, 2H) 1.95 (d, J=12.8, 1H).

Step BG (2): A mixture of 40 mg benzyl (2S,3R)-4-((1S, 3R)-3-(allyloxy)-6-methoxy-2,3-dihydro-1H-inden-1-ylamino)-1-(3,5-dichlorophenyl)-3-hydroxybutan-2-yl-carba-mate, 248 mg 95% barium hydroxide and 3 mL of a 1:1 mixture of H$_2$O/CH$_3$OCH$_2$CH$_2$OH was heated in a sealed vial in an oil bath at 110-115° for 5 days. The reaction mixture was filtered through a short Celite plug, the solid was washed with water and methanol, the solvents were evaporated, and the residue was subjected to preparative HPLC. The fractions containing the component at 7.3 min were collected. The acid was neutralized with triethylamine, and the mobile phase was evaporated in vacuo. The residue was partitioned between water and EtOAc. The organic phase was separated, washed with brine, and dried over MgSO$_4$, filtered, and evaporated in vacuo to give the title compound as a clear oil. Yield 21.8 mg. LC-MS RT 1.76 min; (M+H)$^+$=451.1; $^1$H NMR (500 MHz, CDCl$_3$) δ 7.24 (d, J=8.5, 1H) 7.15 (s, 1H) 7.07 (s, 1H) 7.05 (s, 2H) 6.88 (d of d, J=8.5, 2.1, 1H) 5.85 (m, 1H) 5.23 (d, J=16, 1H) 5.14 (d, J=10.4, 1H) 4.69 (d, J=5.8, 2H) 4.51 (d, J=9.8, 1H) 4.00 (m, 2H) 3.68 (s, 3H) 3.60 (s, 1H) 3.10 (d, J=11, 1H) 2.83 (m, 2H) 2.58 (m, 1H) 2.35 (m, 1H) 2.18 (d, J=15.3, 1H)

Preparation BH (2R,3S)-N$^1$-((1S,3R)-3-(allyloxy)-6-isopropoxy-2,3-dihydro-1H-inden-1-yl)-2-(tert-butyldimethylsilyloxy)-5-methylhexane-1,3-diamine

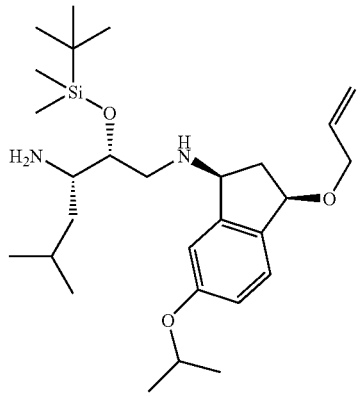

Step BH (1). The product from Step AT (1) (5.0 g, 10.6 mmol) and (1S,3R)-3-(allyloxy)-6-methoxy-2,3-dihydro-1H-inden-1-amine (2.0 g, 8.1 mmol, from Preparation AV) were combined by following a procedure analogous to Step AT (2) to provide 1.3 g (31% yield) of (1S,3R)-3-(allyloxy)-N-((2R,3S)-3-azido-2-(tert-butyldimethylsilyloxy)-5-methylhexyl)-6-isopropoxy-2,3-dihydro-1H-inden-1-amine.

Step BH (2). The product from Step BH (1) (1.3 g, 2.5 mmol) was reduced by following a procedure analogous to Step AT (3) to afford 1.1 g of the title compound. LC-MS (M+H)$^+$ 491.47.

Preparation BI 2-methyloctahydropyrrolo[3,4-c]pyrrole

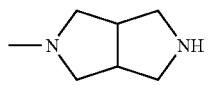

Step BI (1): Sodium triacetoxyborohydride (666 mg, 3.14 mmol) was added to a magnetically stirred solution of tert-butyl hexahydropyrrolo[3,4-c]pyrrole-2(1H)-carboxylate (165 mg, 0.777 mmol) and 37% formaldehyde (144 mg, 1.77 mmol) in 1,2-dichloroethane (10 mL). The resulting mixture was allowed to stir at rt for 16 h. Sodium hydroxide solution (2 mL of a 1 N solution) was added with vigorous stirring. Stirring was stopped and the layers were allowed to separate. The organic layer was removed and concentrated in vacuo with heating. Acetone was added to the residue, and the solution was decanted. The decanted portion was concentrated in vacuo to afford 80 mg (46% yield) of tert-butyl 5-methylhexahydropyrrolo[3,4-c]pyrrole-2(1H)-carboxylate as a colorless oil.

Step BI (2): Trifluoroacetic acid (2 mL, 26.0 mmol) was then added at rt to a solution of the crude product from Step BI (1) (80 mg, 0.353 mmol) dissolved in DCM (10 mL). The reaction was allowed to stir for 16 h at rt. The mixture was concentrated in vacuo to afford 140 mg (quantitative yield) of the TFA salt of the title compound as a pale yellow oil. LC/MS (M+H)$^+$ 127.17. $^1$H NMR (400 MHz, CD$_3$OD) δ ppm 2.94 (s, 3H) 3.25-3.40 (m, 5H) 3.55 (br, 5H).

Preparation BJ 2,2,2-trifluoro-N-((1S,3R)-3-hydroxy-6-methyl-2,3-dihydro-1H-inden-1-yl)acetamide

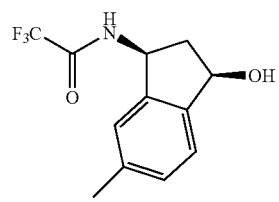

and 2,2,2-trifluoro-N-((1R,3S)-3-hydroxy-6-methyl-2,3-dihydro-1H-inden-1-yl)acetamide

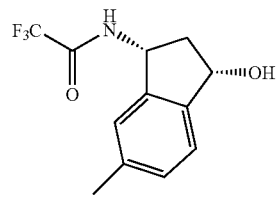

Step BJ (1): L-Selectride (1 M/THF, 18.5 mL, 18.5 mmol) was added dropwise (over 30 min) to a solution of 2,2,2-trifluoro-N-(6-methyl-3-oxo-2,3-dihydro-1H-inden-1-yl)acetamide [Quermonne, M. A.; Dallemagne, P.; Louchahi-Raoul, J.; Pilo, J. C.; Rault, S.; Robba, M. *Eur. J. Med. Chem.* 1992, 27, 961-965] (3.97 g, 15.4 mmol) in THF (80 mL) at −78° C. After 2 hr at −78° C., the reaction mixture was quenched with saturated aqueous NH$_4$Cl solution (2 mL) and allowed to warm to rt. The crude mixture was concentrated in vacuo. The residue was dissolved in EtOAc and washed with saturated aqueous NaHCO$_3$ solution followed by brine. The organic layer was dried over Na$_2$SO$_4$, filtered, and concentrated in vacuo to afford 3.4 g (85% yield) of racemic 2,2,2-trifluoro-N-(3-hydroxy-6-methyl-2,3-dihydro-1H-inden-1-yl)acetamide. LC-MS (M+H)$^+$=260.091H NMR (500 MHz, CDCl3) δ 9.16-9.12 (t, 1H) 7.31-7.29 (m, 1H) 7.02 (m, 1H) 6.94 (s, 1H) 4.98 (t, 1H) 4.10 (bs, 2H) 2.38-2.28 (m, 4H) 2.07-2.01 (m, 1H).

Step BJ (2): The racemic product from Step BJ (1) was purified by chiral HPLC using conditions analogous to Step T (1) to afford 1.49 g (37% yield) of 2,2,2-trifluoro-N-((1S,3R)-3-hydroxy-6-methyl-2,3-dihydro-1H-inden-1-yl)acetamide and 1.49 g (37% yield) of 2,2,2-trifluoro-N-((1R,3S)-3-hydroxy-6-methyl-2,3-dihydro-1H-inden-1-yl)acetamide.

Preparation BK (2R,3S)-1-((1S,3R)-3-(allyloxy)-6-methyl-2,3-dihydro-1H-inden-1-ylamino)-3-amino-4-phenylbutan-2-ol

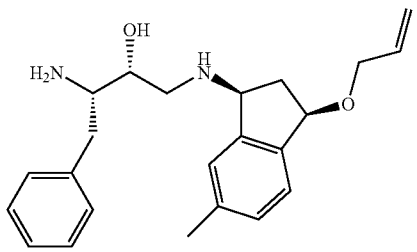

Step BK (1): 2,2,2-Trifluoro-N-((1S,3R)-3-hydroxy-6-methyl-2,3-dihydro-1H-inden-1-yl)acetamide (from Preparation BJ) was O-allylated by a procedure analogous to Step X(1) to afford 0.96 g (58% yield) of N-((1S,3R)-3-(allyloxy)-6-methyl-2,3-dihydro-1H-inden-1-yl)-2,2,2-trifluoroacetamide. LC-MS (M+H)$^+$=260.09; $^1$H NMR (500 MHz, CDCl$_3$) δ ppm 7.31 (d, 1H) 7.25 (bs, 1H) 7.18 (d, 1H) 6.87 (bs, 1H) 5.93-5.88 (m, 1H) 5.40-5.21 (m, 3H) 4.81 (d, 1H) 4.08 (bs, 2H) 2.69-2.65 (m, 1H) 2.37 (s, 3H) 2.08 (d, 1H).

Step BK (2): The product from Step BK (1) was N-deprotected by a procedure analogous to Step U (2) to afford 480 mg (75% yield) of (1S,3R)-3-(allyloxy)-6-methyl-2,3-dihydro-1H-inden-1-amine as a white solid. LC-MS (M+H)$^+$=204.13 $^1$H NMR (500 MHz, CDCl$_3$) δ ppm 7.28 (d, 1H) 7.18 (d, 1H) 7.08 (d, 1H) 6.01-5.94 (m, 1H) 5.32 (d, 1H) 5.18 (d, 1H) 4.77 (t, 1H) 4.16-4.19 (m, 3H) 2.80-2.75 (m, 1H) 2.36 (s, 3H) 1.75-1.70 (m, 3H).

Step BK (3): The product from Step BK (2) was reacted with tert-butyl (S)-1-((S)-oxiran-2-yl)-2-phenylethylcarbamate (271 mg, 1.03 mmol) following a procedure analogous to Step AW (1) to afford 415 mg (86% yield) of tert-butyl (2S,3R)-4-((1S,3R)-3-(allyloxy)-6-methyl-2,3-dihydro-1H-inden-1-ylamino)-3-hydroxy-1-phenylbutan-2-ylcarbamate. LC-MS (M+H)$^+$=467.29; $^1$H NMR (500 MHz, CDCl$_3$) δ ppm 7.39-7.16 (m, 7H) 5.93-5.87 (m, 1H) 5.33-4.60 (m, 8H) 4.08 (d, 2H) 3.94 (m, 1H) 3.62 (m, 1H) 3.46 (d, 1H) 3.10-3.06 (m, 2H) 3.6 (m, 1H) 2.59-2.54 (m, 2H) 2.37 (s, 3H) 1.25 (s, 9H).

Step BK (4): The product from Step BK (3) was converted into 153 mg (48% yield) of the title compound by following procedures analogous to Steps AW (2-3). LC-MS (M+H)$^+$=367.23 $^1$H NMR (500 MHz, CDCl$_3$) δ ppm 7.31-7.26 (m, 1H) 7.09 (bs, 3H) 6.99-9.94 (m, 4H) 5.90-5.80 (M, 1H) 5.23-5.08 (m, 2H) 4.90-4.86 (m, 1H) 4.51-4.47 (m, 3H) 4.05-4.00 (m, 1H) 3.88-3.78 (m, 2H) 3.03-2.98 (m, 1H) 2.88-2.85 (m, 1H) 2.76-2.60 (m, 3H) 2.35-2.28 (m, 4H) 1.98-1.91 (m, 5H).

Preparation BL (2R,3S)-1-((1R,3S)-3-(allyloxy)-6-methyl-2,3-dihydro-1H-inden-1-ylamino)-3-amino-4-phenylbutan-2-ol

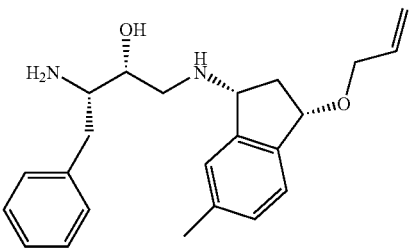

Step BL (1): 2,2,2-Trifluoro-N-((1R,3S)-3-hydroxy-6-methyl-2,3-dihydro-1H-inden-1-yl)acetamide (from Preparation BJ) was converted into the title compound by following a sequence of procedures analogous to Steps BK (1-4). LC-MS (M+H)$^+$=367.23 $^1$H NMR (500 MHz, CDCl$_3$) δ ppm 7.31-7.26 (m, 1H) 7.09 (bs, 3H) 6.99-6.94 (m, 4H) 5.90-5.80 (M, 1H) 5.23-5.08 (m, 2H) 4.90-4.86 (m, 1H) 4.51-4.47 (m, 3H) 4.05-4.00 (m, 1H) 3.88-3.78 (m, 2H) 3.03-2.98 (m, 1H) 2.88-2.85 (m, 1H) 2.76-2.60 (m, 3H) 2.35-2.28 (m, 4H) 1.98-1.91 (m, 5H).

Preparation BM

N-((1S,3R)-3-(allyloxy)-4,6-dimethyl-2,3-dihydro-1H-inden-1-yl)-2,2,2-trifluoroacetamide

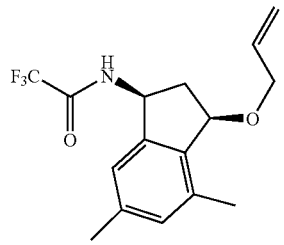

and

N-((1R,3S)-3-(allyloxy)-4,6-dimethyl-2,3-dihydro-1H-inden-1-yl)-2,2,2-trifluoroacetamide

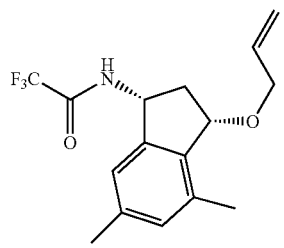

Step BM (1). A solution of 3-amino-3-(3,5-dimethylphenyl)propanoic acid (18 g, 0.078 mol) and TFA (72 mL) was stirred at rt for 30 min. Trifluoroacetic anhydride (72 mL) was added and the resulting mixture was heated at reflux for 2 h. After cooling to rt, the reaction was concentrated in vacuo. The crude residue was dissolved in EtOAc and sequentially washed with 1 N NaOH and brine. The organic layer was dried over $Na_2SO_4$, filtered, and concentrated in vacuo to afford 15 g (71% yield) of N-(4,6-dimethyl-3-oxo-2,3-dihydro-1H-inden-1-yl)-2,2,2-trifluoroacetamide as a white solid. LC-MS (M+H)$^+$=272.09; $^1$H NMR (500 MHz, CDCl$_3$) δ ppm 7.17 (s, 1H) 7.04 (s, 1H) 6.91 (d, J=6.71 Hz, 1H) 5.52-5.59 (m, 1H) 3.15 (dd, J=18.92, 7.93 Hz, 1H) 2.50 (s, 3H) 2.46 (d, J=3.36 Hz, 1H) 2.40 (s, 3H).

Step BM (2): The crude product from Step BM (1) was reduced with L-selectride by following a procedure analogous to Step BJ (1) to afford 6.5 g (85% yield) of trans-2,2,2-trifluoro-N-(3-hydroxy-4,6-dimethyl-2,3-dihydro-1H-inden-1-yl)acetamide (6.5 g, 85% yield). LC-MS (M+H)$^+$=274.10 $^1$H NMR (500 MHz, CDCl$_3$) δ ppm 7.32 (d, 1H) 6.98-7.03 (m, 1H) 6.93-6.97 (m, 1H) 5.22 (t, 1H) 5.12 (d, 1H) 2.81-2.98 (m, 1H) 2.64-2.74 (m, 1H) 2.32-2.37 (m, 3H) 2.27-2.32 (m, 3H) 1.94 (d, 1H).

Step BM (3): The product from Step BM (2) was O-allylated by a procedure analogous to Step X(1) to afford 5.5 g (73% yield) of trans-N-(3-(allyloxy)-4,6-dimethyl-2,3-dihydro-1H-inden-1-yl)-2,2,2-trifluoroacetamide. LC-MS (M+H)$^+$=274.10; $^1$H NMR (500 MHz, CHLOROFORM-D) δ ppm 7.05 (s, 1H) 6.99 (s, 1H) 6.84 (s, 1H) 5.87-5.98 (m, 1H) 5.36 (t, J=7.32 Hz, 1H) 5.25-5.32 (m, 1H) 5.20 (dd, J=10.22, 1.37 Hz, 1H) 4.89 (d, J=4.27 Hz, 1H) 4.01-4.17 (m, 2H) 2.49-2.58 (m, 1H) 2.35 (s, 3H) 2.32 (s, 3H) 2.14 (d, 1H).

Step BM (4): The racemic product from Step BM (3) was purified by chiral HPLC using conditions analogous to Step T (1) to afford 1.4 g (25% yield) of N-((1S,3R)-3-(allyloxy)-4,6-dimethyl-2,3-dihydro-1H-inden-1-yl)-2,2,2-trifluoroacetamide (first to elute) and 1.4 g (25% yield) of N-((1R,3S)-3-(allyloxy)-4,6-dimethyl-2,3-dihydro-1H-inden-1-yl)-2,2,2-trifluoroacetamide (second to elute).

Preparation BN (2R,3S)-1-((1S,3R)-3-(allyloxy)-4,6-dimethyl-2,3-dihydro-1H-inden-1-ylamino)-3-amino-4-phenylbutan-2-ol

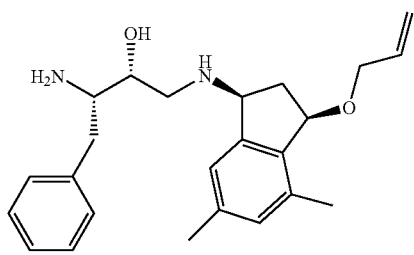

Step BN (1): N-((1S,3R)-3-(allyloxy)-4,6-Dimethyl-2,3-dihydro-1H-inden-1-yl)-2,2,2-trifluoroacetamide from Preparation BM was N-deprotected by a procedure analogous to Step U (2) to afford 900 mg (94% yield) of (1S,3R)-3-(allyloxy)-4,6-dimethyl-2,3-dihydro-1H-inden-1-amine as a white solid. LC-MS (M+H)$^+$=218.15; $^1$H NMR (500 MHz, CDCl$_3$) δ ppm 7.00 (s, 1H) 6.90 (s, 1H) 5.91-6.04 (m, 1H) 5.26-5.34 (m, 1H) 5.13-5.20 (m, J=10.38, 1.53 Hz, 1H) 4.18-4.05 (m, 2H) 4.05-4.00 (m, 1H) 2.57-2.67 (m, 1H) 2.34 (s, 3H) 2.32 (s, 3H) 1.80-1.92 (m, 4H).

Step BN (2): The product from Step BN (1) was reacted with tert-butyl (S)-1-((S)-oxiran-2-yl)-2-phenylethylcarbamate following a procedure analogous to Step AW (1) to afford 1.6 g (80% yield) of tert-butyl (2S,3R)-4-((1S,3R)-3-(allyloxy)-4,6-dimethyl-2,3-dihydro-1H-inden-1-ylamino)-3-hydroxy-1-phenylbutan-2-ylcarbamate. LC-MS (M+H)$^+$=481.30; $^1$H NMR (500 MHz, CDCl$_3$) δ ppm 7.39-7.16 (m, 6H) 5.93-5.87 (m, 1H) 5.33-4.60 (m, 8H) 4.08 (d, 2H) 3.94 (m, 1H) 3.62 (m, 1H) 3.46 (d, 1H) 3.10-3.06 (m, 2H) 3.6 (m, 1H) 2.59-2.54 (m, 2H) 2.37 (s, 3H) 2.35 (s, 3H) 1.25 (s, 9H).

Step BN (3): The product from Step BN (2) was converted into 423 mg (46% yield) of the title compound by following procedures analogous to Steps AW (2-3). LC-MS (M+H)$^+$=381.25; $^1$H NMR (500 MHz, CDCl$_3$) δ ppm 7.26 (t, J=7.48 Hz, 2H) 7.11-7.21 (m, 2H) 7.08 (s, 1H) 6.93 (s, 1H) 5.87-6.02 (m, 1H) 5.29 (dd, J=17.09, 1.53 Hz, 1H) 5.14 (d, J=10.38 Hz, 1H) 4.85 (dd, J=6.26, 1.98 Hz, 1H) 3.97-4.22 (m, 3H) 3.61-3.70 (m, 1H) 3.38 (s, 4H) 3.11-3.21 (m, 1H) 2.95 (dd, J=12.21, 3.36 Hz, 1H) 2.78-2.88 (m, 2H) 2.38-2.54 (m, 2H) 2.33 (d, J=5.80 Hz, 6H) 2.05-2.15 (m, 1H).

Preparation BO (2R,3S)-1-((1R,3S)-3-(allyloxy)-4,6-dimethyl-2,3-dihydro-1H-inden-1-ylamino)-3-amino-4-phenylbutan-2-ol

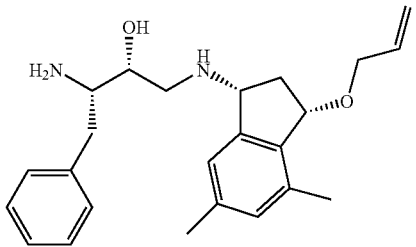

Step BO (1): N-((1R,3S)-3-(allyloxy)-4,6-Dimethyl-2,3-dihydro-1H-inden-1-yl)-2,2,2-trifluoroacetamide from Preparation BM was converted into the title compound by following a sequence of procedures analogous to Steps BN (1-3).

Example 1

2-propyl-pentanoic acid ((1S,4R,5S,8S,14R)-5-benzyl-4-hydroxy-18-methoxy-7-oxo-13-oxa-2,6-diazatricyclo[12.6.1.0$^{15,20}$]henicosa-10,15(20),16,18-tetraen-8-yl)-methyl-amide

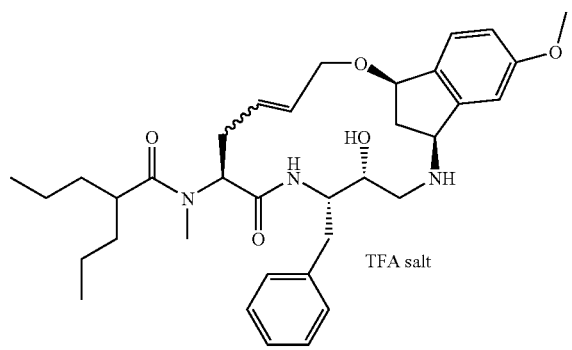

Step CA (1): (2R,3S)-1-((1S,3R)-3-(Allyloxy)-6-methoxy-2,3-dihydro-1H-inden-1-ylamino)-3-amino-4-phenylbutan-2-ol (30 mg, 80 μmol, from Preparation V), (S)-2-

(N,2,2-trimethylhexanamido)pent-4-enoic acid (19 mg, 76 µmol, from Preparation A), EDC (15 mg, 80 µmol), HOBt (11 mg, 80 µmol), and DIEA (70 µL, 380 µmol) were mixed in 2 mL of DMF and stirred for 24 h at rt. The crude reaction mixture was directly injected and purified using reverse phase preparatory-HPLC (MeOH/H$_2$O/TFA) to afford 48.9 mg of the trifluoroacetic acid salt of (S)-N-((2S,3R)-4-((1S,3R)-3-(allyloxy)-6-methoxy-2,3-dihydro-1H-inden-1-ylamino)-3-hydroxy-1-phenylbutan-2-yl)-2-(N-methyl-2-propylpentanamido)pent-4-enamide as a light brown viscous oil. LC-MS (M+H)$^+$=620.62; $^1$H NMR (300 MHz, CDCl$_3$) δ ppm 0.74-0.93 (m, 5H) 1.10-1.58 (m, 7H) 2.30-3.03 (m, 9H) 3.18-3.54 (m, 6H) 3.75-3.88 (m, 3H) 4.01-4.12 (m, 2H) 4.31 (s, 1H) 4.66 (t, J=7.87 Hz, 1H) 4.80 (d, J=5.86 Hz, 1H) 4.87-5.04 (m, 2H) 5.14-5.34 (m, 2H) 5.45-5.63 (m, 1H) 5.82-5.99 (m, 1H) 6.89-7.00 (m, 1H) 7.13-7.38 (m, 8H).

Step CA (2): Hoveyda-Grubb's 2$^{nd}$ generation catalyst (3.4 mg, 5.0 µmol) was added to a flask charged with a solution of the product from Step CA (1) (40 mg, 55 µmol, TFA salt) and DCM at rt. The mixture was stirred for 16 h. The reaction mixture was concentrated in vacuo. The residue was dissolved in a minimal amount of MeOH and filtered through a 5 µm syringe filter. The filtrate was directly purified using reverse phase preparatory-HPLC (MeOH/H$_2$O/TFA) to give 13.4 mg (34% yield) of the trifluoroacetic acid salt of the title compound as a diastereomeric mixture of cis/trans-olefins. LC-MS (M+H)$^+$=592.57; HRMS (M+H)$^+$=633.3652; $^1$H NMR (300 MHz, CDCl$_3$) δ ppm 0.69-0.96 (m, 5H) 1.07-1.63 (m, 7H) 1.90 (s, 1H) 2.23-3.41 (m, 13H) 3.63-3.96 (m, 4H) 3.98-4.28 (m, 2H) 4.55-5.04 (m, 2H) 5.62 (s, 1H) 6.59-6.76 (m, 1H) 6.86-7.02 (m, 1H) 7.04-7.46 (m, 9H).

Example 2

2-ethyl-hexanoic acid ((1S,4R,5S,8S,14R)-5-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide (diastereomer A)

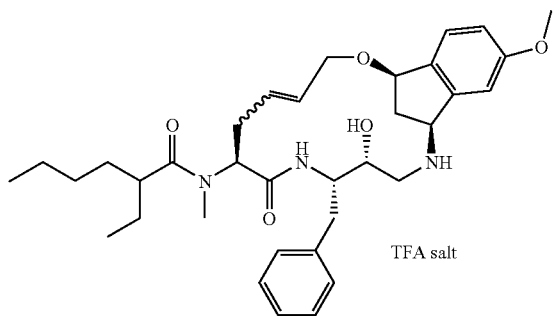

TFA salt

Step CB (1): (2S)-2-(2-Ethyl-N-methylhexanamido)pent-4-enoic acid (19 mg, 75 µmol, diastereomer A from Preparation B) and (2R,3S)-1-((1S,3R)-3-(allyloxy)-6-methoxy-2,3-dihydro-1H-inden-1-ylamino)-3-amino-4-phenylbutan-2-ol (30 mg, 78 µmol, from Preparation V) were coupled following a procedure analogous to Step CA (1) to afford 38 mg (69% yield) of the TFA salt of N-((S)-1-((2S,3R)-4-((1S,3R)-3-(allyloxy)-6-methoxy-2,3-dihydro-1H-inden-1-ylamino)-3-hydroxy-1-phenylbutan-2-ylamino)-1-oxopent-4-en-2-yl)-2-ethyl-N-methylhexanamide (diastereomer A). LC-MS (M+H)$^+$=620.54; $^1$H NMR (300 MHz, CDCl$_3$) δ ppm 0.67-0.93 (m, 6H) 1.06-1.64 (m, 8H) 2.24-3.32 (m, 12H) 3.71-3.91 (m, 4H) 3.94-4.45 (m, 5H) 4.54-4.71 (m, 1H) 4.79 (d, J=4.76 Hz, 1H) 4.85-5.10 (m, 2H) 5.11-5.36 (m, 2H) 5.46-5.66 (m, 1H) 5.78-6.01 (m, 1H) 6.89-7.05 (m, 1H) 7.09-7.42 (m, 8H).

Step CB (2): The product from Step CB (1) (32 mg, 44 µmol) was subject to the ring-closing metathesis procedure described in Step CA (2) to afford 13.2 mg (43% yield) of the TFA salt of the title compound as a diastereomeric mixture of cis/trans-olefins. LC-MS (M+H)$^+$=592.46; HRMS (M+H)$^+$=592.3746; $^1$H NMR (300 MHz, CDCl$_3$) δ ppm 0.61-0.92 (m, 5H) 0.98-1.65 (m, 7H) 2.29-3.20 (m, 9H) 3.35-3.92 (m, 8H) 4.03-4.32 (m, 1H) 4.63-5.08 (m, 1H) 5.55-5.78 (m, 1H) 6.97 (s, 1H) 7.03-7.44 (m, 14H).

Example 3

2-ethyl-hexanoic acid ((1S,4R,5S,8S,14R)-5-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide (diastereomer B)

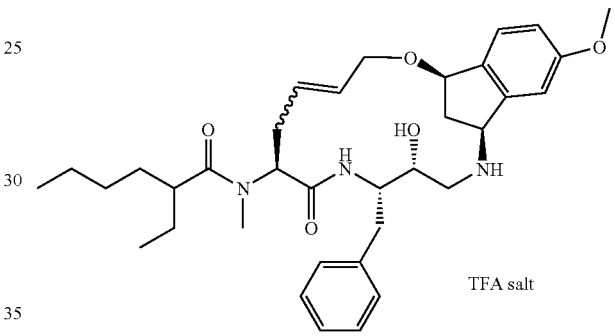

TFA salt

Step CC (1): (2S)-2-(2-Ethyl-N-methylhexanamido)pent-4-enoic acid (19 mg, 75 µmol, diastereomer B from Preparation B) and (2R,3S)-1-((1S,3R)-3-(allyloxy)-6-methoxy-2,3-dihydro-1H-inden-1-ylamino)-3-amino-4-phenylbutan-2-ol (30 mg, 78 µmol, from Preparation V) were coupled following a procedure analogous to Step CA (1) to afford 31 mg (56% yield) of the TFA salt of N-((S)-1-((2S,3R)-4-((1S,3R)-3-(allyloxy)-6-methoxy-2,3-dihydro-1H-inden-1-ylamino)-3-hydroxy-1-phenylbutan-2-ylamino)-1-oxopent-4-en-2-yl)-2-ethyl-N-methylhexanamide (diastereomer B). LC-MS (M+H)$^+$=620.56; $^1$H NMR (300 MHz, CDCl$_3$) δ ppm 0.71-0.95 (m, 6H) 1.07-1.61 (m, 8H) 2.31-3.30 (m, 11H) 3.73-3.90 (m, 4H) 3.99-4.12 (m, 2H) 4.24-4.36 (m, 1H) 4.54-5.09 (m, 6H) 5.12-5.34 (m, 2H) 5.46-5.65 (m, 1H) 5.79-5.98 (m, 1H) 6.89-7.00 (m, 1H) 7.09-7.37 (m, 7H).

Step CC (2): The product from Step CC (1) (24.6 mg, 34 µmol) was subject to the ring-closing metathesis procedure described in Step CA (2) to afford 19 mg (67% yield) of the TFA salt of the title compound as a diastereomeric mixture of cis/trans-olefins. LC-MS (M+H)$^+$=592.47; HRMS (M+H)$^+$=592.3771; $^1$H NMR (300 MHz, CDCl$_3$) δ ppm 0.69-0.90 (m, 5H) 1.04-1.57 (m, 7H) 1.96 (t, J=11.34 Hz, 1H) 2.36-2.50 (m, 2H) 2.59-3.00 (m, 5H) 3.59-3.91 (m, 8H) 4.05-4.17 (m, 1H) 4.18-4.34 (m, 1H) 4.72 (d, J=5.49 Hz, 1H) 4.80 (s, 1H) 4.97 (t, J=15.37 Hz, 1H) 5.58-5.74 (m, 1H) 6.92-7.02 (m, 1H) 7.06-7.41 (m, 13H).

Example 4

2,2-dimethyl-hexanoic acid ((1S,4R,5S,8S,14R)-5-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide

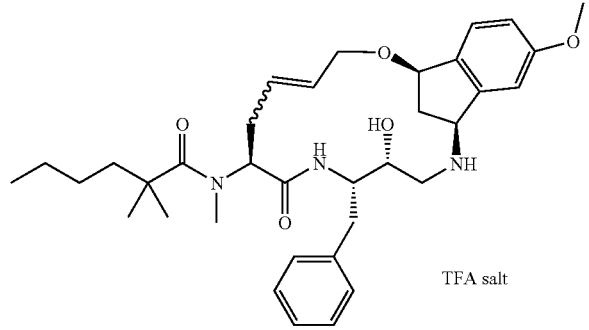

TFA salt

Step CD (1): (S)-2-(N,2,2-Trimethylhexanamido)pent-4-enoic acid (14.9 mg, 58 μmol, from Preparation C) and (2R,3S)-1-((1S,3R)-3-(allyloxy)-6-methoxy-2,3-dihydro-1H-inden-1-ylamino)-3-amino-4-phenylbutan-2-ol (23 mg, 61 μmol, from Preparation V) were coupled using a procedure analogous to Step CA (1) to afford 4.9 mg (11% yield) of the TFA salt of N-((S)-1-((2S,3R)-4-((1S,3R)-3-(allyloxy)-6-methoxy-2,3-dihydro-1H-inden-1-ylamino)-3-hydroxy-1-phenylbutan-2-ylamino)-1-oxopent-4-en-2-yl)-N,2,2-trimethylhexanamide. LC-MS (M+H)$^+$=620.62.

Step CC (2): The product from Step CD (1) (4.9 mg, 7 μmol) was subject to the ring-closing metathesis procedure described in Step CA (2) to afford 1.4 mg (29% yield) of the TFA salt of the title compound as a diastereomeric mixture of cis/trans-olefins. LC-MS (M+H)$^+$=592.46; HRMS (M+H)$^+$=592.3737.

Example 5

5,5,5-Trifluoro-pentanoic acid ((1S,4R,5S,8S,14R)-5-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide

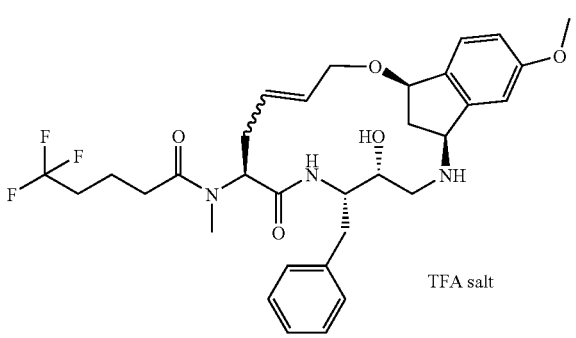

TFA salt

Step CE (1): (S)-2-(5,5,5-Trifluoro-N-methylpentanamido)pent-4-enoic acid (26.2 mg, 98.1 μmol, from Preparation H) and (2R,3S)-1-((1S,3R)-3-(allyloxy)-6-methoxy-2,3-dihydro-1H-inden-1-ylamino)-3-amino-4-phenylbutan-2-ol (37 mg, 98.1 μmol, from Preparation V) were coupled using a procedure analogous to Step CA (1) to afford 48 mg (66% yield) of the TFA salt of (S)-N-((2S,3R)-4-((1S,3R)-3-(allyloxy)-6-methoxy-2,3-dihydro-1H-inden-1-ylamino)-3-hydroxy-1-phenylbutan-2-yl)-2-(5,5,5-trifluoro-N-methylpentanamido)pent-4-enamide. LC-MS (M+H)$^+$=632.6; $^1$H NMR (500 MHz, CDCl$_3$) δ ppm 1.72-1.90 (m, 2H) 2.04-2.49 (m, 8H) 2.51-2.73 (m, 2H) 2.81-3.05 (m, 3H) 3.22 (dd, J=14.80, 3.81 Hz, 1H) 3.75-4.12 (m, 5H) 4.23-4.33 (m, 1H) 4.73-5.34 (m, 9H) 5.46-5.61 (m, 1H) 5.83-5.97 (m, 1H) 6.94-7.00 (m, 1H) 7.10-7.30 (m, 7H) 7.32-7.39 (m, 1H) 8.45 (d, J=60.12 Hz, 1H) 9.42 (s, 1H).

Step CE (2): The product from Step CE (1) (48 mg, 64.4 μmol) was subject to the ring-closing metathesis procedure described in Step CA (2) to afford 16 mg (35% yield) of the TFA salt of the title compound as a diastereomeric mixture of cis/trans-olefins. LC-MS (M+H)$^+$=604.5; HRMS (M+H)$^+$=604.3025; $^1$H NMR (500 MHz, CDCl$_3$) δ ppm 1.49-1.92 (m, 3H) 1.93-2.27 (m, 3H) 2.27-3.18 (m, 8H) 3.28 (d, J=11.29 Hz, 1H) 3.69-3.91 (m, 4H) 3.95-4.45 (m, 2H) 4.55-5.04 (m, 5H) 5.48-5.77 (m, 2H) 6.38-6.62 (m, 1H) 6.86-7.46 (m, 8H).

Example 6

3,3,3-Trifluoro-propane-1-sulfonic acid ((1S,4R,5S,8S,14R)-5-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide

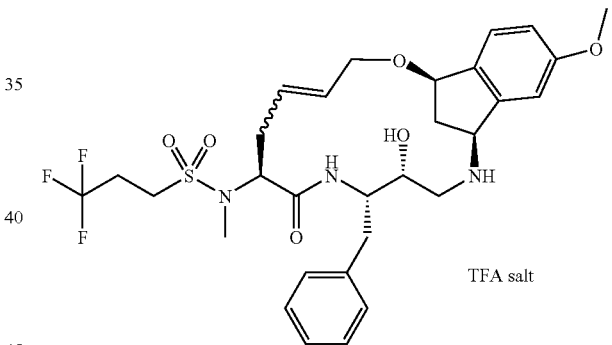

TFA salt

Step CF (1): ((S)-2-(3,3,3-trifluoro-N-methylpropylsulfonamido)pent-4-enoic acid (20 mg, 68.7 μmol, from Preparation I) and (2R,3S)-1-((1S,3R)-3-(allyloxy)-6-methoxy-2,3-dihydro-1H-inden-1-ylamino)-3-amino-4-phenylbutan-2-ol (25 mg, 65.4 μmol, from Preparation V) were coupled using a procedure analogous to Step CA (1) to afford 21 mg (42% yield) of the TFA salt of (S)-N-((2S,3R)-4-((1S,3R)-3-(allyloxy)-6-methoxy-2,3-dihydro-1H-inden-1-ylamino)-3-hydroxy-1-phenylbutan-2-yl)-2-(3,3,3-trifluoro-N-methylpropylsulfonamido)-pent-4-enamide. LC-MS (M+H)$^+$=654.6; $^1$H NMR (500 MHz, CDCl$_3$) δ ppm 2.21-2.43 (m, 4H) 2.44-2.70 (m, 4H) 2.72-2.98 (m, 3H) 2.98-3.32 (m, 3H) 3.74-3.84 (m, 3H) 3.92-3.99 (m, 1H) 4.00-4.12 (m, 2H) 4.12-4.27 (m, 2H) 4.68-4.76 (m, 1H) 4.81 (t, J=4.43 Hz, 1H) 5.04 (d, J=10.07 Hz, 1H) 5.07-5.15 (m, 1H) 5.15-5.24 (m, 1H) 5.30 (d, J=17.40 Hz, 1H) 5.48-5.76 (m, 2H) 5.84-5.96 (m, 1H) 6.63 (d, J=8.55 Hz, 1H) 6.92-6.99 (m, 1H) 7.10-7.22 (m, 3H) 7.22-7.29 (m, 2H) 7.30-7.38 (m, 1H) 8.26 (s, 1H) 8.55 (s, 1H) 9.13 (s, 1H).

Step CF (2): The product from Step CF (1) (21 mg, 27.3 μmol) was subject to the ring-closing metathesis procedure described in Step CA (2) to afford 10.7 mg (54% yield) of the TFA salt of the title compound as a diastereomeric mixture of cis/trans-olefins. LC-MS (M+H)+=626.5; HRMS (M+H)+=626.2512; $^1$H NMR (500 MHz, CDCl$_3$) δ ppm 2.13 (d, J=12.51 Hz, 1H) 2.45-2.58 (m, 3H) 2.58-2.65 (m, 2H) 2.69-2.83 (m, 2H) 2.86-3.14 (m, 4H) 3.25 (s, 1H) 3.76-3.94 (m, 5H) 4.04-4.24 (m, 4H) 4.34 (s, 1H) 4.67-4.77 (m, 2H) 5.56-5.71 (m, 2H) 6.91-7.06 (m, 2H) 7.13-7.21 (m, 3H) 7.20-7.29 (m, 3H) 7.40 (d, J=8.24 Hz, 1H).

Example 7 pentane-1-sulfonic acid ((1S,4R,5S,8S,14R)-5-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide

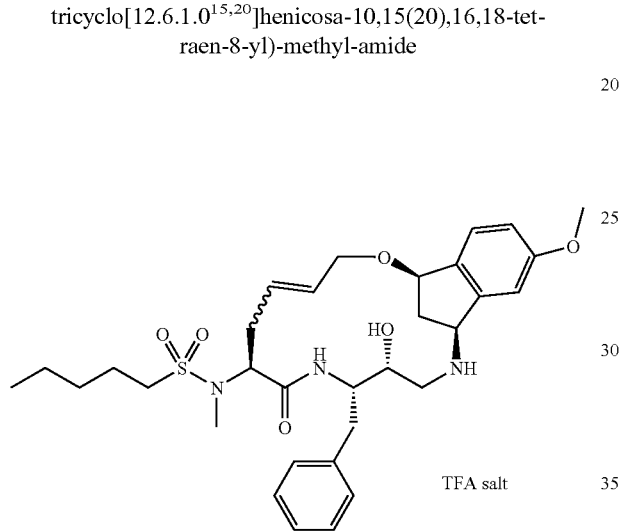

TFA salt

Step CG (1): (S)-2-(N-Methylpentylsulfonamido)pent-4-enoic acid (27 mg, 103 µmol, from Preparation J) and (2R,3S)-1-((1S,3R)-3-(allyloxy)-6-methoxy-2,3-dihydro-1H-inden-1-ylamino)-3-amino-4-phenylbutan-2-ol (25 mg, 65.4 µmol, from Preparation V) were coupled using a procedure analogous to Step CA (1) to afford 40 mg (53% yield) of the TFA salt of (S)-N-((2S,3R)-4-((1S,3R)-3-(allyloxy)-6-methoxy-2,3-dihydro-1H-inden-1-ylamino)-3-hydroxy-1-phenylbutan-2-yl)-2-(N-methylpentylsulfonamido)pent-4-enamide. LC-MS (M+H)+=628.6; $^1$H NMR (500 MHz, CDCl$_3$) δ ppm 0.84-0.93 (m, 3H) 1.21-1.38 (m, 4H) 1.62-1.78 (m, 2H) 2.17-2.41 (m, 4H) 2.54-2.71 (m, 2H) 2.71-3.00 (m, 5H) 3.27 (d, J=11.60 Hz, 1H) 3.74-3.85 (m, 3H) 3.90-4.28 (m, 5H) 4.70-4.82 (m, 2H) 5.03-5.15 (m, 2H) 5.20 (d, J=10.38 Hz, 1H) 5.30 (d, J=17.40 Hz, 1H) 5.47-5.68 (m, 1H) 5.85-5.96 (m, 1H) 6.22 (s, 1H) 6.91-6.97 (m, 1H) 7.13-7.28 (m, 6H) 7.31-7.39 (m, 1H) 8.28 (s, 1H) 8.69 (s, 1H) 9.24 (s, 1H).

Step CG (2): The product from Step CG (1) (80 mg, 108 µmol) was subject to the ring-closing metathesis procedure described in Step CA (2) to afford 34.7 mg (45% yield) of the TFA salt of the title compound as a diastereomeric mixture of cis/trans-olefins. HRMS (M+H)+=600.3096; $^1$H NMR (500 MHz, CDCl$_3$) δ ppm 0.84-0.97 (m, 3H) 1.17-1.43 (m, 5H) 1.62-1.83 (m, 2H) 1.98-2.10 (m, 1H) 2.22-2.92 (m, 9H) 3.01-3.38 (m, 2H) 3.69-3.90 (m, 4H) 4.02-4.31 (m, 3H) 4.67-4.89 (m, 2H) 5.39-5.75 (m, 3H) 6.90-7.01 (m, 1H) 7.06-7.48 (m, 7H) 8.89 (d, J=69.89 Hz, 1H).

Example 8

(1S,4R,5S,8S,14R)-8-butyl-5-(3,5-difluoro-benzyl)-4-hydroxy-18-methoxy-13-oxa-2,6-diaza-tricyclo[12.6.1.0$^{15,20}$]henicosa-10,15(20),16,18-tetraen-7-one

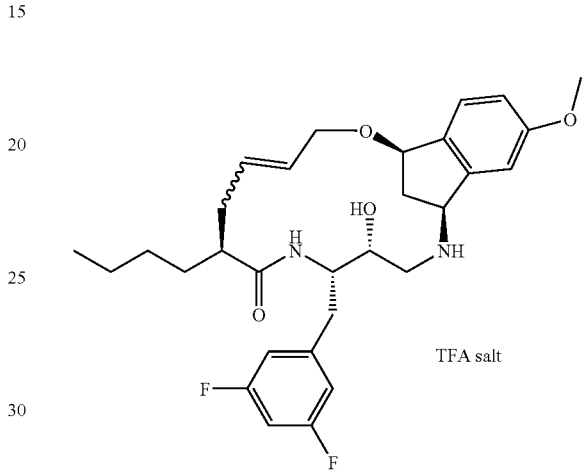

TFA salt

Step CH (1): (S)-2-Allylhexanoic acid (11.4 mg, 73.6 µmol) and (2R,3S)-1-((1S,3R)-3-(allyloxy)-6-methoxy-2,3-dihydro-1H-inden-1-ylamino)-3-amino-4-(3,5-difluorophenyl)butan-2-ol (25 mg, 65.4 µmol, from Preparation W) were coupled using a procedure analogous to Step CA (1) to afford 25 mg (56% yield) of the TFA salt of (S)-2-allyl-N-((2S,3R)-4-((1S,3R)-3-(allyloxy)-6-methoxy-2,3-dihydro-1H-inden-1-ylamino)-1-(3,5-difluorophenyl)-3-hydroxybutan-2-yl) hexanamide. LC-MS (M+H)+=557.1; $^1$H NMR (500 MHz, CDCl$_3$) δ ppm 0.62-0.90 (m, 5H) 0.96-1.45 (m, 5H) 1.97-2.13 (m, 2H) 2.13-2.22 (m, 1H) 2.39 (d, J=14.95 Hz, 1H) 2.52-2.92 (m, 3H) 2.99-3.17 (m, 1H) 3.23-3.31 (m, 1H) 3.73-3.84 (m, 3H) 3.85-3.92 (m, 1H) 3.97-4.17 (m, 3H) 4.66 (t, J=6.26 Hz, 1H) 4.76-4.96 (m, 3H) 5.14-5.43 (m, 2H) 5.54-5.68 (m, 1H) 5.81-5.97 (m, 1H) 6.54 (d, J=7.32 Hz, 1H) 6.58-6.66 (m, 1H) 6.74 (d, J=6.10 Hz, 2H) 6.88-6.97 (m, 1H) 7.15-7.27 (m, 2H) 7.31-7.40 (m, 1H)

Step CH (2): The product from Step CH (1) (25 mg, 37.3 µmol) was subject to the ring-closing metathesis procedure described in Step CA (2) to afford 16 mg (67% yield) of the TFA salt of the title compound as a diastereomeric mixture of cis/trans-olefins. HRMS (M+H)+=529.2874; $^1$H NMR (500 MHz, CDCl$_3$) δ ppm 0.41-0.54 (m, 1H) 0.64-0.92 (m, 3H) 0.99-1.44 (m, 4H) 1.80-2.49 (m, 9H) 2.66-3.15 (m, 2H) 3.17-3.39 (m, 1H) 3.75-3.94 (m, 3H) 3.96-4.05 (m, 1H) 4.14 (dd, J=10.83, 3.81 Hz, 1H) 4.25 (d, J=7.32 Hz, 1H) 4.33-4.45 (m, 1H) 4.58 (s, 1H) 4.66-4.84 (m, 1H) 5.51-5.62 (m, 1H) 5.66-5.78 (m, 1H) 6.57-6.70 (m, 1H) 6.71-6.88 (m, 2H) 6.91-7.02 (m, 1H) 7.43 (t, J=8.24 Hz, 1H) 8.15 (s, 1H).

Example 9 hexanoic acid ((1S,4R,5S,8S,14R)-5-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide

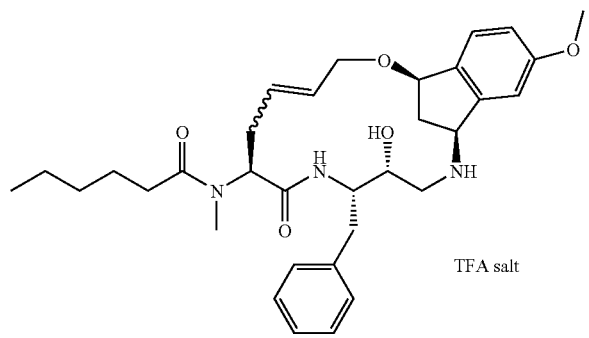

TFA salt

Step CI (1): (S)-2-(N-methylhexanamido)pent-4-enoic acid (18 mg, 78.5 μmol, from Preparation F) and (2R,3S)-1-((1S,3R)-3-(allyloxy)-6-methoxy-2,3-dihydro-1H-inden-1-ylamino)-3-amino-4-phenylbutan-2-ol (30 mg, 78.5 μmol, from Preparation V) were coupled using a procedure analogous to Step CA (1) to afford 37 mg (67% yield) of the TFA salt of N-((S)-1-((2S,3R)-4-((1S,3R)-3-(allyloxy)-6-methoxy-2,3-dihydro-1H-inden-1-ylamino)-3-hydroxy-1-phenylbutan-2-ylamino)-1-oxopent-4-en-2-yl)-N-methylhexanamide. LC-MS (M+H)$^+$=592.2; $^1$H NMR (500 MHz, CDCl$_3$) δ ppm 0.70-0.96 (m, 3H) 1.05-1.39 (m, 4H) 1.51 (dd, J=14.95, 7.32 Hz, 2H) 1.93-3.36 (m, 13H) 3.68-4.61 (m, 9H) 4.68-5.10 (m, 4H) 5.13-5.38 (m, 2H) 5.44-5.62 (m, 1H) 5.83-6.00 (m, 1H) 6.86-7.03 (m, 1H) 7.05-7.49 (m, 7H) 8.94-9.17 (m, 1H) 9.65 (s, 1H).

Step CI (2): The product from Step CI (1) (33.8 mg, 47.9 μmol) was subject to the ring-closing metathesis procedure described in Step CA (2) to afford 16.3 mg (51% yield) of the TFA salt of the title compound as a diastereomeric mixture of cis/trans-olefins. HRMS (M+H)$^+$=564.3425; $^1$H NMR (500 MHz, CDCl$_3$) δ ppm 0.80-0.97 (m, 3H) 1.13-1.61 (m, 6H) 1.76-3.50 (m, 13H) 3.67-3.97 (m, 4H) 3.99-4.20 (m, 1H) 4.48-5.05 (m, 5H) 5.45-5.80 (m, 2H) 6.44-6.61 (m, 1H) 6.92-7.41 (m, 8H).

Example 10

((1S,4R,5S,8S,14R)-5-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-carbamic acid butyl ester

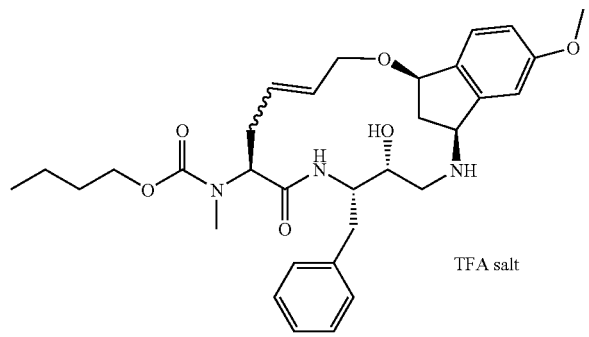

TFA salt

Step CJ (1): (S)-2-(Butoxycarbonyl(methyl)amino)pent-4-enoic acid (12 mg, 52.3 μmol, from Preparation E) and (2R,3S)-1-((1S,3R)-3-(allyloxy)-6-methoxy-2,3-dihydro-1H-inden-1-ylamino)-3-amino-4-phenylbutan-2-ol (20 mg, 52.3 μmol, from Preparation V) were coupled using a procedure analogous to Step CA (1) to afford 22.2 mg (60% yield) of the TFA salt of butyl (S)-1-((2S,3R)-4-((1S,3R)-3-(allyloxy)-6-methoxy-2,3-dihydro-1H-inden-1-ylamino)-3-hydroxy-1-phenylbutan-2-ylamino)-1-oxopent-4-en-2-yl(methyl)carbamate. LC-MS (M+H)$^+$=594.3; $^1$H NMR (500 MHz, CDCl$_3$) δ ppm 0.82-1.03 (m, 3H) 1.25-1.44 (m, 2H) 1.59 (s, 2H) 2.18-3.01 (m, 9H) 3.34 (s, 5H) 3.75-4.32 (m, 9H) 4.63-4.85 (m, 2H) 4.91-5.08 (m, 2H) 5.16-5.36 (m, 2H) 5.49-5.64 (m, 1H) 5.82-5.97 (m, 1H) 6.90-7.00 (m, 1H) 7.05-7.41 (m, 7H).

Step CJ (2): The product from Step CJ (1) (18.0 mg, 25.4 μmol) was subject to the ring-closing metathesis procedure described in Step CA (2) to afford 4.8 mg (28% yield) of the TFA salt of the title compound as a diastereomeric mixture of cis/trans-olefins. HRMS (M+H)$^+$=566.3239; $^1$H NMR (500 MHz, CDCl$_3$) δ ppm 0.79-1.00 (m, 4H) 1.19-1.74 (m, 6H) 2.07-2.86 (m, 12H) 3.12 (d, J=10.99 Hz, 1H) 3.23-3.48 (m, 1H) 3.72-4.17 (m, 6H) 4.25-4.57 (m, 1H) 4.68-4.83 (m, 1H) 4.92 (s, 1H) 5.51-5.79 (m, 2H) 6.94-7.40 (m, 8H).

Example 11

(S)-2-methyl-hexanoic acid ((1S,4R,5S,8S,14R)-5-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide

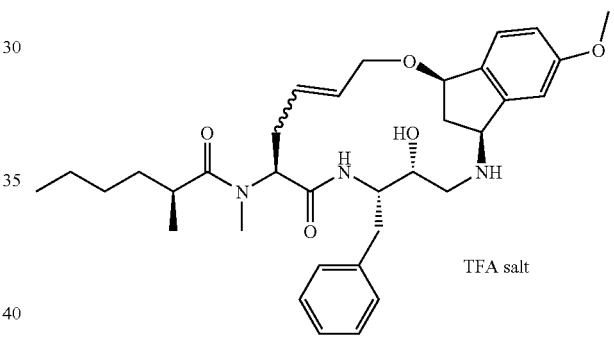

TFA salt

Step CK (1): (S)-2-((S)-N,2-dimethylhexanamido)pent-4-enoic acid (12.6 mg, 52.3 μmol, diastereomer A from Preparation D) and (2R,3S)-1-((1S,3R)-3-(allyloxy)-6-methoxy-2,3-dihydro-1H-inden-1-ylamino)-3-amino-4-phenylbutan-2-ol (20 mg, 52.3 μmol, from Preparation V) were coupled following a procedure analogous to Step CA (1) to afford 25 mg (66% yield) of the TFA salt of (S)-N-((S)-1-((2S,3R)-4-((1S,3R)-3-(allyloxy)-6-methoxy-2,3-dihydro-1H-inden-1-ylamino)-3-hydroxy-1-phenylbutan-2-ylamino)-1-oxopent-4-en-2-yl)-N,2-dimethylhexanamide. LC-MS (M+H)$^+$=606.3; $^1$H NMR (500 MHz, CDCl$_3$) δ ppm 0.81-0.93 (m, 2H) 1.01 (t, J=5.95 Hz, 2H) 1.13-1.38 (m, 5H) 1.51-1.62 (m, 1H) 2.22-2.79 (m, 13H) 2.83-2.98 (m, 4H) 3.21 (dd, J=13.12, 3.97 Hz, 1H) 3.78-3.86 (m, 2H) 3.91 (q, J=4.48 Hz, 1H) 4.02-4.14 (m, 2H) 4.22-4.33 (m, 1H) 4.64 (dd, J=9.16, 7.02 Hz, 1H) 4.71-5.07 (m, 3H) 5.16-5.23 (m, 1H) 5.26-5.35 (m, 1H) 5.50-5.61 (m, 1H) 5.84-5.98 (m, 1H) 6.93-6.98 (m, 1H) 7.14-7.29 (m, 6H) 7.31-7.38 (m, 1H) 7.44 (d, J=2.14 Hz, 1H).

Step CK (2): The product from Step CK (1) (131 mg, 182 μmol) was subject to the ring-closing metathesis procedure described in Step CA (2) to afford 35 mg (28% yield) of the TFA salt of the title compound. HRMS (M+H)$^+$=578.3572; $^1$H NMR (400 MHz, CDCl$_3$) δ ppm 0.66-0.93 (m, 4H) 0.93-1.42 (m, 9H) 1.47-1.63 (m, 1H) 1.79-2.04 (m, 1H) 2.26-3.37

(m, 10H) 3.61-3.93 (m, 4H) 3.96-4.18 (m, 1H) 4.69 (d, J=5.04 Hz, 1H) 4.90 (d, J=5.54 Hz, 1H) 5.44-5.81 (m, 3H) 6.69 (s, 1H) 6.89-7.43 (m, 8H) 8.59-8.90 (m, 1H) 9.20-9.47 (m, 1H).

Example 12

N-((1S,4R,5S,14R)-5-benzyl-4-hydroxy-18-methoxy-7-oxo-13-oxa-2,6-diaza-tricyclo[12.6.1.0$^{15,20}$]henicosa-10,15(20),16,18-tetraen-8-yl)-acetamide

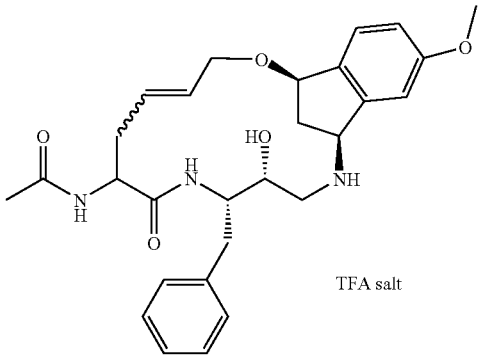

TFA salt

Step CL (1): 2-Acetamidopent-4-enoic acid (8.2 mg, 52.3 µmol) and (2R,3S)-1-((1S,3R)-3-(allyloxy)-6-methoxy-2,3-dihydro-1H-inden-1-ylamino)-3-amino-4-phenylbutan-2-ol (20 mg, 52.3 µmol, from Preparation V) were coupled following a procedure analogous to Step CA (1) to afford 26.1 mg (78% yield) of the TFA salt of 2-acetamido-N-((2S,3R)-4-((1S,3R)-3-(allyloxy)-6-methoxy-2,3-dihydro-1H-inden-1-ylamino)-3-hydroxy-1-phenylbutan-2-yl)pent-4-enamide. LC-MS (M+H)$^+$=522.11; $^1$H NMR (500 MHz, CDCl$_3$) δ ppm 1.94 (d, J=23.50 Hz, 3H) 2.12-2.30 (m, 2H) 2.34-2.46 (m, 1H) 2.61-3.09 (m, 4H) 3.25 (s, 1H) 3.46-4.38 (m, 12H) 4.82 (d, J=5.19 Hz, 1H) 4.92-5.05 (m, 2H) 4.92-5.03 (m, 2H) 5.16-5.46 (m, 2H) 5.79-5.96 (m, 1H) 6.89-7.02 (m, 1H) 7.08-7.43 (m, 7H) 8.75 (s, 1H).

Step CL (2): The product from Step CL (1) (22 mg, 34.3 µmol) was subject to the ring-closing metathesis procedure described in Step CA (2) to afford 13.6 mg (65% yield) of the TFA salt of the title compound as a mixture of diastereomers. HRMS (M+H)$^+$=494.2673; $^1$H NMR (500 MHz, CDCl$_3$) δ ppm 1.82-1.98 (m, 2H) 1.99-2.07 (m, 1H) 2.15-3.40 (m, 13H) 3.72-4.49 (m, 6H) 4.57-4.88 (m, 2H) 5.43-5.75 (m, 1H) 6.91-7.00 (m, 1H) 7.04-7.27 (m, 6H) 7.29-7.46 (m, 2H) 8.89 (s, 1H) 9.12 (s, 1H) 9.83 (s, 1H).

Example 13

(1S,4R,5S,14R)-5-benzyl-4-hydroxy-18-methoxy-8-methyl-13-oxa-2,6-diaza-tricyclo[12.6.1.0$^{15,20}$]henicosa-10,15(20),16,18-tetraen-7-one

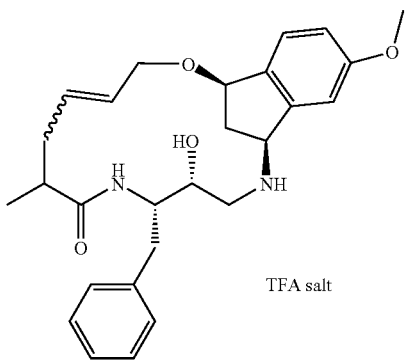

TFA salt

Step CM (1): 2-Methylpent-4-enoic acid (6.0 mg, 52.3 µmol) and (2R,3S)-1-((1S,3R)-3-(allyloxy)-6-methoxy-2,3-dihydro-1H-inden-1-ylamino)-3-amino-4-phenylbutan-2-ol (20 mg, 52.3 µmol, from Preparation V) were coupled following a procedure analogous to Step CA (1) to afford 21.4 mg (69% yield) of the TFA salt of 2-acetamido-N-((2S,3R)-4-((1S,3R)-3-(allyloxy)-6-methoxy-2,3-dihydro-1H-inden-1-ylamino)-3-hydroxy-1-phenylbutan-2-yl)pent-4-enamide. LC-MS (M+H)$^+$=479.1; $^1$H NMR (500 MHz, CDCl$_3$) δ ppm 0.86-1.03 (m, 2H) 1.93-2.68 (m, 11H) 2.93 (s, 2H) 3.04-3.17 (m, 1H) 3.25 (d, J=12.82 Hz, 1H) 3.81 (s, 3H) 4.00-4.24 (m, 2H) 4.69 (t, J=7.02 Hz, 1H) 4.76-4.97 (m, 2H) 5.16-5.32 (m, 1H) 5.84-5.95 (m, 1H) 6.09 (d, J=30.82 Hz, 1H) 6.86-6.97 (m, 1H) 7.13-7.39 (m, 7H) 8.54-8.81 (m, 1H) 9.69-9.91 (m, 1H).

Step CM (2): The product from Step CM (1) (18.4 mg, 31.1 µmol) was subject to the ring-closing metathesis procedure described in Step CA (2) to afford 13.4 mg (77% yield) of the TFA salt of the title compound as a mixture of diastereomers. HRMS (M+H)$^+$=451.2618; $^1$H NMR (500 MHz, CDCl$_3$) δ ppm 0.85 (d, J=6.71 Hz, 2H) 0.94-1.04 (m, 1H) 1.98 (s, 1H) 2.09-2.33 (m, 1H) 2.34-2.51 (m, 2H) 2.62-3.02 (m, 7H) 3.23 (s, 1H) 3.75-3.95 (m, 3H) 4.04-4.17 (m, 1H) 4.21 (dd, J=11.44, 4.12 Hz, 1H) 4.35 (d, J=9.16 Hz, 1H) 4.74 (dd, J=14.80, 3.81 Hz, 1H) 5.50-5.77 (m, 2H) 6.93-7.05 (m, 1H) 7.11-7.30 (m, 5H) 7.38-7.48 (m, 1H) 7.82 (s, 1H) 10.67 (s, 1H).

Example 14

3,3,3-trifluoro-propane-1-sulfonic acid ((1S,4R,5S,8S,15R)-5-benzyl-4-hydroxy-19-methoxy-7-oxo-14-oxa-2,6-diaza-tricyclo[13.6.1.0$^{16,21}$]docosa-11,16(21),17,19-tetraen-8-yl)-methyl-amide

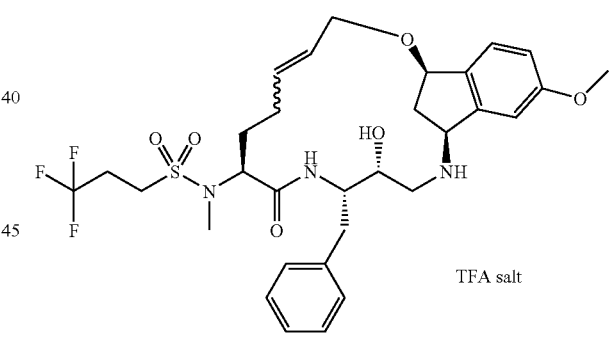

TFA salt

Step CN (1): (S)-2-(3,3,3-Trifluoro-N-methylpropylsulfonamido)hex-5-enoic acid (32 mg, 105 µmol, from Preparation M) and (2R,3S)-1-((1S,3R)-3-(allyloxy)-6-methoxy-2,3-dihydro-1H-inden-1-ylamino)-3-amino-4-phenylbutan-2-ol (40 mg, 105 µmol, from Preparation V) were coupled following a procedure analogous to Step CA (1) to afford 50.3 mg (61% yield) of the TFA salt of (S)-N-((2S,3R)-4-((1S,3R)-3-(allyloxy)-6-methoxy-2,3-dihydro-1H-inden-1-ylamino)-3-hydroxy-1-phenylbutan-2-yl)-2-(3,3,3-trifluoro-N-methylpropylsulfonamido)hex-5-enamide. HRMS (M+H)$^+$=668.3011; $^1$H NMR (400 MHz, CDCl$_3$) δ ppm 1.40-1.77 (m, 2H) 1.78-2.08 (m, 2H) 2.26-3.37 (m, 13H) 3.68-3.85 (m, 3H) 3.89-4.35 (m, 5H) 4.69 (d, J=6.30 Hz, 1H) 4.80 (d, J=5.54 Hz, 1H) 4.87-5.07 (m, 2H) 5.14-5.35 (m, 2H) 5.69 (s, 1H) 5.79-5.99 (m, 1H) 6.86-6.99 (m, 1H) 7.06-7.42 (m, 7H).

Step CN (2): The product from Step CN (1) (50 mg, 64.0 µmol) was subject to the ring-closing metathesis procedure described in Step CA (2) to afford 22.8 mg (47% yield) of the TFA salt of the title compound. HRMS (M+H)$^+$=640.2693; $^1$H NMR (400 MHz, CDCl$_3$) δ ppm 1.24 (s, 2H) 1.96-3.45 (m, 14H) 3.70-4.24 (m, 6H) 4.30-4.47 (m, 1H) 4.66-4.89 (m, 1H) 5.35-5.47 (m, 1H) 5.47-5.60 (m, 1H) 5.65-5.80 (m, 1H) 6.64-7.45 (m, 11H).

Example 15

3,3,3-trifluoro-propane-1-sulfonic acid [(1S,4R,5S,8S,15R)-5-(3,5-difluoro-benzyl)-4-hydroxy-19-methoxy-7-oxo-14-oxa-2,6-diaza-tricyclo[13.6.1.0$^{16,21}$]docosa-11,16(21),17,19-tetraen-8-yl]-methyl-amide

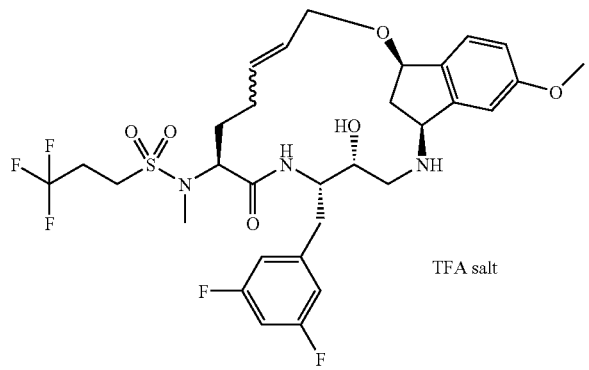

TFA salt

Step CO (1): (S)-2-(3,3,3-Trifluoro-N-methylpropylsulfonamido)hex-5-enoic acid (32 mg, 105 μmol, from Preparation M) and (2R,3S)-1-((1S,3R)-3-(allyloxy)-6-methoxy-2,3-dihydro-1H-inden-1-ylamino)-3-amino-4-(3,5-difluorophenyl)butan-2-ol (33 mg, 79 μmol, from Preparation W) were coupled following a procedure analogous to Step CA (1) to afford 26 mg (40% yield) of the TFA salt of (S)-N-((2S,3R)-4-((1S,3R)-3-(allyloxy)-6-methoxy-2,3-dihydro-1H-inden-1-ylamino)-1-(3,5-difluorophenyl)-3-hydroxybutan-2-yl)-2-(3,3,3-trifluoro-N-methylpropylsulfonamido)hex-5-enamide. LRMS (M+H)$^+$=704.4; $^1$H NMR (500 MHz, CDCl$_3$) δ ppm 1.54-1.67 (m, 1H) 1.86-2.05 (m, 3H) 2.39 (d, J=14.95 Hz, 1H) 2.47-2.74 (m, 6H) 2.76-2.94 (m, 1H) 3.00-3.15 (m, 3H) 3.23-3.32 (m, 1H) 3.79 (s, 3H) 3.94-4.17 (m, 4H) 4.68 (d, 1H) 4.82 (d, J=5.19 Hz, 1H) 4.95-5.07 (m, 2H) 5.22 (d, J=10.38 Hz, 1H) 5.30 (dd, J=17.24, 1.37 Hz, 1H) 5.64-5.79 (m, 1H) 5.83-5.96 (m, J=6.71 Hz, 1H) 6.54-6.86 (m, 5H) 6.95 (dd, J=8.55, 2.14 Hz, 1H) 7.16 (d, J=1.53 Hz, 1H) 7.35 (d, J=8.24 Hz, 1H) 8.14-8.49 (br s, 1H) 9.48-9.81 (br s, 1H).

Step CO (2): The product from Step CO (1) (26 mg, 31.8 μmol) was subject to the ring-closing metathesis procedure described in Step CA (2) to afford 13 mg (52% yield) of the TFA salt of the title compound. LC-MS (M+H)$^+$=676.4; $^1$H NMR (500 MHz, CDCl$_3$) δ ppm 2.05-2.20 (m, 1H) 2.21-2.40 (m, 4H) 2.43-2.71 (m, 3H) 2.86 (d, J=4.58 Hz, 2H) 3.01-3.42 (m, 3H) 3.76-4.19 (m, 6H) 4.25-4.35 (m, 1H) 4.72 (d, J=4.88 Hz, 1H) 4.85 (s, 1H) 5.35-5.55 (m, 1H) 5.69-5.77 (m, 1H) 5.96-6.32 (m, 3H) 6.59-6.77 (m, 3H) 6.86-6.91 (m, 1H) 6.99 (s, 1H) 7.11 (s, 1H) 7.18-7.29 (m, 2H) 7.37 (dd, J=8.24, 1.83 Hz, 1H) 8.13-8.34 (m, 1H) 8.79-9.33 (m, 1H).

Example 16

5,5,5-trifluoro-pentanoic acid [(1S,4R,5S,8S,15R)-5-(3,5-difluoro-benzyl)-4-hydroxy-19-methoxy-7-oxo-14-oxa-2,6-diaza-tricyclo[13.6.1.0$^{16,21}$]docosa-11,16(21),17,19-tetraen-8-yl]-methyl-amide

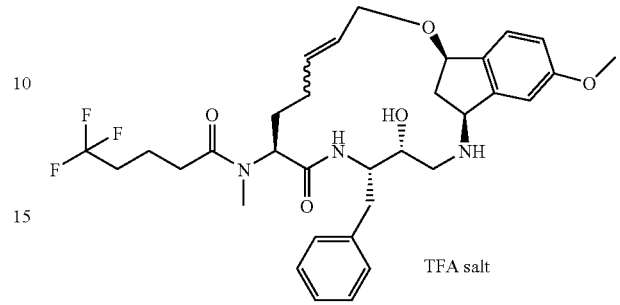

TFA salt

Step CP (1): (S)-2-(5,5,5-Trifluoro-N-methylpentanamido)hex-5-enoic acid (30 mg, 105 μmol, from Preparation L) and (2R,3S)-1-((1S,3R)-3-(allyloxy)-6-methoxy-2,3-dihydro-1H-inden-1-ylamino)-3-amino-4-phenylbutan-2-ol (40 mg, 105 μmol, from Preparation V) were coupled following a procedure analogous to Step CA (1) to afford 68 mg (57% yield) of the TFA salt of (S)-N-((2S,3R)-4-((1S,3R)-3-(allyloxy)-6-methoxy-2,3-dihydro-1H-inden-1-ylamino)-3-hydroxy-1-phenylbutan-2-yl)-2-(5,5,5-trifluoro-N-methylpentanamido)hex-5-enamide. HRMS (M+H)$^+$=646.3471; $^1$H NMR (400 MHz, CDCl$_3$) δ ppm 1.56-1.92 (m, 6H) 2.03-2.23 (m, 3H) 2.28-2.46 (m, 3H) 2.58-2.73 (m, 2H) 2.75-3.00 (m, 3H) 3.11-3.33 (m, 1H) 3.74-3.84 (m, 3H) 3.88-4.14 (m, 3H) 4.21-4.33 (m, 1H) 4.67-5.00 (m, 4H) 5.16-5.23 (m, 1H) 5.24-5.35 (m, 1H) 5.65 (s, 1H) 5.80-5.99 (m, 1H) 6.89-7.01 (m, 1H) 7.04-7.45 (m, 8H) 8.44-8.87 (m, 1H) 9.55-9.87 (m, 1H).

Step CP (2): The product from Step CP (1) (68 mg, 60.3 μmol) was subject to the ring-closing metathesis procedure described in Step CA (2) to afford 16.6 mg (36% yield) of the TFA salt of the title compound. LC-MS (M+H)$^+$=618.4; HRMS (M+H)$^+$=618.3173; $^1$H NMR (400 MHz, CDCl$_3$) δ ppm 0.95-2.70 (m, 16H) 2.75-3.54 (m, 4H) 3.75-3.91 (m, 4H) 3.91-4.11 (m, 1H) 4.10-4.57 (m, 2H) 4.66-4.94 (m, 2H) 5.35-5.74 (m, 2H) 6.96 (d, J=2.01 Hz, 1H) 7.06-7.28 (m, 6H) 7.35 (d, J=8.31 Hz, 1H).

Example 17

2-methyl-hexanoic acid [(1S,4R,5S,8S,14R)-5-(3,5-difluoro-benzyl)-4-hydroxy-18-methoxy-7-oxo-13-oxa-2,6-diaza-tricyclo[12.6.1.0$^{15,20}$]henicosa-10,15(20),16,18-tetraen-8-yl]-methyl-amide

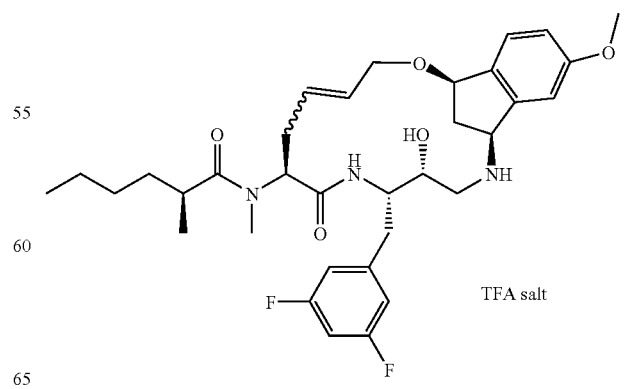

TFA salt

Step CQ (1): (S)-2-((S)-N,2-dimethylhexanamido)pent-4-enoic acid (57 mg, 239 μmol, diastereomer A from Preparation D) and (2R,3S)-1-((1S,3R)-3-(allyloxy)-6-methoxy-2,3-dihydro-1H-inden-1-ylamino)-3-amino-4-(3,5-difluorophenyl)butan-2-ol (100 mg, 239 μmol, from Preparation W) were coupled following a procedure analogous to Step CA (1) to afford 123 mg (68% yield) of the TFA salt of (S)-N-((S)-1-((2S,3R)-4-((1S,3R)-3-(allyloxy)-6-methoxy-2,3-dihydro-1H-inden-1-ylamino)-1-(3,5-difluorophenyl)-3-hydroxybutan-2-ylamino)-1-oxopent-4-en-2-yl)-N,2-dimethylhexanamide. LC-MS (M+H)$^+$=642.5; $^1$H NMR (500 MHz, CDCl$_3$) δ ppm 0.76-0.91 (m, 3H) 0.92-1.05 (m, 3H) 1.08-1.37 (m, 5H) 1.39-1.65 (m, 1H) 2.27-2.99 (m, 10H) 3.28 (s, 1H) 3.71-3.85 (m, 3H) 3.87-4.27 (m, 4H) 4.67-4.87 (m, 3H) 4.92-5.08 (m, 2H) 5.15-5.35 (m, 2H) 5.44-5.66 (m, 1H) 5.81-5.98 (m, 1H) 6.51-7.01 (m, 4H) 7.14-7.40 (m, 2H) 8.21-8.70 (m, 2H) 9.00-9.67 (m, 1H).

Step CQ (2): The product from Step CQ (1) (123 mg, 163 μmol) was subject to the ring-closing metathesis procedure described in Step CA (2) to afford 37 mg (31% yield) of the TFA salt of the title compound. LC-MS (M+H)$^+$=614.5; $^1$H NMR (500 MHz, CDCl$_3$) δ ppm 0.74-0.92 (m, 3H) 0.94-1.66 (m, 9H) 1.82-2.07 (m, 1H) 2.28-3.45 (m, 10H) 3.64-4.18 (m, 6H) 4.71 (d, J=5.49 Hz, 1H) 4.77-5.07 (m, 2H) 5.63 (s, 2H) 6.43-6.86 (m, 5H) 6.90-7.09 (m, 1H) 7.10-7.46 (m, 2H) 8.40-8.66 (m, 1H) 9.31-9.62 (m, 1H).

Example 18

(S)-2-methyl-hexanoic acid [(3R,6R,7S,10S)-7-(3,5-difluoro-benzyl)-6-hydroxy-9-oxo-3-phenyl-1-oxa-4,8-diaza-cyclotetradec-12-en-10-yl]-methyl-amide

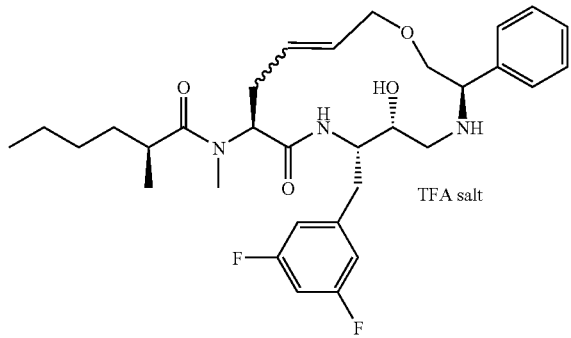

TFA salt

Step CR (1): (S)-2-((S)-N,2-dimethylhexanamido)pent-4-enoic acid (57 mg, 239 μmol, diastereomer A from Preparation D) and (2R,3S)-1-((R)-2-(allyloxy)-1-phenylethylamino)-3-amino-4-(3,5-difluorophenyl)butan-2-ol (59 mg, 160 μmol, from Preparation Q) were coupled following a procedure analogous to Step CA (1) to afford 75 mg (70% yield) of the TFA salt of N-((S)-(S)-N-((S)-1-((2S,3R)-4-((R)-2-(allyloxy)-1-phenylethylamino)-1-(3,5-difluorophenyl)-3-hydroxybutan-2-ylamino)-1-oxopent-4-en-2-yl)-N,2-dimethylhexanamide. LC-MS (M+H)$^+$=600.6; $^1$H NMR (300 MHz, CDCl$_3$) δ ppm 0.71-0.90 (m, 3H) 0.90-1.35 (m, 6H) 1.42-1.63 (m, 1H) 2.28-3.30 (m, 8H) 3.30-4.38 (m, 10H) 4.83-5.32 (m, 2H) 5.42-5.64 (m, 1H) 5.77-5.96 (m, 1H) 6.72 (s, 3H) 7.36-7.55 (m, 5H).

Step CR (2): The product from Step CR (1) (60 mg, 84 μmol) was subject to the ring-closing metathesis procedure described in Step CA (2) to afford 14.7 mg (25% yield) of the TFA salt of the title compound. HRMS (M+H)$^+$=572.3311; $^1$H NMR (300 MHz, CDCl$_3$) δ ppm 0.67-1.62 (m, 12H) 1.68-2.64 (m, 2H) 2.70-3.40 (m, 6H) 3.46-5.21 (m, 9H) 5.61-5.91 (m, 1H) 6.50-6.93 (m, 3H) 7.28-7.61 (m, 5H) 8.53-9.07 (m, 1H).

Example 19

N-((7R,8S,11S)-8-benzyl-7-hydroxy-4-(3-methoxyphenyl)-10-oxo-1-oxa-5,9-diazacyclopentadec-13-en-11-yl)-N-methyl-2-propylpentanamide

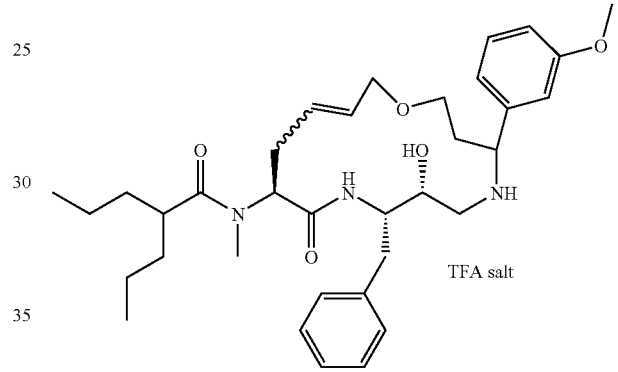

TFA salt

Step CS (1): (S)-2-(N-Methyl-2-propylpentanamido)pent-4-enoic acid (19 mg, 76 μmol, from Preparation A) and (2R,3S)-1-(3-(allyloxy)-1-(3-methoxyphenyl)propylamino)-3-amino-4-phenylbutan-2-ol (27 mg, 80 μmol, from Preparation R) were coupled following a procedure analogous to Step CA (1) to afford 45 mg (7% yield) of the TFA salt of (2S)-N-((2S,3R)-4-(3-(allyloxy)-1-(3-methoxyphenyl)propylamino)-3-hydroxy-1-phenylbutan-2-yl)-2-(N-methyl-2-propylpentanamido)pent-4-enamide as a mixture of diastereomers. LC-MS (M+H)$^+$=622.56; $^1$H NMR (300 MHz, CDCl$_3$) δ ppm 0.67-0.95 (m, 6H) 1.00-1.58 (m, 8H) 1.98-3.20 (m, 11H) 3.34-4.42 (m, 10H) 4.68-5.31 (m, 6H) 5.41-5.62 (m, 1H) 5.77-5.97 (m, 1H) 6.82-7.02 (m, 2H) 7.04-7.34 (m, 7H).

Step CS (2): The product from Step CS (1) (39 mg, 53 μmol) was subject to the ring-closing metathesis procedure described in Step CA (2) to afford 15.3 mg (41% yield) of the TFA salt of the title compound. HRMS (M+H)$^+$=594.3923; $^1$H NMR (300 MHz, CDCl$_3$) δ ppm 0.70-0.98 (m, 6H) 1.07-1.67 (m, 8H) 1.86-2.31 (m, 3H) 2.32-3.33 (m, 12H) 3.33-4.18 (m, 8H) 4.18-4.55 (m, 2H) 5.58-5.93 (m, 2H) 6.78-7.37 (m, 9H).

Example 20

3-ethoxy-thiophene-2-carboxylic acid ((1S,4R,5S,8S,14R)-5-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide

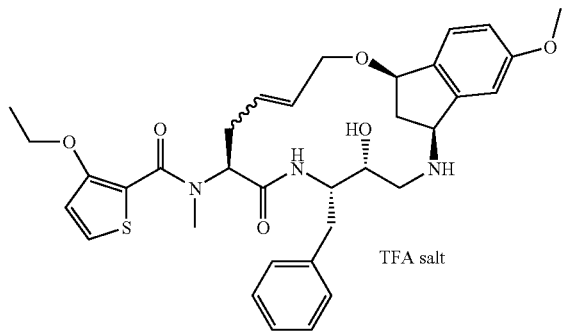

TFA salt

Step CT (1): (S)-2-(3-Ethoxy-N-methylthiophene-2-carboxamido)pent-4-enoic acid (19 mg, 67 µmol, from Preparation M) and (2R,3S)-1-((1S,3R)-3-(allyloxy)-6-methoxy-2,3-dihydro-1H-inden-1-ylamino)-3-amino-4-phenylbutan-2-ol (27 mg, 70 µmol, from Preparation V) were coupled following a procedure analogous to Step CA (1) to afford 30.5 mg (60% yield) of the TFA salt of N-((S)-1-((2S,3R)-4-((1S,3R)-3-(allyloxy)-6-methoxy-2,3-dihydro-1H-inden-1-ylamino)-3-hydroxy-1-phenylbutan-2-ylamino)-1-oxopent-4-en-2-yl)-3-ethoxy-N-methylthiophene-2-carboxamide. LC-MS (M+H)$^+$=648.42; $^1$H NMR (300 MHz, CDCl$_3$) δ ppm 1.26-1.42 (m, 3H) 2.27-3.07 (m, 9H) 3.21-3.44 (m, 1H) 3.68-4.28 (m, 8H) 4.68-4.87 (m, 2H) 4.91-5.35 (m, 3H) 5.51-5.70 (m, 1H) 5.78-5.99 (m, 1H) 6.51-6.79 (m, 4H) 6.85-7.52 (m, 10H).

Step CT (2): The product from Step CT (1) (30.5 mg, 40 µmol) was subject to the ring-closing metathesis procedure described in Step CA (2) to afford 11.2 mg (39% yield) of the TFA salt of the title compound. HRMS (M+H)$^+$=620.2800; $^1$H NMR (300 MHz, CDCl$_3$) δ ppm 1.14-1.46 (m, 4H) 1.91-2.09 (m, 1H) 2.25-2.84 (m, 6H) 3.00-3.52 (m, 3H) 3.69-3.91 (m, 4H) 3.98-4.48 (m, 5H) 4.55-5.04 (m, 3H) 5.50-5.69 (m, 1H) 6.75 (d, J=5.49 Hz, 1H) 6.91-7.50 (m, 10H).

Example 21

N-[(1S,4R,5S,8S,14R)-5-(3,5-difluoro-benzyl)-4-hydroxy-18-methoxy-7-oxo-13-oxa-2,6-diaza-tricyclo[12.6.1.0$^{15,20}$]henicosa-10,15(20),16,18-tetraen-8-yl]-4,4,4-trifluoro-2,N-dimethyl-butyramide (diastereomer A)

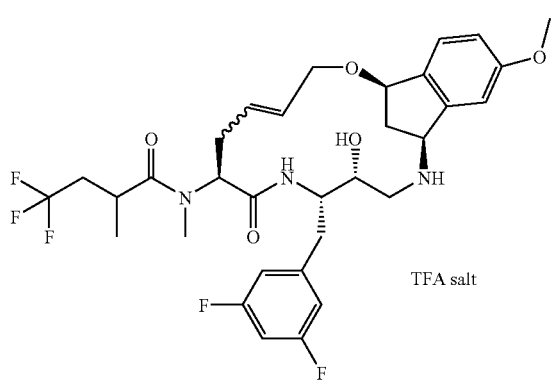

TFA salt

Step CU (1): (2S)-2-(4,4,4-Trifluoro-N,2-dimethylbutanamido)pent-4-enoic acid (64 mg, 239 µmol, diastereomer A from Preparation O) and (2R,3S)-1-((1S,3R)-3-(allyloxy)-6-methoxy-2,3-dihydro-1H-inden-1-ylamino)-3-amino-4-(3,5-difluorophenyl)butan-2-ol (100 mg, 239 µmol, from Preparation W) were coupled following a procedure analogous to Step CA (1) to afford 108 mg (58% yield) of the TFA salt of (2S)-N-((2S,3R)-4-((1S,3R)-3-(allyloxy)-6-methoxy-2,3-dihydro-1H-inden-1-ylamino)-1-(3,5-difluorophenyl)-3-hydroxybutan-2-yl)-2-(4,4,4-trifluoro-N,2-dimethylbutanamido)pent-4-enamide (diastereomer A). HRMS (M+H)$^+$=668.3111; $^1$H NMR (500 MHz, CDCl$_3$) δ ppm 1.05-1.18 (m, 3H) 2.00-2.16 (m, 1H) 2.28-2.46 (m, 2H) 2.53-2.75 (m, 6H) 2.77-3.06 (m, 2H) 3.14 (dd, J=14.65, 3.66 Hz, 1H) 3.28 (d, J=11.29 Hz, 1H) 3.70-4.26 (m, 9H) 4.72 (d, J=6.41 Hz, 1H) 4.82 (d, J=4.88 Hz, 1H) 4.92 (dd, J=10.68, 4.88 Hz, 1H) 4.97-5.09 (m, 2H) 5.22 (dd, J=10.38, 1.22 Hz, 1H) 5.31 (dd, J=17.09, 1.53 Hz, 1H) 5.49-5.62 (m, 1H) 5.83-5.97 (m, 1H) 6.49 (d, J=8.85 Hz, 1H) 6.56-6.77 (m, 3H) 6.95 (dd, J=8.39, 2.29 Hz, 1H) 7.20 (d, J=1.83 Hz, 1H) 7.30-7.39 (m, 1H) 9.73-10.02 (m, 1H).

Step CU (2): The product from Step CU (1) (94 mg, 120 µmol) was subject to the ring-closing metathesis procedure described in Step CA (2) to afford 62 mg (69% yield) of the TFA salt of the title compound. HRMS (M+H)$^+$=640.2826; $^1$H NMR (500 MHz, CDCl$_3$) δ ppm 1.13-1.21 (m, 4H) 1.92 (d, J=7.63 Hz, 1H) 2.08-2.20 (m, 1H) 2.33-2.49 (m, 2H) 2.53-2.73 (m, 3H) 2.76-2.84 (m, 2H) 2.94-3.34 (m, 7H) 3.72-3.89 (m, 4H) 3.97 (s, 1H) 4.08 (dd, J=10.83, 3.51 Hz, 1H) 4.72 (d, J=5.49 Hz, 1H) 4.84 (d, J=10.38 Hz, 1H) 4.89-4.98 (m, 1H) 5.56 (d, J=14.34 Hz, 1H) 5.60-5.70 (m, 1H) 6.52-6.65 (m, 2H) 6.90-7.03 (m, 1H) 7.17 (s, 1H) 7.31-7.37 (m, 1H) 8.51 (s, 1H) 9.24-9.42 (m, 1H).

Example 22

N-[(1S,4R,5S,8S,14R)-5-(3,5-difluoro-benzyl)-4-hydroxy-18-methoxy-7-oxo-13-oxa-2,6-diaza-tricyclo[12.6.1.0$^{15,20}$]henicosa-10,15(20),16,18-tetraen-8-yl]-4,4,4-trifluoro-2,N-dimethyl-butyramide (diastereomer B)

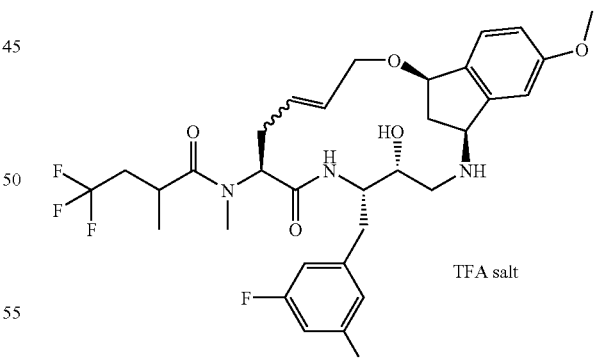

TFA salt

Step CV (1): (2S)-2-(4,4,4-Trifluoro-N,2-dimethylbutanamido)pent-4-enoic acid (64 mg, 239 µmol, diastereomer B from Preparation O) and (2R,3S)-1-((1S,3R)-3-(allyloxy)-6-methoxy-2,3-dihydro-1H-inden-1-ylamino)-3-amino-4-(3,5-difluorophenyl)butan-2-ol (100 mg, 239 µmol, from Preparation W) were coupled following a procedure analogous to Step CA (1) to afford 117 mg (63% yield) of the TFA salt of (2S)-N-((2S,3R)-4-((1S,3R)-3-(allyloxy)-6-methoxy-2,3-dihydro-1H-inden-1-ylamino)-1-(3,5-difluorophenyl)-3-hydroxybutan-2-yl)-2-(4,4,4-trifluoro-N,2-dimethylbutanamido)pent-4-enamide (diastereomer B). HRMS (M+H)+=668.3091; ¹H NMR (500 MHz, CDCl₃) δ ppm 1.98-2.11 (m, 1H) 2.34-2.45 (m, 2H) 2.46-2.75 (m, 6H) 2.85-2.96 (m, 2H) 3.08 (dd, J=14.95, 3.66 Hz, 1H) 3.30 (d, J=12.21 Hz, 1H) 3.75-3.82 (m, 3H) 3.88-3.98 (m, 1H) 4.03-4.12 (m, 2H) 4.13-4.22 (m, 1H) 4.69-4.80 (m, 2H) 4.82 (d, J=4.58 Hz, 1H) 5.02 (d, J=10.68 Hz, 1H) 5.05-5.09 (m, 1H) 5.18-5.61 (m, 6H) 5.84-5.96 (m, 1H) 6.58-6.74 (m, 3H) 6.87 (d, J=8.85 Hz, 1H) 6.95 (dd, J=8.39, 2.29 Hz, 1H) 7.18 (d, J=2.44 Hz, 1H) 7.32-7.38 (m, 1H) 8.37 (s, 1H) 9.43-9.63 (m, 1H).

Step CV (2): The product from Step CV (1) (106 mg, 135 μmol) was subject to the ring-closing metathesis procedure described in Step CA (2) to afford 56 mg (55% yield) of the TFA salt of the title compound. LC-MS (M+H)+=640.17; HRMS (M+H)+=640.2806; ¹H NMR (500 MHz, CDCl₃) δ ppm 1.10 (d, J=6.71 Hz, 4H) 1.93 (s, 1H) 2.03-2.16 (m, 1H) 2.39 (d, J=14.65 Hz, 1H) 2.45-2.53 (m, 1H) 2.54-2.71 (m, 2H) 2.75-2.81 (m, 2H) 2.89-3.33 (m, 9H) 3.76-3.90 (m, 3H) 4.00-4.12 (m, J=10.53, 3.81 Hz, 1H) 4.73 (d, J=5.49 Hz, 1H) 4.86 (d, J=10.38 Hz, 1H) 4.92-4.99 (m, 1H) 5.50-5.59 (m, J=7.32 Hz, 1H) 5.61-5.71 (m, 1H) 6.52-6.69 (m, 2H) 6.93-7.03 (m, 2H) 7.15 (s, 1H) 7.33-7.38 (m, 1H).

Example 23

(S)-2-methyl-hexanoic acid [(1S,4R,5S,8S,14S)-5-(3,5-difluoro-benzyl)-4-hydroxy-18-methoxy-7-oxo-13-oxa-2,6-diaza-tricyclo[12.6.1.0¹⁵,²⁰]henicosa-10,15(20),16,18-tetraen-8-yl]-methyl-amide

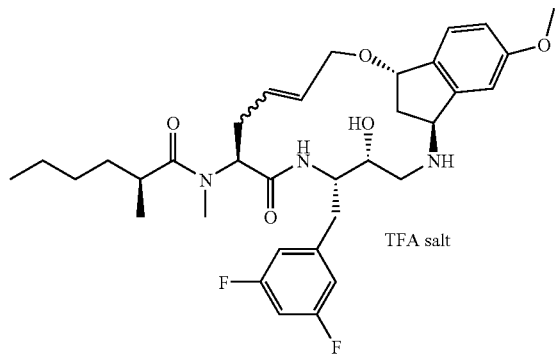

TFA salt and

Example 24

(S)-2-methyl-hexanoic acid [(1R,4R,5S,8S,14R)-5-(3,5-difluoro-benzyl)-4-hydroxy-18-methoxy-7-oxo-13-oxa-2,6-diaza-tricyclo[12.6.1.0¹⁵,²⁰]henicosa-10,15(20),16,18-tetraen-8-yl]-methyl-amide

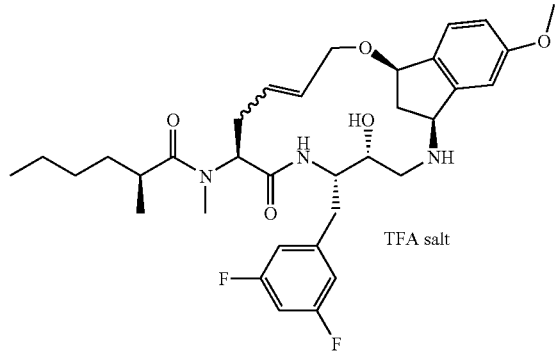

TFA salt

Step CVA (1): (S)-2-((S)-N,2-Dimethylhexanamido)pent-4-enoic acid (147 mg, 610 μmol, diastereomer A from Preparation D) and the product mixture from Preparation X (231 mg, 555 μmol) were coupled following a procedure analogous to Step CA (1) to afford 256 mg (61% yield) of the TFA salt of a diastereomeric mixture of (S)-N-((S)-1-((2S,3R)-4-((1R,3R)-3-(allyloxy)-6-methoxy-2,3-dihydro-1H-inden-1-ylamino)-1-(3,5-difluorophenyl)-3-hydroxybutan-2-ylamino)-1-oxopent-4-en-2-yl)-N,2-dimethylhexanamide and (S)-N-((S)-1-((2S,3R)-4-((1S,3S)-3-(allyloxy)-6-methoxy-2,3-dihydro-1H-inden-1-ylamino)-1-(3,5-difluorophenyl)-3-hydroxybutan-2-ylamino)-1-oxopent-4-en-2-yl)-N,2-dimethylhexanamide. LC-MS (M+H)+=642.5.

Step CVA (2): The product from Step CVA (1) (256 mg, 67.8 μmol) was subject to the ring-closing metathesis procedure described in Step CA (2) to afford the TFA salts of diastereomer A (23 mg) and diastereomer B (34) of the title compound. Data for diastereomer A: LC-MS (M+H)+=614.5; ¹H NMR (500 MHz, CDCl₃) δ ppm 0.62-1.42 (m, 12H) 1.90-3.48 (m, 12H) 3.57-4.11 (m, 5H) 4.39 (d, J=12.21 Hz, 1H) 4.85-5.32 (m, 3H) 5.45-6.08 (m, 3H) 6.39-6.83 (m, 4H) 6.84-7.03 (m, 1H) 7.05-7.53 (m, 2H) 8.62 (s, 1H) 9.40 (s, 1H). Data for diastereomer B: LC-MS (M+H)+=614.4; ¹H NMR (500 MHz, CDCl₃) δ ppm 0.60-1.40 (m, 12H) 1.86-3.46 (m, 12H) 3.54-4.09 (m, 5H) 4.39 (d, J=12.51 Hz, 1H) 4.84-5.37 (m, 3H) 5.48-6.05 (m, 3H) 6.45-6.82 (m, 4H) 6.84-7.04 (m, 1H) 7.08-7.48 (m, 2H) 8.63 (s, 1H) 9.24-9.54 (m, 1H).

Example 25

Diastereomeric Mixture of (S)-2-methyl-hexanoic acid [(1R,4R,5S,8S,14S)-5-(3,5-difluoro-benzyl)-4-hydroxy-7-oxo-13-oxa-2,6-diaza-bicyclo[12.2.1]heptadec-10-en-8-yl]-methyl-amide

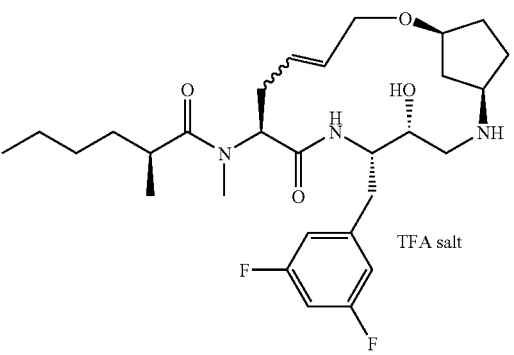

TFA salt

105 and (S)-2-methyl-hexanoic acid [(1S,4R,5S,8S,14R)-5-(3,5-difluoro-benzyl)-4-hydroxy-7-oxo-13-oxa-2,6-diaza-bicyclo[12.2.1]heptadec-10-en-8-yl]-methyl-amide

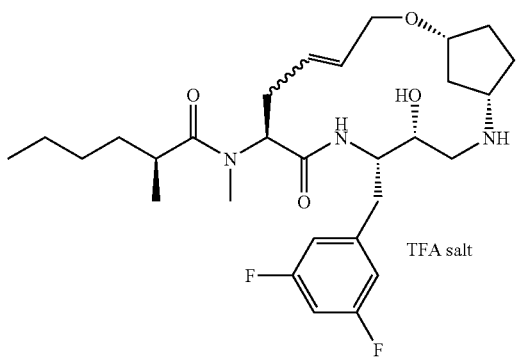

TFA salt

Step CW (1): (S)-2-((S)-N,2-Dimethylhexanamido)pent-4-enoic acid (69 mg, 285 μmol, diastereomer A from Preparation D) and the product mixture from Preparation Y (88 mg, 259 μmol) were coupled following a procedure analogous to Step CA (1) to afford 90 mg (47% yield) of the TFA salt of a diastereomeric mixture of (S)-N-((S)-1-((2S,3R)-4-((1R,3S)-3-(allyloxy)cyclopentylamino)-1-(3,5-difluorophenyl)-3-hydroxybutan-2-ylamino)-1-oxopent-4-en-2-yl)-N,2-dimethylhexanamide and (S)-N-((S)-1-((2S,3R)-4-((1S,3R)-3-(allyloxy)cyclopentylamino)-1-(3,5-difluorophenyl)-3-hydroxybutan-2-ylamino)-1-oxopent-4-en-2-yl)-N,2-dimethylhexanamide. LC-MS (M+H)$^+$=564.4; $^1$H NMR (500 MHz, CDCl$_3$) δ ppm 0.66-1.39 (m, 13H) 1.39-1.81 (m, 2H) 1.85-2.28 (m, 4H) 2.28-3.30 (m, 10H) 3.54-3.70 (m, 1H) 3.80-4.22 (m, 4H) 4.81-5.30 (m, 4H) 5.42-5.92 (m, 2H) 6.54-6.91 (m, 3H) 7.79 (s, 3H) 8.79-9.35 (m, J=79.65 Hz, 1H).

Step CW (2): The product from Step CW (1) (90 mg, 133 μmol) was subject to the ring-closing metathesis procedure described in Step CA (2) to afford 25 mg (29% yield) of the TFA salts of a diastereomeric mixture of the titled compounds. LC-MS (M+H)$^+$=536.4; $^1$H NMR (500 MHz, CDCl$_3$) δ ppm 0.68-1.63 (m, 13H) 1.63-2.28 (m, 6H) 2.39-3.52 (m, 9H) 3.55-4.20 (m, 4H) 4.23-4.81 (m, 1H) 4.85-5.14 (m, 1H) 5.41-5.89 (m, 2H) 6.50-6.81 (m, 3H) 6.96-7.29 (m, 1H) 7.29-8.08 (m, 2H) 8.38 (d, J=81.48 Hz, 1H).

Example 26

Diastereomeric Mixture of pentane-1-sulfonic acid ((1R,7S,10S,11R,14R)-10-benzyl-11-hydroxy-17-methoxy-8-oxo-2-oxa-9,13-diaza-tricyclo[12.7.0.0$^{15,20}$]henicosa-4,15(20),16,18-tetraen-7-yl)-methyl-amide

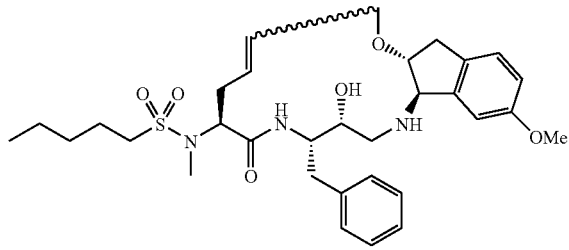

106 and pentane-1-sulfonic acid ((1S,7S,10S,11R,14S)-10-benzyl-11-hydroxy-17-methoxy-8-oxo-2-oxa-9,13-diaza-tricyclo[12.7.0.0$^{15,20}$]henicosa-4,15(20),16,18-tetraen-7-yl)-methyl-amide

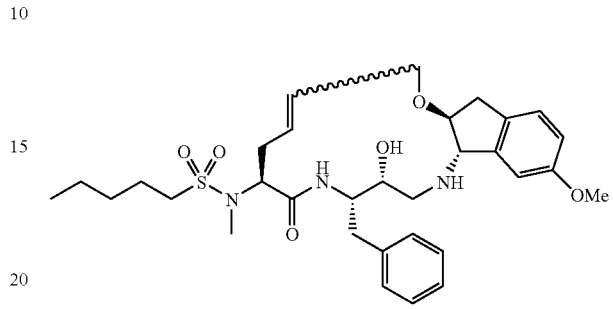

Step CX (1): To a solution of the products from Preparation AB in DCM (0.30 mL) was added (S)-N-methyl-N-(1-oxo-pent-4-en-2-yl)pentane-1-sulfonamide (33 mg, from Preparation J), Py.BOP (96 mg) and DIEA (86 μL). The resulting reaction mixture was stirred at rt for 12 h. Boc$_2$O (40 mg) was added, and the reaction was continued for 4 h. The solvents were evaporated in vacuo, and the residue was purified by preparative TLC eluting with 40% EtOAc/60% hexane to give a 1:1 mixture of tert-butyl (1R,2R)-2-(allyloxy)-6-methoxy-2,3-dihydro-1H-inden-1-yl((2R,3S)-2-hydroxy-3-((S)-2-(N-methylpentylsulfonamido)pent-4-enamido)-4-phenylbutyl)carbamate and tert-butyl(1S,2S)-2-(allyloxy)-6-methoxy-2,3-dihydro-1H-inden-1-yl((2R,3S)-2-hydroxy-3-((S)-2-(N-methylpentylsulfonamido)pent-4-enamido)-4-phenylbutyl)carbamate as a colorless oil (55 mg). LC-MS R$_t$ 2.50 min (method A), (M+H)$^+$ 728.52.

Step CX (2): To a solution of the products from Step CX (1) (50 mg) in DCM (23 mL) at rt was added the 1$^{st}$ generation Grubbs catalyst (11 mg). The resulting reaction mixture was heated at 50° C. for 12 h. The solvents were evaporated in vacuo, and the residue was purified by preparative TLC eluting with 40% EtOAc/60% hexane to give a 1:1 mixture of (3R,4S,7S,13aR,18bR)-tert-butyl 4-benzyl-3-hydroxy-17-methoxy-7-(N-methylpentylsulfonamido)-6-oxo-2,3,4,5,6,7,8,11,12,13a,14,18b-dodecahydro-1H-indeno[2,1-b][1,4,8]oxadiazacyclopentadecine-1-carboxylate and (3R,4S,7S,13aS,18bS)-tert-butyl 4-benzyl-3-hydroxy-17-methoxy-7-(N-methylpentylsulfonamido)-6-oxo-2,3,4,5,6,7,8,11,12,13a,14,18b-dodecahydro-1H-indeno[2,1-b][1,4,8]oxadiazacyclopentadecine-1 carboxylate as a colorless oil (21 mg). LC-MS R$_t$ 2.12 min (method A), (M+H)$^+$ 700.56.

Step CX (3): To a solution of the products from Step CX (2) (10 mg) in DCM (0.10 mL) at rt was added TFA (50 μL), and the resulting reaction mixture was stirred at rt for 30 min. The reaction mixture was evaporated in vacuo to give TFA salt of a mixture of the titled compounds as a colorless oil (10 mg). LC-MS R$_t$ 1.89 min (method A), (M+H)$^+$ 600.43.

Example 27

Diastereomeric Mixture of pentane-1-sulfonic acid ((1R,7S,10S,11R,14R)-10-benzyl-11-hydroxy-17-methoxy-8-oxo-2-oxa-9,13-diaza-tricyclo[12.7.0.0$^{15,20}$]henicosa-15(20),16,18-trien-7-yl)-methyl-amide

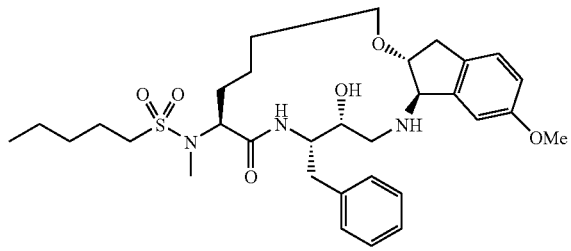

and pentane-1-sulfonic acid ((1S,7S,10S,11R,14S)-10-benzyl-11-hydroxy-17-methoxy-8-oxo-2-oxa-9,13-diaza-tricyclo[12.7.0.0$^{15,20}$]henicosa-15(20),16,18-trien-7-yl)-methyl-amide

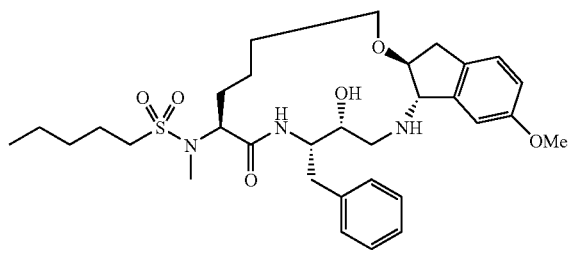

Step CY (1): To a solution of the products from Step CX (2) (10 mg) in EtOAc (0.80 mL) was added 10% Pd/C (one spatula-tip). The resulting mixture was stirred under a hydrogen balloon atmosphere for 12 h. The reaction mixture was passed through a pad of Celite, and the filtrate was evaporated in vacuo to give the reduced product as a colorless oil (10 mg). LC-MS $R_t$ 2.35 min (method A), (M+H)$^+$ 702.53.

Step CY (2): To a solution of the products from Step CY (1) (10 mg) in DCM (0.10 mL) at rt was added TFA (50 μL), and the resulting reaction mixture was stirred at rt for 30 min. The reaction mixture was evaporated in vacuo to give the TFA salt of a mixture of the titled compounds as a colorless oil (10 mg). Isomer A: LC-MS $R_t$ 1.88 min (method A), (M+H)$^+$ 602.37. Isomer B: LC-MS $R_t$ 1.97 min (method A), (M+H)$^+$ 602.37.

Example 28 pentane-1-sulfonic acid ((1S,7S,10S,11R,14R)-10-benzyl-11-hydroxy-17-methoxy-8-oxo-2-oxa-9,13-diaza-tricyclo[12.7.0.0$^{15,20}$]henicosa-4,15(20),16,18-tetraen-7-yl)-methyl-amide

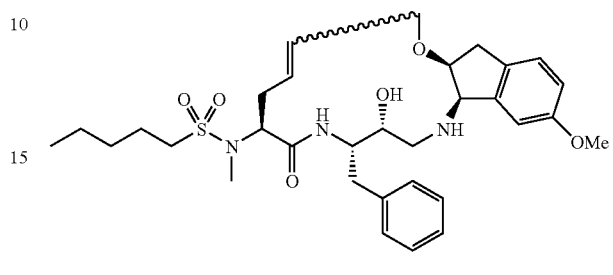

Step CZ (1): The product from Preparation AC was converted to tert-butyl (1R,2S)-2-(allyloxy)-6-methoxy-2,3-dihydro-1H-inden-1-yl((2R,3S)-2-hydroxy-3-((S)-2-(N-methylpentylsulfonamido)pent-4-enamido)-4-phenylbutyl)carbamate (20 mg, colorless oil) by a procedure analogous to Step CX (1). LC-MS $R_t$ 2.52 min (method A), (M+H)$^+$ 728.50.

Step CZ (2): The product from Step CZ (1) were converted to (3R,4S,7S,12aS,17bR,E)-tert-butyl 4-benzyl-3-hydroxy-16-methoxy-7-(N-methylpentylsulfonamido)-6-oxo-3,4,5,6,7,8,11,12a,13,17b-decahydroindeno[2,1-b][1,4,8]oxadiazacyclotetradecine-1(2H)-carboxylate (9 mg, mixture of isomers, colorless oil) by a procedure analogous to Step CX (2). LC-MS $R_t$ 2.38 min (method A), (M+H)$^+$ 700.35.

Step CZ (3): The products from Step CZ (2) were converted to the title compound (4 mg, mixture of isomers, colorless oil) by a procedure analogous to Step CX (3). LC-MS $R_t$ 1.66 min (method A), (M+H)$^+$ 600.46.

Example 29 pentane-1-sulfonic acid ((1S,7S,10S,11R,14R)-10-benzyl-11-hydroxy-17-methoxy-8-oxo-2-oxa-9,13-diaza-tricyclo[12.7.0.0$^{15,20}$]henicosa-15(20),16,18-trien-7-yl)-methyl-amide

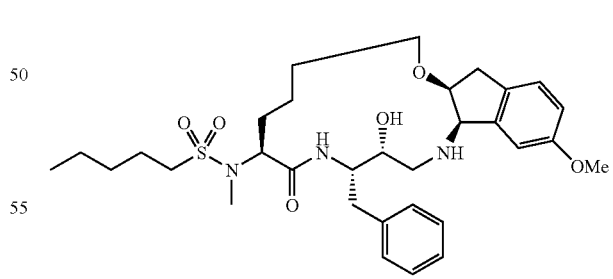

Step DA (1): The product from Step CZ (3) (4 mg) was hydrogenated by a procedure analogous to Step CY (1) to afford the reduced product (4 mg) as a colorless oil. LC-MS $R_t$ 2.18 min (method A), (M+H)$^+$ 702.57.

Step DA (2): The product from Step DA (1) was deprotected by a procedure analogous to Step CY (2) to afford the TFA salt of the titled compound (5 mg) as a colorless oil. LC-MS $R_t$ 2.38 min (method A), (M+H)$^+$ 602.31.

Examples 30

3,3,3-trifluoro-propane-1-sulfonic acid ((1R,8S,11S, 12R,15R)-11-benzyl-12-hydroxy-18-methoxy-9-oxo-2-oxa-10,14-diaza-tricyclo[13.7.0.0$^{16,21}$]docosa-4,16(21),17,19-tetraen-8-yl)-methyl-amide (isomer A)

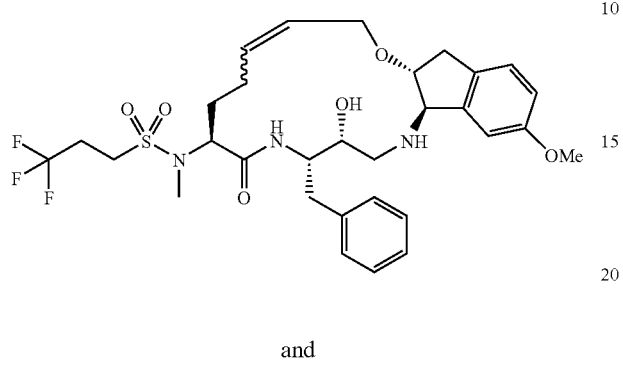

and

Example 31

3,3,3-trifluoro-propane-1-sulfonic acid ((1R,8S,11S, 12R,15R)-11-benzyl-12-hydroxy-18-methoxy-9-oxo-2-oxa-10,14-diaza-tricyclo[13.7.0.0$^{16,21}$]docosa-4,16(21),17,19-tetraen-8-yl)-methyl-amide (isomer B)

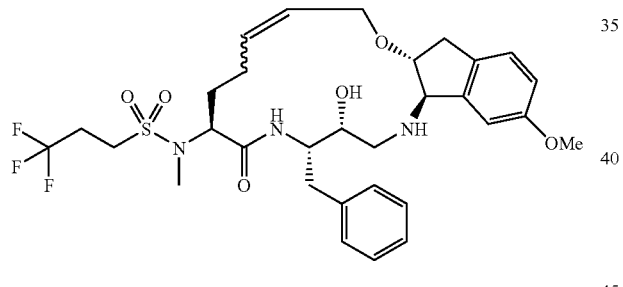

Step DB (1): The product from Preparation AD was coupled with (S)-2-(3,3,3-trifluoro-N-methylpropylsulfonamido)hex-5-enoic acid (45 mg, from Preparation M) following a procedure analogous to Step CX (1) to afford tert-butyl (1R,2R)-2-(allyloxy)-6-methoxy-2,3-dihydro-1H-inden-1-yl((2R,3S)-2-hydroxy-4-phenyl-3-((S)-2-(3,3,3-trifluoro-N-methylpropylsulfonamido)hex-5-enamido)butyl)carbamate as a colorless oil (48 mg). LC-MS R$_t$ 2.53 min (method A), (M+H)$^+$ 768.36.

Step DB (2): The product from Step DB (1) (45 mg) was converted to a separable mixture of two diastereomers of (Z)-(1R,8S,11S,12R,15R)-11-benzyl-12-hydroxy-18-methoxy-8-[methyl-(3,3,3-trifluoro-propane-1-sulfonyl)-amino]-9-oxo-2-oxa-10,14-diaza-tricyclo[13.7.0.0$^{16,21}$]docosa-4,16(21),17,19-tetraene-14-carboxylic acid tert-butyl ester (5 mg of isomer A, and 5 mg of isomer B, colorless oils) by a procedure analogous to Step CX (2). Data for isomer A: HPLC retention time: 2.40 min (method A). MS (ESI) (M+H)$^+$ 740.32. Data for isomer B: LC-MS R$_t$ 2.39 min (method A), (M+H)$^+$ 740.32.

Step DB (3): The product isomers A and B from Step DB (2) were individually converted to isomers A and B of the TFA salts of the title compound (5 mg of isomer A, and 5 mg of isomer B, colorless oils) by a procedure analogous to Step CX (3). Data for isomer A: LC-MS R$_t$ 1.83 min (method A), (M+H)$^+$ 640.30. Data for isomer B: LC-MS R$_t$ 1.84 min (method A), (M+H)$^+$ 640.24.

Example 32

3,3,3-trifluoro-propane-1-sulfonic acid ((Z)-(1S,8S, 11S,12R,15R)-11-benzyl-12-hydroxy-18-methoxy-9-oxo-2-oxa-10,14-diaza-tricyclo[13.7.0.0$^{16,21}$]docosa-4,16(21),17,19-tetraen-8-yl)-methyl-amide

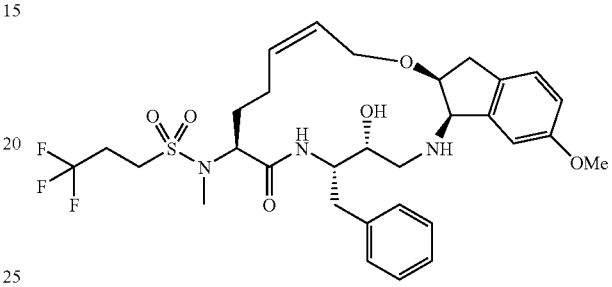

and

Example 33

3,3,3-trifluoro-propane-1-sulfonic acid ((E)-(1S,8S, 11S,12R,15R)-11-benzyl-12-hydroxy-18-methoxy-9-oxo-2-oxa-10,14-diaza-tricyclo[13.7.0.0$^{16,21}$]docosa-4,16(21),17,19-tetraen-8-yl)-methyl-amide

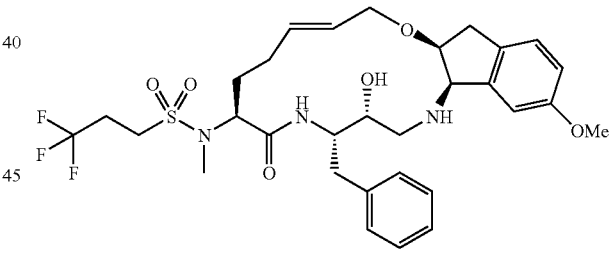

Step DC (1): To a solution of (2R,3S)-1-((1R,2S)-2-(allyloxy)-6-methoxy-2,3-dihydro-1H-inden-1-ylamino)-3-amino-4-phenylbutan-2-ol from Step AE in DCM (1.8 mL) was added (S)-2-(3,3,3-trifluoro-N-methylpropylsulfonamido)hex-5-enoic acid (48 mg), Py.BOP (117 mg) and triethylamine (90 μL), and the resulting reaction mixture was stirred at rt for 12 h. Solvents were evaporated and the residue was purified by HPLC to give (S)-N-((2S,3R)-4-((1R,2S)-2-(allyloxy)-6-methoxy-2,3-dihydro-1H-inden-1-ylamino)-3-hydroxy-1-phenylbutan-2-yl)-2-(3,3,3-trifluoro-N-methylpropylsulfonamido)hex-5-enamide as its TFA salt (65 mg). LC-MS R$_t$ 1.93 min (method B), (M+H)$^+$ 668.33.

Step DC (2): To a solution of the product from Step DC (1) (56 mg) in DCM (23 mL) at rt was added 1$^{st}$ generation Grubbs catalyst (18 mg), and the resulting reaction mixture was heated at 55° C. for 12 h. The solvents were evaporated in vacuo, and the residue was purified by prepHPLC to give the E and Z isomers of the title compound. Data for the Z isomer:

HPLC retention time: 1.83 min (method B). MS (ESI) (M+H)+ 640.34. 1H NMR (C6D6, 400 MHz) δ 7.53 (br. s), 7.33 (br. s), 7.25 (m), 7.05 (m), 6.85 (dd), 6.78 (d), 6.72 (d), 5.40 (m), 5.25 (dt), 4.51 (s), 4.20 (d), 4.10 (dd), 3.70 (m), 3.60 (3H, s), 3.20 (m), 1.6-2.8 (m). Data for the E-isomer: LC-MS R$_t$ 1.81 min (method B), (M+H)+ 640.28. 1H NMR (C6D6, 400 MHz) δ 7.60 (br. s), 7.1-7.4 (m), 7.07 (t), 6.87 (dd), 6.80 (d), 6.67 (d), 5.33-5.42 (m), 5.24-5.32 (dt), 4.45 (br. S), 4.32 (br. S), 4.0 (d), 3.75 (dd), 3.60 (3H, s), 1.7-3.3 (m).

Examples 34

3,3,3-trifluoro-propane-1-sulfonic acid ((1S,8S,11S, 12R,15R)-11-benzyl-12-hydroxy-18-methoxy-9-oxo-2-oxa-10,14-diaza-tricyclo[13.7.0.0$^{16,21}$]docosa-16(21),17,19-trien-8-yl)-methyl-amide

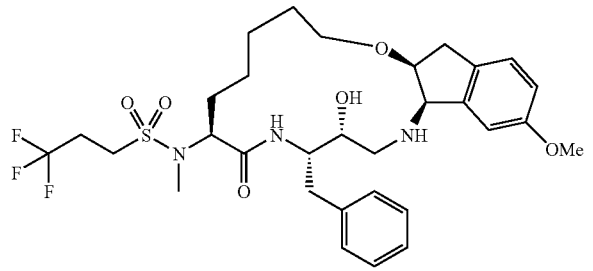

Step DD (1): To a solution of Example 31 (3 mg) in ethyl aceatete (0.20 mL) at rt was added a spatula-tip of 10% Pd/C, and the resulting suspension was stirred at rt for 3 h. The solvent was removed to give the title compound as a colorless oil (3 mg). LC-MS R$_t$ 1.87 min (method B), (M+H)+ 642.35.

Example 35

3,3,3-trifluoro-propane-1-sulfonic acid ((1S,4R,5S, 8S,15R)-5-benzyl-4-hydroxy-19-methoxy-7-oxo-13-oxa-2,6-diaza-tricyclo[13.6.1.0$^{16,21}$]docosa-10,16 (21),17,19-tetraen-8-yl)-methyl-amide (isomer A)

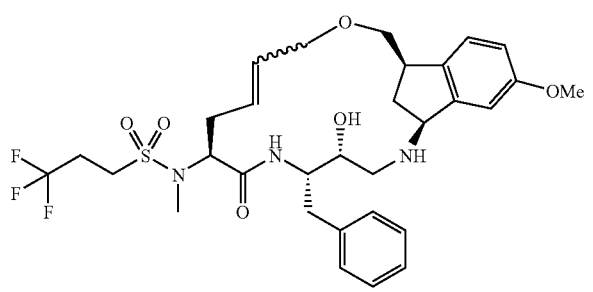

and

Example 36

3,3,3-trifluoro-propane-1-sulfonic acid ((1S,4R,5S, 8S,15R)-5-benzyl-4-hydroxy-19-methoxy-7-oxo-13-oxa-2,6-diaza-tricyclo[13.6.1.0$^{16,21}$]docosa-10,16 (21),17,19-tetraen-8-yl)-methyl-amide (isomer B)

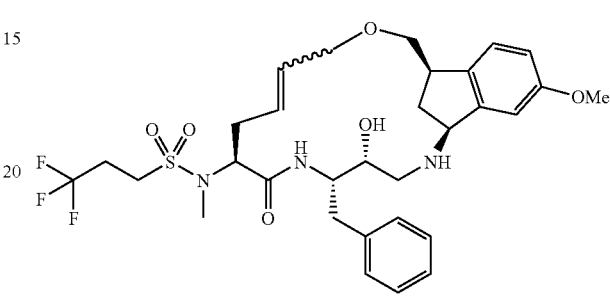

Step DE (1): The product from Preparation AG was coupled with (S)-2-(3,3,3-trifluoro-N-methylpropylsulfonamido)hex-5-enoic acid (21 mg, from Preparation M) by a procedure analogous to Step CX (1) to afford tert-butyl (1S, 3R)-3-(allyloxymethyl)-6-methoxy-2,3-dihydro-1H-inden-1-yl((2R,3S)-2-hydroxy-4-phenyl-3-((S)-2-(3,3,3-trifluoro-N-methylpropylsulfonamido)pent-4-enamido)butyl) carbamate as a colorless oil (45 mg). LC-MS R$_t$ 2.24 min (method A), (M+H)+ 742.77.

Step DE (2): The product from Step DE (1) (43 mg) underwent ring-closing by a procedure analogous to Step CX (2) to afford a separable mixture of two olfin isomers of (1S,4R,5S, 8S,15R)-5-benzyl-4-hydroxy-19-methoxy-8-[methyl-(3,3, 3-trifluoro-propane-1-sulfonyl)-amino]-7-oxo-13-oxa-2,6-diaza-tricyclo[13.6.1.0$^{16,21}$]docosa-10,16(21),17,19-tetraene-2-carboxylic acid tert-butyl ester (14 mg of isomer A, and 14 mg of isomer B, colorless oils). Data for isomer A: 1H NMR (400 MHz), CDCl3) δ 7.2-7.6 (m), 6.85 (dd), 6.20 (br. S), 6.05 (d), 5.65 (br. S), 5.44 (m), 3.78 (3H, s), 3.6-4.2 (m), 3.20 (m), 2.95 (m), 2.5-2.8 (m), 1.9 (m), 1.7 (m), 1.51 (9H, s), 1.26 (m). LC-MS R$_t$ 2.37 min (method A), (M+H)+ 714.47. Data for isomer B: 1H NMR (400 MHz), CDCl3) δ 7.1-7.3 (m), 6.77 (m), 6.48 (d), 5.74 (d), 5.3-5.6 (m), 3.79 (3H, s), 3.4-4.2 (m), 3.20 (m), 2.95 (m), 2.70 (m), 1.90 (m), 1.60 (m), 1.52 (9H, s), 1.30 (m).

Step DE (3): The product isomers A and B from Step DE (2) were individually converted to isomers A and B of the TFA salts of the title compound (4 mg of isomer A, and 4 mg of isomer B, colorless oils) by a procedure analogous to Step CX (3). Data for isomer A: LC-MS R$_t$ 1.70 min (method A), (M+H)+ 614.16. Data for isomer B: LC-MS R$_t$ 1.71 min (method A), (M+H)+ 614.30.

Example 37

3,3,3-trifluoro-propane-1-sulfonic acid ((1S,4R,5S, 8S,15S)-5-benzyl-4-hydroxy-19-methoxy-7-oxo-13-oxa-2,6-diaza-tricyclo[13.6.1.0$^{16,21}$]docosa-10,16(21),17,19-tetraen-8-yl)-methyl-amide

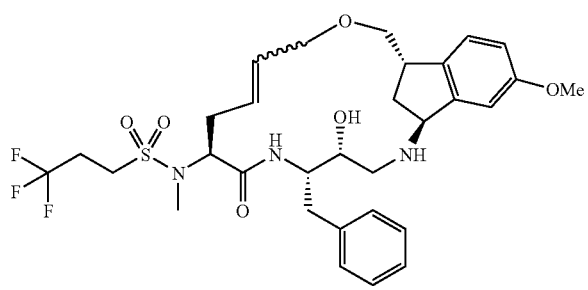

Step DF (1): 2,2,2-Trifluoro-N-((1S,3S)-3-(hydroxymethyl)-6-methoxy-2,3-dihydro-1H-inden-1-yl)acetamide (130 mg) (diasteromer B) from Step AF (3) was converted into the title compound by a series of procedures analogous to Steps AF (4-5), AB (1-2), and CX (1-3). LC-MS R$_t$ 1.92 min (method A), (M+H)$^+$ 614.39.

Example 38

N-((4R,5S,8S)-5-(3,5-difluorobenzyl)-4-hydroxy-17-methyl-7-oxo-1,2,3,4,5,6,7,8,9,12,13,14-dodecahydrobenzo[g][1,5]diazacyclohexadecin-8-yl)-N-methylpentane-1-sulfonamide

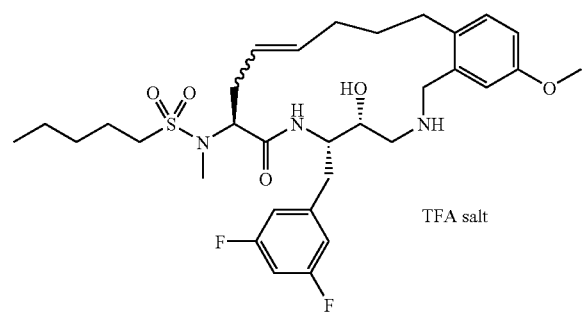

Step DG (1): To a solution of the product from Preparation AH (45.8 mg, 0.072 mmol) and (S)-2-(propylsulfonamido) pent-4-enoic acid (18.0 mg, 0.072 mmol) in DMF (1.2 mL) were added EDC (13.8 mg, 0.072), HOBT monohydrate (9.7 mg, 0.072 mmol) and DIPEA (0.07 mL, 0.396 mmol). The reaction mixture was stirred at rt overnight. The product was isolated by reverse phase chromatography to give (S)-N-((2S, 3R)-1-(3,5-difluorophenyl)-3-hydroxy-4-(5-methoxy-2-(pent-4-enyl)benzylamino)butan-2-yl)-2-(propylsulfonamido)pent-4-enamide trifluoroacetate salt (34.5 mg, 63%) as colorless oil. LC-MS (M+H)$^+$=650.77. $^1$H NMR (CD$_3$OD, 500 MHz) δ 7.30-6.73 (m, 6H) 5.88 (m, 1H) 5.72 (m, 1H) 5.23-4.97 (m, 4H) 4.50-3.80 (m, 6H) 3.50-2.70 (m, 8H) 2.90 (s, 3H) 2.50 (m, 2H) 2.40 (m, 2H) 2.30 (m, 2H) 1.80-1.20 (m, 8H) 0.95 (t, J=7.0 Hz, 3H).

Step DG (2): To a solution of product from Step DG (1) (34.5 mg, 0.045 mmol) in 1,2-dichloroethane (4.0 mL) was added Hoveyda-Grubbs catalyst (7.6 mg, 0.009 mmol). The reaction was stirred at rt overnight. The solvent was removed in vacuum and the residue was purified by silica gel chromatography to give the title compound as a TFA salt (14.4 mg, 44%) as colorless oil. LC-MS (M+H)$^+$=622.62. $^1$H NMR (CD$_3$OD, 500 MHz) δ 7.38-6.70 (m, 6H) 5.85-5.29 (m, 2H) 4.50-3.80 (m, 6H) 3.50-2.30 (m, 14H) 3.02 (s, 3H) 2.15-0.75 (m, 8H) 0.95 (t, J=7.0 Hz, 3H).

Example 39

N-((4R,5S,8S)-5-(3,5-difluorobenzyl)-4-hydroxy-17-methyl-7-oxo-1,2,3,4,5,6,7,8,9,12,13,14-dodecahydrobenzo[g][1,5]diazacyclohexadecin-8-yl)-N-methylpentane-1-sulfonamide

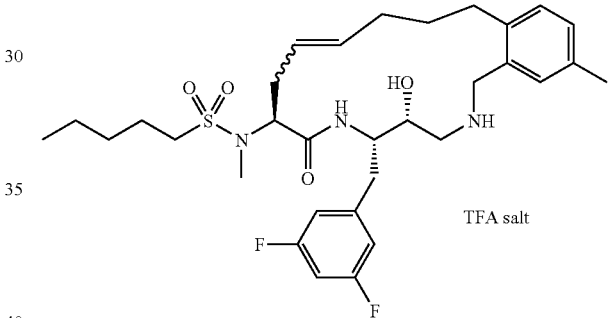

Step DH (1): To a solution of the product from Preparation AL (22 mg, 0.036 mmol) and (S)-2-(N-methylpentylsulfonamido)pent-4-enoic acid (9.0 mg, 0.036 mmol) in DMF (1.0 mL) were added EDC (6.9 mg, 0.036), HOBT monohydrate (4.9 mg, 0.036 mmol), and DIPEA (0.03 mL, 0.198 mmol). The reaction mixture was stirred at rt overnight. The product was isolated by reverse phase chromatography to give (S)-N-((2S,3R)-1-(3,5-difluorophenyl)-3-hydroxy-4-(5-methyl-2-(pent-4-enyl)benzylamino)butan-2-yl)-2-(N-methylpentylsulfonamido) pent-4-enamide trifluoroacetate salt (18.5 mg, 69%) as a colorless oil. LC-MS (M+H)$^+$=634.51.

Step DH (2): To a solution of product from Step DH (1) (18.5 mg, 0.025 mmol) in 1,2-dichloroethane (4.0 mL) was added Hoveyda-Grubbs catalyst (3.1 mg, 0.005 mmol). The reaction was heated to 60° C. and stirred overnight. The product was isolated by reverse phase chromatography to give the title compound as a trifluoroacetate salt (2.7 mg, 18%) as a colorless oil. LC-MS (M+H)$^+$=606.57. $^1$H NMR (CDCl$_3$, 500 MHz) δ 7.62-7.43 (m, 8H) 5.79 (m, 1H) 5.06-4.92 (m, 2H) 3.96-3.93 (m, 3H) 2.69-2.66 (m, 3H) 2.16-2.12 (m, 2H) 2.05 (m, 1H) 1.79-1.14 (m, 17H) 0.96-0.94 (t, J=10 Hz, 2H) 0.88-0.85 (t, J=5 Hz).

Example 40

N-((4R,5S,8S)-5-(3,5-difluorobenzyl)-4-hydroxy-17-(trifluoromethyl)-7-oxo-1,2,3,4,5,6,7,8,9,12,13,14-dodecahydrobenzo[g][1,5]diazacyclohexadecin-8-yl)-N-methylpentane-1-sulfonamide

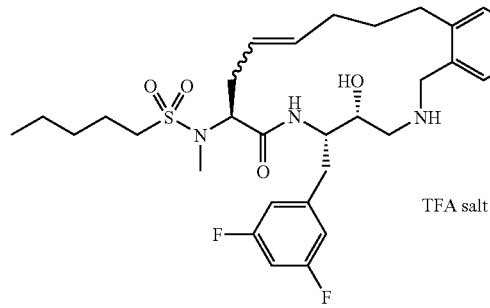

TFA salt

Step DI (1): To a solution of the product from Preparation AM (64 mg, 0.095 mmol) and (S)-2-(N-methylpentylsulfonamido)pent-4-enoic acid (23.7 mg, 0.095 mmol) in DMF (1.5 mL) were added EDC (18.2 mg, 0.095 mmol), HOBT monohydrate (12.8 mg, 0.095), and DIPEA (0.09 mL, 0.525 mmol). The reaction mixture was stirred at rt overnight. The product was isolated by reverse phase chromatography to give (S)-N-((2S,3R)-1-(3,5-difluorophenyl)-3-hydroxy-4-(2-(pent-4-enyl)-5-(trifluoromethyl)benzylamino)butan-2-yl)-2-(N-methylpentyl sulfonamido)pent-4-enamide trifluoroacetate salt (18.0 mg, 27%) as a colorless oil. LC-MS (M+H)$^+$=688.58.

Step DI (2): To a solution of the products from Step DI (1) (18.0 mg, 0.026 mmol) in 1,2-dichloroethane (4.0 mL) was added Hoveyda-Grubbs catalyst (3.3 mg, 0.005 mmol). The reaction was heated to 60° C. and stirred overnight. The product was isolated by reverse phase chromatography to give N-((4R,5S,8S)-5-(3,5-difluorobenzyl)-4-hydroxy-7-oxo-17-(trifluoromethyl)-1,2,3,4,5,6,7,8,9,12,13,14-dodeca hydrobenzo[g][1,5]diazacyclohexadecin-8-yl)-N-methylpentane-1-sulfonamide trifluoroacetate salt (5.4 mg, 32%) as a colorless oil. LC-MS (M+H)$^+$=659.17. $^1$H NMR (CDCl$_3$, 500 MHz) δ 7.76-7.58 (m, 3H) 6.82-6.63 (m, 3H) 5.63 (m, 1H) 5.29-5.12 (m, 1H) 4.17-3.02 (m, 8H) 2.89-2.77 (m, 3H) 2.62-2.59 (m, 2H) 2.48-2.47 (d, J=10 Hz, 2H) 2.28-1.52 (m, 5H) 1.42-1.25 (m, 6H) 0.94-0.82 (m, 5H).

Example 42

N-((3R,6R,7S,10S)-7-(3,5-difluorobenzyl)-6-hydroxy-3-isobutyl-9-oxo-1-oxa-4,8-diazacyclopentadec-13-en-10-yl)-3,3,3-trifluoro-N-methylpropane-1-sulfonamide

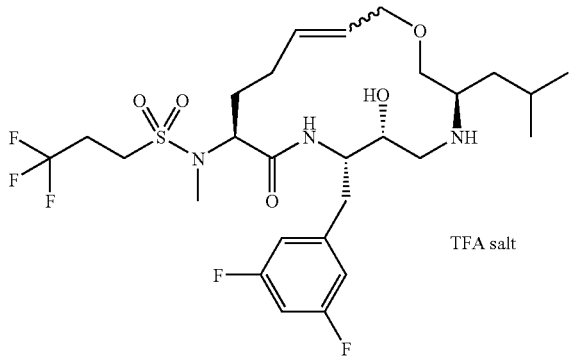

TFA salt

Step DK (1): To a solution of the product from Preparation AO (50 mg, 0.14 mmol) and (S)-2-(3,3,3-trifluoro-N-methylpropylsulfonamido)hex-5-enoic acid (42.5 mg, 0.14 mmol) in DMF (1.5 mL) were added EDC (26.8 mg, 0.14), HOBT monohydrate (18.9 mg, 0.14 mmol), and DIPEA (0.13 mL, 0.77 mmol). The reaction mixture was stirred at rt overnight. The product was isolated by reverse phase chromatography to give (S)-N-((2S,3R)-4-((R)-1-(allyloxy)-4-methylpentan-2-ylamino)-1-(3,5-difluorophenyl)-3-hydroxybutan-2-yl)-2-(3,3,3-trifluoro-N-methylpropylsulfonamido)hex-5-enamide (12.0 mg, 13%) as a colorless oil. LC-MS (M+H)$^+$=642.07. $^1$H NMR (CD$_3$OD, 500 MHz) δ 6.89-6.88 (m, 2H) 6.79 (m, 1H) 6.00-5.82 (m, 2H) 5.38-5.25 (m, 2H) 5.11-5.03 (m, 2H) 4.24 (m, 1H) 4.12-3.93 (m, 4H) 3.76-3.48 (m, 3H) 3.28-2.76 (m, 7H) 2.62-2.56 (m, 2H) 2.13-1.50 (m, 6H) 1.02-0.98 (m, 6H).

Step DK (2): To a solution of the product from Step DK (1) (12.0 mg, 0.019 mmol) in 1,2-dichloroethane (1.0 mL) was added Hoveyda-Grubbs catalyst (2.0 mg, 0.003 mmol). The reaction was heated to 60° C. and stirred overnight. The product was isolated by reverse phase chromatography to give the title compound as a trifluoroacetate salt (2.2 mg, 19%) as a colorless oil LC-MS (M+H)$^+$=614.24. $^1$H NMR (CDCl$_3$, 500 MHz) δ 6.86-6.65 (m, 3H) 5.65-5.45 (m, 2H) 4.26-2.05 (m, 18H) 1.71-1.37 (m, 5H) 0.99-0.95 (m, 6H).

Example 43 pentane-1-sulfonic acid ((1S,4R,5S,8S,14R)-5-(3,5-dichloro-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide

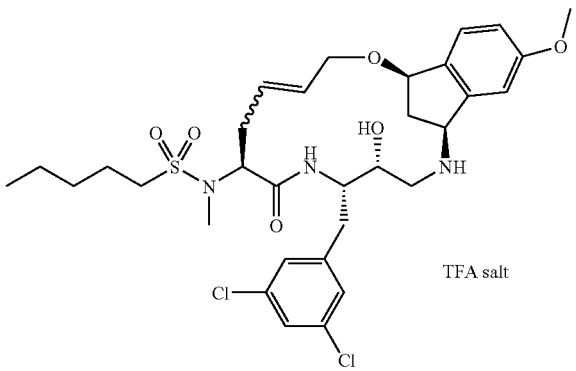

TFA salt

Step DL (1): A mixture of 28.7 mg (S)-2-(N-methylpentylsulfonamido)pent-4-enoic acid (0.11 mmol, from Preparation J), 24.8 mg 1-[3-(dimethyamino)propyl]-3-ethyl carbodiimide methiodide (0.083 mmol), 18 mg 1-hydroxybenzotriazole, 3 drops triethylamine and 1 mL dimethyl-formamide was stirred for 15 minutes at rt. The mixture was then added to 21 mg (2R,3S)-1-((1S,3R)-3-(allyloxy)-6-methoxy-2,3-dihydro-1H-inden-1-ylamino)-3-amino-4-(3,5-dichloro-phenyl)butan-2-ol (0.046 mmoles, from Preparation BG) and the reaction mixture was allowed to stand at rt overnight. The reaction mixture was subjected to preparative HPLC, with the peak at 9.8 min collected to yield 14.1 mg (S)-N-((2S,3R)-4-((1S,3R)-3-(allyloxy)-6-methoxy-2,3-dihydro-1H-inden-1-yl-amino)-1-(3,5-dichlorophenyl)-3-hydroxybutan-2-yl)-2-(N-methylpentyl-sulfonamido)pent-4-enamide as a clear oil. LC-MS R$_t$ 2.18 min (method A), (M+H)$^+$=696.0, 698.0; HRMS (M+H)$^+$=696.2653; $^1$H NMR (500 MHz, CDCl$_3$) δ 7.31 (d, J=8.2, 1H) 7.19 (s, 1H) 7.14 (s, 2H) 6.94 (d, J=2.1, 1H) 6.84 (d of d, J=8.2, 2.4, 1H) 6.68 (d, J=9.1, 1H) 5.95 (m, 1H) 5.69

(m, 1H) 5.31 (d, J=17, 1H) 5.2-5.08 (m, 3H) 4.77 (t, J=5.5, 1H) 4.17 (d of d, J=9.5, 5.7, 1H) 4.10 (m, 1H) 3.80 (s, 3H) 3.51 (m, 1H) 3.12 (d of d, J=14.3, 3.7, 1H) 2.90 (m, 4H) 2.67 (m, 4H) 2.54 (s, 3H) 2.31 (m, 2H) 1.93 (d, J=13.4 of t, J=4.6, 1H) 1.75 (m, 2H) 1.33 (m, 4H) 0.90 (t, J=7, 3H).

Step DL (2): A mixture of 4 mg of the product from Step DL (1), 0.5 mL DCM and 1 mg 1,3-bis-(2,4,6-trimethylphenyl)-2-imidazolidinylidene)dichloro(phenylmethylene)-(tricyclohexylphosphine)-ruthenium was stirred under an atmosphere of nitrogen overnight at rt. The reaction mixture was evaporated and the peak at 10.0 min was collected to give 1.4 mg of the title compound as a white solid (trifluoroacetic acid salt). LC-MS R$_t$ 2.1 min (method A), (M+H)$^+$=668.1; $^1$H NMR (500 MHz, CDCl$_3$) δ 7.38 (d, J=8.2, 1H) 7.17 (s, 1H) 7.10 (s, 2H) 7.06 (s, 1H) 6.99 (d, J=8.2, 1H) 5.64 (m, 2H) 4.74 (d, J=4.6, 2H) 4.26 (br s, 1H) 4.1 (d, J=10.8, 2H) 3.89-3.78 (m, 7H) 3.3-3.2 (br d, J=11, 1H) 3.12-3.02 (m, 2H) 2.95-2.85 (m, 2H) 2.84-2.71 (m, 6H) 2.68 (s, 3H) 2.60-2.45 (m, 3H) 2.10 (br d, J=11, 2H) 1.72 (m, 4H) 1.38-1.27 (m, 7H) 1.24 (s, 1H) 1.19 (d, J=6.4, 1H) 0.89 (dist t, J=7.0, 4H).

Example 44

3,3,3-Trifluoro-propane-1-sulfonic acid ((1S,4R,5S,8S,14R)-5-(3,5-dichloro-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide

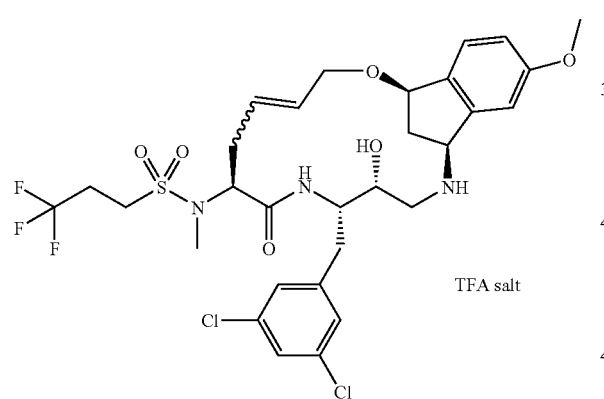

TFA salt

Step DM (1): (S)-2-(3,3,3-Trifluoro-N-methyl-propylsulfonamido)pent-4-enoic acid (33 mg, 0.11 mmol, from Preparation J) was coupled with (2R,3S)-1-((1S,3R)-3-(allyloxy)-6-methoxy-2,3-dihydro-1H-inden-1-ylamino)-3-amino-4-(3,5-dichloro-phenyl)butan-2-ol (50 mg, from Preparation BG) by a procedure analogous to Step DL (1) to afford 19.1 mg of (S)-N-((2S,3R)-4-((1S,3R)-3-(allyloxy)-6-methoxy-2,3-dihydro-1H-inden-1-ylamino)-1-(3,5-dichlorophenyl)-3-hydroxybutan-2-yl)-2-(3,3,3-trifluoro-N-methylpropylsulfonamido)pent-4-enamide as a clear oil. LC-MS R$_t$ 2.10 min (method A), (M+H)$^+$=722.1, 724.0; HRMS (M+H)$^+$=722.2031; $^1$H NMR (500 MHz, CDCl$_3$) δ 7.35 (d, J=8.2, 1H) 7.18 (s, 1H) 7.08 (s, 2H) 6.95 (d of d, J=8.5, 2.1, 1H) 6.78 (d, J=8.8, 1H) 5.91 (m, 1H) 5.66 (m, 1H) 5.31 (d, J=17.4, 1H) 5.24-5/12 (m, 3H) 4.82 (d, J=4.6, 1H) 4.72 (br d, J=6.7, 1H) 4.21 (d of d, J=5.2, 5.2, 1H 3H) 4.01 (m, 3H) 3.80 (s, 3H) 3.26 (d, J=12.2, 1H) 3.10 (m, 5H) 2.90-2.80 (m, 2H) 2.72-2.50 (m, 5H0, 2.56 (s, 3H) 2.44-2.31 (m, 2H) 1.32 (t, J=7.3, 2H) 1.24 (s, 1H).

Step DM (2): The product from Step DM (1) underwent ring-closing metathesis by a procedure analogous to Step DL (2) to afford 9.3 mg of the title compound as a reddish oil. LC-MS R$_t$ 2.02 min (method A), (M+H)$^+$=694, 696; HRMS (M+H)$^+$=694.1715; $^1$H NMR (500 MHz, CDCl$_3$) δ 7.27 (d, J=8.2, 1H) 7.11 (s, 1H) 7.05 (s, 2H) 6.90 (s, 1H) 6.85 (d, J=8.5, 1H) 5.62 (m, 1H) 5.50 (m, 1H) 4.66 (d, J=5.2, 1H) 4.35 (br d, J=6.1, 1H) 4.10-3.98 (m, 3H) 3.85-3.72 (m, 5H) 3.52 (br s, 1H) 3.12-2.98 (m, 3H) 2.92-2.85 (m, 1H) 2.75-2.58 (m, 7H) 2.56-2.45 (m, 3H) 2.37-2.29 (m, 2H) 2.21 (d, J=13.7, 1H) 2.10 (m, 1H).

Example 45

3,3,3-Trifluoro-propane-1-sulfonic acid ((1S,4R,5S,8S,14R)-5-(3,5-dichloro-benzyl-4-hydroxy-18-methoxy-7-oxo-13-oxa-2,6-diaza-tricyclo[12.6.1.0$^{15,20}$]henicosa-15(20),16,18-trien-8-yl)-methyl-amide

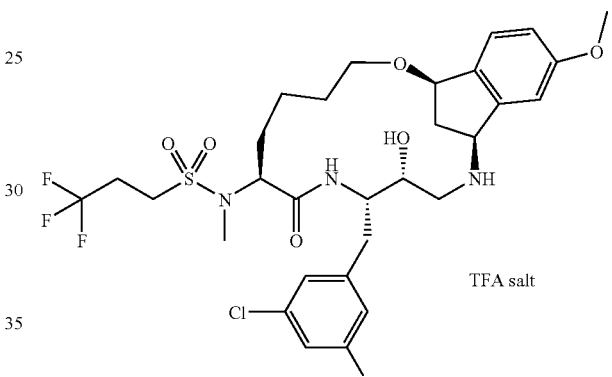

TFA salt and

Example 46

3,3,3-Trifluoro-propane-1-sulfonic acid ((1S,4R,5S,8S,14R)-5-(3-chloro-benzyl-4-hydroxy-18-methoxy-7-oxo-13-oxa-2,6-diaza-tricyclo[12.6.1.0$^{15,20}$]henicosa-15(20),16,18-trien-8-yl)-methyl-amide

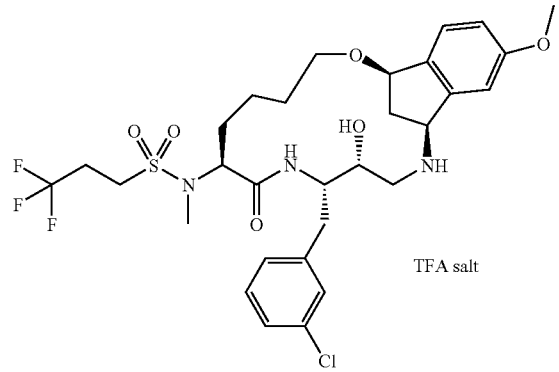

TFA salt

Example 47

3,3,3-Trifluoro-propane-1-sulfonic acid ((1S,4R,5S,8S,14R)-5-(benzyl-4-hydroxy-18-methoxy-7-oxo-13-oxa-2,6-diaza-tricyclo[12.6.1.0^{15,20}]henicosa-15(20),16,18-trien-8-yl)-methyl-amide

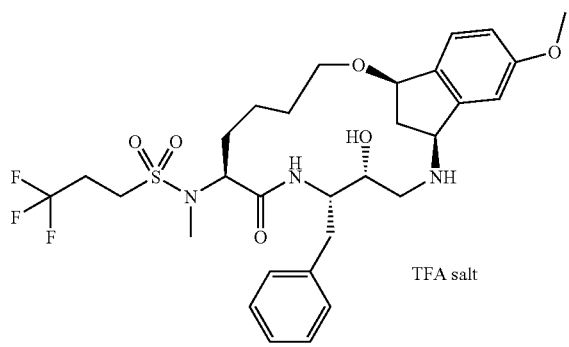

TFA salt

Step DN (1): A mixture of 5 mL methyl alcohol, 3.7 mg 10% palladium on charcoal and 5.5 mg of Example 43 was stirred under a balloon atmosphere of hydrogen for 72 h, then the reaction mixture was filtered and evaporated. The residue was subjected to purification by preparative HPLC to give three components (retention times 9.5 min, 9.0 min, and 8.6 min): 1.1 mg of Example 44 as a clear oil (LC-MS $R_t$ 1.93 min (method A), $(M+H)^+$=696.1), 1.3 mg Example 45 as a clear oil (LC-MS $R_t$ 1.85 min (method A), $(M+H)^+$=662), and 3.2 mg of Example 46 as a clear oil (LC-MS $R_t$ 1.68 min (method A), $(M+H)^+$=628.2).

Example 48

(S)-2-methyl-hexanoic acid ((1S,4R,5S,8S,14R)-5-(3,5-dichloro-benzyl-4-hydroxy-18-methoxy-7-oxo-13-oxa-2,6-diaza-tricyclo[12.6.1.0^{15,20}]henicosa-10,15(20),16,18-tetraen-8-yl)-methyl-amide

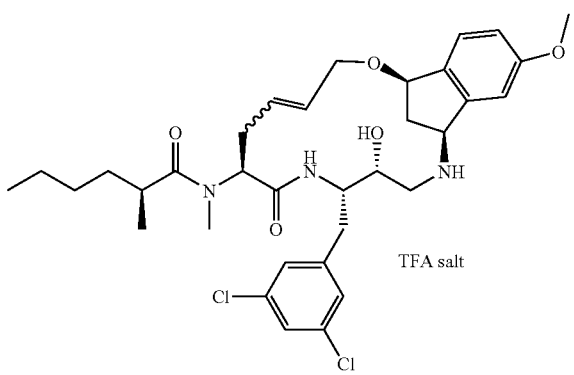

TFA salt

Step DO (1): (S)-2-((S)-N,2-Dimethylhexanamido)pent-4-enoic acid (26.5 mg, 0.11 mmoles, diastereomer A from Preparation D) and (2R,3S)-1-((1S,3R)-3-(allyloxy)-6-methoxy-2,3-dihydro-1H-inden-1-ylamino)-3-amino-4-(3,5-dichloro-phenyl)butan-2-ol (47 mg, from Preparation BG) were coupled by a procedure analogous to Step DL (1) to afford 29.5 mg of (S)-N-((S)-1-((2S,3R)-4-((1S,3R)-3-(allyloxy)-6-methoxy-2,3-dihydro-1H-inden-1-ylamino)-1-(3,5-dichloro-phenyl)-3-hydroxybutan-2-ylamino)-1-oxopent-4-en-2-yl)-N,2-dimethylhexan-amide as a clear oil. LC-MS $R_t$ 2.25 min (method A), $(M+H)^+$=674.2, 676; $^1$H NMR (500 MHz, CDCl$_3$) δ 7.30 (d, J=8.2, 1H) 7.18 (m, 1H) 7.09 (s, 1H) 7.06 (s, 1H) 6.94 (s, 1H) 6.84 (d, J=8.2, 1H) 6.37 (d, J=8.8, 1H) 5.95 (m, 1H) 5.58 (m, 1H) 5.30 (m, 1H) 5.18 (d, J=10.3, 1H) 5.10-4.97 (m, 3H) 4.77 (m, 1H) 4.18-4.05 (m, 3H) 3.81 (s, 1H) 3.80 (s, 3H) 3.46 (m, 1H) 3.13 (d of d, J=15, 2, 3.1, 1H) 3.01 (d of d, J=14.6, 3.6, 1H) 2.87 (s, 1H) 2.86-2.78 (m, 2H) 2.74-2.45 (m, 7H) 2.42-2.32 (m, 1H) 1.93 (m, 1H) 1.65-1.45 (m, 1H) 1.37-1.13 (m, 6H) 1.02 (d, J=7.0, 2H) 0.95 (d, J=7.0, 1H) 0.87 (m, 4H).

Step DO (2): The product from Step DO (1) underwent ring-closing metathesis by a procedure analogous to Step DL (2) to afford 12.4 mg (47% yield) of the title compound as a light brown solid. LC-MS $R_t$ 2.17 min (method A), $(M+H)^+$=646.2; HRMS $(M+H)^+$=646.2833.

Example 49

(S)-2-methyl-hexanoic acid ((1S,4R,5S,8S,14R)-5-(3,5-dichloro-benzyl)-4-hydroxy-18-methoxy-7-oxo-13-oxa-2,6-diaza-tricyclo[12.6.1.0^{15,20}]henicosa-15(20),16,18-trien-8-yl)-methyl-amide

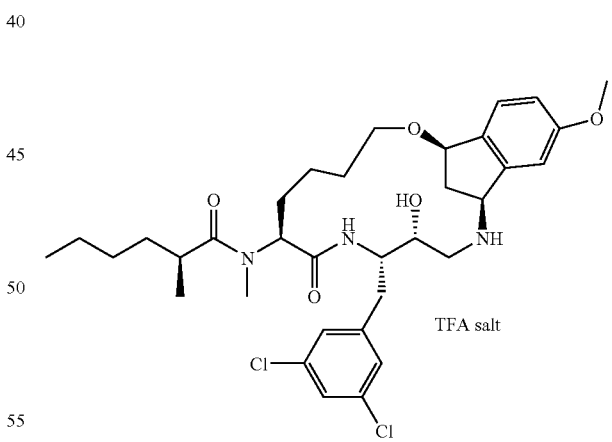

TFA salt

Step DP (1): The product from Example 47 (4.8 mg), 1.2 mg 10% palladium-on-charcoal and 1.5 mL methyl alcohol was stirred for 3 hr at ambient temperature under a balloon atmosphere of hydrogen. The hydrogen was replaced by nitrogen and the catalyst was filtered off and the solvent evaporated. The residue was subjected to preparative HPLC (collecting the peak at 10.2 min) to give 2.8 mg of the title compound as a clear oil. LC-MS $R_t$ 2.01 min (method A), $(M+H)^+$=648.2.

Example 50

(1S,4R,5S,15R)-5-(3,5-dichloro-benzyl)-4-hydroxy-19-methoxy-14-oxa-2,6-diaza-tricyclo[13.6.1.0[16,21]]docosa-11,16(21),17,19-tetraen-7-one

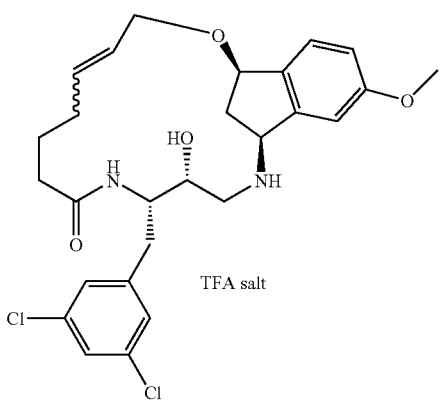

TFA salt

Step DQ (1): 5-Hexenoic acid (Alfa Aesar, 0.096 mmole) and (2R,3S)-1-((1S,3R)-3-(allyloxy)-6-methoxy-2,3-dihydro-1H-inden-1-ylamino)-3-amino-4-(3,5-dichloro-phenyl)butan-2-ol (0.04 mmol, from Preparation BG) were coupled by a procedure analogous to Step DL (1) to afford 20 mg of N-((2S,3R)-4-((1S,3R)-3-(allyloxy)-6-methoxy-2,3-dihydro-1H-inden-1-ylamino)-1-(3,5-dichlorophenyl)-3-hydroxy-butan-2-yl)hex-5-enamide as a clear oil. LC-MS $R_t$ 2.1 min (method A), (M+H)$^+$=547.1.

Step DQ (2): The product from Step DQ (1) underwent ring-closing metathesis by a procedure analogous to Step DL (2) to afford 1.7 mg of the title compound as a red solid. LC-MS $R_t$ 1.8 min (method A), (M+H)$^+$=519.2, 521.

Example 51 pentane-1-sulfonic acid ((4R,5S,8S)-5-benzyl-4-hydroxy-18-methoxy-7-oxo-2,6,13-triaza-tricyclo[12.6.1.0[15,20]]henicosa-15(20),16,18-trien-8-yl)-methyl-amide

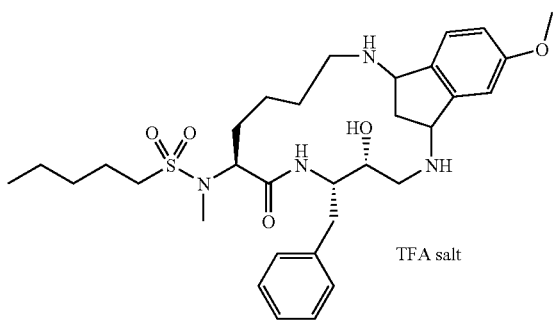

TFA salt

Step DR (1): Diisopropylethylamine (225 μL, 1.29 mmol) and HBTU (108 mg, 0.285 mmol) were added to a solution of the product from Preparation AQ (2) (192 mg, 0.258 mmol), (S)-2-(N-methylpentylsulfonamido)pent-4-enoic acid (68 mg, 0.258 mmol, from Preparation J), and HOBt (39 mg, 0.285 mmol) in 5 mL DCM. The solution was stirred at rt for 1 h. The reaction was diluted with 75 mL EtOAc, then extracted once with 50 mL saturated NaHCO$_3$ and twice with 50 mL brine. The organic layer was dried over Na$_2$SO$_4$ and concentrated to an oil. The crude product was purified by reverse phase prep-HPLC to afford a diasteromeric mixture of benzyl allyl((1R,3S)-3-((2R,3S)-2-hydroxy-3-((S)-2-(N-methylpentylsulfonamido)pent-4-enamido)-4-phenylbutylamino)-5-methoxy-2,3-dihydro-1H-inden-1-yl)carbamate and benzyl allyl((1S,3R)-3-((2R,3S)-2-hydroxy-3-((S)-2-(N-methylpentylsulfonamido)pent-4-enamido)-4-phenylbutylamino)-5-methoxy-2,3-dihydro-1H-inden-1-yl)carbamate as a TFA salt (130 mg, 58%). LC-MS (M+H)$^+$=761.5; $^1$H NMR (400 MHz, CD$_3$OD) δ ppm 0.83-0.96 (m, 3H) 1.18-1.37 (m, 4H) 1.56-1.70 (m, 2H) 2.20-2.41 (m, 2H) 2.43-2.56 (m, 1H) 2.59-2.79 (m, 6H) 2.88-3.17 (m, 2H) 3.19-3.34 (m, 1H) 3.82 (s, 3H) 3.84-4.19 (m, 4H) 4.22-4.35 (m, 1H) 4.69 (m, 1H) 4.97-5.30 (m, 7H) 5.61-5.79 (m, 1H) 5.84-6.01 (m, 1H) 7.00 (td, J=5.60, 3.15 Hz, 1H) 7.13-7.38 (m, 12H) 7.79 (d, J=8.81 Hz, 0.5H) 7.93 (d, J=8.31 Hz, 0.5H).

Step DR (2): A mixture of the products from Step DR (1) (110 mg, 0.126 mmol) and Hoveyda-Grubbs catalyst (2$^{nd}$ Generation) (8.0 mg, 0.013 mmol) in DCM was refluxed for 2 h. After the addition of more catalyst (2.0 mg) the reaction was stirred for an additional 4 h. The reaction was concentrated and purified by reverse phase prep-HPLC to give three purified diastereomers (7.4 mg of A, 20.0 mg of B, and 7.5 mg of C) of (4R,5S,8S)-5-benzyl-4-hydroxy-18-methoxy-8-[methyl-(pentane-1-sulfonyl)-amino]-7-oxo-2,6,13-triaza-tricyclo[12.6.1.0[15,20]]henicosa-10,15(20),16,18-tetraene-13-carboxylic acid benzyl ester. Data for diastereomer A: LC-MS (M+H)$^+$=733.5; $^1$H NMR (400 MHz, CD$_3$OD) δ ppm 0.91 (t, J=7.18 Hz, 3H) 1.24-1.39 (m, 6H) 1.60-1.75 (m, 2H) 2.00-2.19 (m, 2H) 2.32-2.42 (m, 2H) 2.42-2.80 (m, 5H) 2.85 (s, 3H) 2.92-3.01 (m, 1H) 3.16 (q, J=7.13 Hz, 2H) 3.53 (d, J=6.55 Hz, 1H) 3.62-3.72 (m, 1H) 3.82 (s, 3H) 4.13-4.31 (m, 2H) 5.09-5.30 (m, 2H) 5.37-5.57 (m, 1H) 5.74-5.99 (m, 1H) 6.99-7.41 (m, 11H) 7.59 (d, J=9.57 Hz, 1H). Data for diastereomer B: LC-MS (M+H)$^+$=733.5; $^1$H NMR (400 MHz, CD$_3$OD) δ ppm 0.93 (t, J=7.05 Hz, 3H) 1.25-1.42 (m, 4H) 1.70 (ddd, J=14.86, 7.81, 7.55 Hz, 2H) 1.93-2.19 (m, 2H) 2.46 (s, 2H) 2.54-2.71 (m, 3H) 2.73-2.90 (m, 4H) 2.93-3.06 (m, 1H) 3.07-3.20 (m, 1H) 3.36 (dd, J=17.75, 5.41 Hz, 1H) 3.73-3.82 (m, 1H) 3.84 (s, 3H) 4.05-4.18 (m, 2H) 4.22 (dd, J=10.83, 3.27 Hz, 1H) 4.76 (t, J=8.18 Hz, 1H) 5.06-5.31 (m, 3H) 5.52-5.68 (m, 1H) 5.75 (t, J=8.18 Hz, 1H) 7.02 (dd, J=8.44, 1.89 Hz, 1H) 7.08-7.40 (m, 12H) 7.81 (d, J=9.32 Hz, 1H). Data for diastereomer C: LC-MS (M+H)$^+$=733.5; $^1$H NMR (400 MHz, CD$_3$OD) δ ppm 0.91 (t, J=6.92 Hz, 3H) 1.24-1.40 (m, 4H) 1.56-1.71 (m, 2H) 1.73-1.85 (m, 1H) 1.90-2.09 (m, 1H) 2.28 (s, 2H) 2.51-2.77 (m, 4H) 2.85 (s, 3H) 2.86-2.93 (m, 1H) 2.95-3.04 (m, 1H) 3.16 (q, J=7.30 Hz, 1H) 3.36-3.49 (m, 1H) 3.66-3.75 (m, 1H) 3.86 (s, 3H) 3.89-3.98 (m, 1H) 4.11-4.28 (m, 2H) 5.03-5.35 (m, 3H) 5.38-5.50 (m, 1H) 5.74-5.87 (m, 1H) 6.96-7.42 (m, 13H) 7.91-7.99 (m, 1H).

Step DR (3): Diastereomer B from Step DR (2) and 5 mg 10% Pd—C in 5 mL MeOH was hydrogenated at atmospheric pressure for 16 h. After filtration, the filtrate was concentrated and purified by reverse phase prep-HPLC to afford 8 mg of the title compound as a TFA salt. LC-MS (M+H)$^+$=601.5; $^1$H NMR (400 MHz, CD$_3$OD) δ ppm 0.92 (t, J=7.05 Hz, 3H) 1.03-1.10 (m, 1H) 1.24-1.41 (m, 5H) 1.47-1.61 (m, 2H) 1.62-1.73 (m, 2H) 1.74-1.94 (m, 2H) 2.14-2.31 (m, 1H) 2.38 (s, 2H) 2.85 (s, 3H) 2.92-3.01 (m, 1H) 3.05-3.21 (m, 4H) 3.30-3.35 (m, 1H) 3.77-3.92 (m, 3H) 3.88 (s, 3H) 4.04-4.15 (m, 1H) 4.21 (dd, J=10.58, 2.77 Hz, 1H) 4.87-5.11 (m, 1H) 7.09-7.37 (m, 7H) 7.51-7.63 (m, 1H) 8.20 (d, J=9.57 Hz, 1H).

Example 52

3,3,3-trifluoro-propane-1-sulfonic acid ((1S,4R,5S,8S,14R)-5-benzyl-4-hydroxy-18-methoxy-7-oxo-2,6,13-triaza-tricyclo[12.6.1.0$^{15,20}$]henicosa-15(20),16,18-trien-8-yl)-methyl-amide

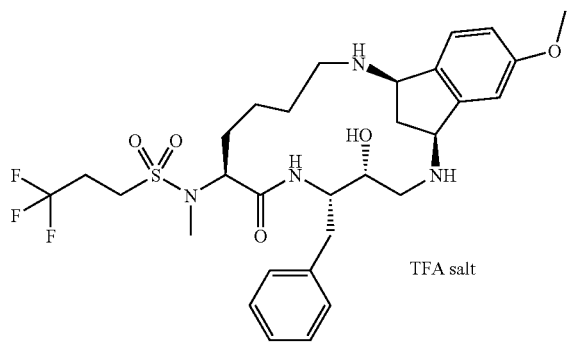

TFA salt and

Example 53

3,3,3-Trifluoro-propane-1-sulfonic acid ((1R,4R,5S,8S,14S)-5-benzyl-4-hydroxy-18-methoxy-7-oxo-2,6,13-triaza-tricyclo[12.6.1.0$^{15,20}$]henicosa-15(20),16,18-trien-8-yl)-methyl-amide

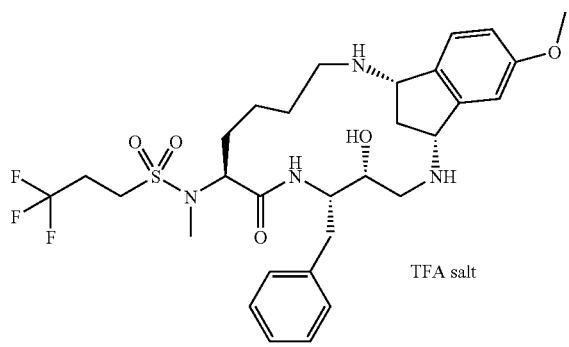

TFA salt

Step DS (1): The product from Preparation AQ (2) (192 mg, 0.258 mmol) and (S)-2-(3,3,3-trifluoro-N-methylpropylsulfonamido)pent-4-enoic acid from Preparation I were coupled by a procedure analogous to Step DR (1) to afford benzyl allyl(3-((2R,3S)-2-hydroxy-4-phenyl-3-((S)-2-(3,3,3-trifluoro-N-methylpropylsulfonamido)pent-4-enamido)butylamino)-5-methoxy-2,3-dihydro-1H-inden-1-yl)carbamate as a mixture of two diastereomers as the TFA salt (504 mg, 66%). This mixture was separated by supercritical fluid chromatography to afford 175 mg of benzyl allyl((1R,3S)-3-((2R,3S)-2-hydroxy-4-phenyl-3-((S)-2-(3,3,3-trifluoro-N-methylpropylsulfonamido)pent-4-enamido)butylamino)-5-methoxy-2,3-dihydro-1H-inden-1-yl)carbamate (diastereomer A) and 145 mg of benzyl allyl((1S,3R)-3-((2R,3S)-2-hydroxy-4-phenyl-3-((S)-2-(3,3,3-trifluoro-N-methylpropylsulfonamido)pent-4-enamido)butylamino)-5-methoxy-2,3-dihydro-1H-inden-1-yl)carbamate (diastereomer B). Data for diastereomer A: LC-MS (M+H)$^+$=787.4; $^1$H NMR (400 MHz, CDCl$_3$) δ ppm 1.62-1.84 (m, 1H) 2.29 (ddd, J=14.98, 9.32, 9.19 Hz, 1H) 2.41 (s, 3H) 2.45-2.85 (m, 7H) 2.98-3.12 (m, 2H) 3.12-3.21 (m, 1H) 3.42-3.68 (m, 2H) 3.80 (s, 3H) 3.86-3.95 (m, 1H) 4.01-4.08 (m, 1H) 4.11-4.17 (m, 1H) 4.21 (dd, J=10.07, 5.54 Hz, 1H) 4.98-5.21 (m, 6H) 5.30-5.60 (m, 1H) 5.61-5.73 (m, 1H) 5.73-5.93 (m, 1H) 6.40-6.60 (m, 1H) 6.80 (dd, J=8.31, 2.27 Hz, 1H) 6.92 (s, 1H) 7.02 (d, J=8.31 Hz, 1H) 7.13-7.40 (m, 9H). Data for diastereomer B: LC-MS (M+H)$^+$=787.4; $^1$H NMR (400 MHz, CDCl$_3$) δ ppm 1.71-1.84 (m, 1H) 2.29 (dt, J=15.05, 8.97 Hz, 1H) 2.44 (s, 3H) 2.47-2.91 (m, 7H) 2.99-3.18 (m, 3H) 3.37-3.70 (m, 2H) 3.79 (s, 3H) 3.86-4.11 (m, 2H) 4.13-4.19 (m, 1H) 4.22 (dd, J=9.82, 5.79 Hz, 1H) 4.97-5.21 (m, 6H) 5.31-5.60 (m, 1H) 5.62-5.74 (m, J=17.12, 10.07, 8.56, 5.79 Hz, 1H) 5.79-5.86 (m, 1H) 6.45-6.53 (m, 1H) 6.80 (dd, J=8.31, 2.27 Hz, 1H) 6.90-6.96 (m, 1H) 7.03 (d, J=8.31 Hz, 1H) 7.12-7.44 (m, 9H).

Step DS (2): The TFA salts of diastereomers A and B from Step DS (1) were independently subjected to ring-closing metathesis following a procedure analogous to that described for Step DR (2). The crude products from each reaction were purified by reverse phase prep-HPLC to afford 75 mg (45% yield) of (1S,4R,5S,8S,14R)-5-benzyl-4-hydroxy-18-methoxy-8-[methyl-(3,3,3-trifluoro-propane-1-sulfonyl)-amino]-7-oxo-2,6,13-triaza-tricyclo[12.6.1.0$^{15,20}$]henicosa-10,15,17,19-tetraene-13-carboxylic acid benzyl ester (diastereomer A) and 31 mg (21% yield) of (1R,4R,5S,8S,14S)-5-benzyl-4-hydroxy-18-methoxy-8-[methyl-(3,3,3-trifluoro-propane-1-sulfonyl)-amino]-7-oxo-2,6,13-triaza-tricyclo[12.6.1.0$^{15,20}$]henicosa-10,15,17,19-tetraene-13-carboxylic acid benzyl ester (diastereomer B) as their TFA salts. Data for diastereomer A: LC-MS (M+H)$^+$=759.4; $^1$H NMR (400 MHz, CD$_3$OD) δ ppm 1.95-2.24 (m, 2H) 2.48 (s, 3H) 2.51-2.71 (m, 4H) 2.73-2.87 (m, 2H) 2.90-3.07 (m, 2H) 3.08-3.20 (m, 2H) 3.30-3.41 (m, 1H) 3.75-3.86 (m, 1H) 3.83 (s, 3H) 4.04-4.17 (m, 2H) 4.24 (d, J=7.30 Hz, 1H) 4.79 (t, J=8.18 Hz, 1H) 5.05-5.31 (m, 3H) 5.61 (d, J=12.09 Hz, 1H) 5.75 (t, J=8.06 Hz, 1H) 6.98-7.40 (m, 13H) 7.94 (d, J=9.32 Hz, 1H). Data for diastereomer B: LC-MS (M+H)$^+$=759.4; $^1$H NMR (400 MHz, CD$_3$OD) δ ppm 2.04-2.22 (m, 2H) 2.35 (s, 3H) 2.44-2.75 (m, 6H) 2.91-3.03 (m, 2H) 3.08-3.24 (m, 2H) 3.35 (dd, J=14.10, 2.77 Hz, 1H) 3.69 (dd, J=10.07, 2.52 Hz, 1H) 3.82 (s, 3H) 4.19-4.28 (m, 3H) 4.91 (t, J=8.56 Hz, 1H) 5.09-5.31 (m, 3H) 5.54 (d, J=12.09 Hz, 1H) 5.81 (t, J=8.06 Hz, 1H) 6.99-7.40 (m, 13H) 7.75 (d, J=9.32 Hz, 1H).

Step DS (3): Diasteremers A and B from Step DS (2) were independently converted into 64 mg (100% yield) of 3,3,3-trifluoro-propane-1-sulfonic acid ((1S,4R,5S,8S,14R)-5-benzyl-4-hydroxy-18-methoxy-7-oxo-2,6,13-triaza-tricyclo[12.6.1.0$^{15,20}$]henicosa-10,15(20),16,18-tetraen-8-yl)-methyl-amide (diastereomer A) and 34 mg (90% yield) of 3,3,3-trifluoro-propane-1-sulfonic acid ((1R,4R,5S,8S,14S)-5-benzyl-4-hydroxy-18-methoxy-7-oxo-2,6,13-triaza-tricyclo[12.6.1.0$^{15,20}$]henicosa-10,15 (20),16,18-tetraen-8-yl)-methyl-amide (diastereomer B), respectively, by following a procedure analogous to step DR (3). Data for diastereomer A: LC-MS (M+H)$^+$=627.4; $^1$H NMR (400 MHz, CD$_3$OD) δ ppm 0.81-0.92 (m, 2H) 1.34-1.56 (m, 4H) 1.67-1.81 (m, 2H) 2.47-2.68 (m, 4H) 2.62 (s, 3H) 2.71-2.83 (m, 2H) 2.93-3.10 (m, 2H) 3.18 (dd, J=14.10, 3.78 Hz, 2H) 3.70 (ddd, J=9.07, 6.80, 3.02 Hz, 1H) 3.83 (s, 3H) 4.04-4.16 (m, 2H) 4.41 (d, J=6.55 Hz, 1H) 4.54 (d, J=6.30 Hz, 1H) 6.98 (dd, J=8.44, 2.39 Hz, 1H) 7.10-7.16 (m, 2H) 7.21 (d, J=4.28 Hz, 4H) 7.43 (d, J=8.31

Hz, 1H). Data for diastereomer B: LC-MS (M+H)+=627.4; 1H NMR (400 MHz, CD3OD) δ ppm 0.81-0.95 (m, 2H) 1.40-1.72 (m, 4H) 1.98-2.14 (m, 1H) 2.25 (d, J=15.36 Hz, 1H) 2.37-2.69 (m, 4H) 2.73-2.92 (m, 3H) 2.80 (s, 3H) 2.96-3.07 (m, 2H) 3.21 (dd, J=14.23, 3.40 Hz, 1H) 3.53 (ddd, J=8.88, 5.60, 3.15 Hz, 1H) 3.83 (s, 3H) 4.03-4.15 (m, 2H) 4.33 (d, J=6.55 Hz, 1H) 4.67 (d, J=7.30 Hz, 1H) 7.01 (dd, J=8.56, 2.52 Hz, 1H) 7.14-7.18 (m, 2H) 7.22-7.25 (m, 4H) 7.45 (d, J=8.56 Hz, 1H).

Example 54

(1S,4R,5S,8S)-5-benzyl-4-hydroxy-19-methoxy-8-[methyl-(3,3,3-trifluoro-propane-1-sulfonyl)-amino]-7-oxo-2,6,14-triaza-tricyclo[13.6.1.0^{16,21}]docosa-10,16(21),17,19-tetraene-14-carboxylic acid benzyl ester

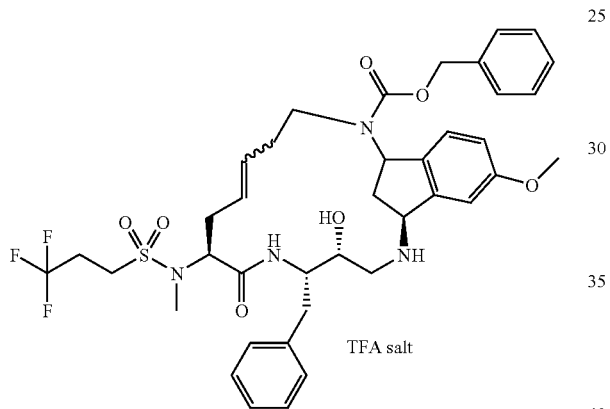

Step DT (1): The product from Preparation AR and (S)-2-(3,3,3-trifluoro-N-methylpropylsulfonamido)pent-4-enoic acid from Preparation I were coupled by a procedure analogous to Step DR (1) to afford 0.43 g (85% yield) of a diastereomeric mixture of benzyl but-3-enyl((3S)-3-((2R,3S)-2-hydroxy-4-phenyl-3-((S)-2-(3,3,3-trifluoro-N-methylpropylsulfonamido)pent-4-enamido)butylamino)-5-methoxy-2,3-dihydro-1H-inden-1-yl)carbamate as a TFA salt. LC-MS (M+H)+=801.4; HRMS (M+H)+=801.3491; 1H NMR (400 MHz, CD3OD) δ 7.05-7.40 (m, 12H) 6.90 (m, 1H) 5.60-5.78 (m, 2H) 4.90-5.18 (m, 6H) 4.10-4.30 (m, 3H) 3.81 (2s, 3H) 2.10-3.50 (m, 21H).

Step DT (2): The TFA salts the product from Step DT (1) was subjected to ring-closing metathesis following a procedure analogous to that described for Step DR (2). The crude product was purified by reverse phase prep-HPLC to afford 10 mg (10% yield) of the title compound as a TFA salt. LC-MS (M+H)+=773.8; HRMS (M+H)+=773.3193; 1H NMR (400 MHz, CD3OD) δ 7.59 (m, 1H) 7.33 (m, 5H) 7.13 (m, 5H) 6.94 (m, 2H) 6.20 (m, 1H) 5.50 (m, 1H) 5.10-5.35 (m, 4H) 4.90 (m, 1H) 4.50 (m, 1H) 4.20 (m, 2H) 3.81 (s, 3H) 3.50 (m, 2H) 1.90-3.30 (m, 16H).

Example 55

3,3,3-trifluoro-propane-1-sulfonic acid ((1S,4R,5S,8S)-5-benzyl-4-hydroxy-19-methoxy-7-oxo-2,6,14-triaza-tricyclo[13.6.1.0^{16,21}]docosa-16(21),17,19-trien-8-yl)-methyl-amide

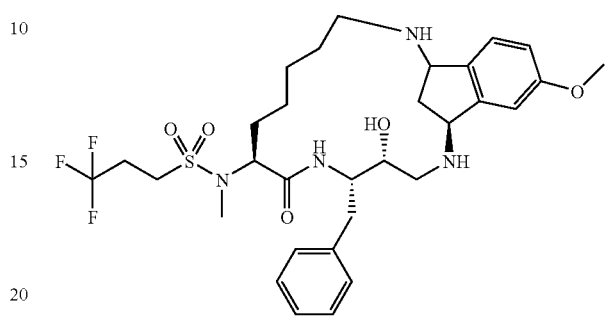

and

Example 56

3,3,3-trifluoro-propane-1-sulfonic acid ((1S,4R,5S,8S)-5-benzyl-4-hydroxy-19-methoxy-14-methyl-7-oxo-2,6,14-triaza-tricyclo[13.6.1.0^{16,21}]docosa-16(21),17,19-trien-8-yl)-methyl-amide

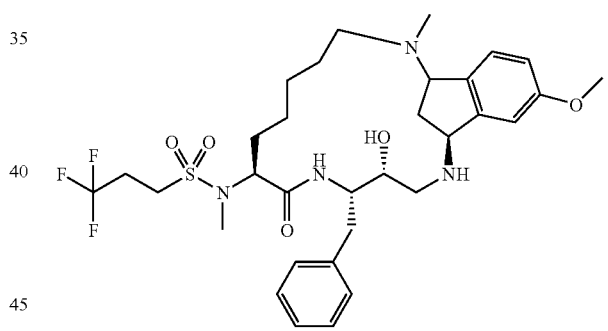

Step DU (1): The product from Step DT (2) (160 mg, 0.2 mmol) and 50 mg of 10% Pd/C was stirred under hydrogen at atmospheric pressure and rt for 3 h, then shaken under hydrogen at 20 psi for 4 h. The reaction was filtered through Celite, concentrated, and purified by reverse phase prep-HPLC to give two products. The two compounds were then separated by preparative TLC, eluting with 10% (2 M ammonia in methanol/EtOAc) to give 8 mg of 3,3,3-trifluoro-propane-1-sulfonic acid ((1S,4R,5S,8S)-5-benzyl-4-hydroxy-19-methoxy-7-oxo-2,6,14-triaza-tricyclo[13.6.1.0^{16,21}]docosa-16(21),17,19-trien-8-yl)-methyl-amide (Example 55) and 10 mg of 3,3,3-trifluoro-propane-1-sulfonic acid ((1S,4R,5S,8S)-5-benzyl-4-hydroxy-19-methoxy-14-methyl-7-oxo-2,6,14-triaza-tricyclo[13.6.1.0^{16,21}]docosa-16(21),17,19-trien-8-yl)-methyl-amide (Example 56). Data for Example 55: LC-MS (M+H)+=641.3; HRMS (M+H)+=641.2999; 1H NMR (400 MHz, CD3OD) δ ppm 0.98-1.08 (m, 1H) 1.25-1.36 (m, 4H) 1.45-1.60 (m, 2H) 1.70-1.80 (m, 1H) 1.96-2.05 (m, 1H) 2.37 (s, 3H) 2.54-2.72 (m, 8H) 2.96-3.05 (m, 1H) 3.08-3.18 (m, 1H) 3.57-3.64 (m, 1H) 3.81 (t, J=2.01 Hz 1H)

3.83 (s, 3H) 4.04-4.14 (m, 2H) 4.45-4.50 (m, 1H) 4.56 (dd, J=7.55, 5.79 Hz, 1H) 6.93 (dd, J=8.56, 2.27 Hz, 1H) 7.06 (d, J=2.27 Hz, 1H) 7.17-7.24 (m, 5H) 7.36 (d, J=8.31 Hz, 1H). Data for Example 56: LC-MS (M+H)⁺=655.3; HRMS (M+H)⁺=655.3145; ¹H NMR (400 MHz, CD₃OD) δ 7.20 (m, 5H) 7.13 (m, 1H) 6.93 (m, 1H) 6.85 (m, 1H) 4.5 (m, 1H) 4.34 (m, 1H) 4.03 (m, 2H) 3.83 (S, 3H) 3.63 (m, 1H) 2.90-3.15 (m, 2H) 2.30-2.70 (m, 15H) 1.90 (s, 3H) 0.95-1.55 (m, 6H).

Example 57

(1S,4R,5S,8S)-8-(acetyl-methyl-amino)-5-benzyl-4-hydroxy-19-methoxy-7-oxo-2,6,14-triaza-tricyclo[13.6.1.0¹⁶,²¹]docosa-10,16(21),17,19-tetraene-14-carboxylic acid benzyl ester

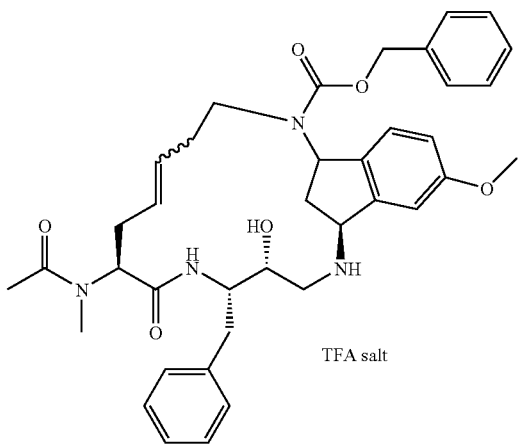

Step DV (1): The product from Preparation AR and (S)-N-methyl-N-acetyl-allygycine from Preparation P were coupled by a procedure analogous to Step DR (1) to afford 80 g (99% yield) of a diastereomeric mixture of benzyl but-3-enyl((3S)-3-((2R,3S)-2-hydroxy-3-((S)-2-(N-methylacetamido)pent-4-enamido)-4-phenylbutylamino)-5-methoxy-2,3-dihydro-1H-inden-1-yl)carbamate as a TFA salt. LC-MS (M+H)⁺=683.4; HRMS (M+H)⁺=683.3816; ¹H NMR (400 MHz, CD₃OD) δ 6.90-7.30 (m, 13H) 5.78 (m, 1H) 5.50 (m, 1H) 4.90-5.12 (m, 7H) 4.68 (m, 1H) 4.10 (m, 1H) 3.86 (m, 1H) 3.83 (s, 3H) 3.45-3.20 (m, 2H) 3.25 (m, 2H) 3.05 (m, 2H) 2.85 (s, 1H) 2.62 (m, 2H) 2.40 (m, 4H) 2.25 (m, 3H) 2.00 (m, 3H).

Step DV (2): The TFA salt of the product from Step DV (1) was subjected to ring-closing metathesis following a procedure analogous to that described for Step DR (2). The crude product was purified by reverse phase prep-HPLC to afford 120 mg (83% yield) of the title compound as a TFA salt. LC-MS (M+H)⁺=655.4; HRMS (M+H)⁺=655.3484; ¹H NMR (400 MHz, CD₃OD) δ 6.90-7.47 (m, 13H) 5.73 (m, 1H) 5.50 (m, 1H) 5.35 (m, 1H) 5.20 (m, 2H) 4.92 (m, 1H) 4.00 (m, 1H) 3.85 (m, 3H) 3.65 (m, 1H) 3.32-3.50 (m, 1H) 1.60-3.20 (m, 18H).

Example 59

(S)-N-((6S,9S,10R)-9-benzyl-10-hydroxy-15-methoxy-7-oxo-2,5,6,7,8,9,10,11,12,13-decahydrobenzo[b][1,5,9]oxadiazacyclopentadecin-6-yl)-N,2-dimethylhexanamide Step DX (1): A pre-mixed suspension of (S)-2-methylhexanoyl(methyl)-(S)-allylglycine (57 mg, 0.24 mmol, diastereomer A from Preparation D), O-benzotriazole-N,N,N',N'-tetramethyl-uronium-hexafluoro-phosphate (HBTU) (99 mg, 0.26 mmol) and N-hydroxybenzotriazole monohydrate (HOBt) (35 mg, 0.26 mmol) in 2 mL DCM was added to a mixture of the product from Preparation AS (138 mg, 0.24 mmol) and diisopropylamine (165 μL, 0.95 mmol) in 3 mL DCM at RT. The mixture was stirred at rt for 2 h. The reaction was concentrated under vacuum and the residue purified by reverse phase prep-HPLC to yield 130 mg (79% yield) of (S)-N-((S)-1-((2S,3R)-4-(2-(allyloxy)-5-methoxybenzylamino)-3-hydroxy-1-phenylbutan-2-ylamino)-1-oxopent-4-en-2-yl)-N,2-dimethylhexanamide as a TFA salt. LC-MS (M+H)⁺=580.4; HRMS (M+H)⁺=580.3762; ¹H NMR (400 MHz, CD₃OD) δ 7.15-7.28 (m, 5H) 7.00 (m, 3H) 6.10 (m, 1H) 5.55 (m, 1H) 5.39 (m, 1H) 5.28 (m, 1H) 4.85-5.00 (m, 3H) 4.63 (m, 2H) 4.20 (m, 2H) 4.00 (m, 1H) 3.78 (m, 1H) 3.75 (s, 1H) 3.25 (m, 1H) 3.10 (m, 1H) 2.95 (m, 1H) 2.83 (S, 1H) 2.58 (m, 2H) 2.50 (s, 2H) 2.10-2.40 (m, 2H) 1.55 (m, 1H) 1.10-1.40 (m, 5H) 0.80-1.03 (m, 6H).

Step DX (2): The product from Step DX (1) (30 mg, 0.043 mmol) and Hoveyda-Grubb's 2ⁿᵈ generation catalyst (5.4 mg, 0.009 mmol) in 10 mL DCM was refluxed for 4 h. The reaction was concentrated and the residue was purified by reverse phase prep-HPLC to yield 14 mg (49% yield) of the title compound as a TFA salt. LC-MS (M+H)⁺=552.4; HRMS (M+H)⁺=552.3419; ¹H NMR (400 MHz, CD₃OD) δ 7.08-7.23 (m, 5H) 7.00 (m, 3H) 5.80 (m, 1H) 5.65 (m, 1H) 4.80 (m, 1H) 4.35 (m, 1H) 4.24 (m, 1H) 4.00 (m, 1H) 3.82 (m, 1H) 3.78 (s, 3H) 3.60 (m, 1H) 2.90-3.20 (m, 3H) 2.45 (m, 2H) 2.24 (S, 3H) 1.20-1.62 (m, 8H) 0.80-1.02 (m, 7H)

Example 60

N-((7S,10S,11R)-10-benzyl-11-hydroxy-16-methoxy-8-oxo-5,6,7,8,9,10,11,12,13,14-decahydro-2H-benzo[b][1,5,9]oxadiazacyclohexadecin-7-yl)-3,3,3-trifluoro-N-methylpropane-1-sulfonamide

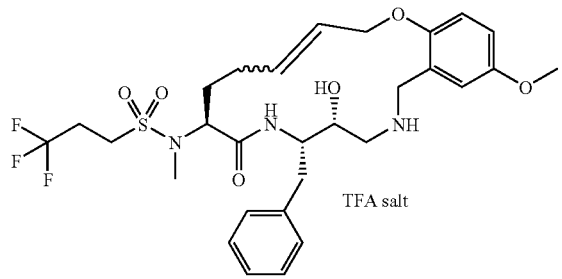

TFA salt

Step DY (1): The product from Preparation AS and (S)-2-(3,3,3-trifluoro-N-methylpropylsulfonamido)hex-5-enoic acid from Preparation M were coupled by a procedure analogous to Step DX (1) to afford 200 mg (94% yield) of (S)-N-((2S,3R)-4-(2-(allyloxy)-5-methoxybenzylamino)-3-hydroxy-1-phenylbutan-2-yl)-2-(3,3,3-trifluoro-N-methylpropylsulfonamido)hex-5-enamide as a TFA salt. LC-MS (M+H)$^+$=642.5; HRMS (M+H)$^+$=642.2851; $^1$H NMR (400 MHz, CD$_3$OD) δ 7.18 (m, 5H) 6.95 (m, 3H) 6.08 (m, 1H) 5.73 (m, 1H) 5.30 (m, 2H) 4.95 (m, 2H) 4.60 (d, 2H) 4.20 (m, 2H) 4.10 (m, 1H) 3.90 (m, 1H) 3.78 (m, 1H) 3.75 (S, 3H) 2.75-3.20 (m, 5H) 2.67 (s, 3H) 2.40-2.60 (m, 3H) 1.95 (m, 2H) 1.65 (m, 1H) 1.50 (m, 1H).

Step DY (2). The product from Step DY (1) was subject to ring-closing metathesis by procedure analogous to Step DX (2) to afford 12 mg (8% yield) of the title compound as a TFA salt. LC-MS (M+H)$^+$=614.4; HRMS (M+H)$^+$=614.2494; $^1$H NMR (400 MHz, CD$_3$OD) δ 7.15 (m, 5H) 6.78-6.92 (m, 3H) 5.70 (m, 2H) 4.44 (m, 2H) 4.12 (m, 1H) 3.90 (m, 3H) 3.72 (m, 1H) 3.70 (S, 3H) 2.90-3.20 (m, 4H) 2.78 (m, 1H) 2.56 (m, 3H) 2.36 (S, 3H) 2.18 (m, 3H) 1.45 (m, 1H).

Example 61

3,3,3-trifluoro-propane-1-sulfonic acid ((1S,4R,5S,8S,15R)-5-benzyl-19-bromo-4-hydroxy-7-oxo-14-oxa-2,6-diaza-tricyclo[13.6.1.0$^{16,21}$]docosa-11,16(21),17,19-tetraen-8-yl)-methyl-amide

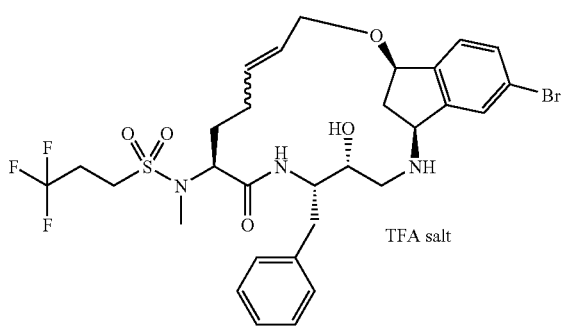

TFA salt

Step DZ (1): (S)-2-(3,3,3-Trifluoro-N-methylpropylsulfonamido)hex-5-enoic acid (32 mg, 105 μmol, from Preparation BD were coupled by following a procedure analogous to Step CA (1) to afford 120 mg (51% yield) of (S)-N-((2S,3R)-4-((1S,3R)-3-(allyloxy)-6-bromo-2,3-dihydro-1H-inden-1-ylamino)-3-hydroxy-1-phenylbutan-2-yl)-2-(3,3,3-trifluoro-N-methylpropylsulfonamido)hex-5-enamide. MS (M+H)$^+$ 716.56. $^1$H NMR (500 MHz, CD$_3$OD) δ ppm 1.69-1.78 (m, 1H) 1.80-1.92 (m, 2H) 2.00-2.10 (m, 2H) 2.49-2.60 (m, 2H) 2.60-2.74 (m, 3H) 2.75-2.76 (m, 3H) 2.76-2.83 (m, 2H) 2.90-2.97 (m, 2H) 3.18 (dd, J=13.89, 3.51 Hz, 1H) 3.61-3.69 (m, 1H) 4.09-4.25 (m, 5H) 4.79-4.85 (m, 1H) 5.01 (d, J=10.07 Hz, 1H) 5.07 (d, J=17.09 Hz, 1H) 5.21 (d, J=10.38 Hz, 1H) 5.32-5.40 (m, 1H) 5.77-5.88 (m, 1H) 5.96-6.06 (m, 1H) 7.14-7.20 (m, 1H) 7.21-7.29 (m, 4H) 7.33 (d, J=8.24 Hz, 1H) 7.45 (d, J=7.93 Hz, 1H) 7.63 (s, 1H).

Step DZ (2): The product from Step DZ (1) was subject to the ring-closing metathesis procedure described in Step CA (2) to afford 32 mg (47% yield) of the title compound as a TFA salt. MS (M+H)$^+$ 688.10; $^1$H NMR (500 MHz, CD$_3$OD, ~6:4 mixture of rotamers). Data for rotamer A (major): δ ppm 1.97-2.13 (m, 2H) 2.21 (d, J=9.46 Hz, 3H) 2.21-2.26 (m, 1H) 2.27-2.34 (m, 1H) 2.38 (t, J=11.75 Hz, 1H) 2.53-2.74 (m, 5H) 2.84-2.93 (m, 1H) 2.95-3.25 (m, 4H) 3.34-3.38 (m, 1H) 3.68-3.80 (m, 1H) 4.00-4.15 (m, 3H) 4.25 (dd, J=10.99, 8.24 Hz, 1H) 4.83-4.95 (m, 1H) 4.98 (t, J=9.00 Hz, 1H) 5.50-5.60 (m, 1H) 5.69-5.81 (m, 1H) 7.12-7.28 (m, 5H) 7.37 (d, J=9.77 Hz, 1H) 7.53 (dd, J=12.67, 8.09 Hz, 1H) 7.66-7.72 (m, 1H) 7.86 (d, J=14.95 Hz, 1H). Data for rotamer B (minor): δ ppm 1.97-2.13 (m, 2H) 2.21 (d, J=9.46 Hz, 3H) 2.21-2.26 (m, 1H) 2.27-2.34 (m, 1H) 2.44-2.52 (m, 1H) 2.53-2.74 (m, 5H) 2.84-2.93 (m, 1H) 2.95-3.25 (m, 5H) 3.34-3.38 (m, 1H) 3.68-3.80 (m, 1H) 4.00-4.15 (m, 3H) 4.83-4.95 (m, 1H) 4.98 (t, J=9.00 Hz, 1H) 5.50-5.60 (m, 2H) 7.12-7.28 (m, 5H) 7.53 (dd, J=12.67, 8.09 Hz, 1H) 7.60 (d, J=9.46 Hz, 1H) 7.66-7.72 (m, 1H) 7.86 (d, J=14.95 Hz, 1H).

Example 62

(1S,4R,5S,16R)-5-(3,5-difluoro-benzyl)-20-bromo-4-hydroxy-15-oxa-2,6-diaza-tricyclo[14.6.1.0$^{17,22}$]tricosa-12,17(22),18,20-tetraen-7-one (isomer A)

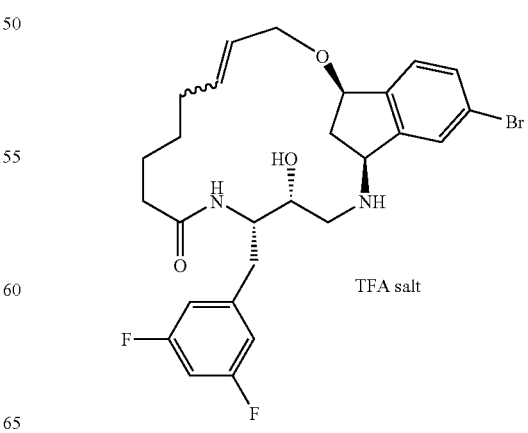

TFA salt

Example 63

(1S,4R,5S,16R)-5-(3,5-difluoro-benzyl)-20-bromo-4-hydroxy-15-oxa-2,6-diaza-tricyclo[14.6.1.0$^{17,22}$]tricosa-12,17(22),18,20-tetraen-7-one (isomer B)

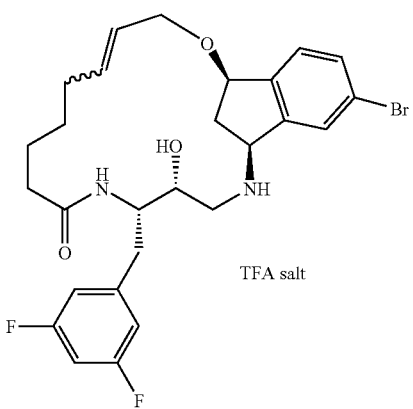

TFA salt

Step EA (1): 2,6-Lutidine (1.7 g, 15.9 mmol) and tert-butyldimethylsilyl trifluoromethanesulfonate (2.1 g, 7.95 mmol) were sequentially added at −78° C. to a solution of tert-butyl (2S,3R)-4-((1S,3R)-3-(allyloxy)-6-bromo-2,3-dihydro-1H-inden-1-ylamino)-1-(3,5-difluorophenyl)-3-hydroxybutan-2-ylcarbamate (1.5 g, 2.65 mmol, from Preparation BE) in anyhydrous DCM. The mixture was warmed to rt over 1 hr, then aged at rt for an additional 1 hr. LC-MS analysis of the crude mixture indicated that all of the starting material was consumed. The crude reaction was concentrated was in vacuo to afford a crude residue. Tetra-butylammonium fluoride (1.0 M solution in THF, 7.95 mL) was added to the crude residue. The mixture was stirred at rt for 18 h and then heated at 55° C. for 4 h. The crude reaction was concentrated in vacuo to afford a residue containing (2R,3S)-1-((1S,3R)-3-(allyloxy)-6-bromo-2,3-dihydro-1H-inden-1-ylamino)-3-amino-4-(3,5-difluorophenyl)butan-2-ol. LC-MS (M+H)$^+$ 467.00. The crude product was used in the next step without purification.

Step EA (2): HATU (1.39 g, 3.66 mmol) was added to a rt solution of hept-6-enoic acid (425 mg, 3.33 mmol) in DCM. After 15 min, the crude product from Step EA (1) was added. The resulting mixture was stirred at rt for 2 h. The crude reaction was concentrated in vacuo. The product was purified by silica gel column chromatography to afford 810 mg (53% yield over 3 steps) of N-((2S,3R)-4-((1S,3R)-3-(allyloxy)-6-bromo-2,3-dihydro-1H-inden-1-ylamino)-1-(3,5-difluorophenyl)-3-hydroxybutan-2-yl)hept-6-enamide. MS (M+H)$^+$ 577.32. $^1$H NMR (500 MHz, CDCl$_3$) δ ppm 1.24-1.32 (m, 2H) 1.46-1.57 (m, 2H) 1.86-1.93 (m, 1H) 1.97-2.15 (m, 5H) 2.64-2.73 (m, 2H) 2.75-2.84 (m, 2H) 3.04 (dd, J=14.34, 4.58 Hz, 1H) 3.50 (td, J=6.26, 3.97 Hz, 1H) 4.04-4.19 (m, 5H) 4.73-4.78 (m, 1H) 4.90-4.99 (m, 2H) 5.20 (ddd, J=10.38, 2.75, 1.22 Hz, 1H) 5.31 (ddd, J=17.24, 3.20, 1.53 Hz, 1H) 5.62 (d, J=8.85 Hz, 1H) 5.69-5.79 (m, J=17.05, 10.34, 6.60, 6.60 Hz, 1H) 5.90-5.99 (m, J=17.17, 10.45, 5.80, 5.65 Hz, 1H) 6.62-6.69 (m, 1H) 6.72-6.78 (m, 2H) 7.28 (d, J=7.94 Hz, 1H) 7.41 (dd, J=8.09, 1.68 Hz, 1H) 7.50 (s, 1H).

Step EA (3): The product from Step EA (2) was subject to the ring-closing metathesis procedure described in Step CA (2) to afford 30 mg (65% yield) of the title compound (isomer A) as a TFA salt and 5 mg (11% yield) of the title compound (isomer B) as a TFA salt. Data for isomer A: MS (M+2H)$^+$ 551.31. $^1$H NMR (500 MHz, CD$_3$OD) δ ppm 1.32-1.58 (m, 5H) 1.58-1.69 (m, 2H) 1.98-2.10 (m, 4H) 2.10-2.19 (m, 2H) 2.71 (dd, J=14.04, 10.68 Hz, 1H) 2.82 (dd, J=12.82, 10.07 Hz, 1H) 3.01 (ddd, J=13.96, 7.32, 7.10 Hz, 1H) 3.21 (dd, J=12.82, 2.75 Hz, 1H) 3.28 (dd, J=14.04, 3.66 Hz, 1H) 3.91 (dd, 1H) 4.01-4.10 (m, 2H) 4.40 (dd, J=12.36, 5.04 Hz, 1H) 4.84 (t, J=7.02 Hz, 1H) 5.64-5.82 (m, 2H) 6.79 (tt, J=9.23, 2.44, 2.29 Hz, 1H) 6.86 (dd, 2H) 7.45 (d, J=7.93 Hz, 1H) 7.65 (dd, 1H) 7.86 (s, 1H). Data for isomer B: MS (M+2H)$^+$ 551.28. $^1$H NMR (500 MHz, CD$_3$OD) δ ppm 1.31-1.44 (m, 3H) 1.44-1.62 (m, 2H) 1.85-1.95 (m, 2H) 2.05-2.17 (m, 3H) 2.18-2.27 (m, 2H) 2.61-2.69 (m, 2H) 2.89 (s, 1H) 2.98-3.07 (m, 1H) 3.12 (dd, J=12.82, 2.75 Hz, 1H) 3.81 (ddd, 1H) 3.87-3.94 (m, 1H) 4.16 (dd, J=10.53, 6.26 Hz, 1H) 4.27 (dd, 1H) 4.90-4.94 (m, 1H) 4.96 (dd, J=7.02, 3.36 Hz, 1H) 5.61-5.69 (m, 1H) 5.72-5.79 (m, 1H) 6.77 (tt, J=9.16, 2.29 Hz, 1H) 6.80-6.83 (m, 2H) 7.48 (d, J=8.24 Hz, 1H) 7.67 (dd, J=8.24, 1.53 Hz, 1H) 7.84 (s, 1H).

Example 64

(1S,4R,5S,16R)-5-(3,5-difluoro-benzyl)-4-hydroxy-20-(3-methyl-butyl)-15-oxa-2,6-diaza-tricyclo[14.6.1.0$^{17,22}$]tricosa-12,17(22),18,20-tetraen-7-one (isomer A)

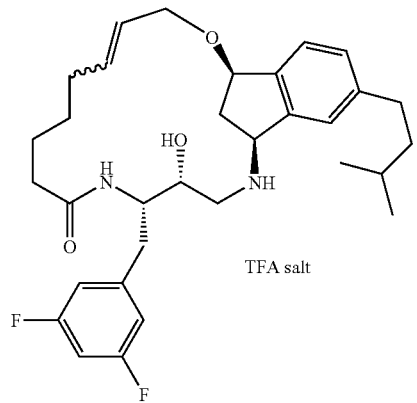

TFA salt

Example 65

(1S,4R,5S,16R)-5-(3,5-difluoro-benzyl)-4-hydroxy-20-(3-methyl-butyl)-15-oxa-2,6-diaza-tricyclo[14.6.1.0$^{17,22}$]tricosa-12,17(22),18,20-tetraen-7-one (isomer B)

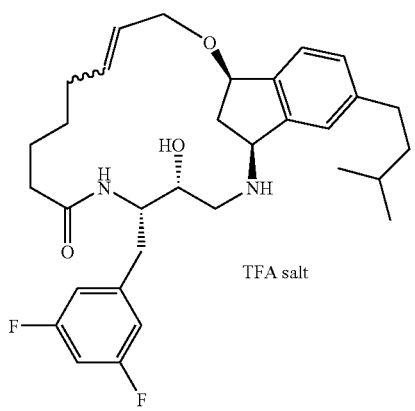

TFA salt

Step EB (1): Palladium(II) acetate (6.5 mg, 0.029 mmol) was added to a solution of (2-biphenyl)di-tert-butylphosphine (4.3 mg, 0.014 mmol) in anhydrous THF. After 15 min, a mixture of isomer A and B from Step EA (3) (0.072 mmol) was added. A solution of isopentylzinc(II) bromide (0.216 mmol) in THF was added. The resulting mixture was stirred at rt for 20 hr. The reaction was concentrated in vacuo. The crude products were purified by reverse phase preparatory HPLC to afford 5.4 mg of the title compound (Example 64, isomer A) and 3.5 mg of the title compound (Example 65, isomer B) as their TFA salts. MS (M+H)$^+$ 541.43. $^1$H NMR (500 MHz, CD$_3$OD) δ ppm 0.98 (t, J=5.95 Hz, 6H) 1.35 (t, J=7.32 Hz, 1H) 1.37-1.65 (m, 3H) 1.86-1.97 (m, 1H) 2.03-2.16 (m, 3H) 2.16-2.24 (m, 1H) 2.59-2.69 (m, 2H) 2.69-2.76 (m, 2H) 2.89 (s, 2H) 2.94-3.02 (m, 1H) 3.10 (dd, J=13.12, 2.14 Hz, 1H) 3.17-3.23 (m, 2H) 3.27-3.30 (m, 1H) 3.43-3.48 (m, 1H) 3.83 (t, J=9.77 Hz, 2H) 4.16-4.21 (m, 1H) 4.22-4.28 (m, 1H) 4.79 (s, 1H) 4.93-5.00 (m, 1H) 5.18 (s, 1H) 5.59-5.69 (m, 1H) 5.70-5.79 (m, 1H) 6.74-6.78 (m, 1H) 6.81 (d, J=8.24 Hz, 1H) 6.86 (d, 1H) 7.35 (d, J=7.63 Hz, 1H) 7.44-7.48 (m, 2H). Data for Example 65, isomer B: MS (M+H)$^+$ 541.43. $^1$H NMR (500 MHz, CD$_3$OD) δ ppm 0.98 (d, J=6.41 Hz, 6H) 1.34 (t, J=7.32 Hz, 1H) 1.39-1.48 (m, 3H) 1.50-1.59 (m, 4H) 1.59-1.67 (m, 2H) 1.99-2.18 (m, 5H) 2.69-2.76 (m, 3H) 2.80 (dd, J=13.12, 10.07 Hz, 1H) 2.89 (s, 1H) 2.97 (q, 1H) 3.27 (dd, J=14.04, 3.66 Hz, 1H) 3.91 (dd, 1H) 3.96-4.03 (m, 1H) 4.07 (dd, J=12.36, 7.48 Hz, 1H) 4.40 (dd, J=12.36, 5.04 Hz, 1H) 4.76-4.82 (m, 1H) 4.90-4.95 (m, 1H) 5.64-5.72 (m, 1H) 5.72-5.80 (m, 1H) 6.80 (tt, J=9.23, 2.44, 2.29 Hz, 1H) 6.83-6.88 (m, 2H) 7.33 (d, J=7.93 Hz, 1H) 7.43 (d, J=7.63 Hz, 1H) 7.48 (s, 1H).

Example 66

(1S,4R,5S,16R)-5-(3,5-difluoro-benzyl)-4-hydroxy-20-isobutyl-15-oxa-2,6-diaza-tricyclo[14.6.1.0$^{17,22}$]tricosa-12,17(22),18,20-tetraen-7-one

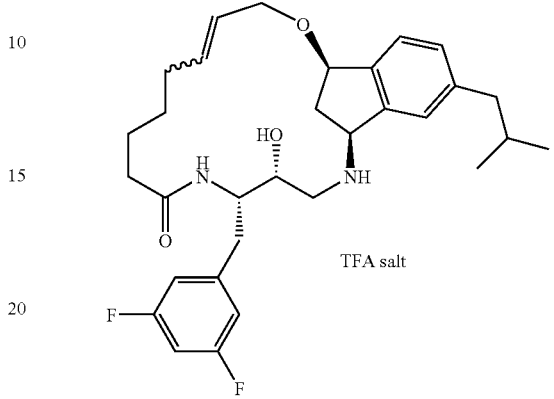

TFA salt

Step EC (1): A mixture of isomer A and B from Step EA (3) was coupled with isobutylzinc(II) bromide by following a procedure analogous to Step EB (1) to afford 1.5 mg of a TFA salt of the title compound as a mixture of olefin isomers. MS (M+H)$^+$ 527.42. $^1$H NMR (500 MHz, CD$_3$OD) δ ppm 0.89-0.99 (m, 6H) 1.35 (t, J=7.32 Hz, 2H) 1.39-1.60 (m, 2H) 1.86-1.96 (m, 1H) 2.01-2.20 (m, 3H) 2.58 (dd, J=7.02, 3.36 Hz, 2H) 2.60-2.77 (m, 2H) 2.82 (dd, J=9.31, 3.51 Hz, 1H) 2.97 (dd, J=14.95, 7.93 Hz, 1H) 3.15-3.26 (m, 3H) 3.44-3.49 (m, 1H) 3.87 (d, J=5.80 Hz, 1H) 3.92 (dd, J=10.07, 2.44 Hz, 1H) 4.07 (dd, J=12.67, 8.09 Hz, 1H) 4.41 (dd, J=12.51, 5.19 Hz, 1H) 4.79 (t, J=7.02 Hz, 1H) 5.19 (dd, J=6.71, 3.97 Hz, 1H) 5.59-5.82 (m, 2H) 6.78-6.84 (m, 2H) 6.86 (t, 2H) 7.24-7.35 (m, 1H) 7.40 (s, 1H) 7.42-7.50 (m, 2H).

Example 67

4-[(1S,4R,5S,16R)-5-(3,5-difluoro-benzyl)-4-hydroxy-7-oxo-15-oxa-2,6-diaza-tricyclo[14.6.1.0$^{17,22}$]tricosa-12,17(22),18,20-tetraen-20-yl]-butyronitrile

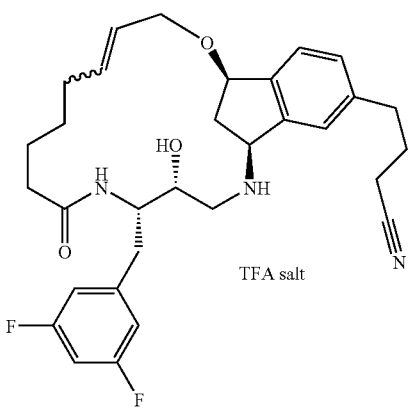

TFA salt

Step ED (1): A mixture of isomer A and B from Step EA (3) was coupled with (3-cyanopropyl)zinc(II) bromide by following a procedure analogous to Step EB (1) to afford 5.1 mg of a TFA salt of the title compound as a mixture of olefin isomers. MS (M+H)+ 538.38. $^1$H NMR (500 MHz, CD$_3$OD) δ ppm 1.28-1.38 (m, 2H) 1.37-1.68 (m, 4H) 1.95-2.21 (m, 6H) 2.41-2.52 (m, 2H) 2.67-2.77 (m, 1H) 2.77-2.87 (m, 3H) 2.92-3.03 (m, 2H) 3.16-3.23 (m, 2H) 3.27 (dd, J=14.19, 3.51 Hz, 1H) 3.88-3.95 (m, 1H) 3.97-4.04 (m, 1H) 4.04-4.12 (m, 1H) 4.39 (dd, J=12.21, 4.88 Hz, 1H) 4.90-4.97 (m, 1H) 5.61-5.83 (m, 2H) 6.74-6.83 (m, 1H) 6.85 (d, J=7.93 Hz, 2H) 7.19 (dd, J=27.01, 7.48 Hz, 1H) 7.38 (d, J=7.93 Hz, 1H) 7.44-7.54 (m, 2H).

Example 68

(1S,4R,5S,15R)-19-Bromo-5-(3,5-difluoro-benzyl)-4-hydroxy-14-oxa-2,6-diaza-tricyclo[13.6.1.0$^{16,21}$]docosa-11,16(21),17,19-tetraen-7-one

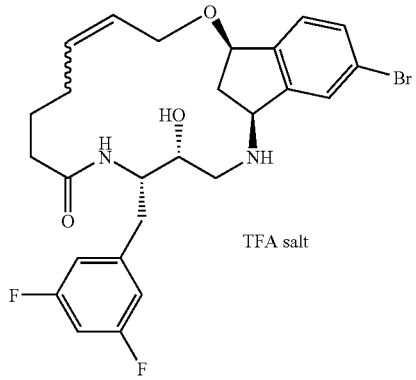

TFA salt

Step EE (1): (2R,3S)-1-((1S,3R)-3-(Allyloxy)-6-bromo-2,3-dihydro-1H-inden-1-ylamino)-3-amino-4-(3,5-difluorophenyl)butan-2-ol from Step EA (1) was coupled with hex-5-enoic acid by following a procedure analogous to Step EA (2) to afford 1.9 g (62% yield) of N-((2S,3R)-4-((1R,3R)-3-(allyloxy)-6-bromo-2,3-dihydro-1H-inden-1-ylamino)-1-(3,5-difluorophenyl)-3-hydroxybutan-2-yl)hex-5-enamide. MS (M+2H)+ 564.95. $^1$H NMR (500 MHz, CDCl$_3$) δ ppm 1.58-1.69 (m, 3H) 1.87-2.00 (m, 4H) 2.03-2.16 (m, 2H) 2.64-2.73 (m, 2H) 2.76-2.85 (m, 2H) 3.04 (dd, J=14.34, 4.58 Hz, 1H) 3.48-3.53 (m, 1H) 4.04-4.21 (m, 4H) 4.76 (t, J=5.80 Hz, 1H) 4.93 (s, 1H) 4.96 (dd, J=3.51, 1.37 Hz, 1H) 5.20 (dd, J=10.38, 1.22 Hz, 1H) 5.28-5.34 (m, 1H) 5.60-5.76 (m, 2H) 5.90-5.99 (m, 1H) 6.63-6.68 (m, 1H) 6.73-6.78 (m, 2H) 7.28 (d, J=8.24 Hz, 1H) 7.41 (dd, J=7.93, 1.83 Hz, 1H) 7.51 (s, 1H).

Step EE (2). The product from Step EE (1) underwent ring-closing metathesis by following a procedure analogous to Step CA (2) to afford 430 mg (53% yield) of a TFA salt of the title compound as a mixture of olefin isomers. MS (M+2H)+ 537.20. Data for the major isomer: $^1$H NMR (500 MHz, CDCl$_3$) δ ppm 0.75-0.90 (m, 1H) 1.52 (dd, J=7.32, 3.66 Hz, 1H) 1.79-1.93 (m, 1H) 1.92-2.03 (m, 1H) 2.03-2.19 (m, 3H) 2.18-2.28 (m, 1H) 2.52 (d, J=15.56 Hz, 1H) 2.58-2.69 (m, 1H) 2.68-2.83 (m, 2H) 2.95 (dd, J=13.58, 3.51 Hz, 1H) 3.34 (d, J=10.99 Hz, 1H) 3.86-4.10 (m, 4H) 4.70 (d, J=5.49 Hz, 1H) 4.82 (dd, J=10.99, 6.71 Hz, 1H) 5.33-5.44 (m, 1H) 5.44-5.57 (m, 1H) 6.50-6.62 (m, 1H) 6.65 (d, J=6.10 Hz, 2H) 7.19-7.27 (m, 1H) 7.27-7.37 (m, 1H) 7.48-7.60 (m, 1H) 7.79 (s, 1H). Data for the minor isomer: $^1$H NMR (500 MHz, CDCl$_3$) δ ppm 0.75-0.90 (m, 1H) 1.52 (dd, J=7.32, 3.66 Hz, 1H) 1.64 (dd, J=7.32, 3.36 Hz, 1H) 1.69-1.81 (m, 1H) 2.03-2.19 (m, 3H) 2.18-2.28 (m, 1H) 2.41 (d, J=15.56 Hz, 1H) 2.58-2.69 (m, 1H) 2.68-2.83 (m, 2H) 3.07 (d, J=11.90 Hz, 1H) 3.26 (d, J=11.90 Hz, 1H) 3.86-4.10 (m, 4H) 4.82 (dd, J=10.99, 6.71 Hz, 2H) 5.44-5.57 (m, 1H) 5.57-5.68 (m, 1H) 6.50-6.62 (m, 1H) 6.65 (d, J=6.10 Hz, 2H) 7.09-7.18 (m, 1H) 7.27-7.37 (m, 1H) 7.48-7.60 (m, 1H) 7.86 (s, 1H).

Example 69

(1S,4R,5S,15R)-5-(3,5-difluoro-benzyl)-4-hydroxy-19-(3-methyl-butyl)-14-oxa-2,6-diaza-tricyclo[13.6.1.0$^{16,21}$]docosa-11,16(21),17,19-tetraen-7-one

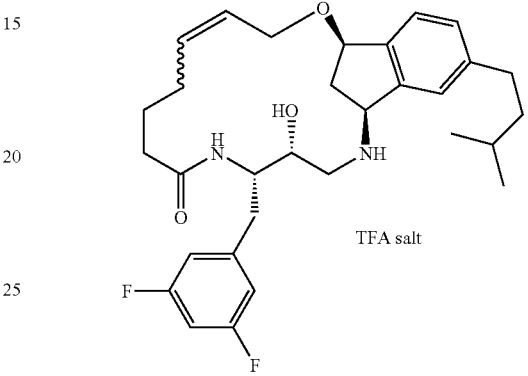

TFA salt

Step EF (1): A mixture of olefin isomers from Step EE (2) was coupled with isopentylzinc(II) bromide by following a procedure analogous to Step EB (1) to afford 2.5 mg of a TFA salt of the title compound as a mixture of olefin isomers. 2.5 mg of the title compound was obtained using the general Negishi coupling procedure. (M+H)+ 527.37. $^1$H NMR (500 MHz, CDCl$_3$) δ ppm 0.90 (dd, J=5.65, 3.81 Hz, 1H) 0.94 (d, J=6.41 Hz, 6H) 1.38 (t, J=7.32 Hz, 2H) 1.42-1.55 (m, 2H) 1.55-1.64 (m, 1H) 1.78-1.96 (m, 1H) 2.01-2.15 (m, 2H) 2.20-2.28 (m, 1H) 2.29-2.42 (m, 1H) 2.48-2.61 (m, 1H) 2.64-2.71 (m, 1H) 3.11-3.34 (m, 3H) 3.93-4.11 (m, 2H) 4.22-4.37 (m, 1H) 4.72 (d, J=3.97 Hz, 1H) 4.82 (d, J=4.88 Hz, 1H) 5.35-5.46 (m, 1H) 5.48-5.66 (m, 1H) 6.61-6.76 (m, 5H) 7.26-7.32 (m, 3H) 7.33-7.44 (m, 3H).

Example 70

3,3,3-trifluoro-propane-1-sulfonic acid ((1S,4R,5S,8S,15R)-4-hydroxy-5-isobutyl-19-methoxy-7-oxo-14-oxa-2,6-diaza-tricyclo[13.6.1.0$^{16,21}$]docosa-11,16(21),17,19-tetraen-8-yl)-methyl-amide TFA salt Step EG (1): (S)-2-(3,3,3-Trifluoro-N-methylpropylsulfonamido)hex-5-enoic acid (from Preparation M) and (2R, 3S)-1-((1S,3R)-3-(allyloxy)-6-methoxy-2,3-dihydro-1H-inden-1-ylamino)-3-amino-5-methylhexan-2-ol (from Preparation AT) were coupled following a procedure analogous to Step CA (1) to afford 160 mg (55% yield) of the TFA salt of (S)-N-((2R,3S)-1-((1S,3R)-3-(allyloxy)-6-methoxy-2,3-dihydro-1H-inden-1-ylamino)-2-hydroxy-5-methylhexan-3-yl)-2-(3,3,3-trifluoro-N-methylpropylsulfonamido)hex-5-enamide. LRMS (M+H)$^+$=634.22; $^1$H NMR (300 MHz, CDCl$_3$) δ ppm 0.6-0.8 (dd, 6H) 1.2-1.8 (m, 3H) 1.8-2.1 (m, 3H) 2.3-2.7 (m, 4H) 2.78 (s, 3H) 2.8-3.3 (m, 6H) 3.78 (s, 3H) 3.8-4.1 (m, 3H) 4.2-4.3 (m, 1H) 4.6-4.8 (m, 2H) 5.0-5.4 (m, 4H) 5.7-5.9 (m, 2H) 6.6-6.7 (m, 1H) 6.8-7.0 (d, 1H) 7.1-7.2 (s, 1H) 7.3-7.4 (d, 1H).

Step EG (2): The product from Step EG (1) (150 mg, 240 μmol) was subject to the ring-closing metathesis procedure described in Step CA (2) to afford 56 mg (31% yield) of the TFA salt of the title compound. LC-MS (M+H)$^+$=606.23; $^1$H NMR (300 MHz, CDCl$_3$) δ ppm 0.7-0.9 (dd, 6H) 1.2-1.6 (m, 4H) 2.1-4.4 (m, 24H) 4.6-4.8 (m, 1H) 5.4-5.8 (m, 1H) 6.9-7.2 (m, 2H) 7.3-7.5 (m, 1H).

Example 71

(1S,4R,5S,15R)-4-hydroxy-5-isobutyl-19-methoxy-14-oxa-2,6-diaza-tricyclo[13.6.1.0$^{16,21}$]docosa-11,16(21),17,19-tetraen-7-one

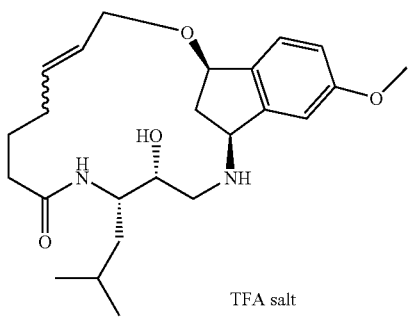

TFA salt

Step EI (1): Hex-5-enoic acid and (2R,3S)-1-((1S,3R)-3-(allyloxy)-6-methoxy-2,3-dihydro-1H-inden-1-ylamino)-3-amino-5-methylhexan-2-ol (from Preparation AT) were coupled following a procedure analogous to Step CA (1) to afford 10 mg (9% yield) of the TFA salt of N-((2R,3S)-1-((1S,3R)-3-(allyloxy)-6-methoxy-2,3-dihydro-1H-inden-1-ylamino)-2-hydroxy-5-methylhexan-3-yl)hex-5-enamide. LRMS (M+H)$^+$=445.4; $^1$H NMR (300 MHz, CDCl$_3$) δ ppm 0.7-0.9 (dd, 6H) 1.0-1.3 (m, 1H) 1.3-1.5 (m, 1H) 1.5-1.8 (m, 3H) 2.0-2.1 (m, 2H) 2.1-2.3 (m, 2H) 2.3-2.6 (m, 2H) 2.9-3.0 (m, 1H) 3.2-3.4 (m, 1H) 3.7 (s, 3H) 3.9-4.0 (m, 2H) 4.6-4.8 (m, 4H) 4.9-5.0 (m, 2H) 5.1-5.3 (m, 2H) 5.6-5.8 (m, 2H) 6.5-6.6 (m, 1H) 6.9-7.0 (d, 1H) 7.1 (s, 1H) 7.3 (d, 1H).

Step EI (2): The product from Step EI (1) (10 mg, 20 μmol) was subjected to the ring-closing metathesis procedure described in Step CA (2) to afford 4.2 mg (44% yield) of the TFA salt of the title compound. LC-MS (M+H)$^+$=417.4; $^1$H NMR (300 MHz, CDCl$_3$) δ ppm 0.8-0.9 (dd, 6H) 1.0-3.4 (m, 15H) 3.8 (s, 3H) 3.9-4.1 (m, 1H) 4.1-4.3 (m, 1H) 4.5-4.8 (m, 2H) 5.3-5.5 (m, 1H) 5.5-5.7 (m, 1H) 6.9-7.0 (m, 2H) 7.4 (d, 1H).

Example 72 pentane-1-sulfonic acid ((1S,4R,5S,8S,14R)-5-benzyl-4-hydroxy-18-isopropoxy-7-oxo-13-oxa-2,6-diaza-tricyclo[12.6.1.0$^{15,20}$]henicosa-10,15(20),16,18-tetraen-8-yl)-methyl-amide

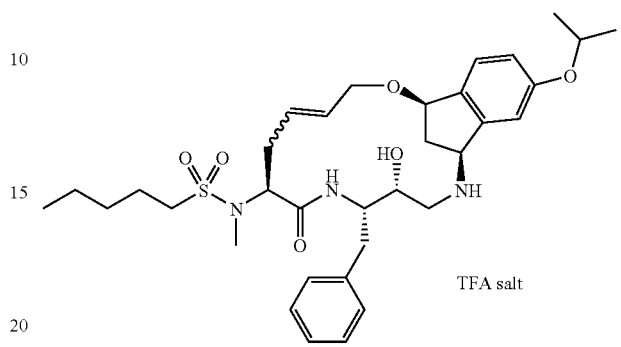

TFA salt

Step EJ (1): (S)-2-(N-Methylpentylsulfonamido)pent-4-enoic acid (130 mg, 490 μmol, from Preparation J) and (2R,3S)-1-((1S,3R)-3-(allyloxy)-6-isopropoxy-2,3-dihydro-1H-inden-1-ylamino)-3-amino-4-phenylbutan-2-ol (200 mg, 480 μmol, from Preparation AW) were coupled using a procedure analogous to Step CA (1) to afford 240 mg (65% yield) of the TFA salt of (S)-N-((2S,3R)-4-((1S,3R)-3-(allyloxy)-6-isopropoxy-2,3-dihydro-1H-inden-1-ylamino)-3-hydroxy-1-phenylbutan-2-yl)-2-(N-methylpentylsulfonamido)pent-4-enamide. LC-MS (M+H)$^+$=656.27; $^1$H NMR (300 MHz, CDCl$_3$) δ ppm 0.8-0.9 (m, 3H) 1.2-1.4 (m, 10H) 1.6-1.8 (m, 2H) 2.1-2.4 (m, 5H) 2.5-2.7 (m, 2H) 2.7-3.0 (m, 3H) 3.1-3.4 (m, 2H) 3.8-4.0 (m, 1H) 4.0-4.2 (m, 4H) 4.5-4.6 (m, 1H) 4.6-4.8 (m, 2H) 5.0-5.4 (m, 5H) 5.0-5.7 (m, 1H) 5.8-6.0 (m, 1H) 6.6-6.8 (m, 1H) 6.8-7.0 (m, 1H) 7.0-7.4 (m, 6H).

Step EJ (2): The product from Step EJ (1) (230 mg, 300 μmol) was subjected to the ring-closing metathesis procedure described in Step CA (2) to afford 81 mg (36% yield) of the TFA salt of the title compound. LC-MS (M+H)$^+$=628.27; $^1$H NMR (300 MHz, CDCl$_3$) δ ppm 0.8-0.9 (m, 3H) 1.2-1.4 (m, 10H) 1.6-1.8 (m, 2H) 2.0-2.2 (m, 1H) 2.4-3.2 (m, 14H) 3.6-3.8 (m, 2H) 4.0-4.2 (m, 2H) 4.2-4.4 (m, 1H) 4.5-4.6 (m, 1H) 4.7 (s, 1H) 5.6 (s, 1H) 6.8-7.4 (m, 8H).

Example 73

3,3,3-trifluoro-propane-1-sulfonic acid ((1S,4R,5S,8S,14R)-5-benzyl-4-hydroxy-18-isopropoxy-7-oxo-13-oxa-2,6-diaza-tricyclo[12.6.1.0$^{15,20}$]henicosa-10,15(20),16,18-tetraen-8-yl)-methyl-amide

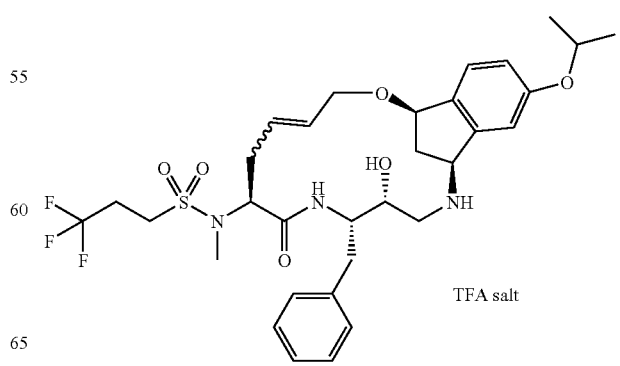

TFA salt

Step EK (1): (S)-2-(3,3,3-Trifluoro-N-methylpropylsulfonamido)pent-4-enoic acid (120 mg, 420 μmol, from Preparation J) and (2R,3S)-1-((1S,3R)-3-(allyloxy)-6-isopropoxy-2,3-dihydro-1H-inden-1-ylamino)-3-amino-4-phenylbutan-2-ol (200 mg, 480 μmol, from Preparation AW) were coupled using a procedure analogous to Step CA (1) to afford 280 mg (70% yield) of the TFA salt of (S)-N-((2S,3R)-4-((1S,3R)-3-(allyloxy)-6-isopropoxy-2,3-dihydro-1H-inden-1-ylamino)-3-hydroxy-1-phenylbutan-2-yl)-2-(3,3,3-trifluoro-N-methylpropylsulfonamido)pent-4-enamide. LC-MS (M+H)⁺=682.23; ¹H NMR (300 MHz, CDCl₃) δ ppm 1.2-1.3 (d, 6H) 2.2-3.3 (m, 15H) 3.9-4.0 (m, 1H) 4.0-4.1 (m, 2H) 4.1-4.3 (m, 2H) 4.5-4.8 (m, 3H) 5.1-5.4 (m, 4H) 5.5-5.7 (m, 1H) 5.8-6.0 (m, 1H) 6.6-6.7 (m, 1H) 6.8-7.0 (m, 1H) 7.1-7.4 (m, 6H).

Step EK (2): The product from Step EK (1) (270 mg, 340 μmol) was subjected to the ring-closing metathesis procedure described in Step CA (2) to afford 190 mg (73% yield) of the TFA salt of the title compound. LC-MS (M+H)⁺=654.22; ¹H NMR (300 MHz, CDCl₃) δ ppm 1.30-1.32 (d, 6H) 2.0-2.2 (m, 1H) 2.5-3.4 (m, 16H) 3.8-3.9 (m, 2H) 4.0-4.2 (m, 2H) 4.2-4.4 (m, 1H) 4.5-4.6 (m, 1H) 4.7 (s, 1H) 5.6 (s, 1H) 6.8-7.4 (m, 8H).

Example 74 pentane-1-sulfonic acid ((1S,4R,5S,8S,15R)-5-benzyl-4-hydroxy-19-isopropoxy-7-oxo-14-oxa-2,6-diaza-tricyclo[13.6.1.0¹⁶,²¹]docosa-11,16(21),17,19-tetraen-8-yl)-methyl-amide

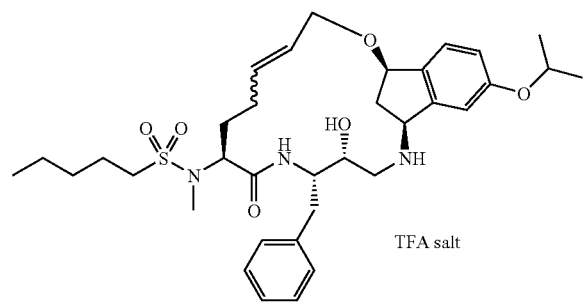

Step EL (1): (S)-2-(N-methylpentylsulfonamido)hex-5-enoic acid (100 mg, 360 μmol) and (2R,3S)-1-((1S,3R)-3-(allyloxy)-6-isopropoxy-2,3-dihydro-1H-inden-1-ylamino)-3-amino-4-phenylbutan-2-ol (120 mg, 290 μmol, from Preparation AW) were coupled using a procedure analogous to Step CA (1) to afford 96 mg (42% yield) of the TFA salt of (S)-N-((2S,3R)-4-((1S,3R)-3-(allyloxy)-6-isopropoxy-2,3-dihydro-1H-inden-1-ylamino)-3-hydroxy-1-phenylbutan-2-yl)-2-(N-methylpentylsulfonamido)hex-5-enamide. LC-MS (M+H)⁺=670.34; ¹H NMR (300 MHz, CDCl₃) δ ppm 0.8-0.9 (m, 3H) 1.2-1.4 (m, 10H) 1.4-1.6 (m, 1H) 1.6-1.8 (m, 2H) 1.8-2.5 (m, 5H) 2.5-2.7 (m, 1H) 2.7-3.0 (m, 4H) 3.1-3.3 (m, 2H) 3.8-4.0 (m, 1H) 4.0-4.2 (m, 4H) 4.5-4.8 (m, 3H) 4.9-5.1 (m, 2H) 5.1-5.3 (m, 4H) 5.6-5.9 (m, 2H) 6.6-6.7 (m, 1H) 6.8-7.0 (m, 1H) 7.0-7.4 (m, 6H).

Step EL (2): The product from Step EL (1) (93 mg, 120 μmol) was subjected to the ring-closing metathesis procedure described in Step CA (2) to afford 38 mg (42% yield) of the TFA salt of the title compound. LC-MS (M+H)⁺=642.26; ¹H NMR (300 MHz, CDCl₃) δ ppm 0.8-1.0 (m, 3H) 1.2-1.4 (m, 10H) 1.6-1.8 (m, 2H) 2.0-3.4 (m, 17H) 3.7-4.2 (m, 4H) 4.3-4.5 (m, 1H) 4.5-4.9 (m, 2H) 5.3-5.8 (m, 1H) 6.8-7.0 (m, 1H) 7.0-7.5 (m, 7H).

Example 75

3,3,3-trifluoro-propane-1-sulfonic acid ((1S,4R,5S,8S,15R)-5-benzyl-4-hydroxy-19-isopropoxy-7-oxo-14-oxa-2,6-diaza-tricyclo[13.6.1.0¹⁶,²¹]docosa-11,16(21),17,19-tetraen-8-yl)-methyl-amide

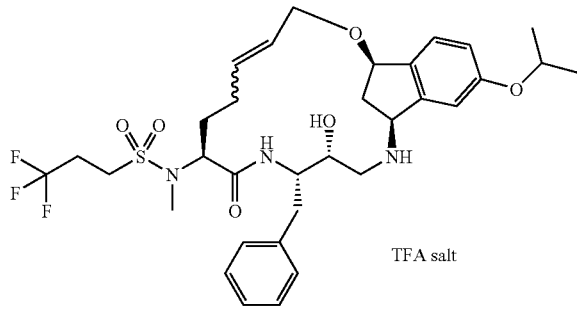

Step EM (1): (S)-2-(3,3,3-Trifluoro-N-methylpropylsulfonamido)hex-5-enoic acid (75 mg, 250 μmol, from Preparation M) and (2R,3S)-1-((1S,3R)-3-(allyloxy)-6-isopropoxy-2,3-dihydro-1H-inden-1-ylamino)-3-amino-4-phenylbutan-2-ol (110 mg, 270 μmol, from Preparation AW) were coupled using a procedure analogous to Step CA (1) to afford 91 mg (42% yield) of the TFA salt of (S)-N-((2S,3R)-4-((1S,3R)-3-(allyloxy)-6-isopropoxy-2,3-dihydro-1H-inden-1-ylamino)-3-hydroxy-1-phenylbutan-2-yl)-2-(3,3,3-trifluoro-N-methylpropylsulfonamido)hex-5-enamide. LC-MS (M+H)⁺=696.25; ¹H NMR (300 MHz, CDCl₃) δ ppm 1.2-1.4 (d, 6H) 1.5-1.7 (m, 1H) 1.8-2.1 (m, 2H) 2.3-3.3 (m, 14H) 3.9-4.2 (m, 5H) 4.5-4.8 (m, 3H) 4.9-5.4 (m, 4H) 5.6-5.9 (m, 2H) 6.6-6.8 (m, 1H) 6.8-7.0 (m, 1H) 7.0-7.4 (m, 6H).

Step EM (2): The product from Step EM (1) (90 mg, 110 μmol) was subjected to the ring-closing metathesis procedure described in Step CA (2) to afford 7.1 mg (9% yield) of the TFA salt of the title compound. LC-MS (M+H)⁺=668.15; ¹H NMR (300 MHz, CDCl₃) δ ppm 1.0-1.4 (m, 6H) 2.0-3.4 (m, 19H) 3.7-4.2 (m, 4H) 4.3-4.5 (m, 1H) 4.5-4.9 (m, 2H) 5.3-5.8 (m, 1H) 6.8-7.0 (m, 1H) 7.0-7.5 (m, 7H).

Example 76

(1S,4R,5S,14R)-5-benzyl-4-hydroxy-18-isopropoxy-13-oxa-2,6-diaza-tricyclo[12.6.1.0¹⁵,²⁰]henicosa-10,15(20),16,18-tetraen-7-one

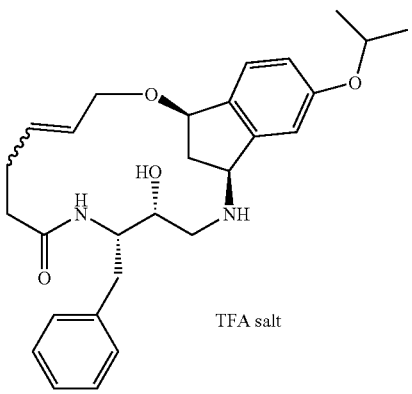

Step EN (1): Pent-4-enoic acid (40 mg, 390 μmol) and (2R,3S)-1-((1S,3R)-3-(allyloxy)-6-isopropoxy-2,3-dihydro-1H-inden-1-ylamino)-3-amino-4-phenylbutan-2-ol (120 mg, 290 μmol, from Preparation AW) were coupled using a procedure analogous to Step CA (1) to afford 43 mg (24% yield) of the TFA salt of N-((2S,3R)-4-((1S,3R)-3-(allyloxy)-6-isopropoxy-2,3-dihydro-1H-inden-1-ylamino)-3-hydroxy-1-phenylbutan-2-yl)pent-4-enamide. LC-MS (M+H)$^+$=493.33; $^1$H NMR (300 MHz, CDCl$_3$) δ ppm 1.2-1.4 (d, 6H) 2.1-3.2 (m, 13H) 3.2-3.3 (m, 1H) 3.8-4.2 (m, 4H) 4.4-4.7 (m, 2H) 4.7-5.0 (m, 2H) 5.1-5.4 (m, 2H) 5.5-6.0 (m, 2H) 6.3-6.5 (m, 1H) 6.8-6.9 (m, 1H) 7.0-7.4 (m, 7H).

Step EN (2): The product from Step EN (1) (40 mg, 70 μmol) was subjected to the ring-closing metathesis procedure described in Step CA (2) to afford 18 mg (46% yield) of the TFA salt of the title compound. LC-MS (M+H)$^+$=465.33; $^1$H NMR (300 MHz, CDCl$_3$) δ ppm 1.2-1.4 (m, 6H) 2.0-2.5 (m, 5H) 2.5-3.0 (m, 3H) 3.0-3.5 (m, 2H) 3.8-4.8 (m, 7H) 5.5-5.8 (m, 2H) 6.8-7.4 (m, 8H).

Example 77

(1S,4R,5S,15R)-5-benzyl-4-hydroxy-19-isopropoxy-14-oxa-2,6-diaza-tricyclo[13.6.1.0$^{16,21}$]docosa-11,16(21),17,19-tetraen-7-one

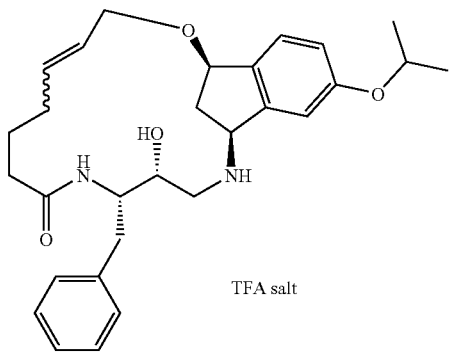

TFA salt

Step EO (1): Hex-5-enoic acid (40 mg, 350 μmol) and (2R,3S)-1-((1S,3R)-3-(allyloxy)-6-isopropoxy-2,3-dihydro-1H-inden-1-ylamino)-3-amino-4-phenylbutan-2-ol (120 mg, 290 μmol, from Preparation AW) were coupled using a procedure analogous to Step CA (1) to afford 74 mg (41% yield) of the TFA salt of N-((2S,3R)-4-((1S,3R)-3-(allyloxy)-6-isopropoxy-2,3-dihydro-1H-inden-1-ylamino)-3-hydroxy-1-phenylbutan-2-yl)hex-5-enamide. LC-MS (M+H)$^+$=507.29.

Step EO (2): The product from Step EO (1) (74 mg, 70 μmol) was subjected to the ring-closing metathesis procedure described in Step CA (2) to afford 10 mg (14% yield) of the TFA salt of the title compound. LC-MS (M+H)$^+$=479.32; $^1$H NMR (300 MHz, CDCl$_3$) δ ppm 1.2-1.4 (m, 6H) 1.4-3.4 (m, 14H) 3.8-4.0 (m, 2H) 4.3-4.8 (m, 3H) 5.3-5.6 (m, 2H) 6.8-7.4 (m, 8H).

Example 78

(1S,4R,5S,15R)-5-(3,5-difluoro-benzyl)-4-hydroxy-19-isopropoxy-14-oxa-2,6-diaza-tricyclo[13.6.1.0$^{16,21}$]docosa-11,16(21),17,19-tetraen-7-one

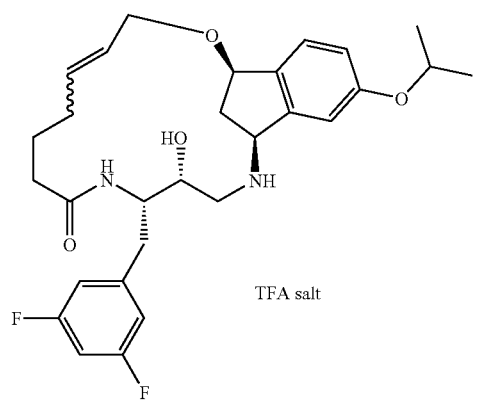

TFA salt

Step EP (1): Hex-5-enoic acid (60 mg, 520 μmol) and (2R,3S)-1-((1S,3R)-3-(allyloxy)-6-isopropoxy-2,3-dihydro-1H-inden-1-ylamino)-3-amino-4-(3,5-difluorophenyl)butan-2-ol (200 mg, 450 μmol, from Preparation AX) were coupled using a procedure analogous to Step CA (1) to afford 180 mg (61% yield) of the TFA salt of N-((2S,3R)-4-((1S,3R)-3-(allyloxy)-6-isopropoxy-2,3-dihydro-1H-inden-1-ylamino)-1-(3,5-difluorophenyl)-3-hydroxybutan-2-yl)hex-5-enamide. LC-MS (M+H)$^+$=507.29.

Step EP (2): The product from Step EP (1) (180 mg, 270 μmol) was subjected to the ring-closing metathesis procedure described in Step CA (2) to afford 32 mg (19% yield) of the TFA salt of the title compound. LC-MS (M+H)$^+$=515.36; $^1$H NMR (300 MHz, CDCl$_3$) δ ppm 1.2-1.4 (m, 6H) 1.4-3.4 (m, 14H) 3.8-4.2 (m, 2H) 4.4-4.8 (m, 3H) 5.3-5.8 (m, 2H) 6.5-7.4 (m, 6H).

Example 79

(1S,4R,5S,15R)-4-hydroxy-5-isobutyl-19-isopropoxy-14-oxa-2,6-diaza-tricyclo[13.6.1.0$^{16,21}$]docosa-11,16(21),17,19-tetraen-7-one

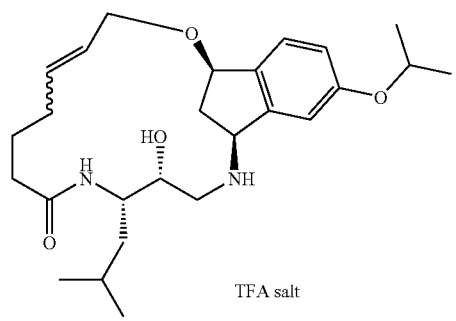

TFA salt

Step EQ (1): Hex-5-enoic acid (240 mg, 2.1 mmol) and (2R,3S)-N$^1$-((1S,3R)-3-(allyloxy)-6-isopropoxy-2,3-dihydro-1H-inden-1-yl)-2-(tert-butyldimethylsilyloxy)-5-methylhexane-1,3-diamine (1.1 g, 2.2 mmol, from Preparation BH) were coupled using a procedure analogous to Step CA (1) to afford N-((2R,3S)-1-((1S,3R)-3-(allyloxy)-6-isopropoxy-2,3-dihydro-1H-inden-1-ylamino)-2-(tert-butyldimethylsilyloxy)-5-methylhexan-3-yl)hex-5-enamide. LC-MS (M+H)$^+$=587.47.

Step EQ (2): Tetrabutylammonium fluoride (1.0 M in THF, 5 mL, 5 mmol) was added to a solution of the crude product from Step EQ (1) in THF (40 mL). The reaction mixture was stirred at rt for 3 h. The resulting mixture was concentrated in vacuo and purified using reverse phase preparatory HPLC to afford 250 mg (17% yield over 3 steps) of the TFA salt of N-((2R,3S)-1-((1S,3R)-3-(allyloxy)-6-isopropoxy-2,3-dihydro-1H-inden-1-ylamino)-2-hydroxy-5-methylhexan-3-yl)hex-5-enamide. LC-MS (M+H)$^+$=473.35.

Step EQ (3): The product from Step EQ (2) was subjected to the ring-closing metathesis procedure described in Step CA (2) to afford 43 mg (18% yield) of the TFA salt of the title compound. LC-MS (M+H)$^+$=445.37; $^1$H NMR (300 MHz, CDCl$_3$) δ ppm 0.8-0.9 (m, 6H) 1.0-3.4 (m, 20H) 3.5-4.3 (m, 4H) 4.5-4.8 (m, 2H) 5.3-5.7 (m, 2H) 6.8-7.0 (m, 2H) 7.3-7.5 (m, 1H).

Example 80

(1S,4R,5S,15R)-5-benzyl-4-hydroxy-19-propoxy-14-oxa-2,6-diaza-tricyclo[13.6.1.0$^{16,21}$]docosa-11,16(21),17,19-tetraen-7-one

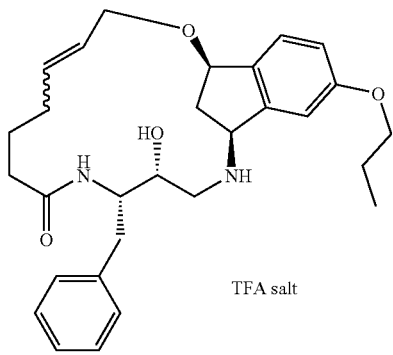

TFA salt

Step ER (1): Hex-5-enoic acid (60 mg, 520 μmol) and (2R,3S)-1-((1S,3R)-3-(allyloxy)-6-propoxy-2,3-dihydro-1H-inden-1-ylamino)-3-amino-4-phenylbutan-2-ol (200 mg, 490 μmol, from Preparation AZ) were coupled using a procedure analogous to Step CA (1) to afford 33 mg (11% yield) of the TFA salt of N-((2S,3R)-4-((1S,3R)-3-(allyloxy)-6-propoxy-2,3-dihydro-1H-inden-1-ylamino)-3-hydroxy-1-phenylbutan-2-yl)hex-5-enamide. LC-MS (M+H)$^+$=507.29. $^1$H NMR (300 MHz, CDCl$_3$) δ ppm 0.9-1.1 (t, 3H) 1.4-1.6 (m, 2H) 1.7-2.0 (m, 4H) 2.0-2.2 (m, 2H) 2.4-3.2 (m, 4H) 3.2-3.3 (m, 1H) 3.8-4.0 (m, 6H) 4.1-4.3 (m, 1H) 4.6-4.7 (m, 1H) 4.7-4.8 (m, 1H) 4.8-5.0 (m, 2H) 5.1-5.3 (m, 2H) 5.6-5.8 (m, 1H) 5.8-6.0 (m, 1H) 6.4-6.5 (m, 1H) 6.8-7.0 (m, 1H) 7.0-7.4 (m, 7H).

Step ER (2): The product from Step ER (1) (30 mg, 50 μmol) was subjected to the ring-closing metathesis procedure described in Step CA (2) to afford 13 mg (44% yield) of the TFA salt of the title compound. LC-MS (M+H)$^+$=479.20; $^1$H NMR (300 MHz, CDCl$_3$) δ ppm 0.9-1.1 (t, 3H) 1.2-1.5 (m, 2H) 1.7-2.0 (m, 3H) 2.0-2.4 (m, 3H) 2.4-2.6 (m, 2H) 2.8-3.0 (m, 2H) 3.1-3.4 (m, 2H) 3.8-4.5 (m, 6H) 4.5-4.9 (m, 2H) 5.3-5.7 (m, 2H) 6.8-7.4 (m, 8H).

Example 81

(1S,4R,5S,15R)-5-(3,5-difluoro-benzyl)-4-hydroxy-19-propoxy-14-oxa-2,6-diaza-tricyclo[13.6.1.0$^{16,21}$]docosa-11,16(21),17,19-tetraen-7-one

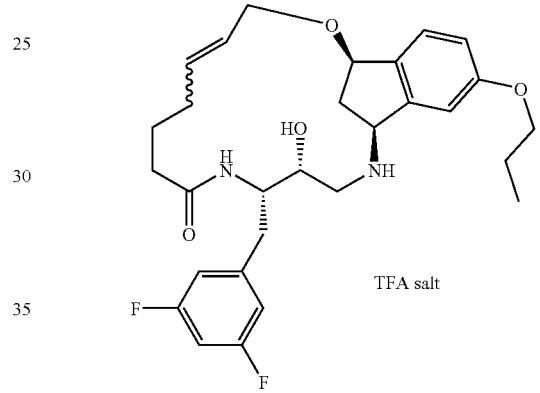

TFA salt

Step ES (1): Hex-5-enoic acid (90 mg, 790 μmol) and (2R,3S)-1-((1S,3R)-3-(allyloxy)-6-propoxy-2,3-dihydro-1H-inden-1-ylamino)-3-amino-4-(3,5-difluorophenyl)butan-2-ol (300 mg, 670 μmol, from Preparation BA) were coupled using a procedure analogous to Step CA (1) to afford 230 mg (52% yield) of the TFA salt of N-((2S,3R)-4-((1S,3R)-3-(allyloxy)-6-propoxy-2,3-dihydro-1H-inden-1-ylamino)-1-(3,5-difluorophenyl)-3-hydroxybutan-2-yl)hex-5-enamide. LC-MS (M+H)$^+$=543.21. $^1$H NMR (300 MHz, CDCl$_3$) δ ppm 0.9-1.1 (t, 3H) 1.4-1.6 (m, 2H) 1.7-2.0 (m, 4H) 2.0-2.2 (m, 2H) 2.4-3.1 (m, 4H) 3.2-3.3 (m, 1H) 3.8-4.0 (m, 4H) 4.0-4.1 (m, 2H) 4.1-4.2 (m, 1H) 4.6-4.7 (m, 1H) 4.7-4.8 (m, 1H) 4.8-5.0 (m, 2H) 5.1-5.4 (m, 2H) 5.5-5.7 (m, 1H) 5.8-6.0 (m, 1H) 6.4-6.6 (m, 1H) 6.6-6.8 (m, 3H) 6.9-7.0 (d, 1H) 7.1 (s, 1H) 7.3-7.4 (d, 1H).

Step ES (2): The product from Step ES (1) (220 mg, 335 μmol) was subjected to the ring-closing metathesis procedure described in Step CA (2) to afford 43 mg (20% yield) of the TFA salt of the title compound. LC-MS (M+H)$^+$=515.18; $^1$H NMR (300 MHz, CDCl$_3$) δ ppm 0.9-1.1 (t, 3H) 1.3-1.6 (m, 2H) 1.6-1.9 (m, 3H) 1.9-2.4 (m, 3H) 2.4-2.6 (m, 4H) 3.1-3.4 (m, 2H) 3.7-4.2 (m, 6H) 4.5-4.9 (m, 2H) 5.3-5.7 (m, 2H) 6.5-7.4 (m, 6H).

Example 82

(1S,4R,5S,15R)-5-(3,5-difluoro-benzyl)-4-hydroxy-19-propoxy-14-oxa-2,6-diaza-tricyclo[13.6.1.0^{16,21}]docosa-16(21),17,19-trien-7-one

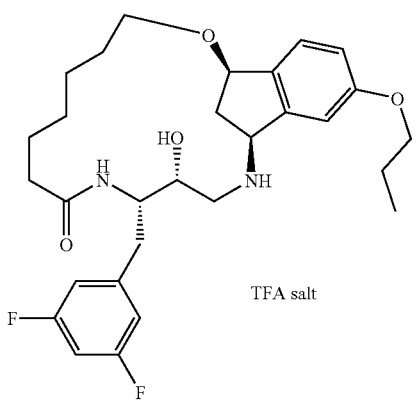

TFA salt

Step ET (1): A mixture of the product from ES (2) (40 mg) and Pd/C (10%, 5 mg) in EtOAc (30 mL) was stirred under hydrogen (balloon) for two h. The catalyst was removed by filtration. The filtrate was concentrated in vacuo. The residue was purified using preparatory reverse phase HPLC to afford 30 mg (75% yield) of the TFA salt of the title compound. LC-MS (M+H)$^+$=517.17; $^1$H NMR (300 MHz, CDCl$_3$) δ ppm 0.9-1.1 (t, 3H) 1.1-1.6 (m, 6H) 1.6-1.9 (m, 2H) 2.0-2.3 (m, 2H) 2.3-3.0 (m, 4H) 3.0-3.4 (m, 3H) 3.4-3.79m, 3H) 3.7-4.0 (m, 3H) 4.2-4.4 (m, 1H) 4.6-4.8 (m, 2H) 6.5-6.8 (m, 3H) 6.9-7.0 (d, 1H) 7.0-7.1 (s, 1H) 7.2-7.4 (d, 1H).

Example 83

(1S,4R,5S,16R)-5-(3,5-difluoro-benzyl)-4-hydroxy-20-propoxy-15-oxa-2,6-diaza-tricyclo[14.6.1.0^{17,22}]tricosa-12,17(22),18,20-tetraen-7-one

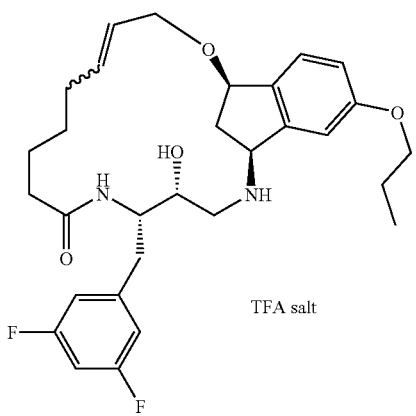

TFA salt

Step EU (1): Hept-6-enoic acid (90 mg, 700 μmol) and (2R,3S)-1-((1S,3R)-3-(allyloxy)-6-propoxy-2,3-dihydro-1H-inden-1-ylamino)-3-amino-4-(3,5-difluorophenyl)butan-2-ol (300 mg, 670 μmol, from Preparation BA) were coupled using a procedure analogous to Step CA (1) to afford 240 mg (54% yield) of the TFA salt of N-((2S,3R)-4-((1S,3R)-3-(allyloxy)-6-propoxy-2,3-dihydro-1H-inden-1-ylamino)-1-(3,5-difluorophenyl)-3-hydroxybutan-2-yl)hept-6-enamide. LC-MS (M+H)$^+$=557.21. $^1$H NMR (300 MHz, CDCl$_3$) δ ppm 0.9-1.1 (t, 3H) 1.1-1.3 (m, 2H) 1.3-1.5 (m, 2H) 1.7-1.9 (m, 2H) 1.9-2.0 (m, 2H) 2.0-2.2 (m, 2H) 2.3-3.3 (m, 5H) 3.8-4.0 (m, 4H) 4.0-4.1 (m, 2H) 4.1-4.2 (m, 1H) 4.6-4.7 (m, 1H) 4.7-4.8 (m, 1H) 4.8-5.0 (m, 2H) 5.1-5.4 (m, 2H) 5.6-6.0 (m, 1H) 6.4-6.6 (m, 1H) 6.6-6.8 (m, 3H) 6.9-7.0 (d, 1H) 7.1 (s, 1H) 7.3-7.4 (d, 1H).

Step EU (2): The product from Step EU (1) (230 mg, 343 μmol) was subjected to the ring-closing metathesis procedure described in Step CA (2) to afford 61 mg (28% yield) of the TFA salt of the title compound. LC-MS (M+H)$^+$=529.41; $^1$H NMR (300 MHz, CDCl$_3$) δ ppm 0.9-1.0 (m, 3H) 1.0-3.4 (m, 16H) 3.7-4.3 (m, 6H) 4.6-5.0 (m, 2H) 5.1-5.8 (m, 2H) 6.5-7.4 (m, 6H).

Example 84

(1S,4R,5S,15R)-5-(3,5-difluoro-benzyl)-4-hydroxy-20-propoxy-15-oxa-2,6-diaza-tricyclo[14.6.1.0^{17,22}]tricosa-17(22),18,20-trien-7-one

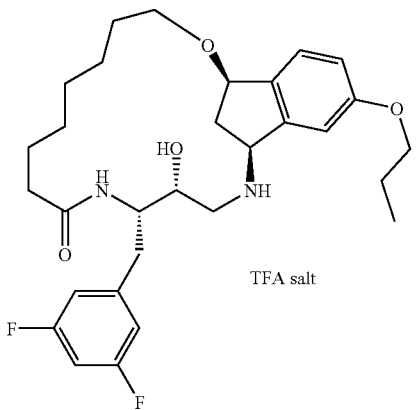

TFA salt

Step EV (1): The product from EU (2) (58 mg) was hydrogenated by following a procedure analogous to Step ET (1) to afford the TFA salt of the title compound. LC-MS (M+H)$^+$=531.30; $^1$H NMR (300 MHz, CDCl$_3$) δ ppm 0.9-1.5 (m, 12H) 1.5-1.8 (m, 2H) 1.9-2.3 (m, 4H) 2.3-3.7 (m, 8H) 3.7-4.2 (m, 3H) 4.5-4.7 (m, 2H) 6.5-6.8 (m, 3H) 6.8-7.0 (d, 1H) 7.0-7.2 (s, 1H) 7.2-7.4 (d, 1H).

Example 85 hexanoic acid ((4R,5S,8S)-5-benzyl-4-hydroxy-7-oxo-18-phenoxy-13-oxa-2,6-diaza-tricyclo[12.6.1.0^{15,20}]henicosa-10,15(20),16,18-tetraen-8-yl)-methyl-amide

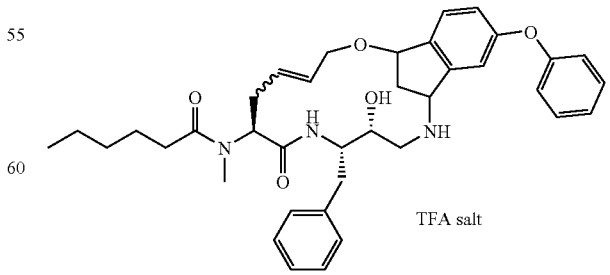

TFA salt

Step EW (1): (S)-2-(N-Methylhexanamido)pent-4-enoic acid (420 mg, 1.8 mmol) and (2R,3S)-N$^1$-(3-(allyloxy)-6- phenoxy-2,3-dihydro-1H-inden-1-yl)-2-(tert-butyldimethyl-silyloxy)-4-phenylbutane-1,3-diamine (1.0 g, 1.8 mmol, from Preparation BC) were coupled using a procedure analogous to Step CA (1) to afford 900 mg (65% yield) of N-((2S)-1-((2S,3R)-4-(3-(allyloxy)-6-phenoxy-2,3-dihydro-1H-inden-1-ylamino)-3-(tert-butyldimethylsilyloxy)-1-phenylbutan-2-ylamino)-1-oxopent-4-en-2-yl)-N-methylhexanamide. LC-MS (M+H)+=768.65; $^1$H NMR (300 MHz, CDCl$_3$) δ ppm 0.0 (m, 6H) 0.7-0.9 (m, 12H) 1.0-1.4 (m, 6H) 1.4-1.7 (m, 3H) 1.7-2.3 (m, 4H) 2.4 (s, 3H) 2.5-3.0 (m, 4H) 3.5-3.8 (m, 1H) 4.0-4.4 (m, 4H) 4.7-4.8 (m, 1H) 4.8-5.4 (m, 4H) 5.5-6.1 (m, 2H) 6.8-7.4 (m, 13H).

Step EW (2): The p-toluenesulfonic acid salt of the product from Step EW (1) was subjected to the ring-closing metathesis procedure described in Step CA (2) to afford a crude mixture containing hexanoic acid [(4R,5S,8S)-5-benzyl-4-(tert-butyl-dimethyl-silanyloxy)-7-oxo-18-phenoxy-13-oxa-2,6-diaza-tricyclo[12.6.1.0$^{15,20}$]henicosa-10,15(20),16,18-tetraen-8-yl]-methyl-amide. LC-MS (M+H)+=740.52.

Step EW (3): Tetrabutylammonium fluoride (1.0 M in THF, 2 mL, 2 mmol) was added to a solution of the crude product from Step EW (2) in THF (30 mL). The reaction mixture was stirred at rt for 18 h. The resulting mixture was concentrated in vacuo and purified using reverse phase preparatory HPLC to afford 250 mg (5% yield over 2 steps) of the TFA salt of the title compound. LC-MS (M+H)+=626.41; $^1$H NMR (300 MHz, CDCl$_3$) δ ppm 0.7-1.0 (m, 3H) 1.0-1.5 (m, 9H) 1.8-2.3 (m, 4H) 2.5 (s, 3H) 2.7-2.9 (m, 4H) 3.5-3.9 (m, 5H) 4.7-4.9 (m, 1H) 5.0-5.2 (m, 1H) 5.6-5.7 (m, 1H) 6.8-7.4 (m, 13H).

Example 86 hexanoic acid ((4R,5S,8S)-5-benzyl-4-hydroxy-7-oxo-19-phenoxy-14-oxa-2,6-diaza-tricyclo[13.6.1.0$^{16,21}$]docosa-11,16(21),17,19-tetraen-8-yl)-methyl-amide

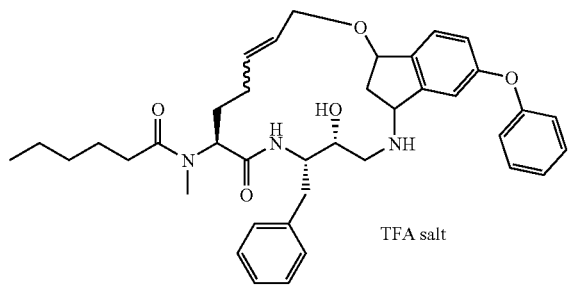

TFA salt

Step EX (1): (S)-2-(N-methylhexanamido)hex-5-enoic acid (500 mg, 2.1 mmol) and (2R,3S)-N$^1$-(3-(allyloxy)-6-phenoxy-2,3-dihydro-1H-inden-1-yl)-2-(tert-butyldimethyl-silyloxy)-4-phenylbutane-1,3-diamine (1.2 g, 2.1 mmol, from Preparation BC) were coupled using a procedure analogous to Step CA (1) to afford 650 mg (40% yield) of (2S)-N-((2S,3R)-4-(3-(allyloxy)-6-phenoxy-2,3-dihydro-1H-inden-1-ylamino)-3-(tert-butyldimethylsilyloxy)-1-phenylbutan-2-yl)-2-(N-methylhexanamido)hex-5-enamide. LC-MS (M+H)+=782.65; $^1$H NMR (300 MHz, CDCl$_3$) δ ppm 0.0 (m, 6H) 0.6-0.9 (m, 12H) 1.1-1.4 (m, 6H) 1.4-1.6 (m, 3H) 1.7-2.3 (m, 6H) 2.3-2.4 (s, 3H) 2.5-2.9 (m, 4H) 3.5-3.8 (m, 1H) 4.0-4.4 (m, 4H) 4.7-4.8 (m, 1H) 4.8-5.4 (m, 4H) 5.6-6.1 (m, 2H) 6.9-7.4 (m, 13H).

Step EX (2): Tetrabutylammonium fluoride (1.0 M in THF, 2 mL, 2 mmol) was added to a solution of the product from Step EX (1) (650 mg, 0.83 mmol) in THF (30 mL). The reaction mixture was stirred for 18 h. The resulting mixture was diluted with water and extracted with EtOAc. The organic layer was washed with brine, dried over Na$_2$SO$_4$, filtered, and concentrated in vacuo to afford a crude mixture containing (2S)-N-((2S,3R)-4-(3-(allyloxy)-6-phenoxy-2,3-dihydro-1H-inden-1-ylamino)-3-hydroxy-1-phenylbutan-2-yl)-2-(N-methylhexanamido)hex-5-enamide. LC-MS (M+H)+=668.51.

Step EX (3): The p-toluenesulfonic acid salt of the product from Step EX (2) was subjected to the ring-closing metathesis procedure described in Step CA (2) to afford 50 mg (8% yield over 2 steps) of the TFA salt of the title compound. LC-MS (M+H)+=640.49; $^1$H NMR (300 MHz, CDCl$_3$) δ ppm 0.8-1.0 (m, 3H) 1.1-1.6 (m, 7H) 2.0-2.5 (m, 13H) 2.5-3.0 (m, 3H) 3.6-4.1 (m, 4H) 4.6-5.0 (m, 2H) 5.4-5.7 (m, 1H) 6.8-7.4 (m, 13H).

Example 87 hexanoic acid ((4R,5S,8S)-5-benzyl-4-hydroxy-7-oxo-19-phenoxy-14-oxa-2,6-diaza-tricyclo[13.6.1.0$^{16,21}$]docosa-16(21),17,19-trien-8-yl)-methyl-amide (isomer A)

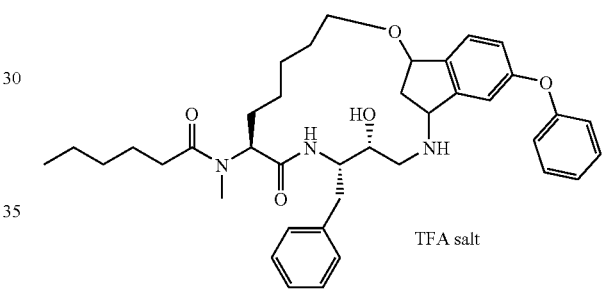

TFA salt and

Example 88 hexanoic acid ((4R,5S,8S)-5-benzyl-4-hydroxy-7-oxo-19-phenoxy-14-oxa-2,6-diaza-tricyclo[13.6.1.0$^{16,21}$]docosa-16(21),17,19-trien-8-yl)-methyl-amide (isomer B)

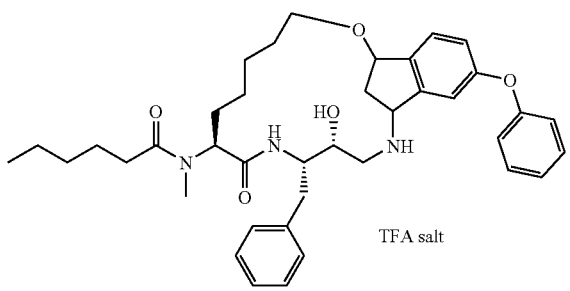

TFA salt

Step EY (1): The product from EX (3) (58 mg) was hydrogenated by following a procedure analogous to Step ET (1) to afford, after reverse phase preparatory HPLC purification, 11 mg of Example 87 (isomer A) and 2.8 mg of Example 88

149

(isomer B) as their TFA salts. Data for Example 87, isomer A: LC-MS (M+H)⁺=642.26; $^1$H NMR (300 MHz, CDCl$_3$) δ ppm 0.7-1.0 (m, 3H) 1.0-1.7 (m, 12H) 1.7-3.0 (m, 12H) 3.0-3.4 (m, 1H) 3.4-4.0 (m, 3H) 4.0-4.3 (m, 1H) 4.6-4.9 (m, 2H) 6.8-7.4 (m, 13H). Data for Example 88, isomer B: LC-MS (M+H)⁺=642.26; $^1$H NMR (300 MHz, CDCl$_3$) δ ppm 0.8-1.0 (m, 3H) 1.2-1.6 (m, 12H) 1.7-2.1 (m, 7H) 2.1-2.5 (m, 5H) 3.0-3.2 (m, 1H) 3.3-3.7 (m, 3H) 3.8-3.9 (m, 1H) 4.2-4.4 (m, 1H) 4.6-4.9 (m, 2H) 7.0-7.4 (m, 13H).

Example 89

(4R,5S)-5-benzyl-4-hydroxy-19-phenoxy-14-oxa-2,6-diaza-tricyclo[13.6.1.0$^{16,21}$]docosa-11,16(21),17,19-tetraen-7-one

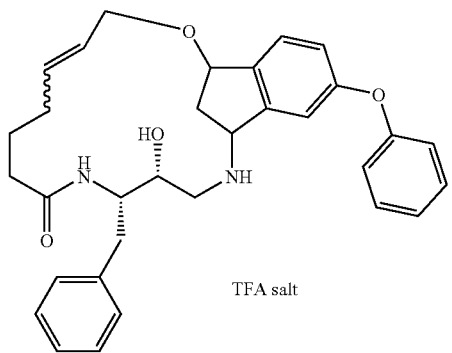

TFA salt

Step EZ (1): Hex-5-enoic acid (65 mg, 0.57 mmol) and (2R,3S)-N$^1$-(3-(allyloxy)-6-phenoxy-2,3-dihydro-1H-inden-1-yl)-2-(tert-butyldimethylsilyloxy)-4-phenylbutane-1,3-diamine (300 mg, 0.54 mmol, from Preparation BC) were coupled using a procedure analogous to Step CA (1) to afford a crude mixture containing N-((2S,3R)-4-(3-(allyloxy)-6-phenoxy-2,3-dihydro-1H-inden-1-ylamino)-3-(tert-butyldimethylsilyloxy)-1-phenylbutan-2-yl)hex-5-enamide.

Step EZ (2): Tetrabutylammonium fluoride (1.0 M in THF, 2 mL, 2 mmol) was added to a solution of the crude product from Step EZ (1) in THF (20 mL). The reaction mixture was stirred for 18 h. The resulting mixture was concentrated in vacuo. The residue was purified using reverse phase preparatory HPLC to afford 170 mg (48% yield over 2 steps) of the TFA salt of N-((2S,3R)-4-(3-(allyloxy)-6-phenoxy-2,3-dihydro-1H-inden-1-ylamino)-3-hydroxy-1-phenylbutan-2-yl)hex-5-enamide. LC-MS (M+H)⁺=541.28; $^1$H NMR (300 MHz, CDCl$_3$) δ ppm 1.3-1.6 (m, 2H) 1.7-1.9 (m, 2H) 1.9-2.2 (m, 2H) 2.4-2.7 (m, 2H) 2.7-2.9 (m, 2H) 2.9-3.3 (M, 2H) 3.8-4.2 (m, 4H) 4.5-4.7 (m, 2H) 4.7-4.9 (m, 2H) 5.1-5.3 (m, 2H) 5.6-5.7 (m, 1H) 5.7-6.0 (m, 1H) 6.9-7.5 (m, 13H).

Step EZ (3): The product from Step EZ (2) was subjected to the ring-closing metathesis procedure described in Step CA (2) to afford 35 mg (40% yield) of the TFA salt of the title compound. LC-MS (M+H)⁺=513.25; $^1$H NMR (300 MHz, CDCl$_3$) δ ppm 1.2-1.6 (m, 2H) 1.8-2.4 (m, 4H) 2.4-3.5 (m, 6H) 3.8-4.1 (m, 3H) 4.1-4.4 (m, 1H) 4.5-4.9 (m, 2H) 5.3-5.7 (m, 2H) 6.9-7.5 (m, 13H).

150

Example 90

(1S,4R,5S,15R)-5-(3,5-difluoro-benzyl)-4-hydroxy-19-(2-methoxy-phenyl)-14-oxa-2,6-diaza-tricyclo[13.6.1.0$^{16,21}$]docosa-11,16(21),17,19-tetraen-7-one

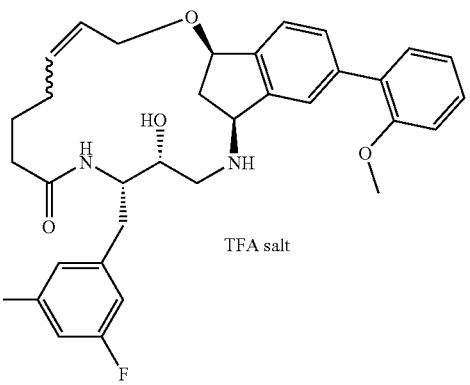

TFA salt

Step FA (1): Palladium tetrakistriphenylphosphine (4.00 mg, 3.46 μmol) and 2-methoxyphenylboronic acid (5.50 μmol) were added to a conical pressure vial charged with a magnetic stirring bar. A solution of (1S,4R,5S,15R)-19-bromo-5-(3,5-difluoro-benzyl)-4-hydroxy-14-oxa-2,6-diaza-tricyclo[13.6.1.0$^{16,21}$]docosa-11,16(21),17,19-tetraen-7-one (18 mg, 28 μmol, TFA salt of Example 68) in benzene (0.5 mL) was added to the reaction vial. Ethanol (0.5 mL) and sodium carbonate (1.0 mmol) were then added. The vial was capped and its contents were mixed by shaking. The vial was placed into an aluminum heating block, preheated to 115° C. The reaction was magnetically stirred for 1.5 h at 115° C. The vial was removed from the heating block and allowed to cool to rt with continued stirring for 16 h. The reaction mixture was filtered through celite to remove solids. The celite was washed sequentially with EtOAc and methanol. The filtrate was concentrated in vacuo. The residue was dissolved in a minimum of methanol and purified by preparative HPLC (methanol/0.1% TFA water, 30×100 mm, 5 micron, AXIA Luna C18 column, 35 mL/min, 220 nm wavelength, 0.5 mL injections). The pure fractions were pooled and concentrated under vacuum to afford 10 mg (42% yield) of the TFA salt of the title compound. LC/MS (M+H)⁺ 536.31. HRMS calculated for C$_{33}$H$_{36}$N$_2$O$_4$F$_2$ 562.2643, found 563.2722 (M+H)⁺; $^1$H NMR (500 MHz, CD$_3$OD) δ ppm 1.29-1.36 (m, 1H) 1.49-1.58 (m, 1H) 1.98-2.03 (m, 2H) 2.16-2.22 (m, 1H) 2.27-2.36 (m, 1H) 2.58-2.67 (m, 2H) 2.90-2.99 (m, 1H) 3.17-3.23 (m, 1H) 3.40-3.47 (m, 2H) 3.66-3.75 (m, 2H) 3.83-3.87 (m, 3H) 3.99-4.06 (m, 2H) 4.06-4.11 (m, 2H) 4.89 (d, J=6.41 Hz, 1H) 5.03 (d, J=8.85 Hz, 1H) 5.46-5.55 (m, 2H) 6.71-6.78 (m, 3H) 7.07 (t, J=7.48 Hz, 1H) 7.13 (d, J=8.24 Hz, 1H) 7.35-7.41 (m, 2H) 7.56-7.61 (m, 1H) 7.62-7.66 (m, 1H) 7.79-7.83 (m, 1H).

Example 91

(1S,4R,5S,15R)-19-(3,5-bis-trifluoromethyl-phenyl)-5-(3,5-difluoro-benzyl)-4-hydroxy-14-oxa-2,6-diaza-tricyclo[13.6.1.0^{16,21}]docosa-11,16(21),17,19-tetraen-7-one

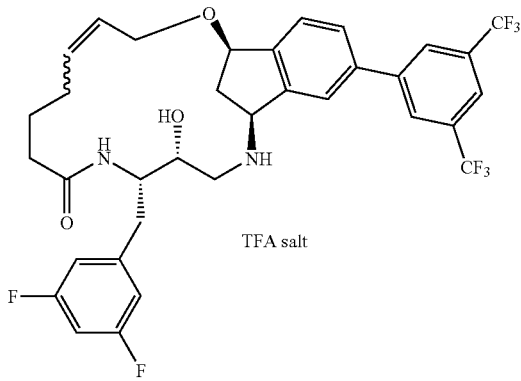

Step FB (1): The TFA salt of the title compound (12 mg) was prepared in 43% yield via Suzuki coupling of (1S,4R,5S,15R)-19-bromo-5-(3,5-difluoro-benzyl)-4-hydroxy-14-oxa-2,6-diaza-tricyclo[13.6.1.0$^{16,21}$]docosa-11,16(21),17,19-tetraen-7-one (TFA salt of Example 68) and 3,5-bis(trifluoromethyl)phenylboronic acid by following a procedure analogous to Step FA (1). LC/MS (M+H)$^+$ 669.18. HRMS calculated for $C_{34}H_{32}N_2O_3F_8$ 668.6220, found 669.2354 (M+H)$^+$; $^1$H NMR (400 MHz, CD$_3$OD) δ ppm 1.22-1.33 (m, 1H) 1.49 (s, 1H) 1.71-1.81 (m, 1H) 1.88-1.99 (m, 3H) 2.15 (dd, J=12.46, 10.20 Hz, 2H) 2.22-2.33 (m, 1H) 2.51-2.63 (m, 1H) 2.85 (s, 1H) 2.93 (ddd, J=16.05, 9.00, 6.92 Hz, 1H) 3.15-3.27 (m, 2H) 3.62-3.73 (m, 2H) 3.99-4.09 (m, 2H) 4.89 (t, J=6.80 Hz, 1H) 5.00-5.07 (m, 1H) 5.40-5.51 (m, 2H) 6.67-6.78 (m, 3H) 7.72 (t, J=7.93 Hz, 1H) 7.85-7.92 (m, 1H) 7.95-8.03 (m, 2H) 8.24 (s, 2H).

Example 92

(1S,4R,5S,15R)-5-(3,5-Difluoro-benzyl)-4-hydroxy-19-(4-trifluoromethoxy-phenyl)-14-oxa-2,6-diaza-tricyclo[13.6.1.0$^{16,21}$]docosa-11,16(21),17,19-tetraen-7-one

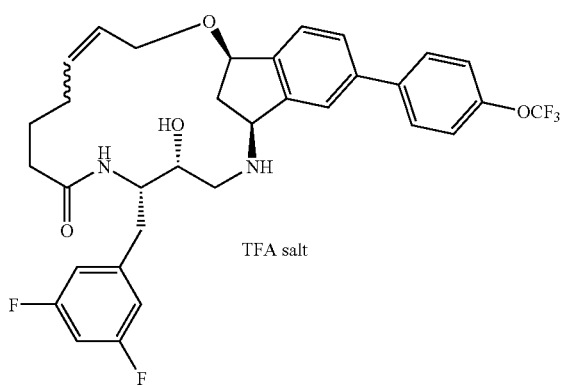

Step FC (1): The TFA salt of the title compound (14 mg) was prepared in 53% yield via Suzuki coupling of (1S,4R,5S,15R)-19-bromo-5-(3,5-difluoro-benzyl)-4-hydroxy-14-oxa-2,6-diaza-tricyclo[13.6.1.0$^{16,21}$]docosa-11,16(21),17,19-tetraen-7-one (TFA salt of Example 68) and 4-(trifluoromethoxy)phenylboronic acid by following a procedure analogous to Step FA (1). LC/MS (M+H)$^+$ 617.20. HRMS calculated for $C_{33}H_{33}N_2O_4F_5$ 616.624. found 617.2439 (M+H)$^+$. $^1$H NMR (400 MHz, CD$_3$OD) δ ppm 1.22-1.33 (m, 2H) 1.49 (s, 1H) 1.77 (d, J=19.39 Hz, 1H) 1.87-1.99 (m, 2H) 2.06-2.18 (m, 2H) 2.20-2.32 (m, 2H) 2.51-2.63 (m, 1H) 2.87-2.99 (m, J=15.64, 15.64, 8.75, 7.05 Hz, 1H) 3.13-3.20 (m, 1H) 3.38-3.49 (m, 1H) 3.61-3.72 (m, 2H) 3.96-4.07 (m, 2H) 4.85-4.89 (m, 1H) 4.97-5.05 (m, 1H) 5.40-5.52 (m, 1H) 6.67-6.78 (m, 3H) 7.37 (t, J=8.56 Hz, 2H) 7.64 (t, J=8.44 Hz, 1H) 7.71-7.81 (m, 4H) 7.82-7.90 (m, 1H).

Example 93

(1S,4R,5S,15R)-5-(3,5-difluoro-benzyl)-4-hydroxy-19-(1H-indol-5-yl)-14-oxa-2,6-diaza-tricyclo[13.6.1.0$^{16,21}$]docosa-11,16(21),17,19-tetraen-7-one

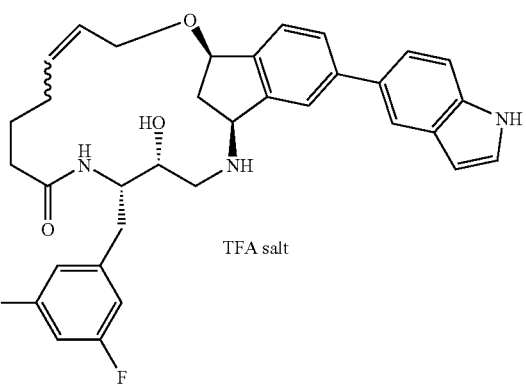

Step FD (1): The TFA salt of the title compound (3 mg) was prepared in 16% yield via Suzuki coupling of (1S,4R,5S,15R)-19-bromo-5-(3,5-difluoro-benzyl)-4-hydroxy-14-oxa-2,6-diaza-tricyclo[13.6.1.0$^{16,21}$]docosa-11,16(21),17,19-tetraen-7-one (TFA salt of Example 68) and 1H-indol-5-ylboronic acid by following a procedure analogous to Step FA (1). LC/MS (M+H)$^+$ 572.29. $^1$H NMR (500 MHz, CD$_3$OD) δ ppm 0.86-0.95 (m, 4H) 1.52 (s, 2H) 1.78 (s, 1H) 1.98 (s, 4H) 2.21 (s, 2H) 2.56 (s, 1H) 3.41-3.51 (m, 3H) 3.73 (s, 3H) 4.08-4.13 (m, 1H) 4.96 (s, 2H) 5.51 (s, 2H) 6.73 (d, J=7.32 Hz, 3H) 7.29-7.36 (m, 1H) 7.42-7.52 (m, 3H) 7.61 (s, 1H) 7.88 (s, 1H).

Example 94

(1S,4R,5S,15R)-5-(3,5-Difluoro-benzyl)-4-hydroxy-19-(4-morpholin-1-yl-phenyl)-14-oxa-2,6-diaza-tricyclo[13.6.1.0$^{16,21}$]docosa-11,16(21),17,19-tetraen-7-one

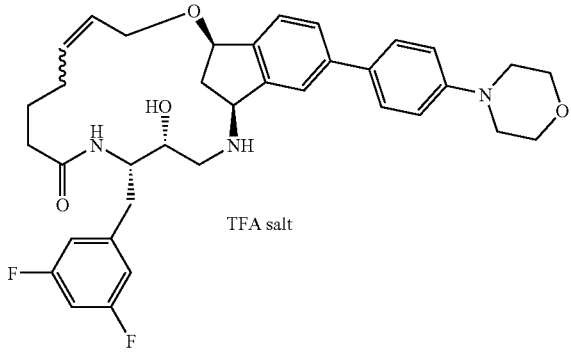

TFA salt

Step FE (1): The TFA salt of the title compound (10 mg) was prepared in 49% yield via Suzuki coupling of (1S,4R,5S,15R)-19-bromo-5-(3,5-difluoro-benzyl)-4-hydroxy-14-oxa-2,6-diaza-tricyclo[13.6.1.0$^{16,21}$]docosa-11,16(21),17,19-tetraen-7-one (TFA salt of Example 68) and 4-morpholinophenylboronic acid by following a procedure analogous to Step FA (1). LC/MS (M+H)$^+$ 628.27. HRMS calculated for $C_{36}H_{41}N_3O_4F_2$ 617.3065, found 618.3144 (M+H)$^+$. $^1$H NMR (400 MHz, CD$_3$OD) δ ppm 1.30 (q, J=7.64 Hz, 2H) 1.70 (d, J=10.32 Hz, 2H) 1.87-1.98 (m, 3H) 2.10-2.20 (m, 2H) 2.22-2.34 (m, 2H) 2.52-2.64 (m, 2H) 3.14-3.26 (m, 6H) 3.68 (dd, J=5.92, 3.65 Hz, 1H) 3.81-3.90 (m, 5H) 3.95-4.06 (m, 1H) 4.94-5.01 (m, 2H) 5.38-5.48 (m, 2H) 6.67-6.74 (m, 2H) 6.74-6.85 (m, 1H) 7.04-7.12 (m, 2H) 7.53-7.63 (m, 3H) 7.68-7.76 (m, 1H) 7.77-7.85 (m, 1H).

Example 95

(1S,4R,5S,15R)-5-(3,5-difluoro-benzyl)-4-hydroxy-19-(1H-pyrazol-4-yl)-14-oxa-2,6-diaza-tricyclo[13.6.1.0$^{16,21}$]docosa-11,16(21),17,19-tetraen-7-one

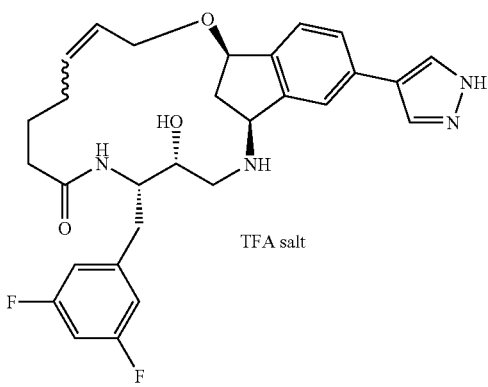

TFA salt

Step FE (1): The TFA salt of the title compound (10 mg) was prepared in 49% yield via Suzuki coupling of (1S,4R,5S,15R)-19-bromo-5-(3,5-difluoro-benzyl)-4-hydroxy-14-oxa-2,6-diaza-tricyclo[13.6.1.0$^{16,21}$]docosa-11,16(21),17,19-tetraen-7-one (TFA salt of Example 68) and 1H-pyrazol-4-ylboronic acid by following a procedure analogous to Step FA (1). LC/MS (M+H)$^+$ 523.23. $^1$H NMR (400 MHz, CD$_3$OD) δ ppm 1.25-1.36 (m, 2H) 1.49 (s, 1H) 1.75 (s, 1H) 1.96 (dd, J=7.05, 4.03 Hz, 2H) 2.17 (s, 1H) 2.25 (d, J=15.86 Hz, 1H) 2.52-2.64 (m, 1H) 2.86-2.97 (m, 1H) 3.11-3.21 (m, 2H) 3.36-3.47 (m, 3H) 3.69 (s, 2H) 3.95-4.06 (m, 2H) 4.91-5.02 (m, 2H) 5.40-5.51 (m, 2H) 6.70 (td, J=6.74, 2.90 Hz, 3H) 7.51-7.58 (m, 1H) 7.71 (dd, J=7.93, 1.64 Hz, 1H) 7.77-7.83 (m, 1H) 8.00 (s, 2H).

Example 96

5-[(1S,4R,5S,15R)-5-(3,5-difluoro-benzyl)-4-hydroxy-7-oxo-14-oxa-2,6-diaza-tricyclo[13.6.1.0$^{16,21}$]docosa-11,16(21),17,19-tetraen-19-yl]-hexahydro-pyrrolo[3,4-c]pyrrole-2-carboxylic acid tert-butyl ester

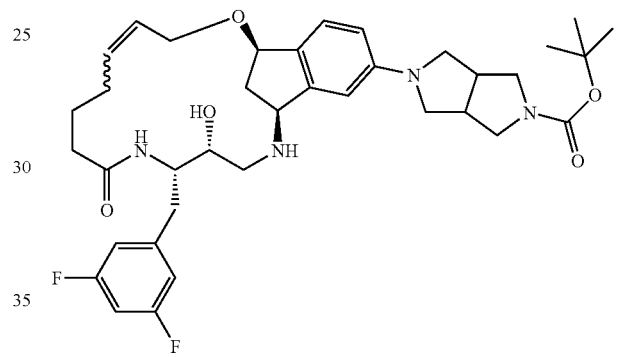

Step FF (1): Copper(I) iodide (20 mg, 0.104 mmol), K$_3$PO$_4$ (67 mg, 0.316 mmol), L-proline (9.2 mg, 0.080 mmol), and DMSO (1 mL) were combined in a 1 dram vial. tert-Butyl hexahydropyrrolo[3,4-c]pyrrole-2(1H)-carboxylate (40.7 mg, 0.192 mmol) and (1S,4R,5S,15R)-19-bromo-5-(3,5-difluoro-benzyl)-4-hydroxy-14-oxa-2,6-diaza-tricyclo[13.6.1.0$^{16,21}$]docosa-11,16(21),17,19-tetraen-7-one (39 mg, 0.073 mmol, TFA salt of Example 68) were added to the mixture. The vial was capped, shaken, and placed into a heating block preheated to 90° C. The reaction was allowed to stir magnetically for 16 h at 90° C. The reaction was cooled to rt, and diluted with water and EtOAc. The mixture was extracted with EtOAc. The combined organic layers were dried over magnesium sulfate, filtered, and concentrated under vacuo. The crude residue was purified by flash column chromatography on a small pre-packed silica gel column, eluted with 30% EtOAc/hexane, then 5-10% methanol/DCM. The pure fractions were pooled (R$_f$=0.54 in 5% methanol/DCM) and concentrated in vacuo to afford 30 mg (55% yield) of the title compound as a brown solid/residue. This material was determined to be a mixture of cis and trans isomers by proton NMR. Analytical HPLC conditions (methanol/0.1% TFA water, 4.6×50 mm, 5 micron, Waters X-Bridge C18 column, 5 mL/min, 254 nm wavelength) showed a purity of 90% and a R$_t$ of 4.79 min.

Example 97

(1S,4R,5S,15R)-5-(3,5-difluoro-benzyl)-4-hydroxy-19-(5-methyl-hexahydro-pyrrolo[3,4-c]pyrrol-2-yl)-14-oxa-2,6-diaza-tricyclo[13.6.1.0$^{16,21}$]docosa-11,16(21),17,19-tetraen-7-one

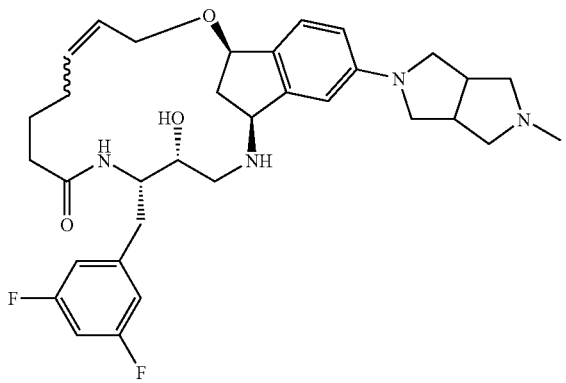

Step FG (1): The title compound (80 mg) was prepared in 46% yield via Ullman type coupling of (1S,4R,5S,15R)-19-bromo-5-(3,5-difluoro-benzyl)-4-hydroxy-14-oxa-2,6-diaza-tricyclo[13.6.1.0$^{16,21}$]docosa-11,16(21),17,19-tetraen-7-one (TFA salt of Example 68) and 2-methyloctahydropyrrolo[3,4-c]pyrrole by following a procedure analogous to Step FF (1). LC/MS (M+H)$^+$ 581.43. $^1$H NMR (400 MHz, CD$_3$OD) δ ppm 1.27 (s, 2H) 1.49 (s, 1H) 1.98-2.06 (m, 2H) 2.23-2.35 (m, 5H) 2.38 (s, 2H) 2.54 (s, 1H) 2.58-2.69 (m, 2H) 2.75 (s, 1H) 2.92 (d, J=12.09 Hz, 4H) 2.99-3.11 (m, 2H) 3.18 (s, 1H) 3.55 (d, J=10.83 Hz, 1H) 3.83 (m, 2H) 3.88-3.98 (m, 2H) 4.05 (d, J=14.10 Hz, 1H) 4.30 (m, 1H) 4.65 (m, 1H) 5.42-5.54 (m, 2H) 6.70-6.77 (m, 5H) 7.19 (t, J=7.43 Hz, 2H). CD$_3$OD

Example 98

(S)-2-methyl-hexanoic acid ((1S,4R,5S,8S,14R)-5-benzyl-4-hydroxy-18-methyl-7-oxo-13-oxa-2,6-diaza-tricyclo[12.6.1.0$^{15,20}$]henicosa-10,15(20),16,18-tetraen-8-yl)-methyl-amide

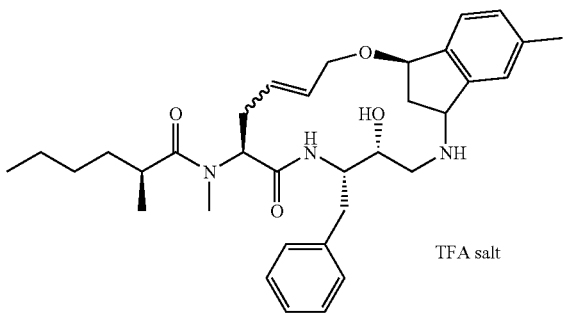

Step FH (1): (S)-2-((S)-N,2-Dimethylhexanamido)pent-4-enoic acid (33 mg, 136 μmol, diastereomer A from Preparation D) and (2R,3S)-1-((1S,3R)-3-(allyloxy)-6-methyl-2,3-dihydro-1H-inden-1-ylamino)-3-amino-4-phenylbutan-2-ol (50 mg, 136 μmol, from Preparation BK) were coupled following a procedure analogous to Step CA (1) to afford 73 mg (91% yield) of the TFA salt of (S)-N-((S)-1-((2S,3R)-4-((1S,3R)-3-(allyloxy)-6-methyl-2,3-dihydro-1H-inden-1-ylamino)-3-hydroxy-1-phenylbutan-2-ylamino)-1-oxopent-4-en-2-yl)-N,2-dimethylhexanamide. LC-MS (method C)R$_t$=2.59 min, (M+H)$^+$=590.32.

Step FH (2): The product from Step FH (1) (73 mg, 124 μmol) was subject to the ring-closing metathesis procedure described in Step CA (2) to afford 3.5 mg (5% yield) of the TFA salt of the title compound. LC-MS (method C) R$_t$=2.52 min, (M+H)$^+$=562.31.

Example 99

(S)-2-Methyl-hexanoic acid ((1R,4R,5S,8S,14S)-5-benzyl-4-hydroxy-18-methyl-7-oxo-13-oxa-2,6-diaza-tricyclo[12.6.1.0$^{15,20}$]henicosa-10,15(20),16,18-tetraen-8-yl)-methyl-amide

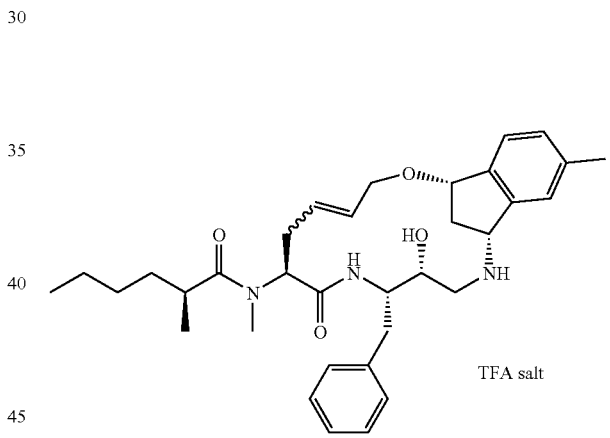

Step FI (1): (S)-2-((S)-N,2-Dimethylhexanamido)pent-4-enoic acid (66 mg, 273 μmol, diastereomer A from Preparation D) and (2R,3S)-1-((1S,3R)-3-(allyloxy)-6-methyl-2,3-dihydro-1H-inden-1-ylamino)-3-amino-4-phenylbutan-2-ol (100 mg, 273 μmol, from Preparation BL) were coupled following a procedure analogous to Step CA (1) to afford 96 mg (59% yield) of the TFA salt of (S)-N-((S)-1-((2S,3R)-4-((1R,3S)-3-(allyloxy)-6-methyl-2,3-dihydro-1H-inden-1-ylamino)-3-hydroxy-1-phenylbutan-2-ylamino)-1-oxopent-4-en-2-yl)-N,2-dimethylhexanamide. LC-MS (method C) R$_t$=2.68 min, (M+H)$^+$=590.31.

Step FI (2): The product from Step FI (1) (92 mg, 156 μmol) was subject to the ring-closing metathesis procedure described in Step CA (2) to afford 30 mg (34% yield) of the TFA salt of the title compound. LC-MS (method C) R$_t$=2.42 min, (M+H)$^+$=562.32.

Example 100

(S)-2-methyl-hexanoic acid ((1S,4R,5S,8S,14R)-5-benzyl-4-hydroxy-16,18-dimethyl-7-oxo-13-oxa-2,6-diaza-tricyclo[12.6.1.0$^{15,20}$]henicosa-10,15(20),16,18-tetraen-8-yl)-methyl-amide

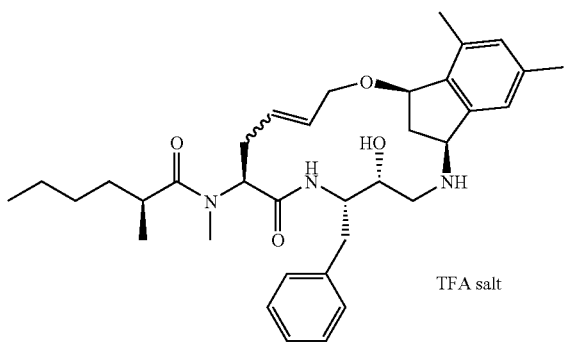

TFA salt

Step FJ (1): (S)-2-((S)-N,2-Dimethylhexanamido)pent-4-enoic acid (64 mg, 263 µmol, diastereomer A from Preparation D) and (2R,3S)-1-((1S,3R)-3-(allyloxy)-4,6-dimethyl-2,3-dihydro-1H-inden-1-ylamino)-3-amino-4-phenylbutan-2-ol (100 mg, 236 µmol, from Preparation BN) were coupled following a procedure analogous to Step CA (1) to afford 139 mg (87% yield) of the TFA salt of (S)-N-((S)-1-((2S,3R)-4-((1S,3R)-3-(allyloxy)-4,6-dimethyl-2,3-dihydro-1H-inden-1-ylamino)-3-hydroxy-1-phenylbutan-2-ylamino)-1-oxo-pent-4-en-2-yl)-N,2-dimethylhexanamide. LC-MS (method C) R$_t$=2.66 min, (M+H)$^+$=604.31.

Step FJ (2): The product from Step FJ (1) (73 mg, 124 µmol) was subjected to the ring-closing metathesis procedure described in Step CA (2) to afford 16.2 mg (12% yield) of the TFA salt of the title compound. LC-MS (method C) R$_t$=2.47 min, (M+H)$^+$=576.32.

Example 101

(S)-2-methyl-hexanoic acid ((1R,4R,5S,8S,14S)-5-benzyl-4-hydroxy-16,18-dimethyl-7-oxo-13-oxa-2,6-diaza-tricyclo[12.6.1.0$^{15,20}$]henicosa-10,15(20),16,18-tetraen-8-yl)-methyl-amide

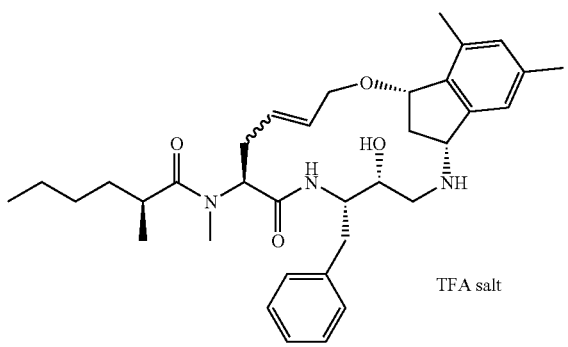

TFA salt

Step FK (1): (S)-2-((S)-N,2-Dimethylhexanamido)pent-4-enoic acid (64 mg, 263 µmol, diastereomer A from Preparation D) and (2R,3S)-1-((1S,3R)-3-(allyloxy)-4,6-dimethyl-2,3-dihydro-1H-inden-1-ylamino)-3-amino-4-phenylbutan-2-ol (100 mg, 236 µmol, from Preparation BO) were coupled following a procedure analogous to Step CA (1) to afford 115 mg (72% yield) of the TFA salt of (S)-N-((S)-1-((2S,3R)-4-((1R,3S)-3-(allyloxy)-4,6-dimethyl-2,3-dihydro-1H-inden-1-ylamino)-3-hydroxy-1-phenylbutan-2-ylamino)-1-oxo-pent-4-en-2-yl)-N,2-dimethylhexanamide. LC-MS (method C) R$_t$=2.60 min, (M+H)$^+$=604.31.

Step FK (2): The product from Step FK (1) (115 mg, 127 µmol) was subject to the ring-closing metathesis procedure described in Step CA (2) to afford 33 mg (45% yield) of the TFA salt of the title compound. LC-MS (method C) R$_t$=2.56 min, (M+H)$^+$=576.32.

Biological Methods

There are a number of methods by which inhibitors of the BACE enzyme can be identified experimentally. The enzyme can be obtained from membrane samples from natural tissues or cultured cells or can be expressed recombinantly in a host cell by well known methods of molecular biology. The whole enzyme or a portion thereof can be expressed, for example, in bacterial, insect or mammalian cells to obtain a catalytically active enzyme species. The enzymatic activity and/or ligand binding capability of the enzyme can be assessed within these membrane samples, or the enzyme can be purified to varying extents. As an illustrative example, the nucleic acid sequence encoding the pro and catalytic domains of human BACE can be appended on the 5' end with an untranslated and signal sequence from the gene for acetylcholinesterase, and on the 3' end with a sequence encoding a poly-histidine tag. This cDNA can then be expressed in *Drosophila melanogaster* S2 cells in which the signal and pro sequences of the transcribed/translated protein are removed by cellular proteases and the catalytic domain, appended by a C-terminal poly-histidine tag, is secreted out into the cellular medium. The enzyme can then be purified from the culture medium by nickel affinity chromatography by methods well known to those trained in the art [Mallender, W. et al., "Characterization of recombinant, soluble beta-secretase from an insect cell expression system." *Mol. Pharmacol.* 2001, 59: 619-626]. Similar strategies for expressing and purifying various forms of BACE in bacterial, mammalian and other cell types would be known to one skilled in the art. A preferred method for determining the potency of a test compound in binding to the BACE enzyme is by monitoring the displacement of a suitable radioligand.

Radioligand displacement assays with a radiolabeled BACE inhibitor (WO 2004 013098, compound 3, where the methoxy group is substituted for C($^3$H)$_3$) were carried out using standard methods (Keen, M. (1999) in *Receptor Binding Techniques* (Walker, J. M. ed) p. 106 Humana Press, Totowa, N.J.). The HEK293-9B.A1 cell line, which overexpresses the BACE1 enzyme, was derived from HEK293 cells (Simmons, N. L. (1990) A cultured human renal epithelioid cell line responsive to vasoactive intestinal peptide. *Exp. Physiol.* 75:309-19.) by RAGE™ (Harrington, J. J. et al. (2001) Creation of genome-wide protein expression libraries using random activation of gene expression. *Nat. Biotechnol.* 19:440-5.; U.S. Pat. Nos. 6,410,266 and 6,361,972). T225 flask cultures of HEK293-9B.A1 were grown to 80% confluency in DMEM supplemented with 2 mM L-glutamine, 10 µg/mL penicillin, 10 µg/mL streptomycin, 3 µg/mL puromycin, 100 nM methotrexate, and 10% fetal bovine serum (Invitrogen, Carlsbad, Calif.), harvested, and resuspended at 2×10$^8$ cells per 10 mL of lysis buffer consisting of 50 mM HEPES pH 7.0 containing a protease inhibitor cocktail of AEBSF 104 µM, aprotinin 80 nM, leupeptin 2 µM, bestatin 4 µM, pepstatin A 1.5 µM, and E-64 1.4 µM (0.1% of protease inhibitor cocktail P8340, Sigma-Aldrich, St. Louis, Mo.) at 4° C. The resuspended cells were homogenized using a Polytron (Brinkman, Westbury, N.Y.) at setting 6 for 10 sec., then centrifuged at 48,000×g for 10 min. The resulting pellet was washed by repeating the resuspension, homogenization and centrifugation steps. The final pellet was resuspended in buffer at 4° C. to yield a total protein concentration of 5 mg/mL, then aliquots were frozen in liquid nitrogen for further storage at −70° C. Immediately before carrying out a binding assay, an aliquot of cell homogenate was thawed and diluted to a concentration of 100 µg/mL in assay buffer consisting of 50 mM HEPES pH 5.0 and 0.1% CHAPSO. Assays were initiated in polypropylene 96-well plates (Costar, Cambridge, Mass.) by the addition of 200 µl of cell homogenate to 50 µl of assay buffer containing 1 nM radioligand (WO 2004 013098, compound 3, where the methoxy group is substituted for C($^3$H)$_3$: 80 Ci/mMol) and various concentrations of unlabelled compounds, and incubated for 1.5 hr. at 25° C. Separation of bound from free radioligand was by filtration on GFF glass fiber filters (Innotech Biosystems International, Lansing, Mich.) using an Innotech cell harvester. Filters were washed three times with 0.3 mL of phosphate buffered saline pH 7.0 at 4° C. and assessed for radioactivity using a Wallac 1450 Microbeta liquid scintillation counter (PerkinElmer, Boston, Mass.). Ki values of competing compounds were derived through Cheng-Prussoff correction of $IC_{50}$ values calculated using XLfit (IDBS, Guildford, UK).

Abbreviations:

AEBSF: 4-(2-Aminoethyl)benzenesulfonyl fluoride hydrochloride

CHAPSO: 3-[(3-Cholamidopropyl)dimethylammonio]-2-hydroxy-1-propanesulfonate

D-MEM: Dulbecco's modified eagle medium

HEPES: 4-(2-Hydroxyethyl)piperazine-1-ethanesulfonic acid

RAGE™: Random Activation of Gene Expression™

The activity of specific compounds described herein and tested in the above assay is provided in Table 1.

TABLE 1

| Compound of Example | Activity Rating[a] |
|---|---|
| 8 | + |
| 18 | + |
| 19 | + |
| 20 | ++ |
| 21 | +++ |
| 25 | ++ |
| 26 | + |
| 29 | ++ |
| 35 | +++ |
| 40 | ++ |
| 42 | + |
| 43 | +++ |
| 49 | +++ |
| 52 | ++ |
| 56 | ++ |
| 59 | + |
| 61 | +++ |
| 69 | ++ |
| 70 | +++ |
| 78 | +++ |
| 79 | + |
| 91 | + |

TABLE 1-continued

| Compound of Example | Activity Rating[a] |
|---|---|
| 96 | ++ |
| 100 | +++ |

[a]Activity based on $IC_{50}$ values:
+++ = <0.01 µM
++ = 0.01-0.5 µM
+ = >0.5 µM In Vitro Assay to Identify β-Secretase Inhibitor Based on the Inhibition of Aβ Formation from Membrane Preparations.

An isolated membrane fraction which contains functionally active β-secretase and β-APP substrates can generate β-secretase cleavage products including Aβ (Roberts, S. B.; Hendrick, J. P.; Vinitsky, A.; Lewis, M.; Smith, D. W.; Pak, R. PCT Publication WO 01/0175435; Fechteler, K.; Kostka, M.; Fuchs, M. Patent Application No. DE 99-19941039; Shearman, M.; Beher, D. et al., *Biochemistry*, 2000, 39, 8698-8704; Zhang, L. Song, L. et al., *Biochemistry* 2001, 40, 5049-5055). An isolated membrane fraction can be prepared from human derived cell lines such as HeLa and H4 which have been transfected with wild type or mutant forms of β-APP or a human alkaline phosphatase β-APP fusion construct, and stably express high levels of β-secretase substrates. The endogenous β-secretase present in the isolated membranes prepared at 0-4° C. cleaves the β-APP substrates when the membranes are shifted from 0-4 to 37° C. Detection of the cleavage products including Aβ can be monitored by standard techniques such as immunoprecipitation (Citron, M.; Diehl, T. S. et al., *Proc. Natl. Acad. Sci. USA*, 1996, 93, 13170-13175), western blot (Klafki, H.-W.; Ambramowski, D. et al., *J. Biol. Chem.* 1996, 271, 28655-28659), enzyme linked immunosorbent assay (ELISA) as demonstrated by Seubert, P.; Vigo-Pelfrey, C. et al., *Nature*, 1992, 359, 325-327, or by a preferred method using time-resolved fluorescence of the homogeneous sample containing membranes and Aβ (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000, 39, 8698-8704). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the β-secretase cleavage. The second antibody binds to any other epitope present on Aβ. For example, antibodies that bind the N-terminal region (e.g., 26D6-B2-B3® SIBIA Neurosciences, La Jolla, Calif.) or bind the C-terminal end (e.g., 9S3.2® antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of β-secretase. The isolated membrane assay can be used to identify candidate agents that inhibit the activity of β-secretase cleavage and Aβ production.

A typical membrane-based assay requires 45 µg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plant or marine samples. All synthetic agents are initially screened at doses ranging from 10-100 μM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantitation of Aβ is described elsewhere (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000. 39, 8698-8704). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. Compounds of the present application are considered active when tested in the above assay if the $IC_{50}$ value for the test compound is less than 50 μM. A preferred $IC_{50}$ value is less than 1 μM. A more preferred $IC_{50}$ value is less than 0.1 μM. If a compound is found to be active then a dose response experiment is performed to determine the lowest dose of compound necessary to elicit the inhibition of the production of Aβ.

In Vivo Assays for the Determination of Aβ Reduction by a β-Secretase Inhibitor.

In vivo assays are available to demonstrate the inhibition of β-secretase activity. In these assays, animals, such as mice, that express normal levels of APP, β- and γ-secretase or are engineered to express higher levels of APP and hence Aβ can be used to demonstrate the utility of β-secretase inhibitors, as demonstrated with γ-secretase inhibitors [Dovey, H. et al., (2001), J. Neurochem. 76: 173-181]. In these assays, β-secretase inhibitors are administered to animals and Aβ levels in multiple compartments, such as plasma, cerebral spinal fluid, and brain extracts, are monitored for Aβ levels using methods previously outlined. For instance, Tg2576 mice, which over-express human APP, are administered β-secretase inhibitors by oral gavage at doses that will cause measurable Aβ lowering, typically less than 100 mg/kg. Three h after dosing plasma, brain, and CSF are collected, frozen in liquid nitrogen, and stored at −80° C. until analysis. For Aβ detection, plasma is diluted 15-fold in PBS with 0.1% Chaps while CSF is diluted 15-fold in 1% Chaps with protease inhibitors (5 μg/mL leupeptin, 30 μg/mL aprotinin, 1 mM phenylmethylsulfonylfluoride, 1 μM pepstatin). Brains are homogenized in 1% Chaps with protease inhibitors using 24 mL solution/g brain tissue. Homogenates were then centrifuged at 100,000×g for 1 hr at 4° C. The resulting supernatants were then diluted 10-fold in 1% Chaps with protease inhibitors. Aβ levels in the plasma, CSF, and brain lysate can then be measured using time-resolved fluorescence of the homogenous sample or one of the other methods previously described.

A β-secretase inhibitor is considered active in one of the above in vivo assays if it reduces Aβ by at least 50% at a dosage of 100 mg/kg.

Dosage and Formulation

The compounds of the present application can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this application can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present application will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present application may be administered in a single daily dose, or the total daily dosage may be administered in divided doses of two, three, or four times daily.

The compounds for the present application can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present application, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present disclosure can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present disclosure may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present disclosure may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of h. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:
1. A compound of Formula (I); or a stereoisomer thereof

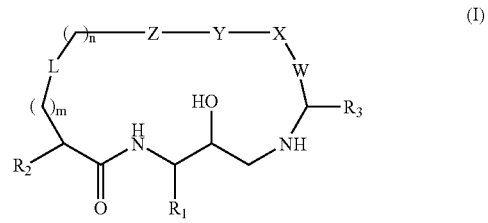

wherein
R$_1$ is C$_{1-6}$alkyl, phenyl or phenyl(C$_{1-4}$alkyl) in which each group is optionally substituted with one or two groups selected from halogen, C$_{1-4}$alkyl, OH, CF$_3$, OCF$_3$ and CN;
R$_2$ is hydrogen, C$_{1-6}$alkyl, C$_{3-6}$alkenyl, C$_{3-6}$cycloalkyl or C$_{3-6}$cyloalkyl(C$_{1-4}$alkyl) in which each group is optionally substituted with a group selected from halogen, C$_{1-4}$alkyl, OH, C$_{1-4}$alkoxy, CF$_3$, CF$_2$H, OCF$_3$ and CN; or NHR$_4$, NR$_4$C(=O)R$_5$, NR$_4$C(=O)OR$_5$ or NR$_4$S(=O)$_2$R$_5$;
R$_3$ is hydrogen, C$_{1-6}$alkyl, phenyl or phenyl(C$_{1-4}$alkyl) in which each group is optionally substituted with one to two groups selected from halogen, C$_{1-4}$alkyl, OH, CF$_3$, OCF$_3$ and CN;
R$_4$ is hydrogen or C$_{1-6}$alkyl;
R$_5$ is C$_{1-6}$alkyl, phenyl or thiophenyl in which each group is optionally substituted with one to two groups selected from halogen, C$_{1-4}$alkyl, OH, CF$_3$, OCF$_3$ and CN;
m is 1 or 2;
n is 1 or 2;
W is CH$_2$; or W and R$_3$ are joined together to form the following ring system

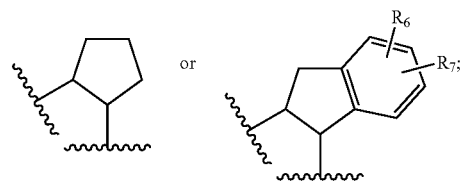

X is a bond or CH$_2$; or when W is CH$_2$, X and R$_3$ are joined together to form the following ring system

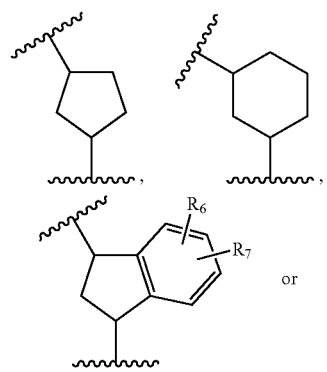

-continued

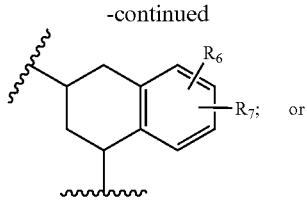

X and W are joined together to form the following ring system

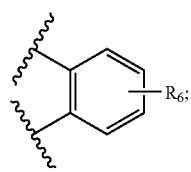

Y is a bond or $C_{1-3}$alkyl;
Z is a bond, oxygen or $NR_8$;
$R_6$ and $R_7$ each are independently hydrogen, halogen, $C_{1-6}$alkyl, $C_{3-6}$cycloalkyl, $C_{3-6}$cyloalkyl($C_{1-4}$alkyl), phenyl, 4-morpholinophenyl, $C_{1-6}$alkoxy, $OCF_3$, phenoxy, indanyl, pyrazoyl, piperizinyl, 4-(5-tert-butoxycarbonyl)-hexahydropyrrolo[3,4-c]pyrrol-2(1H)-yl), 5-methylhexahydropyrrolo[3,4-c]pyrrol-2(1H)-yl and pyrrolidinyl in which each group is optionally substituted with a group selected from halogen, $C_{1-4}$alkyl, $CF_3$, $CF_2H$, OH, $OCF_3$ and $C_{1-4}$alkoxy;
$R_8$ is hydrogen, $C_{1-4}$alkyl or $C(=O)OR_9$;
$R_9$ is $C_{1-6}$alkyl, phenyl or phenyl($C_{1-4}$alkyl);
L is —$CH(R_{10})$—$CH(R_{11})$— or —$C(R_{10})$=$C(R_{11})$—; and
$R_{10}$ and $R_{11}$ are each independently hydrogen or methyl;
or a nontoxic pharmaceutically acceptable salt thereof.

2. The compound according to claim 1 of Formula (I); or a stereoisomer thereof

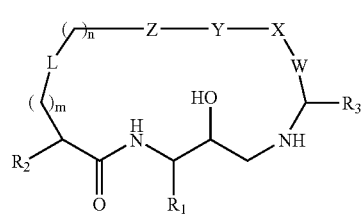

(I)

wherein
$R_1$ is $C_{1-6}$alkyl or phenyl($C_{1-4}$alkyl) in which each group is optionally substituted with one or two groups selected from halogen, $C_{1-4}$alkyl, OH, $CF_3$, $OCF_3$ and CN;
$R_2$ is hydrogen or $C_{1-6}$alkyl optionally substituted with a group selected from halogen, $C_{1-4}$alkyl, OH, $C_{1-4}$alkoxy, $CF_3$, $CF_2H$, $OCF_3$ and CN; or $NHR_4$, $NR_4C(=O)R_5$, $NR_4C(=O)OR_5$ or $NR_4S(=O)_2R_5$;
$R_3$ is hydrogen, $C_{1-6}$alkyl, phenyl or phenyl($C_{1-4}$alkyl) in which each group is optionally substituted with one to two groups selected from halogen, $C_{1-4}$alkyl, OH, $CF_3$, $OCF_3$ and CN;
$R_4$ is hydrogen or $C_{1-6}$alkyl;
$R_5$ is $C_{1-6}$alkyl or phenyl in which each group is optionally substituted with one to two groups selected from halogen, $C_{1-4}$alkyl, OH, $CF_3$, $OCF_3$ and CN;
m is 1 or 2;
n is 1 or 2;
W and $R_3$ are joined together to form the following ring system

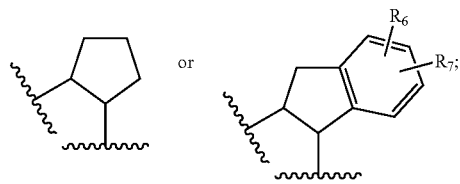

X is a bond;
Y is a bond or $C_{1-3}$alkyl;
Z is oxygen or $NR_8$;
$R_6$ and $R_7$ each are independently hydrogen, halogen, $C_{1-6}$alkyl, phenyl, $C_{1-6}$alkoxy or $OCF_3$ in which each group is optionally substituted with a group selected from halogen, $C_{1-4}$alkyl, $CF_3$, $CF_2H$, OH, $OCF_3$ and $C_{1-4}$alkoxy;
$R_8$ is hydrogen, $C_{1-4}$alkyl or $C(=O)OR_9$;
$R_9$ is $C_{1-6}$alkyl, phenyl or phenyl($C_{1-4}$alkyl);
L is —$CH(R_{10})$—$CH(R_{11})$— or —$C(R_{10})$=$C(R_{11})$—; and
$R_{10}$ and $R_{11}$ are each independently hydrogen or methyl;
or a nontoxic pharmaceutically acceptable salt thereof.

3. The compound according to claim 1 of Formula (I); or a stereoisomer thereof

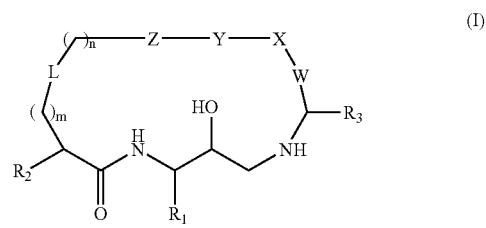

(I)

wherein
$R_1$ is $C_{1-6}$alkyl or phenyl($C_{1-4}$alkyl) in which each group is optionally substituted with one or two groups selected from halogen, $C_{1-4}$alkyl, OH, $CF_3$, $OCF_3$ and CN;
$R_2$ is hydrogen or $C_{1-6}$alkyl optionally substituted with a group selected from halogen, $C_{1-4}$alkyl, OH, $C_{1-4}$alkoxy, $CF_3$, $CF_2H$, $OCF_3$ and CN; or $NHR_4$, $NR_4C(=O)R_5$, $NR_4C(=O)OR_5$ or $NR_4S(=O)_2R_5$,
$R_3$ is hydrogen, $C_{1-6}$alkyl, phenyl or phenyl($C_{1-4}$alkyl) in which each group is optionally substituted with one to two groups selected from halogen, $C_{1-4}$alkyl, OH, $CF_3$, $OCF_3$ and CN;
$R_4$ is hydrogen or $C_{1-6}$alkyl;
$R_5$ is $C_{1-6}$alkyl or phenyl in which each group is optionally substituted with one to two groups selected from halogen, $C_{1-4}$alkyl, OH, $CF_3$, $OCF_3$ and CN;
m is 1 or 2;
n is 1 or 2;
W is $CH_2$;
X and $R_3$ are joined together to form the following ring system

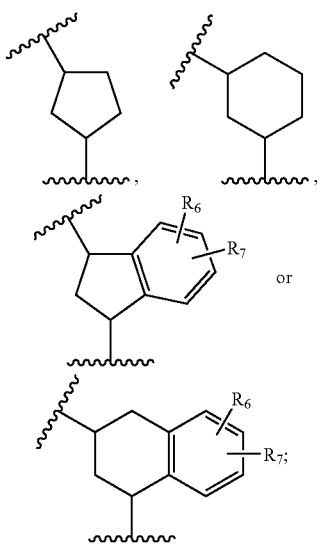

Y is a bond or $C_{1-3}$alkyl;
Z is oxygen or $NR_8$;
$R_6$ and $R_7$ each are independently hydrogen, halogen, $C_{1-6}$alkyl, phenyl, $C_{1-6}$alkoxy or $OCF_3$ in which each group is optionally substituted with a group selected from halogen, $C_{1-4}$alkyl, $CF_3$, $CF_2H$, OH, $OCF_3$ and $C_{1-4}$alkoxy;
$R_8$ is hydrogen, $C_{1-4}$alkyl or $C(=O)OR_9$;
$R_9$ is $C_{1-6}$alkyl, phenyl or phenyl($C_{1-4}$alkyl);
L is —CH($R_{10}$)—CH($R_{11}$)— or —C($R_{10}$)=C($R_{11}$)—; and
$R_{10}$ and $R_{11}$ are each independently hydrogen or methyl;
or a nontoxic pharmaceutically acceptable salt thereof.

4. The compound according to claim 1 of Formula (I); or a stereoisomer thereof

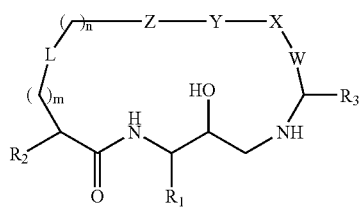

wherein
$R_1$ is $C_{1-6}$alkyl or phenyl($C_{1-4}$alkyl) in which each group is optionally substituted with one or two groups selected from halogen, $C_{1-4}$alkyl, OH, $CF_3$, $OCF_3$ and CN;
$R_2$ is hydrogen or $C_{1-6}$alkyl optionally substituted with a group selected from halogen, $C_{1-4}$alkyl, OH, $C_{1-4}$alkoxy, $CF_3$, $CF_2H$, $OCF_3$ and CN; or $NHR_4$, $NR_4C(=O)R_5$, $NR_4C(=O)OR_5$ or $NR_4S(=O)_2R_5$,
$R_3$ is hydrogen, $C_{1-6}$alkyl, phenyl or phenyl($C_{1-4}$alkyl) in which each group is optionally substituted with one to two groups selected from halogen, $C_{1-4}$alkyl, OH, $CF_3$, $OCF_3$ and CN;
$R_4$ is hydrogen or $C_{1-6}$alkyl;
$R_5$ is $C_{1-6}$alkyl or phenyl in which each group is optionally substituted with one to two groups selected from halogen, $C_{1-4}$alkyl, OH, $CF_3$, $OCF_3$ and CN;

m is 1 or 2;
n is 1 or 2;
X and W are joined together to form the following ring system

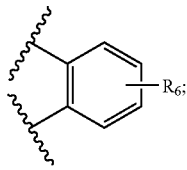

Y is a bond or $C_{1-4}$alkyl;
Z is a bond, oxygen or $NR_8$;
$R_6$ is hydrogen, halogen, $C_{1-6}$alkyl, phenyl, $C_{1-6}$alkoxy or $OCF_3$ in which each group is optionally substituted with a group selected from halogen, $C_{1-4}$alkyl, $CF_3$, $CF_2H$, OH, $OCF_3$ and $C_{1-4}$alkoxy;
$R_8$ is hydrogen, $C_{1-6}$alkyl or $C(=O)OR_9$;
$R_9$ is $C_{1-6}$alkyl, phenyl or phenyl($C_{1-4}$alkyl);
L is —CH($R_{10}$)—CH($R_{11}$)— or —C($R_{10}$)=C($R_{11}$)—; and
$R_{10}$ and $R_{11}$ are each independently hydrogen or methyl;
or a nontoxic pharmaceutically acceptable salt thereof.

5. The compound according to claim 2 having the following Formula; or a stereoisomer thereof

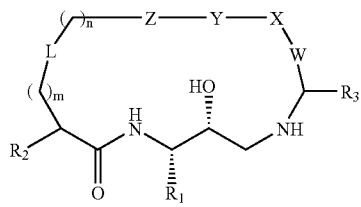

wherein
$R_1$ is phenyl($C_{1-4}$alkyl) optionally substituted with one or two groups selected from halogen, $C_{1-4}$alkyl, OH, $CF_3$, $OCF_3$ and CN;
$R_2$ is hydrogen, $C_{1-6}$alkyl, $NR_4C(=O)R_5$, $NR_4C(=O)OR_5$ or $NR_4S(=O)_2R_5$;
$R_3$ is hydrogen or phenyl optionally substituted with one to two groups selected from halogen, $C_{1-4}$alkyl, OH, $CF_3$, $OCF_3$ and CN;
$R_4$ is hydrogen or $C_{1-6}$alkyl;
$R_5$ is $C_{1-6}$alkyl optionally substituted with one to two groups selected from halogen, $C_{1-4}$alkyl, OH, $CF_3$, $OCF_3$ and CN;
m is 1 or 2;
n is 1;
W and $R_3$ are joined together to form the following ring system

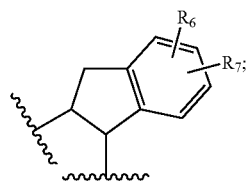

X is a bond;

Y is a bond or $C_{1-3}$alkyl;

Z is oxygen;

$R_6$ and $R_7$ each are independently hydrogen, halogen, $C_{1-6}$alkyl, phenyl, $C_{1-6}$alkoxy or $OCF_3$ in which each group is optionally substituted with a group selected from halogen, $C_{1-4}$alkyl, $CF_3$, $CF_2H$, OH, $OCF_3$ and $C_{1-4}$alkoxy; and L is —$CH_2$—$CH_2$— or —CH=CH—;

or a nontoxic pharmaceutically acceptable salt thereof.

6. The compound according to claim 3 having the following Formula; or a stereoisomer thereof

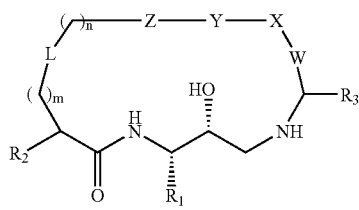

wherein $R_1$ is phenyl($C_{1-4}$alkyl) optionally substituted with one or two groups selected from halogen, $C_{1-4}$alkyl, OH, $CF_3$, $OCF_3$ and CN;

$R_2$ is hydrogen, $NR_4C(=O)R_5$, $NR_4C(=O)OR_5$ or $NR_4S(=O)_2R_5$;

$R_3$ is hydrogen or phenyl optionally substituted with one to two groups selected from halogen, $C_{1-4}$alkyl, OH, $CF_3$, $OCF_3$ and CN;

$R_4$ is hydrogen or $C_{1-6}$alkyl;

$R_5$ is $C_{1-6}$alkyl optionally substituted with one to two groups selected from halogen, $C_{1-4}$alkyl, OH, $CF_3$, $OCF_3$ and CN;

m is 1 or 2;

n is 1;

W is $CH_2$;

X and $R_3$ are joined together to form the following ring system

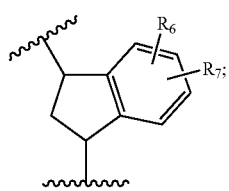

Y is a bond or $C_{1-3}$alkyl;

Z is oxygen;

$R_6$ and $R_7$ each are independently hydrogen, halogen, $C_{1-6}$alkyl, phenyl, $C_{1-6}$alkoxy or $OCF_3$ in which each group is optionally substituted with a group selected from halogen, $C_{1-4}$alkyl, $CF_3$, $CF_2H$, OH, $OCF_3$ and $C_{1-4}$alkoxy; and L is —$CH_2$—$CH_2$— or —CH=CH—;

or a nontoxic pharmaceutically acceptable salt thereof.

7. The compound according to claim 4 having the following Formula; or a stereoisomer thereof

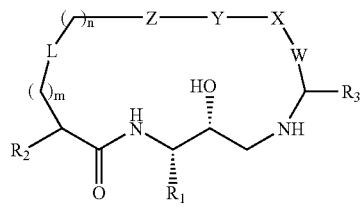

wherein $R_1$ is phenyl($C_{1-4}$alkyl) in which each group is optionally substituted with one or two groups selected from halogen, $C_{1-4}$alkyl, OH, $CF_3$, $OCF_3$ and CN;

$R_2$ is hydrogen, $NR_4C(=O)R_5$, $NR_4C(=O)OR_5$ or $NR_4S(=O)_2R_5$;

$R_3$ is hydrogen or phenyl optionally substituted with one to two groups selected from halogen, $C_{1-4}$alkyl, OH, $CF_3$, $OCF_3$ and CN;

$R_4$ is hydrogen or $C_{1-6}$alkyl;

$R_5$ is $C_{1-6}$alkyl optionally substituted with one to two groups selected from halogen, $C_{1-4}$alkyl, OH, $CF_3$, $OCF_3$ and CN;

m is 1 or 2;

n is 1;

X and W are joined together to form the following ring system

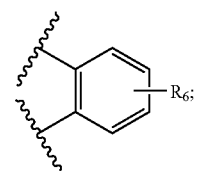

Y is a bond or $C_{1-3}$alkyl;

Z is a bond or oxygen;

$R_6$ is hydrogen, halogen, $C_{1-6}$alkyl, phenyl, $C_{1-6}$alkoxy or $OCF_3$ in which each group is optionally substituted with a group selected from halogen, $C_{1-4}$alkyl, $CF_3$, $CF_2H$, OH, $OCF_3$ and $C_{1-4}$alkoxy; and L is —$CH_2$—$CH_2$— or —CH=CH—;

or a nontoxic pharmaceutically acceptable salt thereof.

8. The compound according to claim 1 of Formula (I); or a stereoisomer thereof

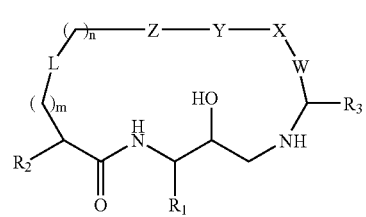

(I)

wherein $R_1$ is $C_{1-6}$alkyl, phenyl or phenyl($C_{1-4}$alkyl) in which each group is optionally substituted with one or two groups selected from halogen, $C_{1-4}$alkyl, OH, $CF_3$, $OCF_3$ and CN;

R₂ is hydrogen;
R₃ is hydrogen, C₁₋₆alkyl, phenyl or phenyl(C₁₋₄alkyl) in which each group is optionally substituted with one to two groups selected from halogen, C₁₋₄alkyl, OH, CF₃, OCF₃ and CN;
R₄ is hydrogen or C₁₋₆alkyl;
R₅ is C₁₋₆alkyl, phenyl or thiophenyl in which each group is optionally substituted with one to two groups selected from halogen, C₁₋₄alkyl, OH, CF₃, OCF₃ and CN;
m is 1 or 2;
n is 1 or 2;
W is CH₂;
X and R₃ are joined together to form the following ring system

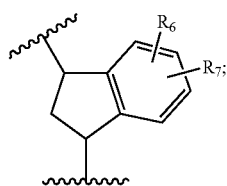

Y is a bond or C₁₋₃alkyl;
Z is a bond, oxygen or NR₈;
R₆ and R₇ each are independently hydrogen, halogen, C₁₋₆alkyl, C₃₋₆cycloalkyl, C₃₋₆cyloalkyl(C₁₋₄alkyl), phenyl, 4-morpholinophenyl, C₁₋₆alkoxy, OCF₃, phenoxy, indanyl, pyrazoyl, piperizinyl, 4-(5-tert-butoxycarbonyl)-hexahydropyrrolo[3,4-c]pyrrol-2(1H)-yl), 5-methylhexahydropyrrolo[3,4-c]pyrrol-2(1H)-yl and pyrrolidinyl in which each group is optionally substituted with a group selected from halogen, C₁₋₄alkyl, CF₃, CF₂H, OH, OCF₃ and C₁₋₄alkoxy;
R₈ is hydrogen, C₁₋₄alkyl or C(=O)OR₉;
R₉ is C₁₋₆alkyl, phenyl or phenyl(C₁₋₄alkyl);
L is —CH(R₁₀)—CH(R₁₁)— or —C(R₁₀)=C(R₁₁)—; and
R₁₀ and R₁₁ are each independently hydrogen or methyl;
or a nontoxic pharmaceutically acceptable salt thereof.

9. The compound according to claim 8 having the following Formula; or a stereoisomer thereof

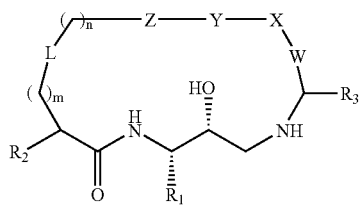

wherein
R₁ is phenyl(C₁₋₄alkyl) optionally substituted with one or two groups selected from halogen, C₁₋₄alkyl, OH, CF₃, OCF₃ and CN;
R₂ is hydrogen;
R₃ is hydrogen or phenyl optionally substituted with one to two groups selected from halogen, C₁₋₄alkyl, OH, CF₃, OCF₃ and CN;
R₄ is hydrogen or C₁₋₆alkyl;
R₅ is C₁₋₆alkyl optionally substituted with one to two groups selected from halogen, C₁₋₄alkyl, OH, CF₃, OCF₃ and CN;
m is 1 or 2;
n is 1;
W is CH₂;
X and R₃ are joined together to form the following ring system

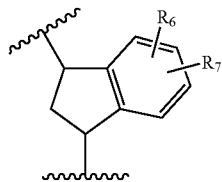

Y is a bond or C₁₋₃alkyl;
Z is oxygen;
R₆ and R₇ each are independently hydrogen, halogen, C₁₋₆alkyl, phenyl, C₁₋₆alkoxy or OCF₃ in which each group is optionally substituted with a group selected from halogen, C₁₋₄alkyl, CF₃, CF₂H, OH, OCF₃ and C₁₋₄alkoxy; and
L is —CH₂—CH₂— or —CH=CH—;
or a nontoxic pharmaceutically acceptable salt thereof.

10. The compound of claim 1 selected from the group consisting of:
2ethyl-hexanoic acid ((1S,4R,5S,8S,14R)-5-benzyl-4-hydroxy-18-methoxy-7-oxo-13-oxa-2,6-diaza-tricyclo[12.6.1.0¹⁵,²⁰]henicosa-10,15(20),16,18-tetraen-8-yl)-methyl-amide;
5,5,5-Trifluoro-pentanoic acid ((1S,4R,5S,8S,14R)-5-benzyl-4-hydroxy-18-methoxy-7-oxo-13-oxa-2,6-diaza-tricyclo[12.6.1.0¹⁵,²⁰]henicosa-10,15(20),16,18-tetraen-8-yl)-methyl-amide;
3,3,3-Trifluoro-propane-1-sulfonic acid ((1S,4R,5S,8S,14R)-5-benzyl-4-hydroxy-18-methoxy-7-oxo-13-oxa-2,6-diaza-tricyclo[12.6.1.0¹⁵,²⁰]henicosa-10,15(20),16,18-tetraen-8-yl)-methyl-amide;
pentane-1-sulfonic acid ((1S,4R,5S,8S,14R)-5-benzyl-4-hydroxy-18-methoxy-7-oxo-13-oxa-2,6-diaza-tricyclo[12.6.1.0¹⁵,²⁰]henicosa-10,15(20),16,18-tetraen-8-yl)-methyl-amide;
hexanoic acid ((1S,4R,5S,8S,14R)-5-benzyl-4-hydroxy-18-methoxy-7-oxo-13-oxa-2,6-diaza-tricyclo[12.6.1.0¹⁵,²⁰]henicosa-10,15(20),16,18-tetraen-8-yl)-methyl-amide;
(S)-2-methyl-hexanoic acid ((1S,4R,5S,8S,14R)-5-benzyl-4-hydroxy-18-methoxy-7-oxo-13-oxa-2,6-diaza-tricyclo[12.6.1.0¹⁵,²⁰]henicosa-10,15(20),16,18-tetraen-8-yl)-methyl-amide;
3,3,3-trifluoro-propane-1-sulfonic acid ((1S,4R,5S,8S,15R)-5-benzyl-4-hydroxy-19-methoxy-7-oxo-14-oxa-2,6-diaza-tricyclo[13.6.1.0¹⁶,²¹]docosa-11,16(21),17,19-tetraen-8-yl)-methyl-amide;
3,3,3-trifluoro-propane-1-sulfonic acid [(1S,4R,5S,8S,15R)-5-(3,5-difluoro-benzyl)-4-hydroxy-19-methoxy-7-oxo-14-oxa-2,6-diaza-tricyclo[13.6.1.0¹⁶,²¹]docosa-11,16(21),17,19-tetraen-8-yl]-methyl-amide;
5,5,5-trifluoro-pentanoic acid [(1S,4R,5S,8S,15R)-5-(3,5-difluoro-benzyl)-4-hydroxy-19-methoxy-7-oxo-14-oxa-2,6-diaza-tricyclo[13.6.1.0¹⁶,²¹]docosa-11,16(21),17,19-tetraen-8-yl]-methyl-amide;
2-methyl-hexanoic acid [(1S,4R,5S,8S,14R)-5-(3,5-difluoro-benzyl)-4-hydroxy-18-methoxy-7-oxo-13-oxa-2,6-diaza-tricyclo[12.6.1.0¹⁵,²⁰]henicosa-10,15(20),16,18-tetraen-8-yl]-methyl-amide;

N-[(1S,4R,5S,8S,14R)-5-(3,5-difluoro-benzyl)-4-hydroxy-18methoxy-7-oxo-13-oxa-2,6-diaza-tricyclo[12.6.1.0 15,20]henicosa-10,15(20),16,18-tetraen-8-yl]-4,4,4-trifluoro-2,N-dimethyl-butyramide;

(S)-2-methyl-hexanoic acid [(1S,4R,5S,8S,14S)-5-(3,5-difluoro-benzyl)-4-hydroxy-18-methoxy-7-oxo-13-oxa-2,6-diaza-tricyclo[12.6.1.0 15,20]henicosa-10,15(20),16,18-tetraen-8-yl]-methyl-amide;

3,3,3-trifluoro-propane-1-sulfonic acid ((1S,4R,5S,8S,15R)-5-benzyl-4-hydroxy-19-methoxy-7-oxo-13-oxa-2,6-diaza-tricyclo[13.6.1.0$^{16,21}$]docosa-10,16(21),17,19-tetraen-8-yl)-methyl-amide;

pentane-1-sulfonic acid ((1S,4R,5S,8S,14R)-5-(3,5-dichloro-benzyl-4-hydroxy-18-methoxy-7-oxo-13-oxa-2,6-diaza-tricyclo[12.6.1.0 15,20]henicosa-10,15(20),16,18-tetraen-8-yl)-methyl-amide;

3,3,3-Trifluoro-propane-1-sulfonic acid ((1S,4R,5S,8S,14R)-5-(3,5-dichloro-benzyl-4-hydroxy-18-methoxy-7-oxo-13-oxa-2,6-diaza-tricyclo[12.6.1.0 15,20]henicosa-10,15(20),16,18-tetraen-8-yl)-methyl-amide;

3,3,3-Trifluoro-propane-1-sulfonic acid ((1S,4R,5S,8S,14R)-5-(3,5-dichloro-benzyl-4-hydroxy-18-methoxy-7-oxo-13-oxa-2,6-diaza-tricyclo[12.6.1.0 15,20] henicosa-15(20),16,18-trien-8-yl)-methyl-amide;

3,3,3-Trifluoro-propane-1-sulfonic acid ((1S,4R,5S,8S,14R)-5-(3-chloro-benzyl-4-hydroxy-18-methoxy-7-oxo-13-oxa-2,6-diaza-tricyclo[12.6.1.0 15,20] henicosa-15(20),16,18-trien-8-yl)-methyl-amide;

3,3,3-Trifluoro-propane-1-sulfonic acid ((1S,4R,5S,8S,14R)-5-(benzyl-4-hydroxy-18methoxy-7-oxo-13-oxa-2,6-diaza-tricyclo[12.6.1.0 15,20]henicosa-15(20),16,18-trien-8-yl)-methyl-amide;

(S)-2-methyl-hexanoic acid ((1S,4R,5S,8S,14R)-5-(3,5-dichloro-benzyl-4-hydroxy-18-methoxy-7-oxo-13-oxa-2,6-diaza-tricyclo[12.6.1.0 15,20]henicosa-10,15(20),16,18-tetraen-8-yl)-methyl-amide;

(S)-2-methyl-hexanoic acid ((1S,4R,5S,8S,14R)-5-(3,5-dichloro-benzyl)-4-hydroxy-18-methoxy-7-oxo-13-oxa-2,6-diaza-tricyclo[12.6.1.0 15,20]henicosa-15(20),16,18-trien-8-yl)-methyl-amide;

3,3,3-trifluoro-propane-1-sulfonic acid ((1S,4R,5S,8S,15R)-5-benzyl-19-bromo-4-hydroxy-7-oxo-14-oxa-2,6-diaza-tricyclo[13.6.1.0$^{16,21}$]docosa-11,16(21),17,19-tetraen-8-yl)-methyl-amide;

(1S,4R,5S,16R)-5-(3,5-difluoro-benzyl)-4-hydroxy-20isobutyl-15-oxa-2,6-diaza-tricyclo[14.6.1.0$^{17,22}$]tricosa-12,17(22),18,20-tetraen-7-one;

3,3,3-trifluoro-propane-1-sulfonic acid ((1S,4R,5S,8S,15R)-4-hydroxy-5-isobutyl-19-methoxy-7-oxo-14-oxa-2,6-diaza-tricyclo[13.6.1.0$^{16,21}$]docosa-11,16(21),17,19-tetraen-8-yl)-methyl-amide;

pentane-1-sulfonic acid ((1S,4R,5S,8S,14R)-5-benzyl-4-hydroxy-18-isopropoxy-7-oxo-13-oxa-2,6-diaza-tricyclo[12.6.1.0 15,20]henicosa-10,15(20),16,18-tetraen-8-yl)-methyl-amide;

3,3,3-trifluoro-propane-1-sulfonic acid ((1S,4R,5S,8S,14R)-5-benzyl-4-hydroxy-18-isopropoxy-7-oxo-13-oxa-2,6-diaza-tricyclo[12.6.1.0 15,20]henicosa-10,15(20),16,18-tetraen-8-yl)-methyl-amide;

pentane-1-sulfonic acid ((1S,4R,5S,8S,15R)-5-benzyl-4-hydroxy-19-isopropoxy-7-oxo-14-oxa-2,6-diaza-tricyclo[13.6.1.0$^{16,21}$]docosa-11,16(21),17,19-tetraen-8-yl)-methyl-amide;

3,3,3-trifluoro-propane-1-sulfonic acid ((1S,4R,5S,8S,15R)-5-benzyl-4-hydroxy-19-isopropoxy-7-oxo-14-oxa-2,6-diaza-tricyclo[13.6.1.0 16,21]docosa-11,16(21),17,19-tetraen-8-yl)-methyl-amide;

(1S,4R,5S,15R)-5-(3,5-difluoro-benzyl)-4-hydroxy-19-isopropoxy-14-oxa-2,6-diaza-tricyclo[13.6.1.0$^{16,21}$]docosa-11,16(21),17,19-tetraen-7-one;

(1S,4R,5S,15R)-5-(3,5-difluoro-benzyl)-4-hydroxy-19-propoxy-14-oxa-2,6-diaza-tricyclo[13.6.1.0$^{16,21}$]docosa-11,16(21),17,19-tetraen-7-one;

hexanoic acid ((4R,5S,8S)-5-benzyl-4-hydroxy-7-oxo-19-phenoxy-14-oxa-2,6-diaza-tricyclo[13.6.1.0$^{16,21}$]docosa-11,16(21),17,19-tetraen-8-yl)-methyl-amide;

(S)-2-methyl-hexanoic acid ((1S,4R,5S,8S,14R)-5-benzyl-4-hydroxy-18-methyl-7-oxo-13-oxa-2,6-diaza-tricyclo[12.6.1.0$^{15,20}$]henicosa-10,15(20),16,18-tetraen-8-yl)-methyl-amide; and (S)-2-methyl-hexanoic acid ((1S,4R,5S,8S,14R)-5-benzyl-4-hydroxy-16,18-dimethyl-7-oxo-13-oxa-2,6-diaza-tricyclo[12.6.1.0$^{15,20}$]henicosa-10,15(20),16,18-tetraen-8-yl)-methyl-amide;

or a nontoxic pharmaceutically acceptable salt thereof.

11. A pharmaceutical composition comprising a therapeutically effective amount of a compound of claim 1 in association with a pharmaceutically acceptable carrier or diluent.

12. A method for the treatment of Alzheimer's Disease, cerebral amyloid angiopathy and Down's Syndrome which comprises administering to a mammal in need thereof a therapeutically effective amount of a compound of claim 1.

13. The compound which is pentane-1-sulfonic acid ((1S,4R,5S,8S,14R)-5-(3,5-dichloro-benzyl-4-hydroxy-18-methoxy-7-oxo-13-oxa-2,6-diaza-tricyclo[12.6.1.0$^{15,20}$]henicosa-10,15(20),16,18-tetraen-8-yl)-methyl-amide, or a nontoxic pharmaceutically acceptable salt thereof.

* * * * *